(12) United States Patent
Beachy et al.

(10) Patent No.: US 8,071,733 B2
(45) Date of Patent: *Dec. 6, 2011

(54) ANTIBODIES THAT SPECIFICALLY BIND HEDGEHOG-DERIVED POLYPEPTIDES

(75) Inventors: Philip A. Beachy, Stanford, CA (US);
Jeffrey A. Porter, Lexington, MA (US);
Randall T. Moon, Kenmore, WA (US)

(73) Assignees: The Johns Hopkins University School of Medicine, Baltimore, MD (US);
University of Washington, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/790,611

(22) Filed: May 28, 2010

(65) Prior Publication Data
US 2011/0002941 A1 Jan. 6, 2011

Related U.S. Application Data

(60) Continuation of application No. 11/804,733, filed on May 18, 2007, now Pat. No. 7,741,451, which is a continuation of application No. 10/460,594, filed on Jun. 11, 2003, now Pat. No. 7,220,838, which is a division of application No. 09/562,914, filed on May 2, 2000, now Pat. No. 6,911,528, which is a division of application No. 08/946,329, filed on Oct. 7, 1997, now Pat. No. 6,057,091, which is a continuation-in-part of application No. 08/729,743, filed on Oct. 7, 1996, now Pat. No. 6,214,794, which is a continuation-in-part of application No. 08/567,357, filed on Dec. 4, 1995, now Pat. No. 6,132,728, which is a continuation-in-part of application No. 08/349,498, filed on Dec. 2, 1994, now Pat. No. 6,281,332.

(60) Provisional application No. 60/061,323, filed on Oct. 2, 1997.

(51) Int. Cl.
*C07K 16/00* (2006.01)
*C07K 16/18* (2006.01)

(52) U.S. Cl. ............... 530/389.2; 530/389.1; 530/388.1; 530/388.24; 424/184.1

(58) Field of Classification Search ............. None
See application file for complete search history.

(56) References Cited

U.S. PATENT DOCUMENTS

| 5,143,830 A | 9/1992 | Holland et al. |
| 5,789,543 A | 8/1998 | Ingham et al. |
| 5,844,079 A | 12/1998 | Ingham et al. |

FOREIGN PATENT DOCUMENTS

| EP | 0 020 029 | 12/1980 |
| WO | WO 96/16668 | 6/1996 |

OTHER PUBLICATIONS

Clarke and Armstrong, "Cellular Lipid Binding Proteins: Expression, Function, and Nutritional Regulation," *FASEB J.* (1989), 3:2480-2487.
Echelard et al., "Sonic Hedgehog, a Member of a Family of Putative Signaling Molecules, is Implicated in the Regulation of CNS Polarity," *Cell* (1993), 75:1417-1430, Cell Press.
Ericson et al., "Two Critical Periods of Sonic Hedgehog Signaling Required for the Specification of Motor Neuron Identity," *Cell* (1996), 87:661-673, Cell Press.
Farese, Jr. and Herz, "Cholesterol Metabolism and Embryogenesis," *TIG* (1998), 14(3):115 -120.
Ganong, William F., "Review of Medical Physiology," A Lange Medical Book, (1995) 273, 438, Appleton & Lange, Norwalk, Connecticut.
Hammerschmidt et al., "The World According to Hedgehog," *TIG*. (1997), 13(1):14-15, Elsevier Science Ltd.
Hynes et al., "Induction of Midbrain Dopaminergic Neurons by Sonic Hedgehog," *Neuron* (1995), 15:35-44.
Ingham, Philip W., "Signalling by Hedgehog Family Proteins in *Drosophila* and Vertebrate Development," *Curr. Opin. Genetics Dev.* (1995), 5:492-498, Current Biology Ltd.
Kolf-Clauw et al., "Abnormal Cholesterol Biosynthesis as in Smith-Lemli-Opitz Syndrome Disrupts Normal Skeletal Development in the Rat," *J. Lab. Clin. Med.* (1998), 131:222-227, Mosby, Inc.
Krauss et al., "A Functionally Conserved Homolog of the Drosophila Segment Polarity Gene hh is Expressed in Tissues with Polarizing Activity in Zebrafish Embryos," *Cell* (1993), 75:1431-1444, Cell Press.
Lange and Steck, "Cholesterol Homeostasis," *J. Biol. Chem.* (1994), 269(47):29371-29374, The American Society for Biochemistry and Molecular Biology, Inc.
Lee et al., "Secretion and Localized Transcription Suggest a Role in Positional Signaling for Products of the Segmentation Gene *hedgehog*," *Cell* (1992), 71:33-50, Cell Press.
Lee et al., "Autoproteolysis in *hedgehog* Protein Biogenesis," *Science* (1994), 266:1528-1537.
Mohler and Vani, "Molecular Organization and Embryonic Expression of the *hedgehog* Gene Involved in Cell-Cell Communication in Segmental Patterning of *Drosophila*," *Development* (1992), 115:957-971.
Ngo et al., "Computational Complexity, Protein Structure Prediction, and the Levinthal Paradox," In Merz, Jr. and Le Grand (eds.), *The Protein Folding Problem and Tertiary Structure Prediction* (1994), 433, 492-495, Birkhauser Boston.
Placzek et al., "Induction of Floor Plate Differentiation by Contact-Dependent, Homeogenetic Signals," *Development* (1993), 117:205-218, The Company of Biologists Limited.

(Continued)

*Primary Examiner* — Daniel C Gamett
(74) *Attorney, Agent, or Firm* — DLA Piper LLP (US)

(57) ABSTRACT

The present invention provides two novel polypeptides, referred to as the "N" and "C" fragments of hedgehog, or N-terminal and C-terminal fragments, respectively, which are derived after specific cleavage at a G'CF site recognized by the autoproteolytic domain in the native protein. Also included are sterol-modified hedgehog polypeptides and functional fragments thereof. Methods of identifying compositions which affect hedgehog activity based on inhibition of cholesterol modification of hedgehog protein are described.

15 Claims, 54 Drawing Sheets

OTHER PUBLICATIONS

Porter et al., "Cholesterol Modification of Hedgehog Signaling Proteins in Animal Development," *Science* (1996), 274:255-259.

Porter et al., "Hedgehog Patterning Activity: Role of a Lipophilic Modification Mediated by the Carbodxy-Terminal Autoprocessing Domain," *Cell* (1996), 86:21-34, Cell Press.

Prickett et al., "A Calcium-Dependent Antibody for Identification and Purificaiton of Recombinant Proteins," *Biotechniques* (1989), 7(6):580-589.

Reeck et al., ""Homology" in Proteins and Nucleic Acids: A Terminology Muddle and a Way Out of It," *Cell* (1987), 50:667, Cell Press.

Tabata and Kornberg, Hedgehog is a Signaling Protein with a Key Role in Patterning Drosophila Imaginal "Discs," *Cell* (1994), 76:89-102, Cell Press.

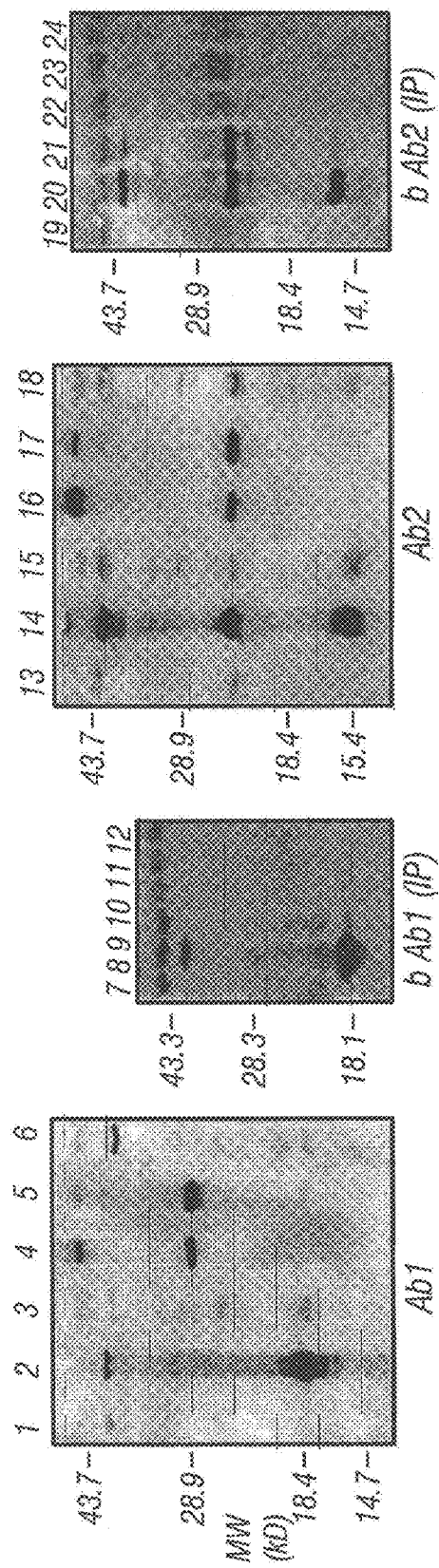

|  | 1 | 2 | 3 | 4 | 5 | 6 | 7 |  |
|---|---|---|---|---|---|---|---|---|
| D. mel. hh | L | T | V | T | P | A | H | SEQ ID NO:23 |
| D. hydei hh | L | T | V | T | P | A | H | SEQ ID NO:23 |
| C-Shh | L | L | L | T | A | A | H | SEQ ID NO:19 |
| M-Shh/Hhg-1 | L | L | L | T | A | A | H | SEQ ID NO:20 |
| R vhh-1 | L | L | L | T | A | A | H | SEQ ID NO:24 |
| Z-Shh/Zf vhh-1 | I | T | L | T | A | A | H | SEQ ID NO:18 |
| twhh | L | T | L | T | A | A | H | SEQ ID NO:17 |
| M-Dhh | L | L | L | T | P | W | H | SEQ ID NO:25 |
| M-Ihh | L | A | L | T | P | A | H | SEQ ID NO:26 |

*FIG. 2A*

| CHT | W | V | V | T | A | A | H | SEQ ID NO:27 |
|---|---|---|---|---|---|---|---|---|
| TRP | W | V | V | S | A | A | H | SEQ ID NO:28 |
| ELA | W | V | M | T | A | A | H | SEQ ID NO:29 |
| UKH | W | V | I | S | A | T | H | SEQ ID NO:30 |
| C1R | W | I | L | T | A | A | H | SEQ ID NO:31 |
| C1S | W | V | L | T | A | A | H | SEQ ID NO:32 |
| MCP | F | V | L | T | A | A | H | SEQ ID NO:33 |
| FAX | Y | V | L | T | A | A | H | SEQ ID NO:34 |
| TPA | W | I | L | S | A | A | H | SEQ ID NO:35 |

*FIG. 2B*

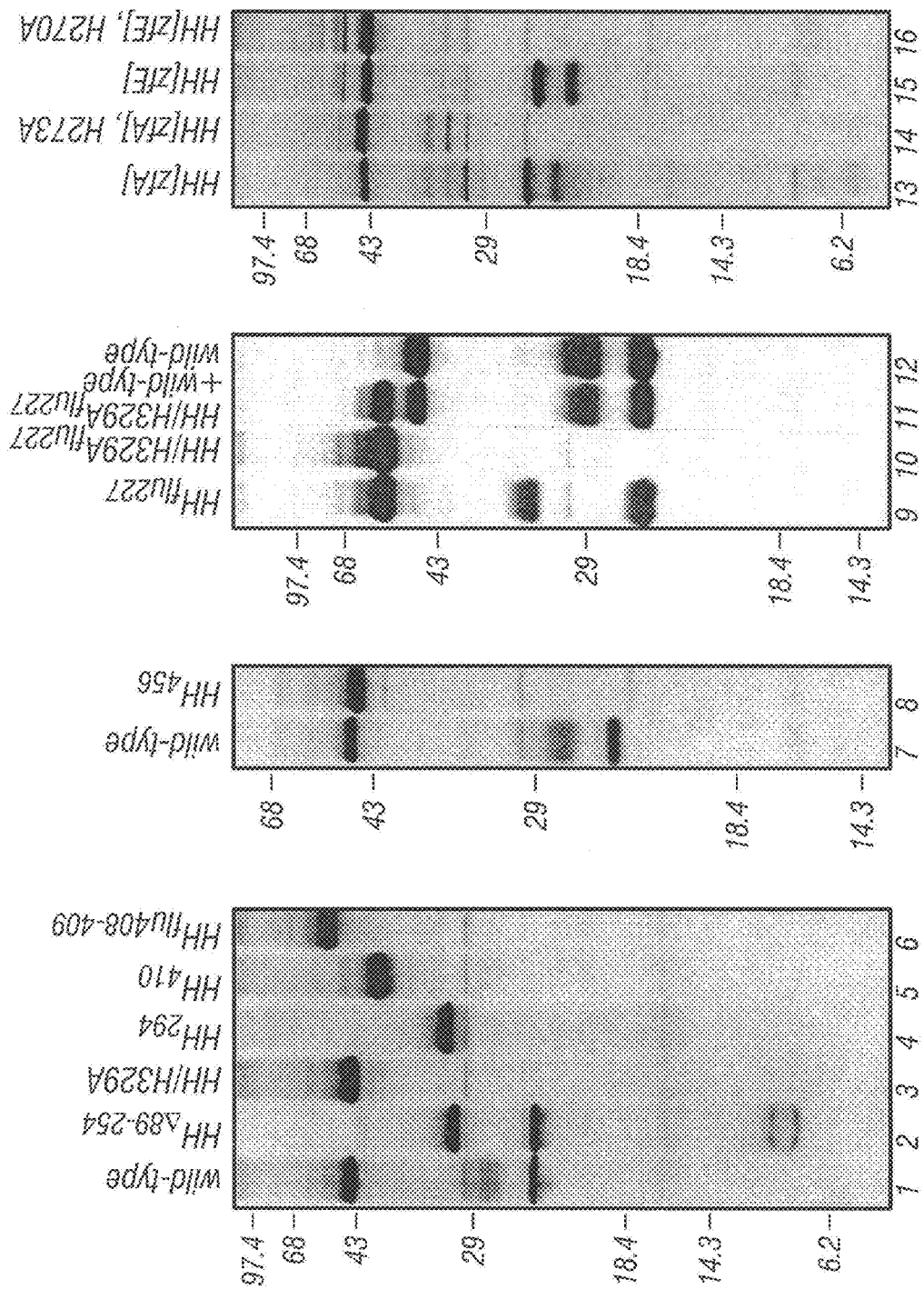

*Ab2*

*Ab1*

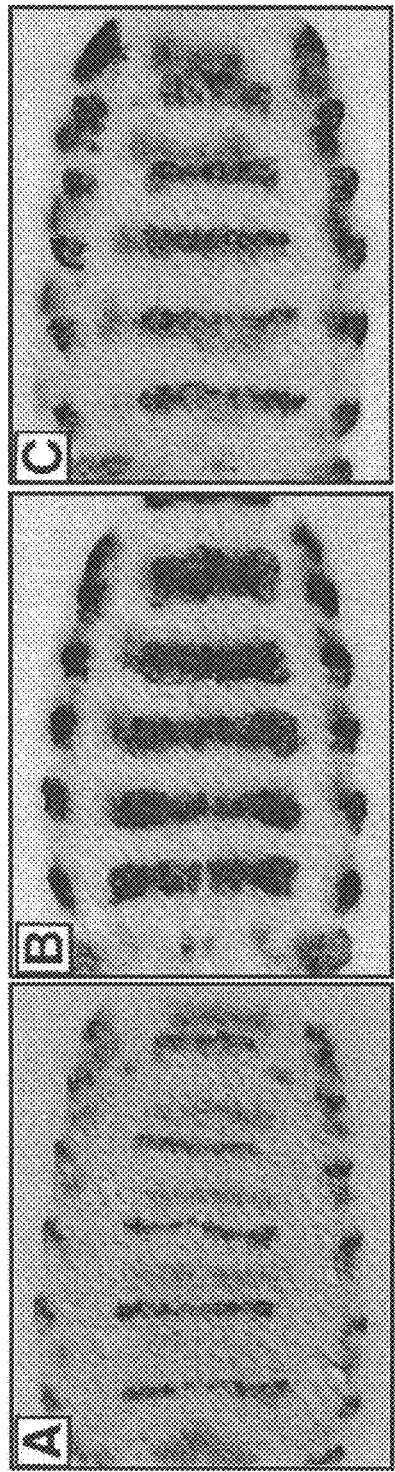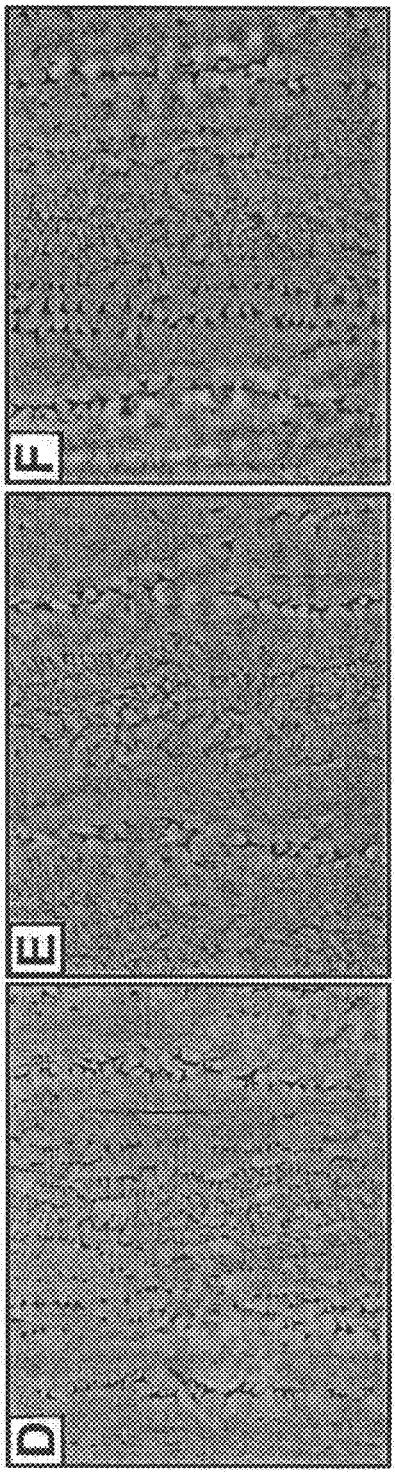
FIG. 6A     FIG. 6B     FIG. 6C     FIG. 6D     FIG. 6E     FIG. 6F

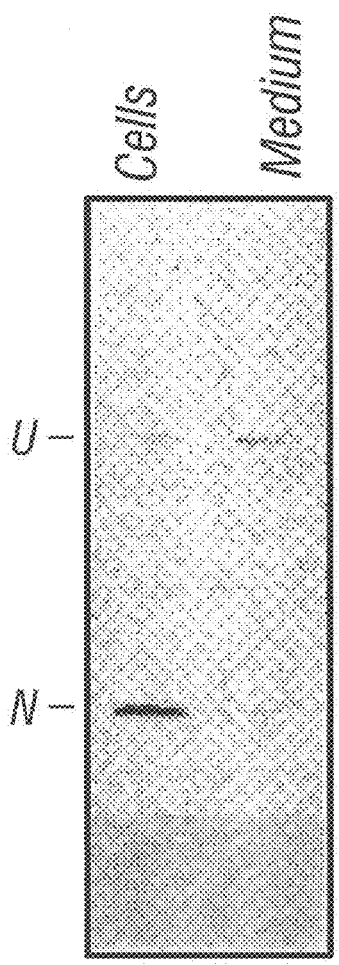 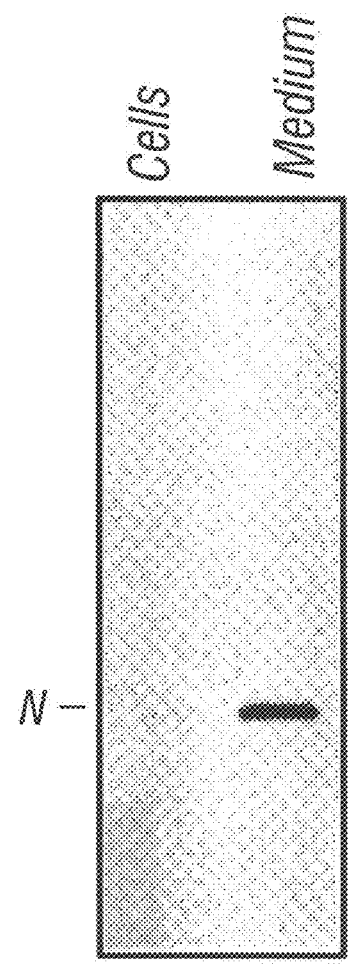
*FIG. 10C*          *FIG. 10D* human hh B -> 1-phase Translation Sonic HHG1
(SEQ ID NO:1) DNA sequence 144 b.p. GTGAAACTGCGG ... CTGGCGGTGGAG linear

```
1/1                                                              31/11
GTG AAA CTG CGG GTG CTG GAG GGC TGG GAC GAA GAT GGC CAC CAC TCA CAG GAG TCT CTG
Val Lys Leu Arg Val Leu Glu Gly Trp Asp Glu Asp Gly His His Ser Gln Glu Ser Leu
61/21                                                            91/31
CAC TAC GAG GGC CGC GGC CGC GCA GTG ACC GAC ATC ACC ACG TCT GAC CGC AGC AAG TAC GGC
His Tyr Glu Gly Arg Gly Arg Ala Val Thr Asp Ile Thr Thr Ser Asp Arg Ser Lys Tyr Gly
121/41
ATG CTG GCC CGC CTG GCG GTG GAG
Met Leu Ala Arg Leu Ala Val Glu
```

FIG. 11A human hh A -> 1-phase Translation HHG2 (probably Desert or Indian)
(SEQ ID NO:2) DNA sequence 144 b.p. GTGAAGGGCTGCGG ... TTGGCAGTGGAG linear

```
1/1                                                              31/11
GTG AAG CTG CGG GTG ACC GAG GGC TGG GAC GAG GAC GGC CAC CAC TCA GAG GAG TCC CTG
Val Lys Leu Arg Val Thr Glu Gly Trp Asp Glu Asp Gly His His Ser Glu Glu Ser Leu
61/21                                                            91/31
CAT TAT GAG GGC CGC GCC GTG GAC ATC ACC ACA TCA GAC CGC AAT AAG TAT GGA
His Tyr Glu Gly Arg Ala Val Asp Ile Thr Thr Ser Asp Arg Asn Lys Tyr Gly
121/41
CTG CTG GCG CGC TTG GCA GTG GAG
Leu Leu Ala Arg Leu Ala Val Glu
```

FIG. 11B

Cleavage Site Sequence
...SHVHG CFTPE...
253          262

| | | |
|---|---|---|
| D. melanogaster hh | ISSHVHGCFTPEST | SEQ ID NO.3 |
| D. hydei hh | SISHMHGCFTPEST | SEQ ID NO.4 |
| m-sonic hh | VAAKSGGCFPGSAT | SEQ ID NO.5 |
| r-sonic hh | VAAKSDGCFPGSAT | SEQ ID NO.6 |
| c-sonic hh | VAAKSGGCFPGSAL | SEQ ID NO.7 |
| z-sonic hh | VAAKSGGCFPGSGT | SEQ ID NO.8 |
| z-twhh | VAAKSGGCFPAGAR | SEQ ID NO.9 |
| x-sonic hh | VAAKTGGCFPAGAQ | SEQ ID NO.10 |
| m-indian hh | VAAKTGGCFPGEAL | SEQ ID NO.11 |
| x-bhh | LGVRSGGCFPGTAM | SEQ ID NO.12 |
| x-hh4 | LGVRSGGCFPGTAM | SEQ ID NO.37 |
| x-hh3 | LGVRSGGCFPGTAM | |
| m-desert hh | LAVRAGGCFPGNAT | SEQ ID NO.13 |

*FIG. 12C*

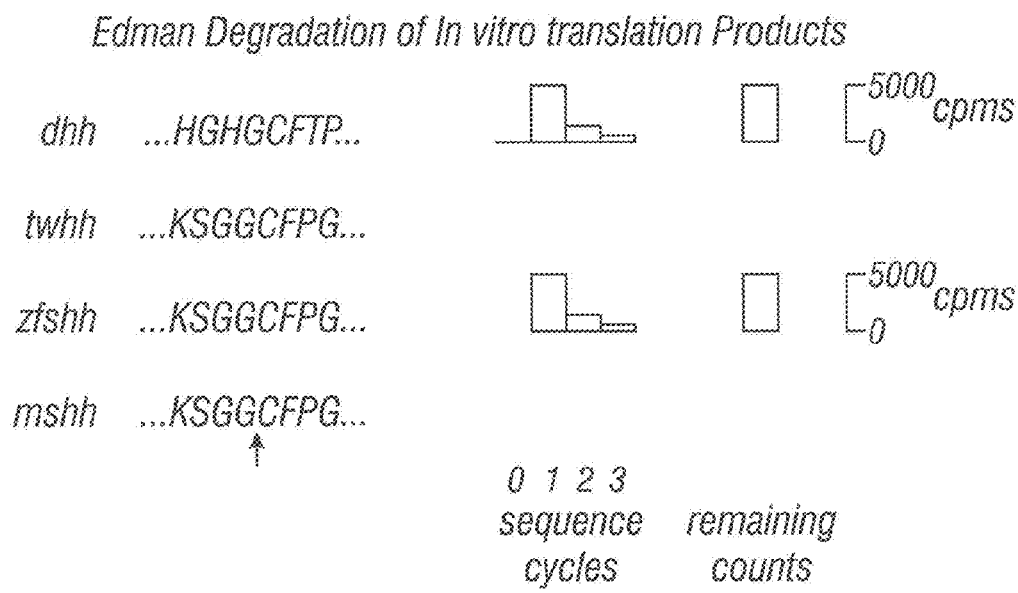

```
Zebrafish twhh  VKLRVTEGWDEDGHHLEESLHYEGRAVDITTSDRDKSKYG
hh[zfB]         .R.............S...................RN..A
hh[zfC]         .R.....A........PPG.................TK...
hh[zfD]         .............N.P.D..................RN...
Zebrafish shh   ..............F.........................
```

```
Zebrafish twhh  MDVRLHLQFALLCFISLLLTPGLACGPGRGYGKRRHPK
Zebrafish shh   M--RL-LTRVLLVSLLTLSLVVSGLACGPGRGYGRRHPK
Chicken   shh   MVEMLLLTRILLVGFICALLVSSGLTCGPGRGIGKRRHPK
Mouse     shh   M--LLLLARCFLVILASSLLVCPGLACGPGRGFGKRRHPK Zebrafish twhh  FKELIPNYNPDIIFKDEENINADRLMTKRCKDKLNSLAIS
Zebrafish shh   FKELIPNYNPDIIFKDEENIGADRLMTQRCKDKLNSLAIS
Chicken   shh   FKELIPNYNPDIIFKDEENIGADRLMTQRCKDKLNALAIS
Mouse     shh   FKELIPNYNPDIIFKDEENIGADRLMTQRCKDKLNALAIS Zebrafish twhh  ITTSDRDKSKYGMLSRLAVEAGFDWVYYESKAHIHCSVKA
Zebrafish shh   ITTSDRDKSKYGTLSRLAVEAGFDWVYYESKAHIHCSVKA
Chicken   shh   ITTSDRDRSKYGMLARLAVEAGFDWVYYESKAHIHCSVKA
Mouse     shh   ITTSDRDRSKYGMLARLAVEAGFDWVYYESKAHIHCSVKA Zebrafish twhh  RVLAADEKGNVLISDFIMFIDHDPTTRRQFIVIETSEPFT
Zebrafish shh   KVLAADSAGNLVFSDFIMFIDRDSTIRRVFMVIETQEFVE
Chicken   shh   RVLAADADGRLLYSDFLTFLDRMDSSRKLPMVIETRQPRA
Mouse     shh   RVLAADDQGRLLYSDFLTFLDREGAKKVFMVIETLEPRE Zebrafish twhh  KPGDIVLWEDTCESLKSV--TMKRI-YTEEHEGSEAFMT
Zebrafish shh   RAGQKMMV-VDDSGQLKSV--IVQRI-YTEEQRGSFAFMT
Chicken   shh   KPGQRVMVLGEGGQQLLPA--SVHSVSLREFASCAYAPLT
Mouse     shh   RPGQRVYVVAERGGDRRLLPAAVHSVTLREFEAGAYAPLT Zebrafish twhh  KLMIWLFF--------ARESNVNFQED---------GIHWY
Zebrafish shh   YVSSFLFF-----QNSSSRSNATLQQE---------GVHWY
Chicken   shh   GLLAALCF------D--GAIPTAATTTT--------GIHWY
Mouse     shh   ALLAALAPARTDGGQGSIPAAQSATEARGAEPTAGIHWY
```

| | | | | | |
|---|---|---|---|---|---|
| MLSRLAVE | | Z-twhh | | | |
| ..A.... | Z-twhh | 100 | Z-shh | | |
| L.AQ... | Z-shh | 73 | 100 | C-Shh | |
| ..A.... | C-Shh | 69 | 68 | 100 | M-Shh |
| T...... | M-Shh | 66 | 68 | 82 | 100 |

```
KLTPLAYKQFTPNVAEKTLGASGKYEGKTTRNSER    75
KLTPLAYKQFTPNVAEKTLGASGRYEGKTTRNSER    72
KLTPLAYKQFTPNVAEKTLGASGRYEGKTTRNSER    75
KLTPLAYKQFTPNVAEKTLGASGRYEGKTTRNSER    73

VMNHWPGVKLRVTEGWDEDGHHLEESLHYEGRAVD   150
VMNHWPGVKLRVTEGWDEDGHHFEESLHYEGRAVD   147
VMNQWPGVKLRVTEGWDEDGHHSEESLHYEGRAVD   150
VMNQWPGVRLRVTEGWDEDGHHSEESLHYEGRAVD   148

ENSVAAKSGGCFPGSGIVTLGDGTRKPIKDLKVGD   225
ENSVAAKSGGCFPGSAIVSLQDGGQKAVKDLNPGD   222
ENSVAAKSGGCFPGSATVHLEHGGTKLVKDLSPGD   225
ENSVAAKSGGCFPGSATVHLEQGGTKLVKDLRPGD   223

KLILITAAHLMFVG-NSSAAS--GITAT---FASNV   294
KTILITAAHLLFVL-DNSTEDLHIMTAA---YASSV   293
RLLLITAAHLLFVAPQHNQSEATGSTSGQALFASNV   300
RLLLITAAHLLFVAPHNDSGPTPGPSAL---FASRV   295

AHGTIIVDQVLASCYAVIENHKWAHWAFAPVRLCH   366
AHGTIVVDRILASCYAVIEDQGLAHLAFAPARLYY   364
ACGTILINRVLASCYAVIEEHSWAHWAFAPERLAQ   373
AHGTILINRVLASCYAVIEEHSWAHRAFAPFRLAH   370

SNMLFHIGSWLLDRDSFHPLGI-LHLS           416
SRLLYQMGTWLLDSNMLHPLGMSVNSS           418
SRLLYRIGSWVLDGDALHPLGMVAPAS           425
SQLLYHIGTWLLDSETMHPLGMAVKSS           437
```

FIG. 13B

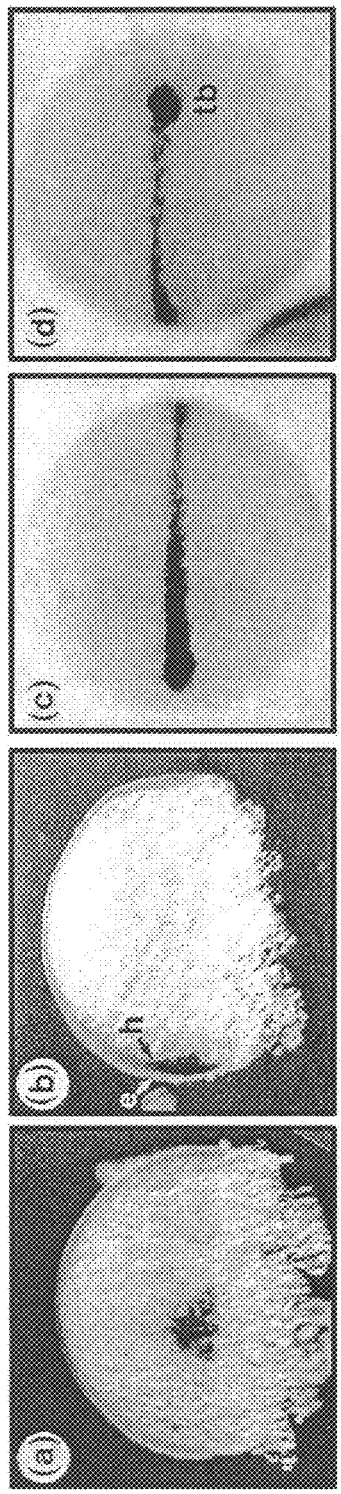
FIG. 14A  FIG. 14B  FIG. 14C  FIG. 14D
FIG. 14E  FIG. 14F  FIG. 14G

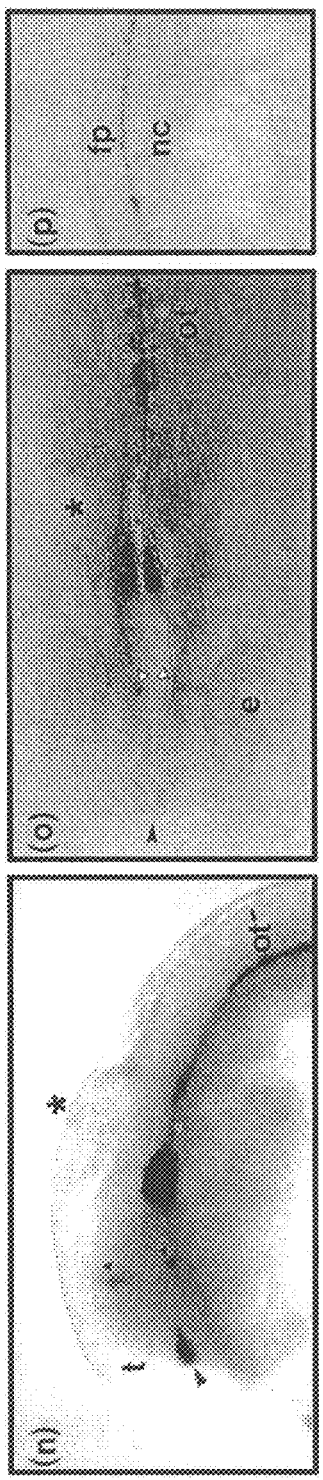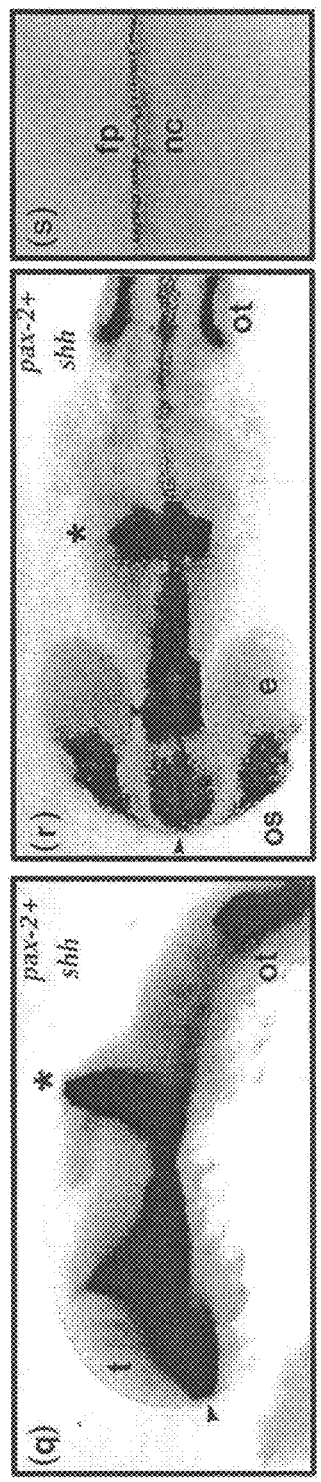

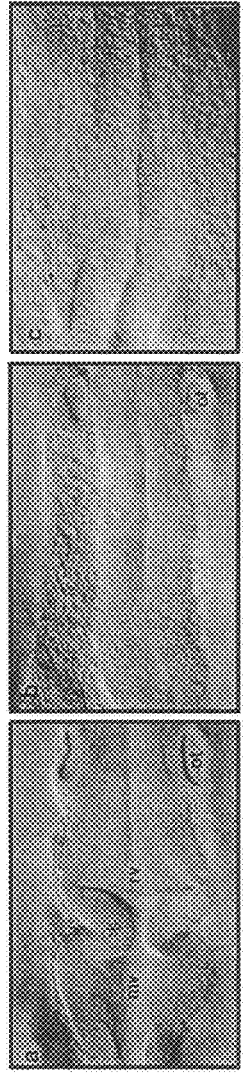
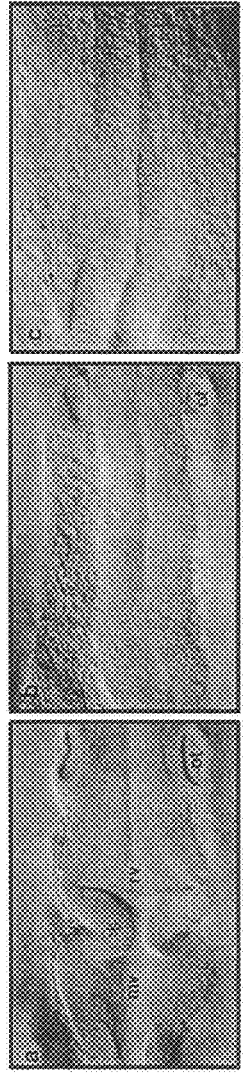
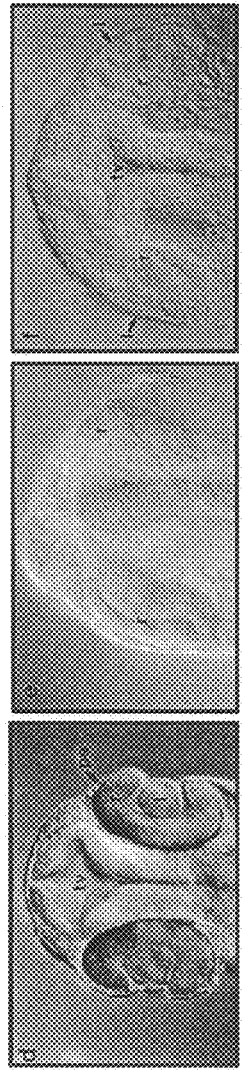
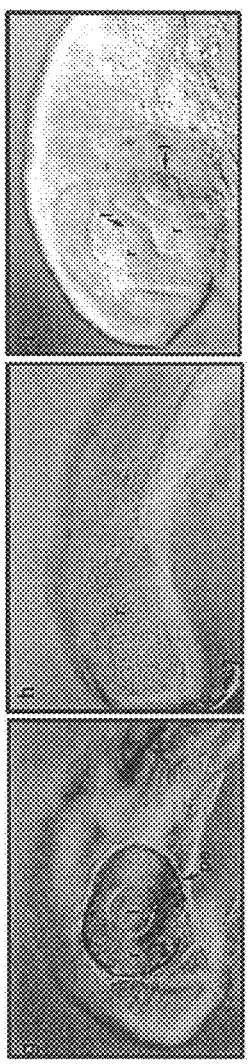

Table 1. Effects of ectopic expression of ssh, twhh, twhh-N, twhh-$U_{HA}$ and lacZ on zebrafish embryonic development.

| Injected mRNA | shh | twhh | twhh-N | twhh-$U_{HA}$ | lac-Z |
|---|---|---|---|---|---|
| 12.5 h | | | | | |
| Ectopic pax-2 in eye | 89% (35) | 82% (22) | 92% (26) | 90% (30) | 0% (31) |
| 22h | | | | | |
| Ectopic pax-2 in eye | 22% (54) | 62% (50) | 76% (42) | 21% (39) | 0% (34) |
| Reduced pax-6 in eye | 20% | 68% | 54% | 1% | 0% |
| Reduced pax-6 in ventral forebrain | 0% | 43% | 79% | 0% | 0% |
| Reduced pax-6 in hindbrain | 0% (35) | 18% (40) | 61% (28) | 0% (68) | 0% (14) |
| 28h | | | | | |
| Lens absent | 16% | 86% | 100% | 9% | 0% |
| Lens smaller | 48% | 9% | 0% | 36% | 0% |
| Reduced eye pigment | 80% | 91% | 100% | 64% | 0% |
| No midbrain-hindbrain constriction | 48% (25) | 77% (44) | 100% (16) | 22% (45) | 3% (37) |

FIG. 16

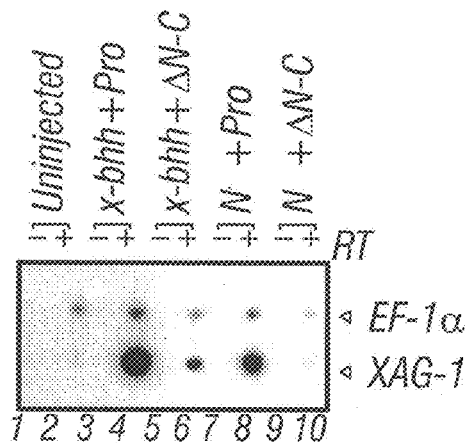
FIG. 21
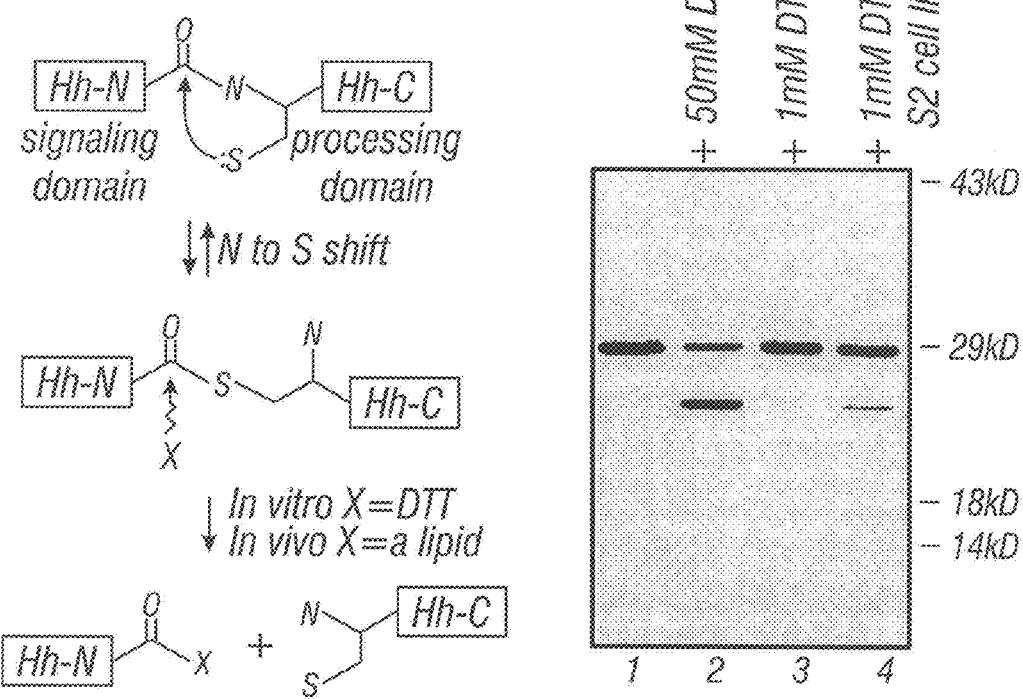
FIG. 22A
FIG. 22B

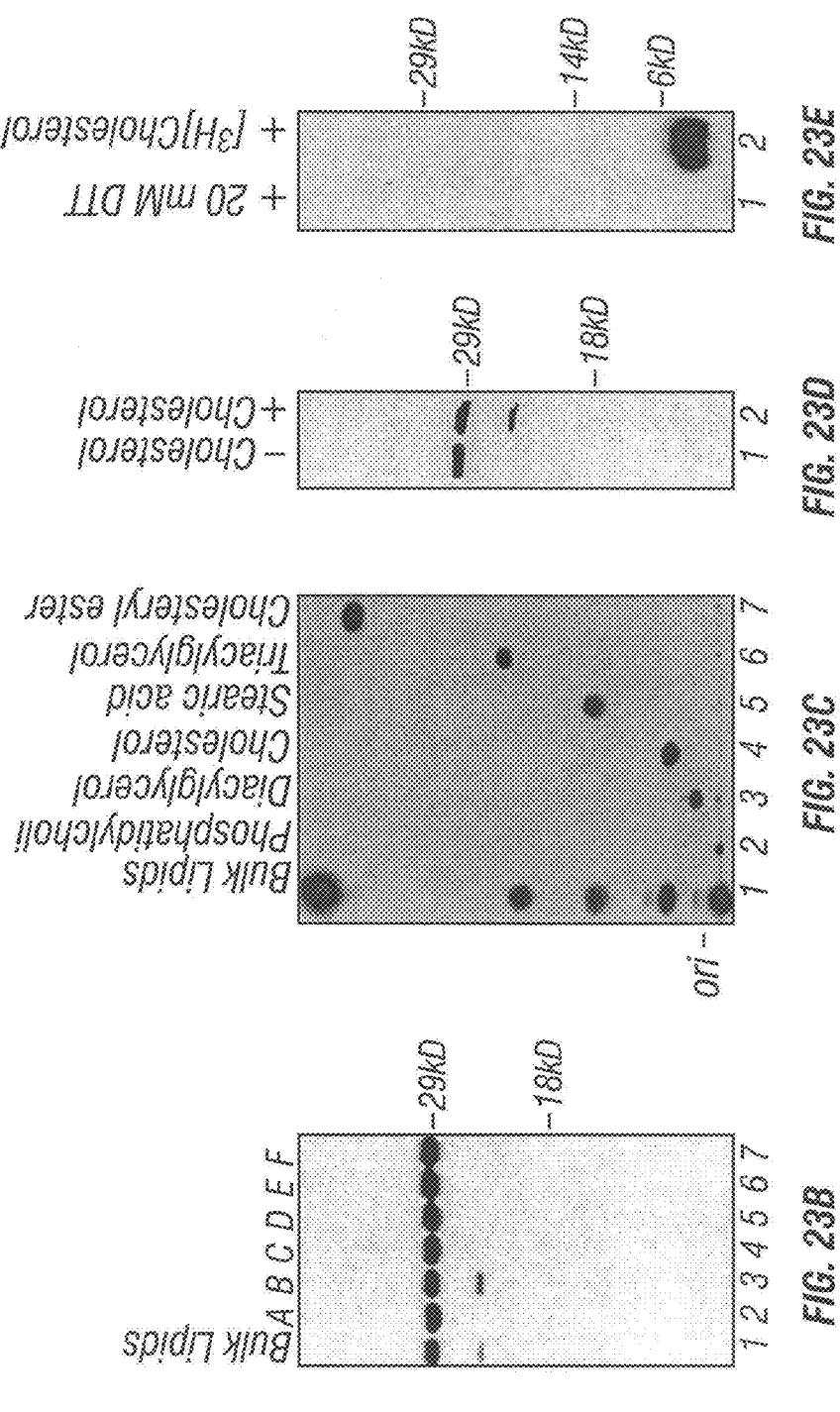

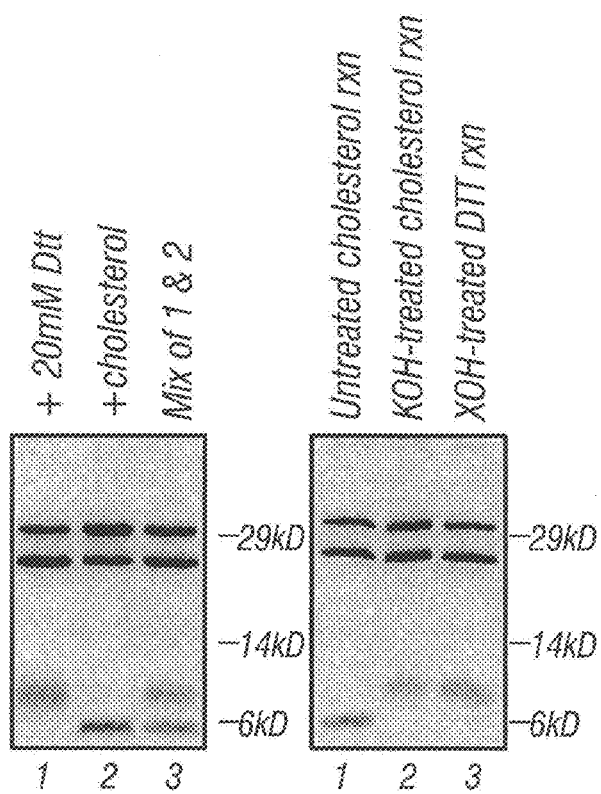
*FIG. 24A*  *FIG. 24B*
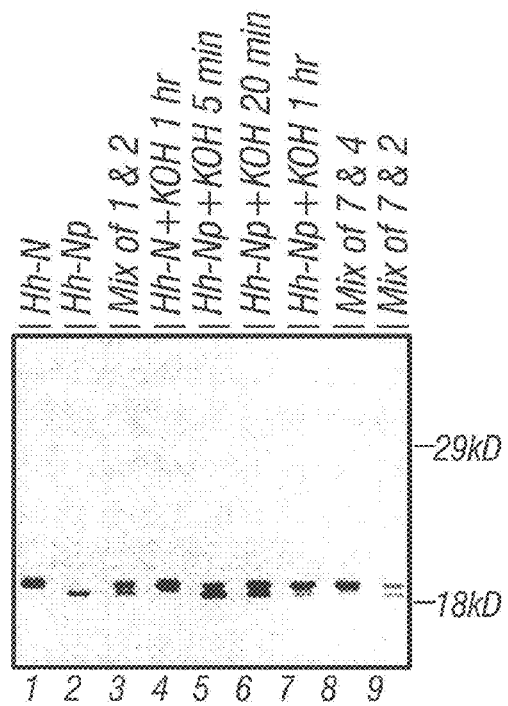
*FIG. 24C*

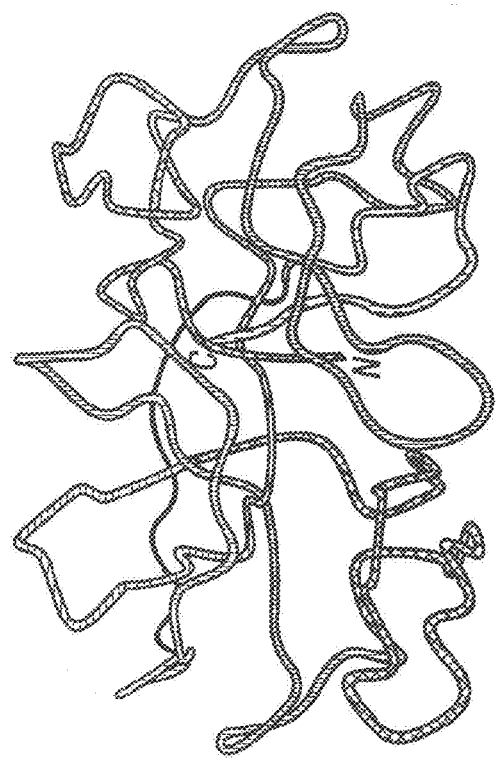
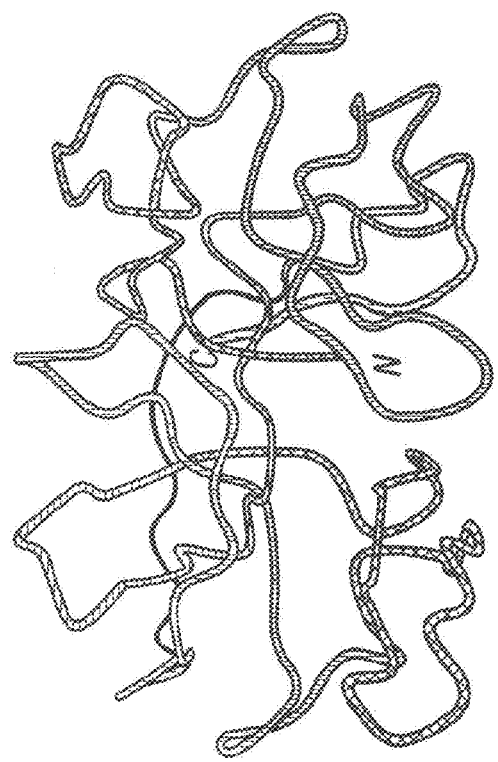
FIG. 29A

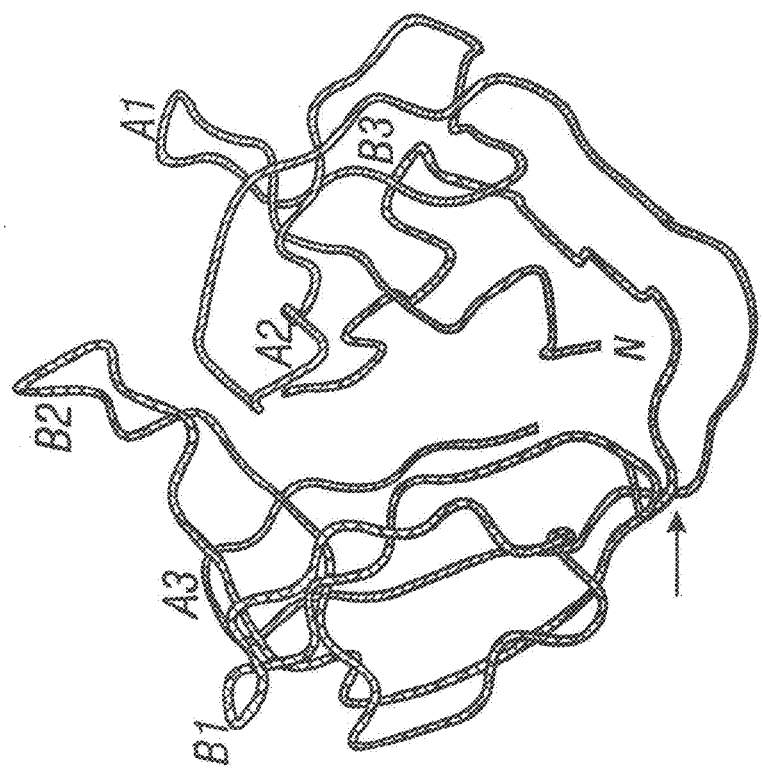
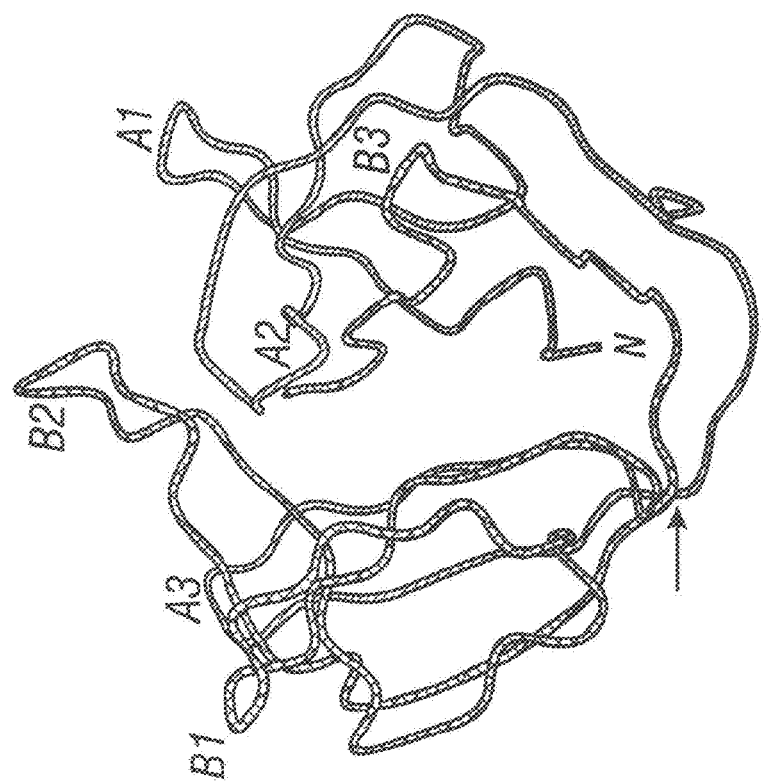
FIG. 29B

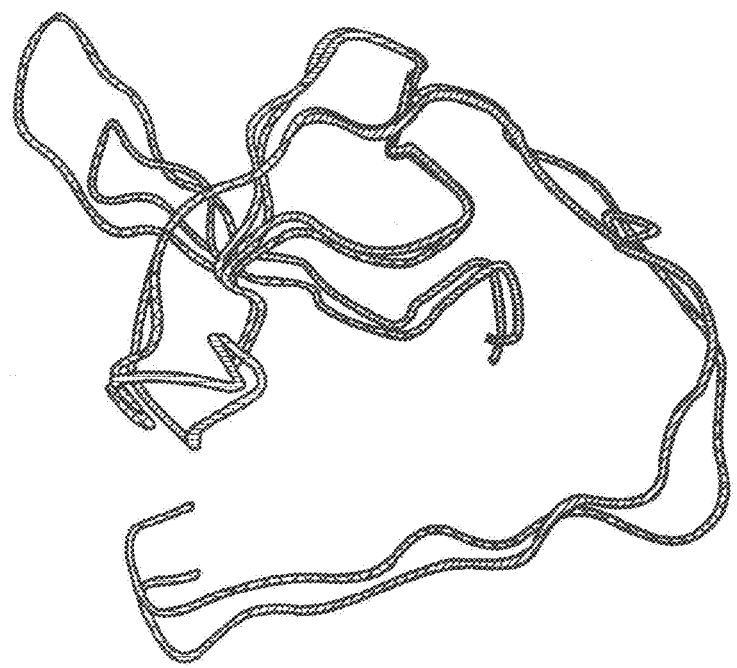
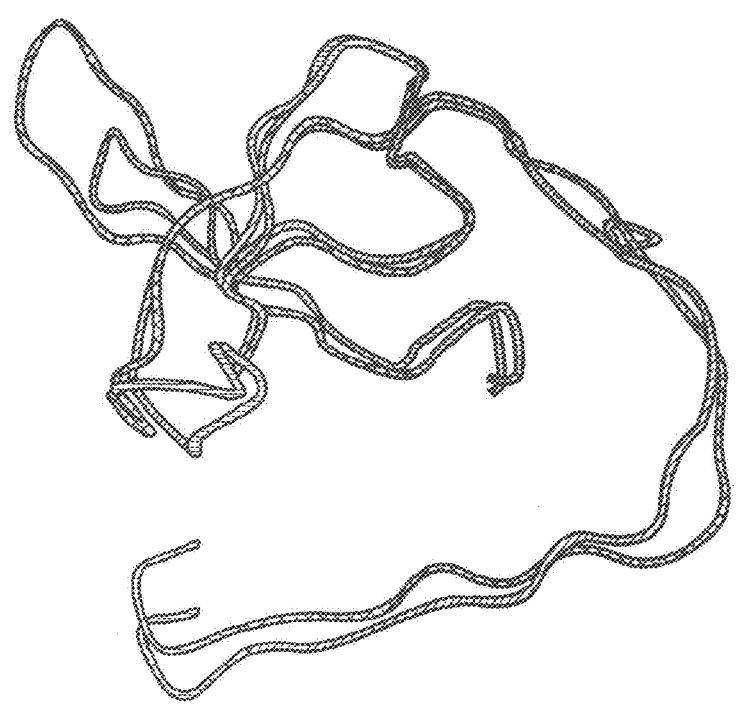
FIG. 29C

```
        β1a/β1b                    β2b/β2a                  β3a/β3b
    ───────────▶               ──────────────▶         ──────────────▶
      0007020114            66672401606542400029
259 F TPESTALLE 268   269 SGVRKPLGELSIGDR VI SMTA 289
325 V TPAHLVSVW 334   340 KLTFVFADRIEEKN QVI VRDV 360
      0147020002            61333304608592100239

β4a/β4b                    β4a/β4b
    ───────────▶               ───────────▶
      6232030361                  002020377
292 QAVYSE VILF 301   312 F VQLH TDGG 320
364 ELRPQR VVKV 373   381 VV APL TREG 389
      6053160362                  000030633
```

ANTIBODIES THAT SPECIFICALLY BIND HEDGEHOG-DERIVED POLYPEPTIDES

CROSS REFERENCE TO RELATED APPLICATIONS

This application is a continuation application of U.S. application Ser. No. 11/804,733 filed May 18, 2007, now U.S. Pat. No. 7,741,451; which is a continuation application of U.S. application Ser. No. 10/460,594 filed Jun. 11, 2003, now issued as U.S. Pat. No. 7,220,838; which is a divisional application of U.S. application Ser. No. 09/562,914 filed May 2, 2000, now issued as U.S. Pat. No. 6,911,528; which is a divisional application of U.S. application Ser. No. 08/946,329 filed Oct. 7, 1997, now issued as U.S. Pat. No. 6,057,091; which is a continuation-in-part application of U.S. application Ser. No. 08/729,743 filed Oct. 7, 1996, now issued as U.S. Pat. No. 6,214,794; which is a continuation-in-part application of U.S. application Ser. No. 08/567,357 filed Dec. 4, 1995, now issued as U.S. Pat. No. 6,132,728; which is a continuation-in-part application of U.S. application Ser. No. 08/349,498 filed Dec. 2, 1994, now issued as U.S. Pat. No. 6,281,332. U.S. application Ser. No. 08/946,329 filed Oct. 7, 1997, now issued as U.S. Pat. No. 6,057,091 also claims the benefit under 35 USC §119(e) to U.S. Application Ser. No. 60/061,323 filed Oct. 2, 1997, now expired. The disclosure of each of the prior applications is considered part of and is incorporated by reference in the disclosure of this application.

BACKGROUND OF THE INVENTION

1. Field of the Invention

This invention relates generally to the field of protein processing and protein signalling pathways and specifically to two novel proteins having distinct activities, which are derived from a common hedgehog protein precursor.

2. Background Information

Embryologists have long performed experimental manipulations that reveal the striking abilities of certain structures in vertebrate embryos to impose pattern upon surrounding tissues. Speculation on the mechanisms underlying these patterning effects usually centers on the secretion of signaling molecule that elicits an appropriate response from the tissues begin patterned. More recent work aimed at the identification of such signaling molecules implicates secreted proteins encoded by individual members of a small number of gene families. One such family of proteins which may have an influential effect upon patterning activities are those proteins encoded by the hedgehog gene family.

The hedgehog (hh) gene was initially identified based on its requirement for normal segmental patterning in *Drosophila* (Nusslein-Volhard, C. & Wieschaus, E, *Nature* 287:795-801, 1980). Its functions include local signaling to coordinate the identities of adjacent cells within early embryonic segments (Hooper, J. E., & Scott, M. P. *Early Embryonic Development of Animals*, pp. 1-48, 1992) and a later function in cuticle patterning that extends across many cell diameters (Heernskerk, J. & DiNardo, S., *Cell*, 76:449-460, 1994). The hh gene also functions in the patterning of imaginal precursors of adult structures, including the appendages and the eye (Mohler, J. *Genetics*, 120:1061-1072, 1988; Ma, et al, *Cell*, 75:927-938, 1993; Heberlein, et al, *Cell*, 75:913-926, 1993; Tabata, T. & Kornberg, T. D., *Cell*, 76:89-102, 1992; Basler, K. & Struhl, G., *Nature*, 368:208-214, 1994). Genetic and molecular evidence indicates that hedgehog proteins are secreted and function in extracellular signaling (Mohler, J., supra; Lee, et al, *Cell*, 71:33-50, 1992; Taylor, et al, *Mech. Dev.*, 42:89-96, 1993).

In vertebrates activities encoded by hh homologues have been implicated in anterior/posterior patterning of the limb (Riddle, et al, *Cell*, 75:1401-1416, 1993; Chang, et al, *Development*, 120:3339, 1994), and in dorsal/ventral patterning of the neural tube (Echelard, et al, *Cell*, 75:1417-1430, 1993; Krauss, et al. *Cell*, 75:1431-1444, 1993; Roelink, et al. *Cell*, 76:761-775, 1994).

The vertebrate ventral midbrain contains neurons whose degeneration or abnormal function are linked to a number of diseases, including Parkinson's disease and schizophrenia. It is known that motor neurons develop in close proximity to the floor plate in the ventral midbrain. Midbrain projections to the striatum are involved in the control of voluntary movement (Bjorklund and Lindvall, In: *Handbook of Chemical Neuroanatomy*, eds., Borklund, et al., Amsterdam: Elsevier, pp 55-122, 1984) and loss of these neurons results in the motor disorders of Parkinson's disease (Hirsch, et al, *Nature*, 334: 345, 1988). Midbrain dopaminergic neurons that innervate limbic structures and the cortex influence emotional and cognitive behavior, respectively, and abnormal function of these neurons has been associated with schizophrenia and drug addiction (Seeman, et al, *Nature*, 365:441, 1993).

While the molecular nature of the factors that specify neuronal cell fate have not been established, members of the transforming growth factor-$\beta$ (TGF-$\beta$) (Lyons, et al, *Trends in Genetics*, 7:408, 1991) or the hedgehog protein family (Smith, J. C., *Cell*, 76:193, 1994) may possess the characteristics expected from such factors as they participate in specification of cell fate, mediate inductive interactions between tissues, and in many cases act at a distance of only a few cell diameters.

The present invention establishes that hh activities encoded by these genes play a crucial role in early patterning of the developing eye and in patterning of the brain. For the first time, the invention shows that internal cleavage of hedgehog protein product is critical for full function, and that the two novel products of this auto-proteolytic cleavage display distinguishable activities, thus demonstrating that hh signaling activity is a composite effect of two separate signaling proteins that derive from a common hh protein precursor. In so doing, the invention provides the means for specific patterning and proliferation of desired neuronal cell types for addressing disorders which arise from neuronal degeneration or abnormal function.

SUMMARY OF THE INVENTION

The present invention is based on the seminal discovery that hedgehog proteins undergo auto-proteolytic cleavage which results in two separate proteins having distinct functional and structural characteristics. The two polypeptides, referred to as the "N" and "C" fragments of hedgehog, or N-terminal and C-terminal fragments, respectively, are produced after specific cleavage at a $G^1CF$ site recognized by the autoproteolytic domain in the native protein. The "C" fragment functions as a cholesterol transferase during autoproteolysis thus allowing cholesterol modification of the "N" fragment.

Thus, in one embodiment, the invention provides a substantially pure polypeptide characterized by having an amino acid sequence derived from amino terminal amino acids of a hedgehog protein and having at its carboxy terminus, a G↓CF cleavage site specifically recognized by a proteolytic activity of the carboxy terminal fragment of the native hedgehog polypeptide. The invention also provides a substantially pure polypeptide characterized by having an amino acid sequence of a hedgehog polypeptide or a fragment derived from amino terminal amino acids of a hedgehog polypeptide, wherein the polypeptide or fragment thereof comprises a sterol moiety. Fragments derived from a native hedgehog polypeptide are included and preferably include extracellular amino acid residues, such as those derived from the N fragment. In one embodiment of the invention, the sterol moiety is cholesterol In another embodiment, the invention provides a substantially pure polypeptide characterized by having an amino acid sequence derived from carboxy terminal amino acids of a hedgehog protein and having at its amino terminus, a G↓CF cleavage site specifically recognized by a proteolytic activity of the carboxy terminal fragment of the native hedgehog polypeptide.

The invention also provides a method for modulating proliferation or differentiation of neuronal cells, comprising contacting the cells with a hedgehog polypeptide. The native hedgehog polypeptide, the N, or the C fragment, or functional fragments derived therefrom, are most useful for the induction of proliferation or differentiation of neuronal cells substantially derived from floor plate neuronal cells.

In yet another embodiment, the invention provides a method for identifying a compound which affects hedgehog activity comprising incubating the compound with hedgehog polypeptide, or with biologically active fragments thereof, or with a recombinant cell expressing hedgehog, under conditions sufficient to allow the components to interact; and determining the effect of the compound on hedgehog activity or expression. For example, cholesterol level (e.g., biosynthesis or transport) is measured as an indicator of hedgehog activity. In one aspect of the invention, the method provides a means for affecting cholesterol biosynthesis or transport in a cell comprising contacting a cell with an effective amount of a compound that affects hedgehog, thereby affecting cholesterol biosynthesis or transport. The effect may be inhibition or stimulation of cholesterol biosynthesis or transport.

BRIEF DESCRIPTION OF THE DRAWINGS

FIGS. 1A and 1C show processing of the hh protein by immunoblots with antibodies against amino (Ab1) and carboxy-terminal (Ab2) epitopes. FIGS. 1B and 1D are blots of samples immuno-precipitated with Ab1 (FIG. 1B, lanes 7-9), Ab2 (FIG. 1D, lanes 19-21), or pre-immune serum (FIG. 1B, lanes 10-12, and FIG. 1D, lanes 22-24).

FIGS. 2A and 2B show sequence similarity between hh proteins and serine proteases. hh protein sequences are aligned to residues 323 to 329 of the *D. melanogaster* protein and numbered as positions 1 to 7 (group A) (SEQ ID Nos: 15, 23, 24, 25, 26 and 37). The catalytic histidines of mammalian serine proteinases (group B) (SEQ ID Nos: 27-35) are aligned to the invariant histidine at position 7 in hh proteins.

FIG. 3A shows a Coomasie blue stained polyacryl-amide gel showing production and purification of $His_6$-U and $His_6$-$UH_{329A}$ proteins from *E. coli*. Samples were molecular weight markers (lanes 1 and 2); lysates of *E. coli* cells carrying the $His_6$-U expression construct without (lane 3) and with (lane 4) induction by IPTG; purified $His_6$-U protein (lane 5); lysates of *E. coli* cells that carry the $His_6$-$UH_{329A}$ expression construct without (lane 6) and with (lane 7) induction by IPTG; purified $His_6$-$UH_{329A}$ protein (lane 8). FIG. 3B is an immunoblot detected with Ab2 showing transfected S2 cells induced to express hh (lane 1); $His_6$-U and $His_6$-$UH_{329A}$ proteins incubated in cleavage reaction buffer for 0 hours (lanes 2 and 5), for 20 hours (lanes 3 and 6), and for 20 hours in the presence of 20 mM TAME (a serine protease inhibitor) (lanes 4 and 7).

FIGS. 4A through 4D show autoproteolytic functions of *Drosophila* (FIGS. 4A, 4B and 4C) and zebrafish (FIG. 4D) hh proteins map to the carboxy terminal fragments by in vitro translations of wild-type and mutant hh proteins. The locations of mutations and cleavage sites (arrows) in these proteins are illustrated schematically in FIG. 4E.

FIGS. 5A and 5B are immunoblots developed using Ab1 and Ab2 antibodies, respectively. Lanes 1 and 6, induced untransfected S2 cells; lanes 2 and 7, transfected S2 cells induced to express hh; lanes 3 and 8, heat shocked wild-type embryos; lanes 4 and 9, heat shocked hshh embryos; lanes 5 and 10, heat shocked hshh H329A embryos.

FIGS. 6A through 6F show in situ hybridization showing the embryonic effects of ubiquitously expressed wild type and H329A hh proteins. FIGS. 6A through 6C show the embryonic distribution of wingless (wg) RNA as revealed by in situ hybridization is shown in FIG. 6A wild-type (homozygous $y^1 w^{1118}$), FIG. 6B hshh, and FIG. 6C hshh H329A embryos that were exposed to two 10 minute heat shocks separated by a 90-minute recovery period (33). Wild-type embryos showed little change in wg expression (Table 1). FIGS. 6D, 6E and 6F show the dorsal surfaces of $y^1 w^{1118}$, and hshh H329A larvae, respectively, at the level of the fourth abdominal segment. These larvae were shocked for 30 minutes as embryos and allowed to complete embryogenesis. Cuticle cell types (1°, 2°, 3°, and 4° are labeled as described (J. Heemskerk and S. DiNardo, *Cell* 76, 449, 1994). Note the expansion of 2° cell types (naked cuticle) at the expense of 3° and some 4° types in the hshh embryo (FIG. 6E) under conditions where the phenotype of hshh H329A embryos (FIG. 6F) is identical to that of control embryos (FIG. 6D).

FIG. 9A is shown in comparison to the distribution of N and C epitopes detected with Ab1 and Ab2 in FIGS. 9B and 9C, respectively. Note that the distribution of N and C epitopes span approximately one-third and one-half of each segmental unit respectively, while the transcript is limited to approximately one-quarter of each unit.

In FIG. 10A, the long-range effects of hh signaling are achieved indirectly through short-range induction of a second signaling molecule (X). Based on its biochemical properties and its restricted tissue localization, N is presumed to represent the active short-range signal while the role of C would be limited to supplying the catalytic machinery required for biogenesis of N. In FIG. 10B, the long- and short-range signaling functions of hh are supplied by the N and C proteins derived by internal auto-proteolysis of the U precursor. N is implicated in short-range signaling by retention near its cellular site of synthesis, while C is less restricted in its distribution and would execute long-range signaling functions. In both models, auto-proteolysis is required to generate fully active signaling proteins.

FIGS. 10C and 10D show an immunoblot of the N fragment synthesized from a wild type construct (FIG. 10C) or a construct lacking the C domain (FIG. 10D).

FIGS. 11A (SEQ ID Nos:1 and 21) and 11B (SEQ ID Nos:2 and 22) show the nucleotide and deduced amino acid sequences for partial human hh clones.

FIG. 12A shows a time course of cleavage after initiation by addition of DTT. FIG. 12B shows incubations of concentrations ranging over three order of magnitude for a fixed time period (four hours), with no difference in the extent of conversion to the cleaved form. FIG. 12C shows the sequence around the cleavage site as determined by amino-terminal sequence of the cleaved fragment C. The cleavage site is denoted by the arrow, and the actual residues sequenced by Edman degradation of the C fragment are underlined. FIG. 12C also shows an alignment of all published vertebrate hh sequences plus some of unpublished sequences from fish and *Xenopus* (SEQ ID NOS:3-13). The sequences shown correspond to the region of *Drosophila* hh where the cleavage occurs, and demonstrates the absolute conservation of the Gly-Cys-Phe sequence at the site of cleavage. FIG. 12E shows that Edman degradation of the C fragments releases $^{35}$S counts on the first but not subsequent rounds for all these proteins, indicating that the site of auto-proteolytic cleavage for all of these hh proteins (SEQ ID NOS:14 AND 16) is the amide bond to the amino-terminal side of the Cys residue that forms the center of the conserved Gly-Cys-Phe sequence highlighted in FIG. 12C.

FIGS. 13A and 13B show the predicted amino acid sequences in single letter code. The amino acid sequences of twhh and shh are aligned with those of the Shh/vhh-1/Hhg-1 class from chick and mouse. Residues identical to all four sequences are boxed, and a dash indicates a gap in the alignment. The arrow indicates the end of the predicted signal sequence. The asterisk (*) denotes invariant amino acid residues associated with the proteolytic domain of C fragment from various species.

FIGS. 15A through 15I show the effects of ectopic hh on zebrafish development. Wild type zebrafish, *Danio rerio* (Ekkwill Waterlife Resources), were maintained at 28.5° C., some embryos were then cultured overnight at RT. Zebrafish embryos were injected at the 1-8 cell stage with twhh, shh, or lacZRNA and examined at 28 h of development. FIGS. 15A through 15C show dorsal view of the midbrain-hindbrain region; anterior is left, lacZ (FIG. 15A), twhh (FIG. 15B) and shh (FIG. 15C). Frontal optical sections of the forebrain region are shown in FIGS. 15D through 15F; anterior is up, lacZ (FIG. 15D), twhh (FIG. 15E) and shh (FIG. 15F). FIGS. 15G through 15L show lateral views of the eye region; anterior is left, lacZ (FIG. 15G), twhh (FIG. 15H) and twhh (FIG. 15I).

FIG. 16 is a table showing the effects of ectopic expression of shh, twhh and twhh mutants on zebrafish embryonic development.

FIG. 17A shows cartoons of various twhh open reading frames. SS (shaded) is the predicted N-terminal signal sequence for secretion of these proteins and encompasses the first 27 amino acids of each open reading frame. The arrow indicates the predicted internal site of auto-proteolytic cleavage. Amino acid residue numbers are according to FIG. 13B. The filled triangle denotes the normal termination codon for the twhh open reading frame. Construct U$_{HA}$ contains a mutation that blocks auto-proteolysis (the histidine at residue 273 is changed to an alanine; see Lee, J. J., et al., supra.). Construct U356$_{HA}$ contains a stop codon in place of amino acid residue 357 as well as the H273A mutation in U$_{HA}$ Construct N encodes just the first 200 amino acids of twhh. Construct C has had the codons for residues 31-197 deleted.

FIG. 17B shows in vitro translation of the expression constructs shown schematically in FIG. 17A. Constructs were translated in vitro in the presence of $^{35}$S methionine and analyzed by autoradiography after SDS-PAGE.

FIG. 21 shows ΔN-C interferes with X-bhh and N-activity in animal cap explants as shown by RT-PCR analysis.

FIG. 22A is an illustration of lipid stimulation of hedgehog autoprocessing.

FIG. 22B shows a Coomassie blue stained SDS-PAGE of autocleavage reactions in bacterially expressed His$_6$Hh-C protein.

FIG. 23A is a thin layer chromatography (TLC) plate coated with silica gel G (Merck) showing the fractionation of bulk S2 cell lipids using a heptane:ether:formic acid solvent (80:20:2).

FIG. 23B is a Coomassie blue-stained SDS-polyacrylamide gel showing in vitro autocleavage reactions of the bacterially expressed His6Hh-C protein incubated with 1 mMDTT plus either unfractionated S2 cell lipids (lane 1), or spots A through F (lanes 2-7, respectively).

FIG. 23C is TLC of S2 cell lipids (lane 1) along with selected lipid standards: phosphatidylcholine (lane 2), a diacylglycerol (lane 3), cholesterol (lane 4), stearic acid (lane 5), a triacylglycerol (lane 6), and cholesteryl ester (lane 7). Lipid spot B comigrates with cholesterol, as also demonstrated by mixing radio-labeled cholesterol with S2 lipids before TLC fractionation.

FIG. 23D is a Coomassie blue stained SDS-polyacrylamide gel showing that relative to 1 mMDTT alone (lane 1) cholesterol (0.35 mM)+1 mMDTT (lane 2) stimulates His2Hh-C autocleavage in vitro.

FIG. 23E is an autoradiogram of electrophoretically-resolved products of His6Hh-C autocleavage reactions driven by 20 mMDTT (lane 1) or 1 mMDTT+0.35 mM cholesterol (lane 2).

FIG. 24A shows Coomassie stained gels of His6Hh-C autocleavage reactions carried out in the presence of 20 mMDTT (lane 1), or 1 mMDTT+0.35 mM cholesterol (lane 2). Lane 3 contains a mixture of the samples loaded in lanes 1 and 2.

FIG. 24B is Coomassie stained gels showing protein products of His6Hh-C autocleavage reactions carried out in the presence of 1 mM DTT+0.35 mM cholesterol (lanes 1 and 2) or with 20 mM DTT (lane 3).

FIG. 24C is an autoradiogram of immunoblotted Hh amino-terminal domains purified from cultured S2 cells.

FIGS. 28B-1 through 28B-3 were prepared using the output of the program PROMOTIF.

FIG. 29A is a pseudo two-fold symmetry in $Hh-C_{17}$. A stereodiagram of a trace of the α-carbon backbone of residues 258-393 of Hh-C17 viewed along the pseudo-twofold symmetry axis is shown. Equivalent loops are marked identically. Checkered regions denote residues 258-276 and 324-347, vertical lines denote residues 276-301 and 347-373, and diagonal lines denote residues 312-320 and 381-389. The pseudo two-fold axis is indicated with a closed circle.

FIG. 29B is a stereodiagram of a backbone trace of $Hh-C_{17}$ wherein horizontal lines denote residues 258-323 and checkered lines denote residues 324-395. The extended loops that make up the $Hh-C_{17}$ structure are labeled in the order in which they appear in the amino-acid sequence, A1-A2-A3-B1-B2-B3. Two structurally cohesive subdomains are apparent, one comprising loops A1, A2, and B3 and another comprising loops B1, B2, and A3. $Hh-C_{17}$ appears to have arisen from a tandem duplication of a primordial gene to produce the 'A' and 'B' sequence regions coupled with exchange of the homologous A3 (residues 310-323) and B3 (residues 379-395) loops to form structural subdomains that are hybrids of 'A' and 'A' sequences. A pivot about which exchange of these loops appears to have occurred is indicated by an arrow.

FIG. 29C is a stereodiagram of backbone traces of the regions of $Hh-C_{17}$ corresponding to the sequence duplication (residues 259-320 indicated with diagonal lines and residues 325-389 indicated with checkered lines) following superposition is shown. The structures were aligned with the program QUANTA (Polygen). The r.m.s. deviation in α-carbon position for 50 matched residues in the subdomains is 1.38 Å. Horizontal lines denote conserved 13 turns (see below). FIGS. 29A, 29B and 29C were prepared with MOLSCRIPT (Kraulis, 1991, supra).

FIGS. 30A and 30B were prepared with MOLSCRIPT (Kraulis, 1991, supra).

FIGS. 31A-1 through 31A-4 are an alignment of the Hh-$C_{17}$ amino-acid sequence (residues 258-402) with other Hh sequences, with nematode sequences homologous to Hh-C, and intein sequences. The alignment was constructed by superimposing the Hh-C and intein alignments produced by the CLUSTALW program using the results of the PSI-BLAST analysis as a guide (Thompson et al., 1994). Additionally, the alignment was verified by analyzing a subset of the sequences containing fifteen diverse intein sequences and three Hh-C sequences with the MACAW program (Schuler et al., 1991, supra). In this analysis the alignment of the blocks containing the cysteine and histidine residues implicated in catalysis was significant with $p<10^{-8}$, and the block including β2b of Hh-C with $p<10^{-4}$. The exact counterpart of β4a in the intein sequences remained uncertain; the respective region is replaced by the number of amino-acid residues. The position of the endonuclease domain (ENDO—domain II according to Duan et al., 1997) inserted in the intein sequences is shown and the number of amino acid residues in these domains is indicated. A second inserted domain in the PI-SceI/YEAST intein thought to be involved in DNA recognition (DRR) is located between β1b and β2b. Three inteins, GYRA/MYCXE, DNAB/PORPU, and KLBA/METJA, contain a short insert replacing the endonuclease domain. The yeast HO endonuclease does not undergo self-splicing, but contains a vestigial, inactive intein domain. The KLBA/METJA intein homologue in which the amino-terminal nucleophile is replaced by alanine is likely inactive as well. A consensus sequence is shown above the aligned sequences and shows amino acid residues conserved in at least one half of the sequences in each of the two aligned sets. 'U' indicates a bulky hydrophobic residue (I, L, V, M, F, Y, W), and "–" indicates a negatively-charged residue (D or E). Catalytic site residues are in bold; hydrophobic residues are shaded; other residues that conform with the consensus are both in bold and shaded. The secondary structure elements and for Hh-$C_{17}$ are shown. Every tenth residue in the Hh-$C_{17}$ sequence is indicated with a dot. The leftmost column shows abbreviated protein and species names, and the second column shows the gene identification number in the NCBI protein database. Protein name abbreviations: CE(R084B4.1) (SEQ ID NO: 47), F46B3 (F46B3.C) (SEQ ID NO: 48), M75 (ZK678.5) (SEQ ID NO: 49), M89 (C29F3.d) (SEQ ID NO: 50), ZK (ZK1290.5) (SEQ ID NO: 51), ZK377 (ZK377.1) (SEQ ID NO: 52), M110 (T05C12.10) (SEQ ID NO: 53)—uncharacterized nematode proteins containing Hh carboxy-terminal domain homologues; HH—hedgehog; EHH—Echidna hedgehog; CHH—Cephalic hedgehog; DHH—Desert hedgehog; IHH—Indian hedgehog; BHH—Banded hedgehog; TWHH—Tiggy-winkle hedgehog; XHH—*Xenopus* hedgehog; SHH—Sonic hedgehog; PI-SeeI, PI-CtrI—yeast intein endonucleases; GYRA, GYRB—DNA gyrase A and B subunits; RECA—recombinase; DNAB—replicative DNA helicase; POLC—DNA polymerase III a subunit; CLPP—endopeptidase; IF-2—translation initiation factor 2; HELI—putative helicase; RFC—replication factor C; ORF—uncharacterized open reading frame product; G6PT—glucose-6-phosphate transaminase; RPO-A', PRO-A"—DNA-dependent RNA-polymerase subunits; RGYR—reverse gyrase; PEPS—phosphoenolpyruvate synthase; UDGD—uridine diphosphate glucose dehydrogenase; RNR—ribonucleotide reductase; DPOL—DNA polymerase, B family; TFIIB—transcription factor IIB; KLBA—predicted ATPase; HO—homothallic endonuclease. Species abbreviations: CAEEL—*Caenorhabditis elegans*; DANRE—*Danio rerio*; XENLA—*Xenopus laevis*; Cynpy—*Cynops pyrrhogaster*; DROHY—*Drosophila hydei*; DROME—*Drosophila melanogaster*; CANTR—*Candida tropicalis*; MYCLE—*Mycobacterium leprae*; MYCXE—*Mycobacterium xenopi*; MYCTU—*Mycobacterium tuberculosis*; PORPU—*Porphyra purpurea*; SYNSP—*Synechocystis* sp; CHLEU—*Chlamydomonas*; METJA—*Methanococcus jannaschii*; PYRFU—*Pyrococcus furiosus*; PYRSP—*Pyrococcus* sp.; THELI—*Thermococcus litoralis*. Accordingly, EHH/DANRE (SEQ ID NO: 54), CHHXENLA (SEQ ID NO: 55), HH4/XENLA (SEQ ID NO: 56), DHH/MOUSE (SEQ ID NO: 57), 1HH/MOUSE (SEQ ID NO: 58), IHH/HUMAN (SEQ ID NO: 59), 1HH/CHICK (SEQ ID NO: 60), BHH/ XENLA (SEQ ID NO: 61), TWHH/DANRE (SEQ ID NO: 62), SHH/DANRE (SEQ ID NO: 63), XHH/XENLA (SEQ ID NO: 64), HH1A/XENLA (SEQ ID NO: 65), HH/CYNPY (SEQ ID NO: 66), SHH/HUMAN (SEQ ID NO: 67), HH/DROHY (SEQ ID NO: 68), and HH/DROME (SEQ ID NO: 69) are shown. Several Hh and intein sequences closely related to those included were omitted.

DETAILED DESCRIPTION OF THE INVENTION

The present invention provides two novel polypeptides originally derived from a single precursor protein, both of which have distinct structural and functional characteristics. The proteins are derived from a hedgehog protein and can be naturally produced by auto-proteolytic cleavage of the full-length hedgehog protein. Based on evidence provided herein, which indicates that hedgehog precursor protein and the auto-proteolytic products of hedgehog precursor protein are expressed in the floorplate of the ventral midline of the neural tube and notochord, the invention now provides a method for the induction of proliferation or differentiation of neuronal cells associated with or in close proximity to the floorplate and notochord. The invention also provides cholesterol modified hedgehog polypeptides and function fragments thereof.

In a first embodiment, the invention provides a substantially pure polypeptide characterized by having an amino acid sequence derived from amino terminal amino acids of a hedgehog protein and having at its carboxy terminus, a glycine-cysteine-phenylalanine (G↓CF) cleavage site specifically recognized by a proteolytic activity of the carboxy terminal fragment of the native hedgehog polypeptide. This fragment is denoted the N-terminal fragment or polypeptide or "N", herein. For example, in the case of the Drosophila hedgehog, the N fragment includes amino acids 1-257 of hedgehog protein, wherein amino acids 85-257 have a molecular weight of about 19 kD by non-reducing SDS-PAGE (Amino acid residue numbers 1-257 include nonstructural features such as signal sequences.). The G↓CF cleavage site in Drosophila hedgehog precursor protein occurs at ammo acid residues 257-259. Those of skill in the art will be able to identify the G↓CF cleavage site in other hedgehog genes, as the amino acid location will be similar and the site will be specifically recognized by the autoproteolytic activity of the corresponding C fragment.

Figure 1E:
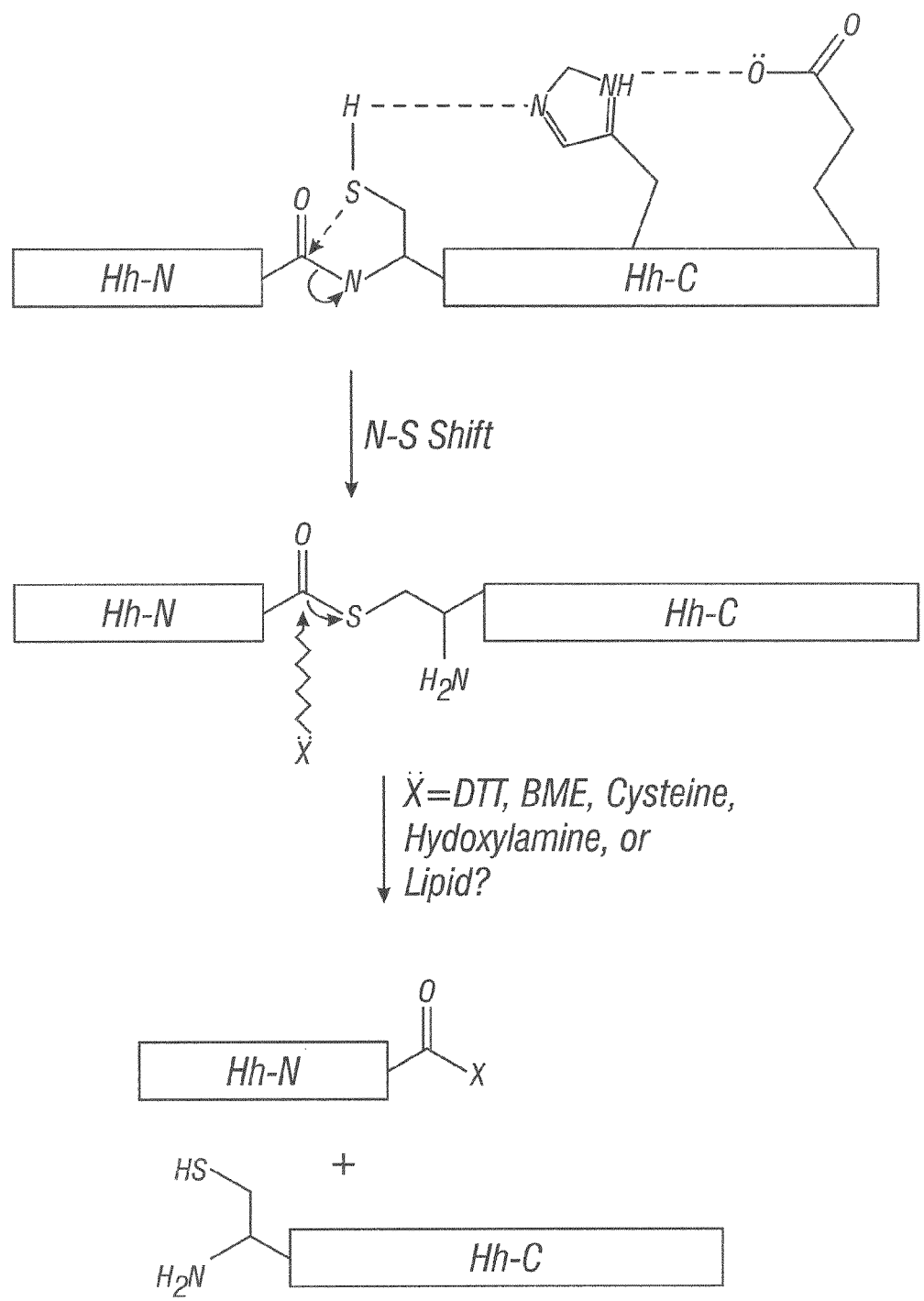
FIGS. 1E and 1F show a schematic illustration of the hedgehog cleavage mechanism.
Figure 1F:
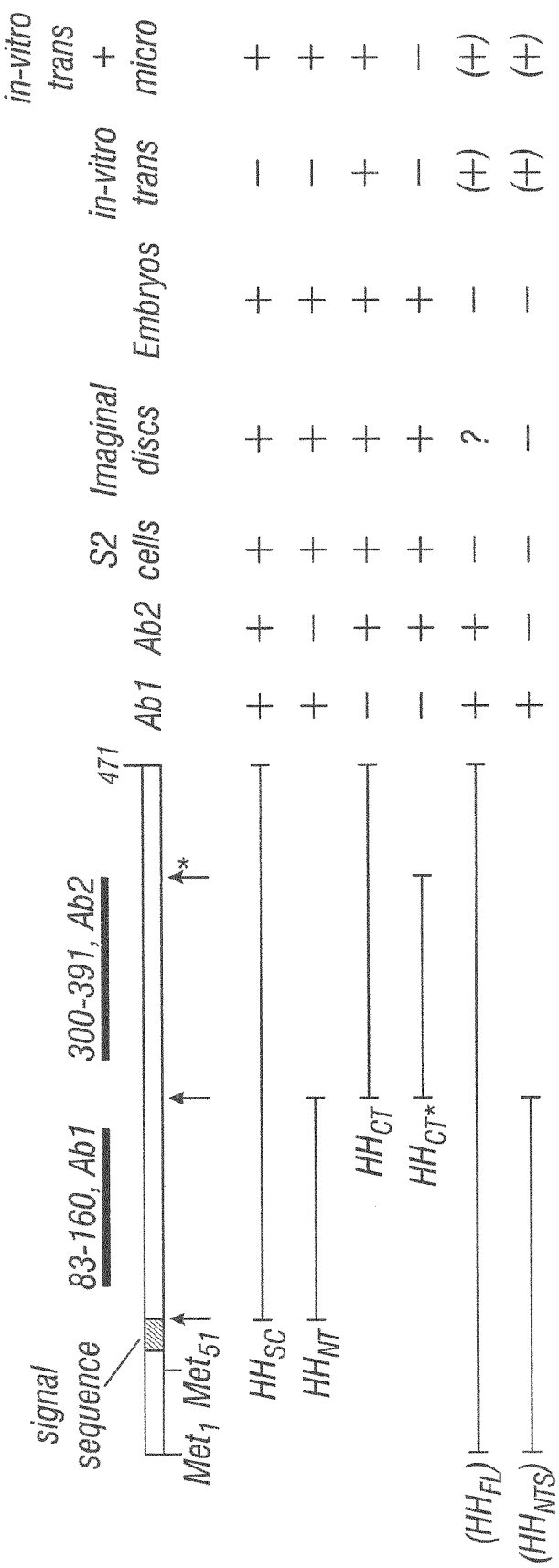

The N-terminal polypeptide is also characterized by being cell-associated in cells expressing the polypeptide in vitro, and being specifically localized in vertebrate or Drosophila cells or embryos, for example. In other words, this N-terminal fragment of hedgehog, remains close to the site of cellular synthesis. The association of N with the cell is a result of the processing event which involves lipophilic modification of the amino terminal domain. (See FIG. 1E and Example 19) This modification is initiated by the action of the carboxy terminal domain, generating a thioester intermediate; the carboxy-terminal domain thus does not act simply as a protease, although cleavage of a peptide bond does ultimately result from its action. Specifically, the lipid modification is a cholesterol moiety. In addition, the N fragment binds to heparin agarose in vitro.

The N polypeptide of the invention is characterized by having an amino acid sequence derived from amino terminal amino acids of hedgehog protein, e.g., 1-257 in Drosophila, wherein amino acids 1-257 have a molecular weight of about 19 kD by non-reducing SDS-PAGE. The N polypeptide includes smaller fragments which retain the functional characteristics of full length N, e.g., bind to heparin. The hedgehog protein from which N is derived includes, but is not limited to Drosophila, Xenopus, chicken, zebrafish, mouse, and human. Crystallographic analysis shows the structure of SHH-N includes the presence of a zinc ion. While not wanting to be bound by a particular theory, the presence of the zinc ion is suggestive of zinc hydrolase activity. Zinc hydrolases include proteases such as carboxypeptidase A and thermolysin, lipases such as phospholipase C, and other enzymes such as carbonic anhydrase. Alterations in the zinc hydrolase site of the amino terminal signaling domain may be useful for modulating the range of diffusion of a hedgehog protein or to alter the signaling characteristics of the amino terminal signaling domain. For example, a mutation in the zinc hydrolase site may result in a tethered protein where ordinarily the protein is secreted at a distance. The result would be induction of a cell type not typically induced. Alteration in the zinc site may result in a molecule capable of inducing motor neurons and not floor plate, and vice versa.

The identification of a cell-surface, or extracellular matrix localization of N and its expression in notochord and floor plate-associated cells, provides a means for isolation or specific selection of cells expressing N, e.g., to isolate a notochord sample or to isolate floor plate cells. In addition, antibodies directed to N are useful for histological analysis of tissues suspected of expressing N protein.

The invention also provides a substantially pure polypeptide characterized by having an amino acid sequence derived from carboxy terminal amino acids of a hedgehog protein and having at its amino terminus a G↓CF cleavage site specifically recognized by a proteolytic activity of the carboxy terminal fragment of the native hedgehog polypeptide. This fragment is denoted the C-terminal fragment or polypeptide or "C", herein. For example, in Drosophila this "C" polypeptide derives from the C-terminal domain of hedgehog precursor protein beginning at amino acid residue 258, wherein the full length C-terminal domain has a molecular weight of about 25 kD by non-reducing SDS-PAGE, a histidine residue at position 72, and has protease activity. The G↓CF cleavage site specifically recognized by the proteolytic activity of the carboxy terminal fragment of the native hedgehog polypeptide is located at amino acid residues 257-259. As described above for the N fragment, now that the present invention has shown the precise cleavage recognition site for the autoproteolytic domain of hedgehog, those of skill in the art can readily discern the cleavage site in other hedgehog proteins thereby allowing the ready identification of any N or C polypeptide of any hedgehog precursor protein.

The "C" polypeptide of the invention is derived from the C-terminus of a hedgehog precursor protein, beginning at the autoproteolytic cleavage site identified at the GCF amino acid sequence, which in *Drosophila* corresponds to amino acids 257-259. In *Drosophila* the histidine residue found invariably at amino acid residue 329 of the native hedgehog protein, and at amino acid residue 72 of the C polypeptide, is essential for auto-proteolytic cleavage between amino acids 257 and 258 (G and C). Corresponding C-polypeptides of the invention will likewise contain a similarly located histidine residue which can be readily identified, such as by comparison to the *Drosophila* C-polypeptide. Among various species, the proteolytic domain can be characterized by the amino acid sequence -XTXXHLXX-.

The C polypeptide of the invention, unlike N, does not significantly bind to heparin agarose. C is characterized by being released into the culture supernatant of cells expressing C polypeptide in vitro and by being localized diffusely in cells and embryos. Because C polypeptide diffuses freely, it would be detectable in various body fluids and tissues in a subject. Identification of C polypeptide expression near the midline of the neural tube, as described herein, provides a useful assay for neural tube closure in an embryo/fetus, for example. The presence of C polypeptide in amniotic fluid would be diagnostic of a disorder in which the neural tube may be malformed.

Altered levels of C polypeptide in cerebrospinal fluid may be indicative of neuro-degenerative disorders, for example. Because C polypeptide is released from the cell after synthesis and autoproteolysis of native hedgehog precursor polypeptide, tumors synthesizing and releasing high levels of C polypeptide would be detectable without prior knowledge of the exact location of the tumor.

C fragment is effective in inducing genes of the pituitary and anterior brain as well. In particular, induction is increased by the addition of a member of the TGF-β family of growth factors. For example, human activin in combination with C fragment may be effective in enhancing pituitary cell growth and activity or development. C fragment possesses cholesterol transferase activity thereby effecting precursor cleavage and transfer of a cholesterol moiety to N fragment, resulting in a biologically active N fragment.

C fragment is effective in inducing posterior markers of the brain by inhibiting N. Such a fragment is exemplified in Example 18 as ΔN-C. Therefore in another embodiment, the invention includes a polypeptide deleting amino acid residues 28-194 of X-bhh. (Autoproteolysis gives a C domain of 198-409 as well as a seven amino acid peptide, representing aa 24-27 and 195-197). This polypeptide blocks the activity of X-bhh and N in explants and reduces dorsoanterior structures in embryos. Also included are polynucleotide sequences encoding ΔN-C. ΔN-C is useful for increasing expression of posterior neural markers (e.g., En-2, Krox-20, Xlttbox-6) and decreasing expression of anterior neural markers (e.g., XANF-2, XAG-1, Otx-A) when desirable to do so to modulate neural patterning.

The term "substantially pure" as used herein refers to hedgehog N or C polypeptide which is substantially free of other proteins, lipids, carbohydrates, nucleic acids or other materials with which if is naturally associated. One skilled in the art can purify hedgehog N or C polypeptide using standard techniques for protein purification. The substantially pure polypeptide will yield a single major band on a non-reducing polyacrylamide gel. The purity of the hedgehog N or C polypeptide can also be determined by amino-terminal amino acid sequence analysis.

The invention includes a functional N or C polypeptide, and functional fragments thereof. As used herein, the term "functional polypeptide" or "functional fragment" refers to a polypeptide which possesses a biological function or activity which is identified through a defined functional assay and which is associated with a particular biologic, morphologic, or phenotypic alteration in the cell. Functional fragments of the hedgehog N or C polypeptide include fragments of N or C polypeptide as long as the activity, e.g., proteolytic activity or cholesterol transferase activity of C polypeptide remains. Smaller peptides containing the biological activity of N or C polypeptide are therefore included in the invention. The biological function, for example, can vary from a polypeptide fragment as small as an epitope to which an antibody molecule can bind to a large polypeptide which is capable of participating in the characteristic induction or programming of phenotypic changes within a cell. A "functional polynucleotide" denotes a polynucleotide which encodes a functional polypeptide as described herein.

Biologically active or functional fragments of hedgehog, as described herein, are included in the invention and can be identified as such by functional assays. For example, fragments of hedgehog are identified as inducing differentiation of neuronal cells; regulating differentiation of chondrocytes; able to complement a loss of function mutation of hedgehog, for example in a transgenic *Drosophila*; binding to Patched (Ptc); or having cholesterol transferase activity (e.g., C fragment). Fragments of the invention may be from about 30 to 450 amino acids in length; from about 50 to 300 amino acids in length; from about 75 to 250 amino acids in length; or from about 100 to 200 amino acids in length, as long as a biological activity of hedgehog is retained therein.

Minor modifications of the N or C polypeptide primary amino acid sequence may result in polypeptides which have substantially equivalent activity as compared to the N or C polypeptide described herein. Such modifications may be deliberate, as by site-directed mutagenesis, or may be spontaneous. All of the polypeptides produced by these modifications are included herein as long as the proteolytic activity of C polypeptide, for example, is present. Further, deletion of one or more amino acids can also result in a modification of the structure of the resultant molecule without significantly altering its activity. This can lead to the development of a smaller active molecule which would have broader utility. For example, it is possible to remove amino or carboxy terminal amino acids which may not be required for N or C polypeptide activity.

The N or C polypeptide of the invention also includes conservative variations of the polypeptide sequence. The term "conservative variation" as used herein denotes the replacement of an amino acid residue by another biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The N fragment of the invention includes both the active form of the polypeptide and the N fragment including the uncleaved signal sequence. For example, in *Drosophila* where the signal sequence is internal (at about amino acids 60-80), the entire uncleaved N fragment beginning at the initiating methionine is included in the invention. Those of skill in the art can readily ascertain the nature and location of the signal sequence by using, for example, the algorithm described in von Heijne, G., *Nucl. Acids Res.* 14:4683, (1986).

Hedgehog polypeptides of the invention include polypeptides having at least about 50%-100% homology with the hedgehog polypeptides provided herein, for example 52%, 64%, 68%, 70%, 75%, 80%, 85%, 90%, 95% and up to 100% homology. Preferably homologous polypeptides are derived from vertebrate species, most preferably mammalian species, such as humans.

The invention also provides an isolated polynucleotide sequence encoding a polypeptide having the amino acid sequence of N or C polypeptide of the invention. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode N or C polypeptide. It is understood that all polynucleotides encoding all or a portion of N or C polypeptide are also included herein, as long as they encode a polypeptide with N or C polypeptide activity. Such polynucleotides include naturally occurring, synthetic, and intentionally manipulated polynucleotides. For example, N or C polypeptide polynucleotide may be subjected to site-directed mutagenesis. The polynucleotide sequence for N or C polypeptide also includes antisense sequences. The polynucleotides of the invention include sequences that are degenerate as a result of the genetic code. There are 20 natural ammo acids, most of which are specified by more than one codon. Therefore, all degenerate nucleotide sequences are included in the invention as long as the amino acid sequence of N or C polypeptide encoded by the nucleotide sequence is functionally unchanged. In addition, the invention also includes a polynucleotide consisting essentially of a polynucleotide sequence encoding a polypeptide having an amino acid sequence of N or C and having at least one epitope for an antibody immunoreactive with N or C polypeptide.

The polynucleotide encoding N or C polypeptide includes the entire polypeptide or fragments thereof, as well as nucleic acid sequences complementary to that sequence. A complementary sequence may include an antisense nucleotide. When the sequence is RNA, the deoxynucleotides A, G, C, and T are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein under physiological conditions.

Hedgehog encoding polynucleotides of the invention include nucleic acid sequences identified by hybridization to a hedgehog nucleic acid described herein. In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions).

Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences; 2) antibody screening of expression libraries to detect cloned DNA fragments with shared structural features; and 3) PCR amplification of a desired nucleotide sequence using oligonucleotide primers.

Preferably the hedgehog, N, or C polynucleotide of the invention is derived from a vertebrate organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate.

This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

The development of specific DNA sequences encoding hedgehog can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of ammo acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A preferred method for obtaining genomic DNA, for example, is Polymerase Chain Reaction (PCR), which relies on an in vitro method of nucleic acid synthesis by which a particular segment of DNA is specifically replicated. Two oligonucleotide primers that flank the DNA fragment to be amplified are utilized in repeated cycles of heat denaturation of the DNA, annealing of the primers to their complementary sequences, and extension of the annealed primers with DNA polymerase. These primers hybridize to opposite strands of the target sequence and are oriented so that DNA synthesis by the polymerase proceeds across the region between the primers. Since the extension products themselves are also complementary to and capable of binding primers, successive cycles of amplification essentially double the amount of the target DNA synthesized in the previous cycle. The result is an exponential accumulation of the specific target fragment, approximately $2^n$, where n is the number of cycles of amplification performed (see PCR Protocols, Eds. Innis, et al., Academic Press, Inc., 1990, incorporated herein by reference).

A cDNA expression library, such as λgt11, can be screened indirectly for hedgehog, N, or C polypeptides having at least one epitope, using antibodies specific for hedgehog, N, or C. Such antibodies can be either polyclonally or monoclonally derived and used to detect expression product indicative of the presence of the desired hedgehog cDNA.

The polynucleotide sequence for hedgehog, N, or C, also includes sequences complementary to the polynucleotide encoding hedgehog, N or C (antisense sequences). Antisense nucleic acids are DNA or RNA molecules that are complementary to at least a portion of a specific mRNA molecule (Weintraub, *Scientific American*, 262:40, 1990). The invention embraces all antisense polynucleotides capable of inhibiting production of hedgehog, N, or C polypeptide. In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target hedgehog, N, or C-producing cell. The use of antisense methods to inhibit the translation of genes is well known in the art (Marcus-Sakura, *Anal. Biochem.*, 172:289, 1988). Inhibition of target nucleotide would be desirable, for example, in inhibiting cell-proliferative disorders, such as certain tumors, which are mediated by hedgehog, N or C.

In addition, ribozyme nucleotide sequences for hedgehog, N or C are included in the invention. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, *tetrahymena*-type (Hasselhoff, Nature, 334:585, 1988) and "hammerhead"-type. *Tetrahymena*-type ribozymes recognize sequences which are four bases in length, while "hammerhead"-type ribozymes recognize base sequences 11-18 bases in length. The longer the recognition sequence, the greater the likelihood that sequence will occur exclusively in the target mRNA species. Consequently, hammerhead-type ribozymes are preferable to *tetrahymena*-type ribozymes for inactivating a specific mRNA species and 18-based recognition sequences are preferable to shorter recognition sequences.

DNA sequences encoding hedgehog, N or C can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the hedgehog, N or C polynucleotide sequences may be inserted into a recombinant expression vector. The term "recombinant expression vector" refers to a plasmid, virus or other vehicle known in the art that has been manipulated by insertion or incorporation of the hedgehog, N or C genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding hedgehog, N or C can be expressed in either prokaryotes or eukaryotes, although post-translational modification of eukaryotically derived polypeptides, such as carboxylation, would occur in a eukaryotic host. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Methods which are well known to those skilled in the art can be used to construct expression vectors containing the hedgehog, N or C coding sequence and appropriate transcriptional/translational control signals. These methods include in vitro recombinant DNA techniques, synthetic techniques, and in vivo recombination/genetic techniques. See, for example, the techniques described in Maniatis, et al., 1989 Molecular Cloning A Laboratory Manual, Cold Spring Harbor Laboratory, N.Y.

A variety of host-expression vector systems may be utilized to express the hedgehog, N or C coding sequence. These include but are not limited to microorganisms such as bacteria transformed with recombinant bacteriophage DNA, plasmid DNA or cosmid DNA expression vectors containing the hedgehog, N or C coding sequence; yeast transformed with recombinant yeast expression vectors containing the hedgehog, N or C coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Hedgehog, N or C coding sequence; insect cell systems infected with recombinant virus expression vectors (e.g., baculovirus) containing the hedgehog, N or C coding sequence; or animal cell systems infected with recombinant virus expression vectors (e.g., retroviruses, adenovirus, vaccinia virus) containing the hedgehog, N or C coding sequence, or transformed animal cell systems engineered for stable expression.

Depending on the host/vector system utilized, any of a number of suitable transcription and translation elements, including constitutive and inducible promoters, transcription enhancer elements, transcription terminators, etc., may be used in the expression vector (see e.g., Bitter, et al., 1987, Methods in Enzymology, 153:516-544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted hedgehog, N or C coding sequence.

In bacterial systems a number of expression vectors may be advantageously selected depending upon the use intended for the expressed. For example, when large quantities of hedgehog, N or C are to be produced, vectors which direct the expression of high levels of fusion protein products that are readily purified may be desirable. Those which are engineered to contain a cleavage site to aid in recovering are preferred. Such vectors include but are not limited to the *E. coli* expression vector pUR278 (Ruther, et al., *EMBO J.,* 2:1791, 1983), in which the Hedgehog, N or C coding sequence may be ligated into the vector in frame with the lac Z coding region so that a hybrid -lac Z protein is produced; pIN vectors (Inouye and Inouye, *Nucleic Acids Res.,* 13:3101, 1985; Van Heeke and Schuster, *J. Biol. Chem.* 264:5503, 1989) and the like.

In yeast, a number of vectors containing constitutive or inducible promoters may be used. For a review see, Current Protocols in Molecular Biology, Vol. 2, 1988, Ed. Ausubel, et al., Greene Publish. Assoc. Wiley Interscience, Ch. 13; Grant, et al., 1987, Expression and Secretion Vectors for Yeast, in Methods in Enzymology, Eds. Wu and Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger and Kimmel, Acad. Press, N.Y., Vol. 152, pp. 673-684; and The Molecular Biology of the Yeast *Saccharomyces,* 1982, Eds. Strathern, et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 1, A Practical Approach, Ed. DM Glover, 1986, IRL Press, Wash., DC). Alternatively, vectors may be used which promote integration of foreign DNA sequences into the yeast chromosome.

In cases where plant expression vectors are used, the expression of the hedgehog, N or C coding sequence may be driven by any of a number of promoters. For example, viral promoters such as the 35S RNA and 19S RNA promoters of CaMV (Brisson, et al., *Nature,* 310:511, 1984), or the coat protein promoter to TMV (Takamatsu, et al, *EMBO J.,* 6:307, 1987) may be used; alternatively, plant promoters such as the small subunit of RUBISCO (Coruzzi, et al., *EMBO J.,* 3:1671-1680, 1984; Broglie, et al., *Science,* 224:838, 1984); or heat shock promoters, e.g., soybean hsp17.5-E or hsp17.3-B (Gurley, et al., *Mol. Cell. Biol.,* 6:559, 1986) may be used. These constructs can be introduced into plant cells using Ti plasmids, Ri plasmids, plant virus vectors, direct DNA transformation, microinjection, electroporation, etc. For reviews of such techniques see, for example, Weissbach and Weissbach, 1988, Methods for Plant Molecular Biology, Academic Press, NY, Section VIII, pp. 421-463; and Grierson and Corey, 1988, Plant Molecular Biology, 2d Ed., Blackie, London, Ch. 7-9.

An alternative expression system which could be used to express is an insect system. In one such system, *Autographa californica* nuclear polyhedrosis virus (AcNPV) is used as a vector to express foreign genes. The virus grows in *Spodoptera frugiperda* cells. The hedgehog, N or C coding sequence may be cloned into non-essential regions (for example the polyhedrin gene) of the virus and placed under control of an AcNPV promoter (for example the polyhedrin promoter). Successful insertion of the hedgehog, N or C coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, (e.g., see Smith, et al., *J. Viol.,* 46:584, 1983; Smith, U.S. Pat. No. 4,215,051).

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, secretion of the gene product may be used as host cells for the expression of hedgehog, N or C. Mammalian cell lines may be preferable. Such host cell lines may include but are not limited to CHO, VERO, BHK, HeLa, COS, MDCK, -293, and WI38.

Mammalian cell systems which utilize recombinant viruses or viral elements to direct expression may be engineered. For example, when using adenovirus expression vectors, the hedgehog, N or C coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the protein in infected hosts (e.g., see Logan and Shenk, *Proc. Natl. Acad. Sci. USA,* 81:3655, 1984). Alternatively, the vaccinia virus 7.5K promoter may be used, (e.g., see, Mackett, et al., *Proc. Natl. Acad. Sci. USA,* 79:7415, 1982; Mackett, et al., *J. Virol,* 49: 857, 1984; Panicali, et al., *Proc. Natl. Acad. Sci. USA,* 79:4927, 1982). Of particular interest are vectors based on bovine papilloma virus which have the ability to replicate as extrachromosomal elements (Sarver, et al., *Mol. Cell. Biol.,* 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the hedgehog, N or C gene in host cells (Cone and Mulligan, *Proc. Natl. Acad. Sci. USA*, 81:6349, 1984). High level expression may also be achieved using inducible promoters, including, but not limited to, the metallothionine ILA promoter and heat shock promoters.

For long-term, high-yield production of recombinant proteins, stable expression is preferred. Rather than using expression vectors which contain viral origins of replication, host cells can be transformed with the hedgehog, N or C cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., *Cell*, 11: 223, 1977), hypoxanthine-guanine phosphoribosyltransferase (Szybalska and Szybalski, *Proc. Natl. Acad. Sci. USA*, 48:2026, 1962), and adenine phosphoribosyltransferase (Lowy, et al., *Cell*, 22: 817, 1980) genes can be employed in tk⁻, hgprt⁻ or aprt⁻ cells respectively. Also, antimetabolite resistance can be used as the basis of selection for dhfr, which confers resistance to methotrexate (Wigler, et al. *Natl. Acad. Sci. USA*, 77: 3567, 1980; O'Hare, et al., *Proc. Natl. Acad. Sci. USA*, 78: 1527, 1981); gpt, which confers resistance to mycophenolic acid (Mulligan and Berg, *Proc. Natl. Acad. Sci. USA*, 78: 2072, 1981; neo, which confers resistance to the aminoglycoside G-418 (Colberre-Garapm, et al., *J. Mol. Biol.*, 150:1, 1981); and hygro, which confers resistance to hygromycin (Santerre, et al., *Gene*, 30:147, 1984) genes. Recently, additional selectable genes have been described, namely trpB, which allows cells to utilize indole in place of tryptophan; hisD, which allows cells to utilize histinol in place of histidine (Hartman and Mulligan, *Proc. Natl. Acad. Sci. USA*, 85:8047, 1988); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the hedgehog, N or C of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with or which bind to hedgehog, N or C polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature*, 256:495, 1975). The term antibody as used in this invention is meant to include intact molecules as well as fragments thereof, such as Fab and $F(ab')_2$, which are capable of binding an epitopic determinant on hedgehog, N or C. The antibodies of the invention include antibodies winch bind to the N or C polypeptide and which bind with immunoreactive fragments N or C.

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies winch bind to the hedgehog, N or C polypeptide of the invention can be prepared using an intact polypeptide or fragments containing small peptides of interest as the immunizing antigen. The polypeptide such as N or C, or fragments thereof used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Antibodies as described herein as having specificity for N polypeptide, e.g., Ab1 (residues 83-160), are useful for specific identification of cells or tissues expressing the N fragment of hedgehog. Similarly, antibodies described herein as having specificity for C polypeptide, e.g., Ab2 (residues 300-391), are useful for specific identification of cells or tissues expressing the C fragment of hedgehog. Both antibodies, naturally, will also detect native hedgehog polypeptide.

The N and C-specific antibodies of the invention are useful for purification of N and C polypeptide, respectively, especially using the antibodies immobilized on solid phase. By contacting a sample with anti-N antibody, both N and native hedgehog polypeptides can be isolated. By next contacting the sample removed by anti-N antibodies, with anti-C antibodies, the native hedgehog polypeptide is removed, thus allowing purification of N polypeptide. In a similar manner, C polypeptide can be antibody purified from a sample.

Monoclonal antibodies of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and noncompetitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of N or C polypeptide. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

For purposes of the invention, N or C polypeptide may be detected by the monoclonal antibodies when present in biological fluids and tissues. Any sample containing a detectable amount of N or C can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis. C polypeptide in particular is detectable in biological samples, since it tends to diffuse more readily than N polypeptide.

In performing the assays it may be desirable to include certain "blockers" in the incubation medium (usually added with the labeled soluble antibody). The "blockers" are added to assure that nonspecific proteins, proteases, or anti-heterophilic immunoglobulins to anti-C or N immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

The invention also provides a method for modulating proliferation or differentiation of neuronal cells comprising contacting the cells with a hedgehog polypeptide. The hedgehog polypeptide may be a native hedgehog polypeptide, or a N or C polypeptide, or functional fragments thereof. Preferably, the modulation is induction of proliferation or differentiation of a particular cell type. This can involve either synergistic positive induction of neuronal cells by N, or negative modulation by delta N—C for example (Lai, et al., *Development* 121:2349, 1995). Delta N—C enhances expression of posteder relative to anterior neural genes and does so through inhibition of N (see EXAMPLE 18 and FIG. 18D). In addition to hedgehog polypeptide, a TGF-β factor may also be utilized in the method of the invention.

Previous studies with the rat hedgehog gene showed that co-culture of cells expressing rat hedgehog precursor gene, with explant from neural tube, was sufficient to induce formation of motor neurons and floor plate from the explant (Jessesl, T., and Dodd, J., In *Cell-Cell Signaling in Vertebrate Development* (ed. E. J. Robertson, et al., pp 139-155, San Diego, Calif.), 1993). Therefore, based on the Examples herein showing that hedgehog is expressed near the floorplate of the ventral midline of the neural tube and notochord, neuronal cells substantially derived from floorplate cells can be induced by contacting the cells with hedgehog, N or C polypeptide. As used herein, the term "substantially derived", refers to those cells from the floor plate or proximate to the floor plate. For example, such cells include motor neurons and dopaminergic neurons. Those of skill in the art will be able to identify other neuronal cells substantially derived from the floorplate. Preferably the cells are vertebrate cells and most preferably, human cells.

In addition, as described herein in the Examples, hedgehog, and particularly C fragment, induces the expression of pituitary genes. Hedgehog is also effective in inducing anterior brain gene expression as exemplified by the OTX-A marker. Further, the addition of a TGF-β family member, for example activin, may be used to further induce expression of such genes. Other TGF-β family members will be known to those of skill in the art. This apparent synergy of hh fragments with TGF-β family members occurs through the TGF-β protein inducing expression of neural inducers such as noggin and follistatin. The hh fragment then synergizes with these inducers to pattern neural gene expression.

hh fragments may also be useful as nerve-sparing agents or in restoring or promoting appropriate patterning during the healing of major limb trauma. In addition, the N and C fragments may be useful in the area of genetic counseling. Specifically, familial midline defects such as cyclopia, Polydactyly or neural tube defects may be diagnosed by mapping close to hh. Since autoproteolytic defects may be responsible for the disorders, N or C therapy could be provided.

The invention also provides an autoproteolytic fusion protein comprising a first polypeptide including the proteolytic domain of the C polypeptide of the invention, a cleavage site recognized by the first polypeptide, and a second polypeptide. (It is understood that the first and second polypeptides can be reversed.) The auto-proteolytic activity of the native hedgehog protein is found entirely within the C polypeptide, therefore, the C polypeptide is useful for producing a fusion polypeptide which can then be cleaved at the junction of the C polypeptide and the second polypeptide. The fusion protein may optionally have a purification tag, such as a poly-histidine tag for isolation on a nickel column, or an antibody epitope tag, preferably on the C fragment. The cleavage site includes the sequence "GCF", which is recognized by the proteolytic domain of the C polypeptide and is utilized to cleave the second polypeptide from the C fragment. Also included in the invention is a polynucleotide encoding the fusion protein of the invention.

The invention also provides a method for producing an autoproteolytic fusion protein comprising operably linking a first polynucleotide, wherein the first polynucleotide encodes a first polypeptide including the proteolytic domain of the C polypeptide of the invention and the cleavage site recognized by the proteolytic domain, and a second polynucleotide encoding a second polypeptide. As described above, the fusion protein may also include a carrier peptide and/or a purification tag.

The C polypeptide or functional fragment thereof is useful as a fusion partner to cause lipophilic modification and tethering of other proteins in vivo or in vitro. Such fusion proteins may be desirable for factors whose activity is required in a localized manner, either by targeting DNA constructs to specific cells or by introducing cells transfected with specific DNA constructs, for example. It may be desirable to lipid-modify a normally secreted protein in order to produce a cell-associated protein. For example, it may be desirable to produce a viral antigen that remains cell associated. Specifically, cholesterol is covalently attached to the N-terminal protein during autoprocessing and the C polypeptide acts as an intramolecular cholesterol transferase.

Alternatively, the C polypeptide or functional fragments thereof can be used as a fusion partner with a protein of interest (e.g., Protein X fused to hh-C domain). Such fusions form thioesters at the junction between Protein X and hh-C (via an S to N shift). The thioesters are then available as substrates for a peptide ligation reaction in which any peptide or protein having an amino terminal cysteine (Peptide Y) is added and undergoes spontaneous rearrangement (S to N shift) that generates a stable peptide bond between Protein X and Peptide Y (Protein X-peptide bond-Peptide Y). For example, a protein that is toxic when produced in vivo could be produced in vitro using the hh-C domain fusion protein method.

The fusion polypeptide may also include an optional carrier peptide. The "carrier peptide", or signal sequence, is located at the amino terminal end of the fusion peptide sequence. In the case of eukaryotes, the carrier peptide is believed to function to transport the fusion polypeptide across the endoplasmic reticulum. The secretory protein is then transported through the Golgi apparatus, into secretory vesicles and into the extracellular space or, preferably, the external environment. Carrier peptides which can be utilized according to the invention include pre-pro peptides which contain a proteolytic enzyme recognition site. Acceptable carrier peptides include the amino terminal pro-region of calcitonin or other hormones, which undergo cleavage at the flanking dibasic sites. However, it should be noted that the invention is not limited to the use of any particular peptide as a carrier. Other carrier peptides are known to those skilled in the art or can be readily ascertained without undue experimentation.

In one embodiment of the invention, a carrier peptide which is a signal sequence is included in the expression vector, specifically located adjacent to the N-terminal end of the fusion polypeptide. This signal sequence allows the fusion protein to be directed toward the endoplasmic reticulum. Typically, the signal sequence consists of a leader of from about 16 to about 29 amino acids, starting with two or three polar residues and continuing with a high content of hydrophobic amino acids; there is otherwise no detectable conservation of sequence known. Such signal sequences are known to those of skill in the art, and include the naturally occurring signal sequence derived from a hedgehog protein.

The fusion polypeptide of the invention includes a polypeptide encoded by a structural gene, preferably at the amino-terminus of the fusion polypeptide. Any structural gene is expressed in conjunction with the C-polypeptide (polynucleotide) and optionally a carrier peptide. The structural gene is operably linked with the carrier in an expression vector so that the fusion polypeptide is expressed as a single unit.

Figure 12A:
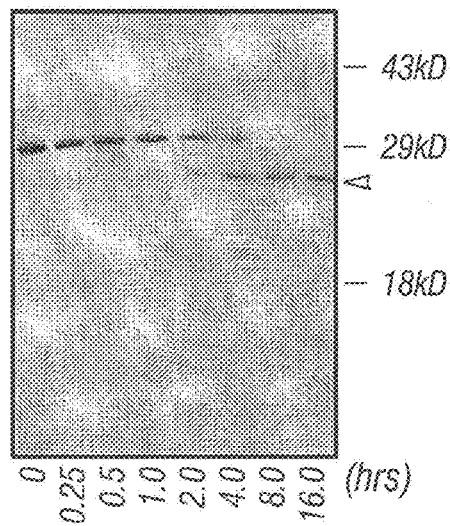
FIGS. 12A and 12B show in vitro cleavage reactions of a *Drosophila* hh protein produced in *E. coli* and purified to homogeneity.
Figure 12B:
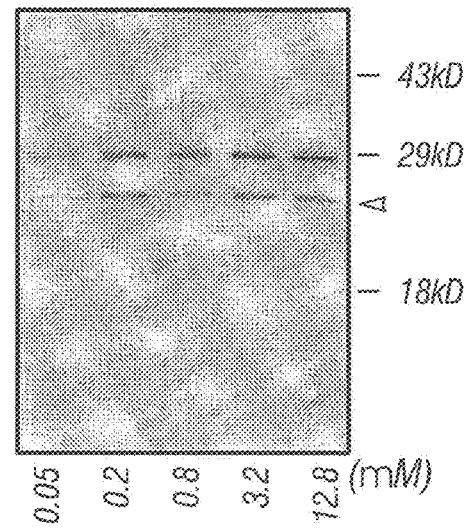

The identification of the autoproteolysis of hedgehog into the N and C domains is useful in a screening method to identify compounds or compositions which affect this processing activity. Thus, in another embodiment, the invention provides a method for identifying a composition which affects hh processing, which can be determined by activity or gene expression, comprising incubating the components, which include the composition to be tested (e.g., a drug, a small molecule, a protein) and a hh polypeptide or a recombinant cell expressing hedgehog or a gene encoding a C domain or functional fragment thereof operably linked to an N domain or functional fragment thereof, under conditions sufficient to allow the components to interact, then subsequently measuring the effect the composition has on hedgehog activity or expression. Fragments of hedgehog polypeptide or polynucleotide can be used in the method of the invention as long as autoproteolytic activity remains (e.g., the construct exemplified in FIGS. 12*a* and 12*b*, Example 10). The observed effect on hh may be either inhibitory or stimulatory. For example, one can determine whether the N domain is associated with the cell, or whether the N domain is secreted into the medium, in other words, whether incomplete processing has occurred. Such methods for determining the effect of the compound or composition on hh processing include those described herein (see Example 10, FIG. 12*a* and 12*b*) such as time course of autoproteolytic cleavage or course of cleavage based on concentration ranges. Alternatively, the effect of the composition on hh can be determined by the expression of anterior or posterior neural markers. Other methods for determining the effect of a composition on processing of N and C will be known to those of skill in the art. Various labels can be used to detect the N and C domains, for example, a radioisotope, a fluorescent compound, a bioluminescent compound, a chemiluminescent compound, a metal chelator or an enzyme could be used. Those of ordinary skill in the art will know of other suitable labels or will be able to ascertain such, using routine experimentation.

The identification of the lipid modification of the N domain of hedgehog by the C domain, resulting in a biologically active N domain, is useful in a screening method to identify compounds or compositions which affect the cholesterol transferase/processing activity of hedgehog. In a broader aspect, the modification may be a general sterol or lipid modification, and not limited to cholesterol. Thus, in another embodiment, the invention provides a method for identifying a composition which affects hh biological activity, which can be determined by activity or lipid modification (e.g., cholesterol), comprising incubating the components, which include the composition to be tested (e.g., a drug, a small molecule, a protein) and a hh polypeptide or a recombinant cell expressing hedgehog or a gene encoding a C domain or functional fragment thereof operably linked to an N domain or functional fragment thereof, under conditions sufficient to allow the components to interact, then subsequently measuring the effect the composition has on hedgehog activity. Fragments of hedgehog polypeptide or polynucleotide can be used in the method of the invention as long as cholesterol transferase activity remains, for example. The effect on hh may be either inhibitory or stimulatory. For example, one can determine whether the N domain is associated with the cell, or whether the N domain is secreted into the medium, in other words, whether incomplete processing and modification has occurred. Such methods for determining the effect of the compound or composition on hh processing include those described herein (see Example 10, FIGS. 12a and 12b) such as time course of autoproteolytic cleavage or course of cleavage based on concentration ranges. Alternatively, the effect of the composition on hh can be determined by the level of cholesterol modification as determined by thin layer chromatography (e.g., Example 19, FIG. 23) or incorporation of labeled cholesterol into hh protein (e.g., Example 19, FIG. 25) or into a fragment appended to the transferase (c) domain. Other methods for determining the effect of a composition on processing and cholesterol modification of N and C will be known to those of skill in the art. Various labels can be used to detect the N and C domains, for example, a radioisotope, a fluorescent compound, a bioluminescent compound, a chemiluminescent compound, a metal chelator or an enzyme could be used. Those of ordinary skill in the art will know of other suitable labels or will be able to ascertain such, using routine experimentation.

As used herein, "hh activity" as described in the screening method refers preferably to auto-proteolytic activity. However, it is understood, that one of skill in the art could use the above-described screening assay to identify a composition having an affect on other hh activities, for example, zinc hydrolase activity or cholesterol transferase activity; or induction or regulation of differentiation of neuronal cells or chondrocytes. Appropriate assays for determining the effect on such activities will be known to those of skill in the art. Example 19 provides lipophilic modification assays useful in the described screening methods above.

Now that the present invention describes the cholesterol modification of N by C, it is possible to design various diagnostic and therapeutic approaches for treatment of hh associated disorders due to defective or altered sterol modification. For example, Smith-Lemli-Optiz syndrome (SLOS) is characterized by a loss of hh function and a sterol profile indicating a cholesterol deficiency. Therefore, SLOS may be diagnosed and/or treated based on the cholesterol profile. Further, a defect in Desert hh in the testes is associated with male sterility (M. Bitgood, L. Shen, A. P. McMahon, *Current Biology* 6, 298, 1996; A. Vortkamp et al., *Science* 273, 613, 1996), consequently, it may be possible to design male contraceptives based on defective cholesterol modification of hh. On the other hand, if sterility or decreased fertility was desirable, hh cholesterol transferase activity could be altered to reduce cholesterol modification. Processing of the C and N fragments of hh is required for hh activity, therefore alterations in cholesterol modification of the amino terminal fragment may also be related to developmental defects in vertebrate embryos.

Another aspect of the present invention concerns three-dimensional molecular models of the subject hedgehog proteins, and their use as templates for the design of agents able to inhibit or potentiate at least one biological activity of the hedgehog, particularly the autoproteolytic. An integral step to our approach to designing inhibitors of the subject hegehog proteins, for example, involves construction of computer graphics models of the hegehog protein which can be used to design pharmacophores by rational drug design. For instance, for an inhibitor to interact optimally with the subject proteolytic domain of hedgehog, it will generally be desirable that it have a shape which is at least partly complimentary to that of a particular binding site of the enzyme, as for example those portions of the human hegehog protein which are involved in the autoproteolytic activity. Additionally, other factors, including electrostatic interactions, hydrogen bonding, hydrophobic interactions, desolvation effects, and cooperative motions of ligand and enzyme, all influence the binding effect and should be taken into account in attempts to design bioactive inhibitors.

A computer-generated molecular model of the subject hedgehog proteins can be created. In preferred embodiments, at least the $C\alpha$-carbon positions of the hedgehog sequence of interest are mapped to a particular coordinate pattern, such as the coordinates for hedgehog determined by x-ray crystallography, by homology modeling, and the structure of the protein and velocities of each atom are calculated at a simulation temperature ($T_o$) at which the docking simulation is to be determined. Typically, such a protocol involves primarily the prediction of side-chain conformations in the modeled protein, while assuming a main-chain trace taken from a tertiary structure such as provided in x-crystallographic model described herein. Computer programs for performing energy minimization routines are commonly used to generate molecular models. For example, both the CHARMM (Brooks et al. (1983) *J Comput Chem* 4:187-217) and AMBER (Weiner et al (1981) *J. Comput. Chem.* 106: 765) algorithms handle all of the molecular system setup, force field calculation, and analysis (see also, Eisenfield et al. (1991) *Am J Physiol* 261:C376-386; Lybrand (1991) *J Pharm Belg* 46:49-54; Froimowitz (1990) *Biotechniques* 8:640-644; Burbam et al. (1990) *Proteins* 7:99-111; Pedersen (1985) *Environ Health Perspect* 61:185-190; and Kini et al. (1991) *J Biomol Struct Dyn* 9:475-488). At the heart of these programs is a set of subroutines that, given the position of every atom in the model, calculate the total potential energy of the system and the force on each atom. These programs may utilize a starting set of atomic coordinates, such as the model coordinates provided in crystallographic-derived models, the parameters for the various terms of the potential energy function, and a description of the molecular topology (the covalent structure). Common features of such molecular modeling methods include: provisions for handling hydrogen bonds and other constraint forces; the use of periodic boundary conditions; and provisions for occasionally adjusting positions, velocities, or other parameters in order to maintain or change temperature, pressure, volume, forces of constraint, or other externally controlled conditions.

Most conventional energy minimization methods use the input data described above and the fact that the potential energy function is an explicit, differentiable function of Cartesian coordinates, to calculate the potential energy and its gradient (which gives the force on each atom) for any set of atomic positions. This information can be used to generate a new set of coordinates in an effort to reduce the total potential energy and, by repeating this process over and over, to optimize the molecular structure under a given set of external conditions. These energy minimization methods are routinely applied to molecules similar to the subject hedgehog proteins as well as nucleic acids, polymers and zeolites.

In general, energy minimization methods can be carried out for a given temperature, $T_i$, which may be different than the docking simulation temperature, $T_o$. Upon energy minimization of the molecule at $T_i$, coordinates and velocities of all the atoms in the system are computed. Additionally, the normal modes of the system are calculated. It will be appreciated by those skilled in the art that each normal mode is a collective, periodic motion, with all parts of the system moving in phase with each other, and that the motion of the molecule is the superposition of all normal modes. For a given temperature, the mean square amplitude of motion in a particular mode is inversely proportional to the effective force constant for that mode, so that the motion of the molecule will often be dominated by the low frequency vibrations.

After the molecular model has been energy minimized at $T_i$, the system is "heated" or "cooled" to the simulation temperature, $T_o$, by carrying out an equilibration run where the velocities of the atoms are scaled in a step-wise manner until the desired temperature, $T_o$, is reached. The system is further equilibrated for a specified period of time until certain properties of the system, such as average kinetic energy, remain constant. The coordinates and velocities of each atom are then obtained from the equilibrated system.

Further energy minimization routines can also be carried out. For example, a second class of methods involves calculating approximate solutions to the constrained EOM for the protein. These methods use an iterative approach to solve for the Lagrange multipliers and, typically, only need a few iterations if the corrections required are small. The most popular method of this type, SHAKE (Ryckaert et al. (1977) *J Comput Phys* 23:327; and Van Gunsteren et al. (1977) *Mol Phys* 34:1311) is easy to implement and scales as O(N) as the number of constraints increases. Therefore, the method is applicable to macromolecules such as the Hedgehog proteins of the present invention. An alternative method, RATTLE (Anderson (1983) *J Comput Phys* 52:24) is based on the velocity version of the Varlet algorithm. Like SHAKE, RATTLE is an iterative algorithm and can be used to energy minimize the model of the subject hedgehog protein.

The increasing availability of biomacromolecule structures of potential pharmacophoric molecules that have been solved crystallographically has prompted the development of a variety of direct computational methods for molecular design, in which the steric and electronic properties of catalytic and substrate recognition sites are use to guide the design of potential inhibitors (Cohen et al. (1990) *J. Med. Cam.* 33: 883-894; Kuntz et al. (1982) *J. Mol. Biol.* 161: 269-288; DesJarlais (1988) *J Med. Cam.* 31: 722-729; Bartlett et al. (1989) (*Spec. Publ., Roy. Soc. Chem.*) 78: 182-196; Goodford et al. (1985) *J. Med. Cam.* 28: 849-857; DesJarlais et al. *J Med. Cam.* 29: 2149-2153). Directed methods generally fall into two categories: (1) design by analogy in which 3-D structures of known molecules (such as from a crystallographic database) are docked to the enzyme structure and scored for goodness-of-fit; and (2) de novo design, in which the ligand model is constructed piece-wise in the enzyme. The latter approach, in particular, can facilitate the development of novel molecules, uniquely designed to bind to, and, e.g., inhibit the proteolytic activity of a hegehog protein.

In an illustrative embodiment, the design of potential hedgehog inhibitors begins from the general perspective of shape complimentary for the active site and substrate specificity subsites of the enzyme, and a search algorithm is employed which is capable of scanning a database of small molecules of known three-dimensional structure for candidates which fit geometrically into the target protein site. It is not expected that the molecules found in the shape search will necessarily be leads themselves, since no evaluation of chemical interaction necessarily be made during the initial search. Rather, it is anticipated that such candidates might act as the framework for further design, providing molecular skeletons to which appropriate atomic replacements can be made. Of course, the chemical complimentary of these molecules can be evaluated, but it is expected that atom types will be changed to maximize the electrostatic, hydrogen bonding, and hydrophobic interactions with the enzyme. Most algorithms of this type provide a method for finding a wide assortment of chemical structures that are complementary to the shape of a binding site of the subject enzyme. Each of a set of small molecules from a particular data-base, such as the Cambridge Crystallographic Data Bank (CCDB) (Allen et al. (1973) *J. Chem. Doc.* 13: 119), is individually docked to the binding site of the hedgehog proteolytic domain in a number of geometrically permissible orientations with use of a docking algorithm. In a preferred embodiment, a set of computer algorithms called DOCK, can be used to characterize the shape of invaginations and grooves that form the active sites and recognition surfaces of the subject protein (Kuntz et al. (1982) *J. Mol. Biol.* 161: 269-288). The program can also search a database of small molecules for templates whose shapes are complementary to particular binding sites of the enzyme (DesJarlais et al. (1988) *J Med Chem* 31: 722-729). These templates normally require modification to achieve good chemical and electrostatic interactions (DesJarlais et al. (1989) *ACS Symp Ser* 413: 60-69). However, the program has been shown to position accurately known cofactors for inhibitors based on shape constraints alone.

The orientations are evaluated for goodness-of-fit and the best are kept for further examination using molecular mechanics programs, such as AMBER or CHARMM. Such algorithms have previously proven successful in finding a variety of molecules that are complementary in shape to a given binding site of a receptor-enzyme, and have been shown to have several attractive features. First, such algorithms can retrieve a remarkable diversity of molecular architectures. Second, the best structures have, in previous applications to other proteins, demonstrated impressive shape complementarity over an extended surface area. Third, the overall approach appears to be quite robust with respect to small uncertainties in positioning of the candidate atoms.

Goodford (1985, *J Med Chem* 28:849-857) and Boobbyer et al. (1989, *J Med Chem* 32:1083-1094) have produced a computer program (GRID) which seeks to determine regions of high affinity for different chemical groups (termed probes) on the molecular surface of the binding site. GRID hence provides a tool for suggesting modifications to known ligands that might enhance binding. It may be anticipated that some of the sites discerned by GRID as regions of high affinity correspond to "pharmacophoric patterns" determined inferentially from a series of known ligands. As used herein, a pharmacophoric pattern is a geometric arrangement of features of the anticipated ligand that is believed to be important for binding. Attempts have been made to use pharmacophoric patterns as a search screen for novel ligands (Jakes et al. (1987) *J Mol Graph* 5:41-48; Brint et al. (1987) *J Mol Graph* 5:49-56; Jakes et al. (1986) *J Mol Graph* 4:12-20); however, the constraint of steric and "chemical" fit in the putative (and possibly unknown) receptor binding site is ignored. Goodsell and Olson (1990, *Proteins: Struct Funct Genet.* 8:195-202) have used the Metropolis (simulated annealing) algorithm to dock a single known ligand into a target protein. They allow torsional flexibility in the ligand and use GRID interaction energy maps as rapid lookup tables for computing approximate interaction energies. Given the large number of degrees of freedom available to the ligand, the Metropolis algorithm is time-consuming and is unsuited to searching a candidate database of a few thousand small molecules.

Yet a further embodiment of the present invention utilizes a computer algorithm such as CLIX which searches such databases as CCDB for small molecules which can be oriented in the receptor binding site in a way that is both sterically acceptable and has a high likelihood of achieving favorable chemical interactions between the candidate molecule and the surrounding amino acid residues. The method is based on characterizing the receptor site in terms of an ensemble of favorable binding positions for different chemical groups and then searching for orientations of the candidate molecules that cause maximum spatial coincidence of individual candidate chemical groups with members of the ensemble. The current availability of computer power dictates that a computer-based search for novel ligands follows a breadth-first strategy. A breadth-first strategy aims to reduce progressively the size of the potential candidate search space by the application of increasingly stringent criteria, as opposed to a depth-first strategy wherein a maximally detailed analysis of one candidate is performed before proceeding to the next. CLIX conforms to this strategy in that its analysis of binding is rudimentary—it seeks to satisfy the necessary conditions of steric fit and of having individual groups in "correct" places for bonding, without imposing the sufficient condition that favorable bonding interactions actually occur. A ranked "shortlist" of molecules, in their favored orientations, is produced which can then be examined on a molecule-by-molecule basis, using computer graphics and more sophisticated molecular modeling techniques. CLIX is also capable of suggesting changes to the substituent chemical groups of the candidate molecules that might enhance binding.

The algorithmic details of CLIX is described in Lawerence et al. (1992) *Proteins* 12:31-41, and the CLIX algorithm can be summarized as follows. The GRID program is used to determine discrete favorable interaction positions (termed target sites) in the binding site of the protein for a wide variety of representative chemical groups. For each candidate ligand in the CCDB an exhaustive attempt is made to make coincident, in a spatial sense in the binding site of the protein, a pair of the candidate's substituent chemical groups with a pair of corresponding favorable interaction sites proposed by GRID. All possible combinations of pairs of ligand groups with pairs of GRID sites are considered during this procedure. Upon locating such coincidence, the program rotates the candidate ligand about the two pairs of groups and checks for steric hindrance and coincidence of other candidate atomic groups with appropriate target sites. Particular candidate/orientation combinations that are good geometric fits in the binding site and show sufficient coincidence of atomic groups with GRID sites are retained.

Consistent with the breadth-first strategy, this approach involves simplifying assumptions. Rigid protein and small molecule geometry is maintained throughout. As a first approximation rigid geometry is acceptable as the energy minimized coordinates of the hedgehog deduced structure, describe an energy minimum for the molecule, albeit a local one. If the surface residues of the site of interest are not involved in crystal contacts then the crystal configuration of those residues. We believe that the deduced crystal structure described in herein should reasonably mimic the mean solution configuration. Moreover, the equivalent models of hedgehog isoforms (Ihh, Dhh, etc) can be derived by the same method.

A further assumption implicit in CLIX is that the potential ligand, when introduced into the active site of hegehog protein, does not induce change in the protein's stereochemistry or partial charge distribution and so alter the basis on which the GRID interaction energy maps were computed. It must also be stressed that the interaction sites predicted by GRID are used in a positional and type sense only, i.e., when a candidate atomic group is placed at a site predicted as favorable by GRID, no check is made to ensure that the bond geometry, the state of protonation, or the partial charge distribution favors a strong interaction between the protein and that group. Such detailed analysis should form part of more advanced modeling of candidates identified in the CLIX shortlist.

Yet another embodiment of a computer-assisted molecular design method for identifying inhibitors of the subject hedgehog protein comprises the de novo synthesis of potential inhibitors by algorithmic connection of small molecular fragments that will exhibit the desired structural and electrostatic complementarity with the active site of the enzyme. The methodology employs a large template set of small molecules with are iteratively pieced together in a model of the hedgehog active site. Each stage of ligand growth is evaluated according to a molecular mechanics-based energy function, which considers van der Waals and coulombic interactions, internal strain energy of the lengthening ligand, and desolvation of both ligand and enzyme. The search space can be managed by use of a data tree which is kept under control by pruning according to the binding criteria.

In an illustrative embodiment, the search space is limited to consider only amino acids and amino acid analogs as the molecular building blocks. Such a methodology generally employs a large template set of amino acid conformations, though need not be restricted to just the 20 natural amino acids, as it can easily be extended to include other related fragments of interest to the medicinal chemist, e.g. amino acid analogs. The putative ligands that result from this construction method are peptides and peptide-like compounds rather than the small organic molecules that are typically the goal of drug design research. The appeal of the peptide building approach is not that peptides are preferable to organics as potential pharmaceutical agents, but rather that: (1) they can be generated relatively rapidly de novo; (2) their energetics can be studied by well-parameterized force field methods; (3) they are much easier to synthesize than are most organics; and (4) they can be used in a variety of ways, for peptidomimetic inhibitor design, protein-protein binding studies, and even as shape templates in the more commonly used 3D organic database search approach described above.

Such a de novo peptide design method has been incorporated in a software package called GROW (Moon et al. (1991) *Proteins* 11:314-328). In a typical design session, standard interactive graphical modeling methods are employed to define the structural environment in which GROW is to operate. For instance, environment could be the active site cleft of hedgehog, or it could be a set of features on the protein's surface to which the user wishes to bind a peptide-like molecule, a peptide sequence based on the cleavage site of hedgehog itself (e.g., to represent the autoproteolytic event). The GROW program then operates to generate a set of potential ligand molecules. Interactive modeling methods then come into play again, for examination of the resulting molecules, and for selection of one or more of them for further refinement.

To illustrate, GROW operates on an atomic coordinate file generated by the user in the interactive modeling session, such as the coordinates provided in the crystallographic-derived models, plus a small fragment (e.g., an acetyl group) positioned in the active site to provide a starting point for peptide growth. These are referred to as "site" atoms and "seed" atoms, respectively. A second file provided by the user contains a number of control parameters to guide the peptide growth (Moon et al. (1991) *Proteins* 11:314-328).

The operation of the GROW algorithm is conceptually fairly simple. GROW proceeds in an iterative fashion, to systematically attach to the seed fragment each amino acid template in a large preconstructed library of amino acid conformations. When a template has been attached, it is scored for goodness-of-fit to the receptor site, and then the next template in the library is attached to the seed. After all the templates have been tested, only the highest scoring ones are retained for the next level of growth. This procedure is repeated for the second growth level; each library template is attached in turn to each of the bonded seed/amino acid molecules that were retained from the first step, and is then scored. Again, only the best of the bonded seed/dipeptide molecules that result are retained for the third level of growth. The growth of peptides can proceed in the N-to-C direction only, the reverse direction only, or in alternating directions, depending on the initial control specifications supplied by the user. Successive growth levels therefore generate peptides that are lengthened by one residue. The procedure terminates when the user-defined peptide length has been reached, at which point the user can select from the constructed peptides those to be studied further. The resulting data provided by the GROW procedure include not only residue sequences and scores, but also atomic coordinates of the peptides, related directly to the coordinate system of the receptor site atoms.

In yet another embodiment, potential pharmacophoric compounds can be determined using a method based on an energy minimization-quenched molecular dynamics algorithm for determining energetically favorable positions of functional groups in the binding sites of the subject hegehog protein. The method can aid in the design of molecules that incorporate such functional groups by modification of known ligands or de novo construction.

For example, the multiple copy simultaneous search method (MCSS) described by Miranker et al. (1991) *Proteins* 11: 29-34. To determine and characterize a local minima of a functional group in the forcefield of the protein, multiple copies of selected functional groups are first distributed in a binding site of interest on the hedgehog protein. Energy minimization of these copies by molecular mechanics or quenched dynamics yields the distinct local minima. The neighborhood of these minima can then be explored by a grid search or by constrained minimization. In one embodiment, the MCSS method uses the classical time dependent Hartee (TDH) approximation to simultaneously minimize or quench many identical groups in the forcefield of the protein.

Implementation of the MCSS algorithm requires a choice of functional groups and a molecular mechanics model for each of them. Groups must be simple enough to be easily characterized and manipulated (3-6 atoms, few or no dihedral degrees of freedom), yet complex enough to approximate the steric and electrostatic interactions that the functional group would have in binding to the site of interest in the hedgehog protein. A preferred set is, for example, one in which most organic molecules can be described as a collection of such groups (*Patai's Guide to the Chemistry of Functional Groups*, ed. S. Patai (New York: John Wiley, and Sons, (1989)). This includes fragments such as acetonitrile, methanol, acetate, methyl ammonium, dimethyl ether, methane, and acetaldehyde.

Determination of the local energy minima in the binding site requires that many starting positions be sampled. This can be achieved by distributing, for example, 1,000-5,000 groups at random inside a sphere centered on the binding site; only the space not occupied by the protein needs to be considered. If the interaction energy of a particular group at a certain location with the protein is more positive than a given cut-off (e.g. 5.0 kcal/mole) the group is discarded from that site. Given the set of starting positions, all the fragments are minimized simultaneously by use of the TDH approximation (Elber et al. (1990) *J Am Chem Soc* 112: 9161-9175). In this method, the forces on each fragment consist of its internal forces and those due to the protein. The essential element of this method is that the interactions between the fragments are omitted and the forces on the protein are normalized to those due to a single fragment. In this way simultaneous minimization or dynamics of any number of functional groups in the field of a single protein can be performed. Minimization is performed successively on subsets of, e.g. 100, of the randomly placed groups. After a certain number of step intervals, such as 1,000 intervals, the results can be examined to eliminate groups converging to the same minimum. This process is repeated until minimization is complete (e.g. RMS gradient of 0.01 kcal/mole/Å). Thus the resulting energy minimized set of molecules comprises what amounts to a set of disconnected fragments in three dimensions representing potential pharmacophores.

The next step then is to connect the pharmacophoric pieces with spacers assembled from small chemical entities (atoms, chains, or ring moieties). In a preferred embodiment, each of the disconnected can be linked in space to generate a single molecule using such computer programs as, for example, NEWLEAD (Tschinke et al. (1993) *J Med Chem* 36: 3863, 3870). The procedure adopted by NEWLEAD executes the following sequence of commands (1) connect two isolated moieties, (2) retain the intermediate solutions for further processing, (3) repeat the above steps for each of the intermediate solutions until no disconnected units are found, and (4) output the final solutions, each of which is single molecule. Such a program can use for example, three types of spacers: library spacers, single-atom spacers, and fuse-ring spacers. The library spacers are optimized structures of small molecules such as ethylene, benzene and methylamide. The output produced by programs such as NEWLEAD consist of a set of molecules containing the original fragments now connected by spacers. The atoms belonging to the input fragments maintain their original orientations in space. The molecules are chemically plausible because of the simple makeup of the spacers and functional groups, and energetically acceptable because of the rejection of solutions with van-der Waals radii violations.

The three-dimensional structure of hedgehog is useful to aid in screening and development of diagnostic and therapeutic protein fragments as in rational drug design, to search for structural analogs of known protein structures, or to aid in an analysis of biological function and activity. Also, the method may be used to predict protein secondary structures and protein subsecondary structures from amino acid sequences alone, and to predict those regions of a protein molecule that are on the outside and those that are on the inside.

Compounds can also be prepared using the three-dimensional structure provided herein and tested using assays known to those of skill in the art. For example, compounds can be synthesized and screened for hedgehog autoproteolytic activity by cleavage assays (see for example, Porter et al., Cell 86:21, 1996; WO96/17924, herein incorporated by reference).

Compounds of the invention include drugs, small molecules, peptides, peptidomimetics, polypeptides, chemical compounds and biologic agents. For example, peptidomimetics are synthetic compounds having a three-dimensional structure (i.e., a "peptide motif") based upon the three-dimensional structure of a selected peptide. The peptide motif provides the peptidomimetic compound with Hedgehog agonist or antagonist activity that is substantially the same as, or greater than, the Hedgehog agonist or antagonist activity of the peptide from which the peptidomimetic was derived. Peptidomimetic compounds can have additional characteristics that enhance their therapeutic application, e.g., enhanced cell permeability, increased receptor or polypeptide binding affinity and/or avidity, and prolonged biological half-life. The design of peptidomimetic compounds having agonist or antagonist activity can be aided through computer modeling techniques well known in the art. Other methods for the design, as well as the preparation of, peptidomimemtic compounds are well known in the art.

Atomic coordinates and structure factors have been deposited in the Brookhaven Protein Data Bank. Applicant assures complete access and disclosure of these coordinates and factors upon issuance of a patent.

The following examples are intended to illustrate but not limit the invention. While they are typical of those that might be used, other procedures known to those skilled in the art may alternatively be used.

Example 1

Hedgehog Protein Processing

Figure 28A:
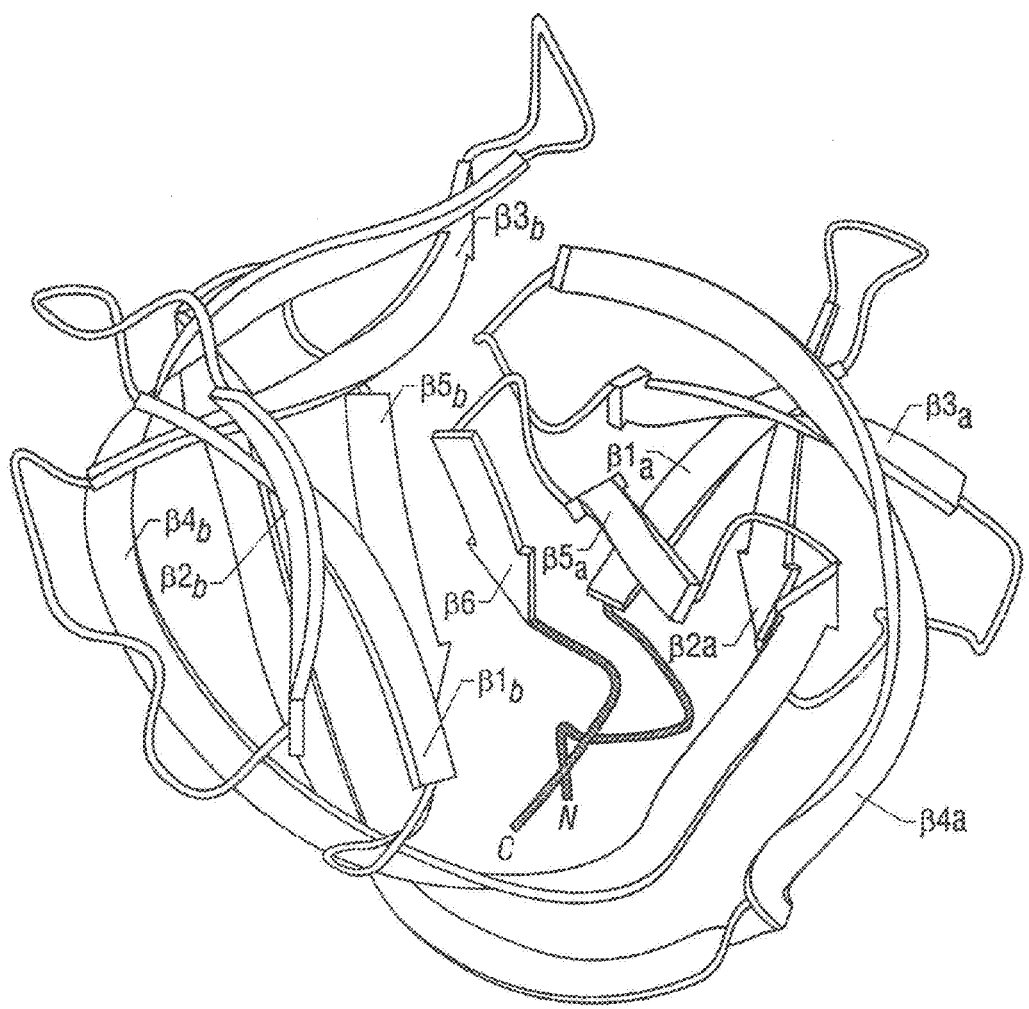
FIG. 28A is a ribbon diagram of $Hh-C_{17}$. The amino-(N) and carboxy-(C) termini are labeled. This figure was prepared with MOLSCRTPT (Kraulis, 1991).
Figures 1, 28B:
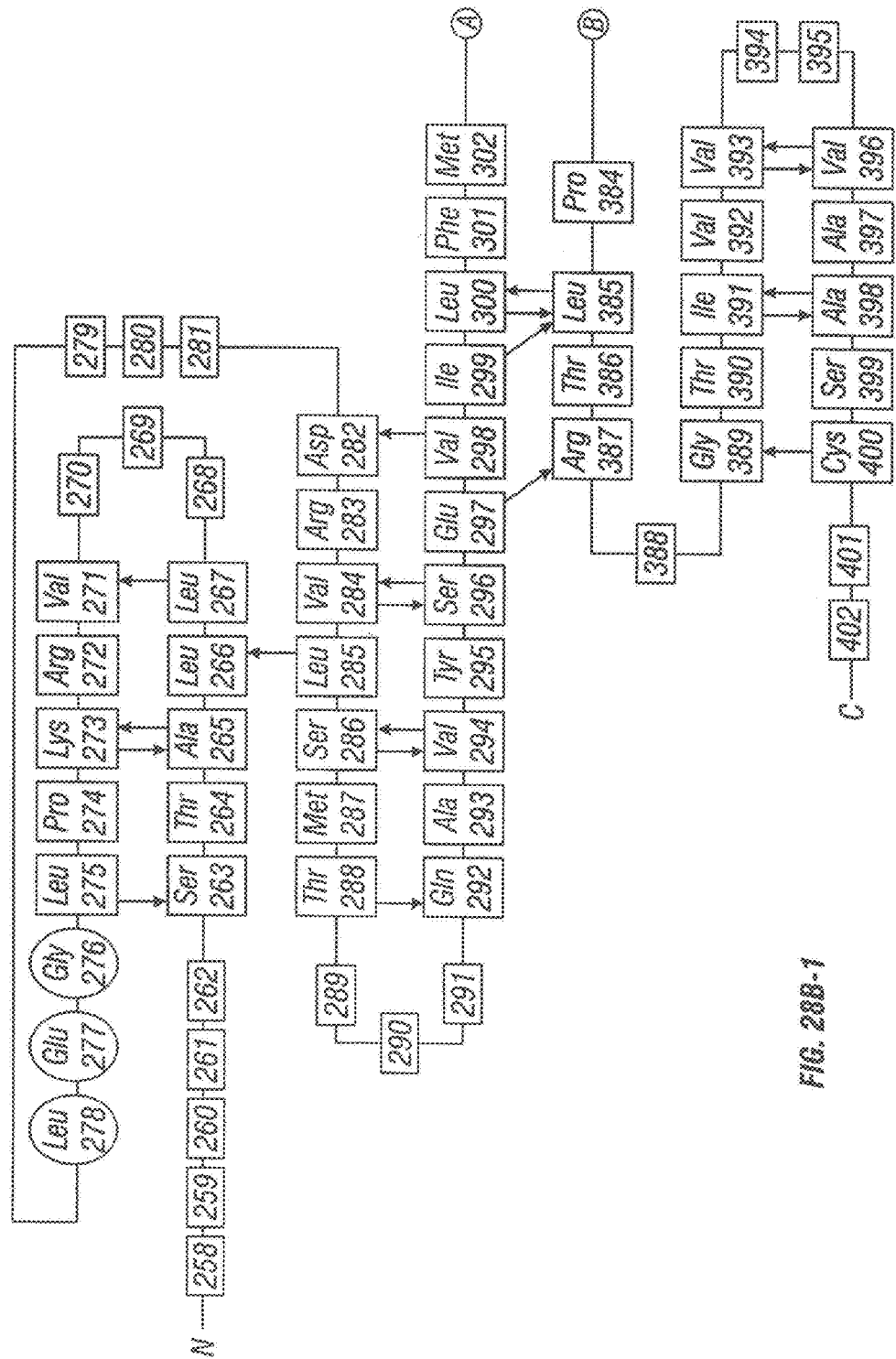
FIGS. 28B-1 through 28B-3 are topology diagrams of $Hh-C_{17}$ (SEQ ID NO:46). Residues in β strands are in boxes with amino-acid type and number indicated. Residues in turns of $3_{10}$ helix are ovals with amino-acid type and number indicated. Other residues in the structure are in boxes with amino-acid number indicated. Hydrogen bonds between β strands are indicated with arrows. A pseudo two-fold axis of symmetry is indicated with a diamond.

The full length form of the hh protein (F) migrates with a mobility corresponding to a relative molecular mass of 46 kD. FIGS. 1 (A) and (C) are immunoblots with antibodies against amino- (Ab1) and carboxy-terminal (Ab2) epitopes. GST fusion proteins containing either residues 83 to 160 or 300 to 391 from HH protein were expressed in *Escherichia coli*, purified as recommended [F. M. Ausubel, et al., *Current Protocols in Molecular Biology* (Greene and Wiley-Interscience, New York, 1991)], and used to immunize rabbits by standard methods. The antibodies were affinity purified on a column of $His_6$-U protein [E. Harlow and D. Lane, *Antibodies: A Laboratory Manual* (Cold Spring Harbor Laboratory, Cold Spring Harbor, N.Y., 1988)] linked to Affi-Gel 10 beads (Bio-Rad). The purification was performed as described (Harlow and Lane, supra) except that the acid and base elutions contained 10 percent dioxane. Biotinylated hh antibodies were prepared by purifying the rabbit antisera over a protein A column, followed by biotinylation with the use of the Immunoprobe biotinylation kit (Sigma). Immunoprecipitations were performed as described [Harlow and Lane] with the use of cold RIPA lysis buffer containing 0.25 mM phenylmethylsulfonyl fluoride (PMSF) and 5 mM EDTA for tissue homogenization. Lysates were precleared twice with pre-immune rabbit serum plus protein A beads (Gibco-BRL). Affinity-purified antibodies or preimmune serum was then added, and the immunoprecipitation was performed with protein A beads, with the use of NP-40 lysis buffer for the washes.

Immunoblots were performed with affinity purified Ab1 or Ab2 by either of two chemiluminescence based protocols. In the first protocol (used in FIGS. 1, 3, and 5) samples were resolved on 15 percent or 12 percent SDS-polyacrylamide gels (F. M. Ausubel et al., supra) and transferred to Magnagraph nylon membranes (MSI) by electroblotting. Blots were developed with the use of an alkaline phosphatase conjugated donkey anti-rabbit IgG secondary antibody and Lumi-Phos 530 (Boehringer Mannheim) under recommended conditions. In the second protocol (used in FIG. 8), samples were transferred to nitrocellulose filters (Schleicher and Schuell), and blots were developed using ECL reagents (Amersham) as recommended. The secondary antibody in this case was horseradish peroxidase conjugated goat anti-rabbit IgG (Jackson Immuno-Research). Lanes contain protein from induced untransfected S2 cells (lanes 1 and 13), transfected S2 cells induced to express hh (lanes 2 and 14), imaginal discs (lanes 3 and 15), wild type embryos (lanes 6 and 18), and in vitro translations of synthetic h mRNA both in the presence (lanes 5 and 17) and absence of microsomes (lanes 4 and 16).

cDNAs encoding various hh protein species were cloned into the pMK33 vector, which allows for inducible expression under metallothionein promoter control (M. R. Koelle et al., *Cell* 67:59, 1991). Stable S2 cell lines were made by transfection of the hh/pMK33 plasmids with constant selection for hygromycin resistance. Proteins were expressed by plating a log phase culture of cells diluted to $0.1 A_{595}$ units, waiting 48 hours, inducing with $CuSO_4$ at 0.2 mM final concentration, and harvesting the cells and/or supernatant 24 hours later. Cell samples for immunoblotting were made by adding 10 volumes of 1×SDS PAGE loading buffer to pelleted cells.

In vitro translations were performed with the use of the TNT coupled transcription-translation system (Promega). $^{35}S$ methionine (DuPont NEN) was used for detection by autoradiography. In the heparin binding experiment in vitro translation lysate with microsomes that produce wild-type hh protein was added to heparin agarose (Sigma) or Sepharose CL-4B (Pharmacia) beads pre-equilibrated with heparin binding buffer (HBB; 20 mM Tris (7.4), 150 mM NaCl, 0.1 percent Triton X-100). Samples were incubated at 4° C. for four hours with gentle rocking. After pelleting the beads, supernatants in some samples were analyzed (lanes 2 and 4). The beads were then washed 5 times with chilled HBB and samples (lanes 3 and 5) were subsequently eluted at 80° C. for 10 minutes in SDS PAGE loading buffer (F. M. Ausubel et al., supra).

Embryos from the wild-type Canton-S line and from the matings, hshh/hshh or hshh H329A-/hshh H329A X y; Sco/ CyO, enlacZ11::wg (Kassis, et al., *Proc. Natl. Acad. Sci. U.S.A.* 89: 1919, 1992), were collected 0 to 16 hours after egg laying (AEL) at 25° C. They were heat shocked for 30 minutes at 37° C. and allowed to recover for 1 hour at 25° C. Embryos in FIG. 1 (Canton-S) were collected 4 to 8 hours AEL at 25° C. In preparation for immuno-blotting, all embryos were dechorionated in 2.6 percent sodium hypochlorite and homogenized in 10 volumes of 1×SDS PAGE loading buffer.

Multiple species were detected and minor cross reactive bands are seen in most samples including extracts of induced untransfected S2 cells (lanes 1 and 13). One of these bands (occurring in both panels) co-migrates with U (at 39 kD) and is particularly abundant in lane 6 of FIG. 1 (A).

FIGS. 1 (B) and (D) are blots of samples immunoprecipitated with Ab1 (B, lanes 7-9), Ab2 (D, lanes 19-21), or preimmune serum (B, lanes 10-12 and D, lanes 22-24). Detection was with biotinylated derivatives of Ab1 (B) and Ab2 (D). Samples used were: induced untransfected S2 cells, lanes 7, 10, 19 and 22; transfected S2 cells induced to express hh, lanes 8, 11, 20 and 23; and embryos, lanes 9, 12, 21 and 24. For either antibody, hh protein fragments were specifically immunoprecipitated from hh expressing cells and embryos, but not from untransfected cells. (E) In the schematic diagram, cleavage sites are denoted by arrows. The cleavage site marked by the asterisk is inferred by identification of only one cleavage product and may therefore occur at another location within the C fragment. The first two columns to the right of the diagram indicate the reactivity of Ab1 and Ab2 to each hh fragment. The other columns indicate the presence (+) or absence (−) of each hh fragment in the various samples. Parentheses around F and $N_{ss}$ indicate that these species are detected in in vitro translation reactions but not in vivo.

The 46 kD species was detected from in vitro translation extracts by Ab1 and Ab2 (FIG. 1, lanes 4 and 16), and was partially converted to a species of 39 kD (U) when translation occurred in the presence of microsomes (FIG. 1, lanes 5 and 17). A 39 kD species co-migrating with U is also present in extracts from all in vivo sources, but none of these extracts contain detectable levels of F. U represents the signal-cleaved form of F; signal cleavage thus appears to be relatively inefficient in vitro, as reported previously, (J. J. Lee, et al., *Cell*, 71:33, 1992), but is highly efficient in vivo. To confirm that signal cleavage indeed is occurring at this unusual internal location, a mutation that changes residue $S_{84}$ to N at the predicted signal cleavage site was introduced. This mutation prevented conversion by microsomes of F to U and also produced a species that comigrated with F upon transfection into cultured S2 cells. The effects of independently mutating the two methionine codons present upstream of the signal sequence were also examined. In vitro translation of the sequence in which the first methionine is removed produces a protein species intermediate in mobility between F and U, and this species is converted to a species that comigrates with U in the presence of microsomes or when produced in vivo. Alteration of the second methionine codon caused no change in the electrophoretic mobility of Hh protein produced in vivo or in vitro.

Smaller species of Hh proteins from in vivo sources have been reported previously (T. Tabata and T. B. Kornberg, *Cell* 76: 89, 1994). The latter study examined not endogenous proteins, but proteins induced to express at high levels from exogenously introduced constructs. The antibody used did not distinguish epitopes from distinct portions of the molecule.

In addition to signal cleavage, a further cleavage of the U precursor is responsible for generating other forms of hh protein observed in vivo. This was deduced from the observation that Ab1 and Ab2 both detected the U (uncleaved) species, but also interacted individually with smaller protein species expressed endogenously in embryos and imaginal discs or with species expressed upon introduction of the hh gene into S2 cells. Ab1 thus interacts with a 19 kD species from all of these tissues (FIG. 1, lanes 2, 3, 6, 8, 9), while Ab2 interacts with a 25 kD species and a 16 kD species (FIG. 1, lanes 14, 15, 18, 20, 21). The 19 kD species hereafter is referred to as N(N-terminal fragment), the 25 kD species as C(C-terminal fragment) and the 16 kD species as C*; these species represent the major forms of endogenous hh protein present in vivo.

The proposed cleavages by which these species arise are shown schematically in the bottom portion of FIG. 1. The N and C species are uniquely detected by Ab1 and Ab2, respectively, and the sum of the relative masses of the two smaller species is roughly equivalent to the relative mass of U. The electrophoretic mobilities of the F and U species are somewhat at variance with their predicted relative masses (52.1 kD and 43.3 kD, respectively). The identities of these species were confirmed by in vitro translation of a variety of hedgehog open reading frames modified to contain different extents of sequence at the $NH_2$- or COOH-terminus, and by insertion of epitope tags. The migration anomalies appear to be associated with protein species in which sequences from both the $NH_2$- and COOH-terminal fragments are simultaneously present. The mobilities of the $NH_2$- and COOH-terminal fragments, in contrast, correspond to relative masses (19 kD and 25 kD, respectively) that sum to yield 44 kD, roughly equivalent to the expected relative mass of U.

A simple mechanism that could account for the derivation of the two smaller species therefore would be a single internal cleavage of the U precursor. Processing of the hh protein when translated in vitro also yields a 25 kD species (C; lanes 16 and 17) and either a 29 kD or 19 kD (N) species (lanes 4 and 5). The 19 kD species comigrates with N, and its formation depends upon the presence of microsomes, consistent with the proposal that N derives from F by signal cleavage and a further internal cleavage. The overall pathway for formation of the predominant forms of hh protein observed in vivo thus appears to involve signal cleavage of F to generate U. U is then cleaved internally to form N and C, which are the predominant forms found in vivo. Further processing of the kD C species might then generate the 16 kD C* species, but whether this processing is a single cleavage event or not is not clear since Ab2 does not recognize the smaller 9 kD fragment that would result. The processing of C to generate C* appears to occur with greater efficiency in imaginal discs as compared to embryos (compare lanes 15 and 18); this may be caused by the more extended mass isolation procedure of imaginal discs (O. M. Eugene, et al., *Tissue Culture Assn. Man.*, 5: 1055, 1979).

Example 2

Auto-Proteolysis of the Hedgehog Protein

Figures 2, 28B:
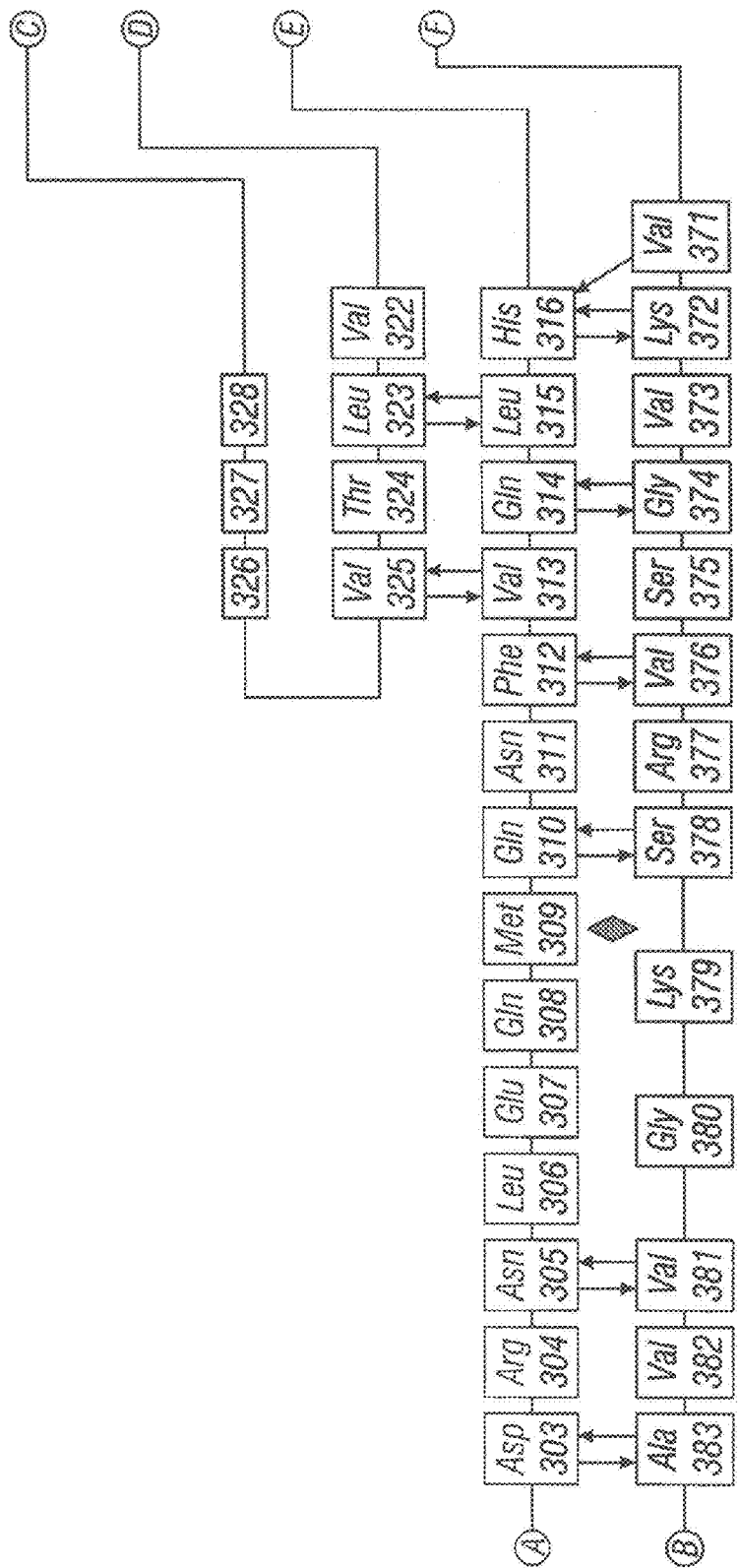

The comigration of endogenous and in vitro-generated hh protein species suggested that in vitro processing is similar to that observed in vivo. FIG. 2 shows limited sequence similarity between hh proteins and serine proteinases. hh protein sequences are aligned to residues 323 to 329 of the *D. melanogaster* protein and numbered as positions 1 to 7 (group A). Conserved hh residues are in bold letters. The catalytic histidines (A. J. Barrett, in *Proteinase inhibitors* A. J. Barrett, G. Salvesen, Eds. (Elsevier, Amsterdam, 1986) pp. 3-22) of mammalian serine proteinases (group B) are aligned to the invariant histidine at position 7 in Hh proteins. Abbreviations are as follows: C-Shh, chicken Sonic hh (R. D. Riddle, et al., *Cell* 75: 1401, 1993); M-Shh, mouse Sonic hh (Y. Echelard et al., *Cell* 75: 1417, 1993) (identical to Hhg-1; R vhh-1, rat vhh-1 (H. Roelink et al., *Cell* 76: 761, 1994); Z-Shh, zebrafish Sonic hh (S. Krauss, et al., *Cell* 75: 1431, 1993) (identical to shh) and zebrafish vhh-1, (H. Roelink et al., supra); twhh, no other abbreviation; M-Dhh, mouse Desert hh (Y. Echelard et al., *Cell* 75: 1417, 1993); M-Ihh, mouse Indian hh (Y. Echelard et al., supra); CHT, bovine chymotrypsin; TRP, bovine trypsin; ELA, porcine elastase; UKH, human urokinase; CIR, human complement factor 1R; CIS, human complement factor IS; MCP, rat mast cell protease; FAX, human blood clotting factor X; TPA, human tissue plasminogen activator.

FIG. 2 shows that a seven residue region of hh coding sequence (residues 323 to 329 in the *Drosophila* protein) displays some similarity to the sequences of serine proteases. This region lies approximately two thirds of the distance from the signal cleavage site to the carboxy-terminus, and includes Thr and His, residues (positions 4 and 7 in FIG. 2) that are invariant among all hh sequences from all species. In the serine proteases, this conserved sequence contains an invariant His that acts as a general base in catalysis (A. J. Barrett, in *Proteinase inhibitors* Å. J. Barrett, G. Salvesen, Eds. Elsevier, Amsterdam, 1986, pp. 3-22).

Figures 3, 28D:
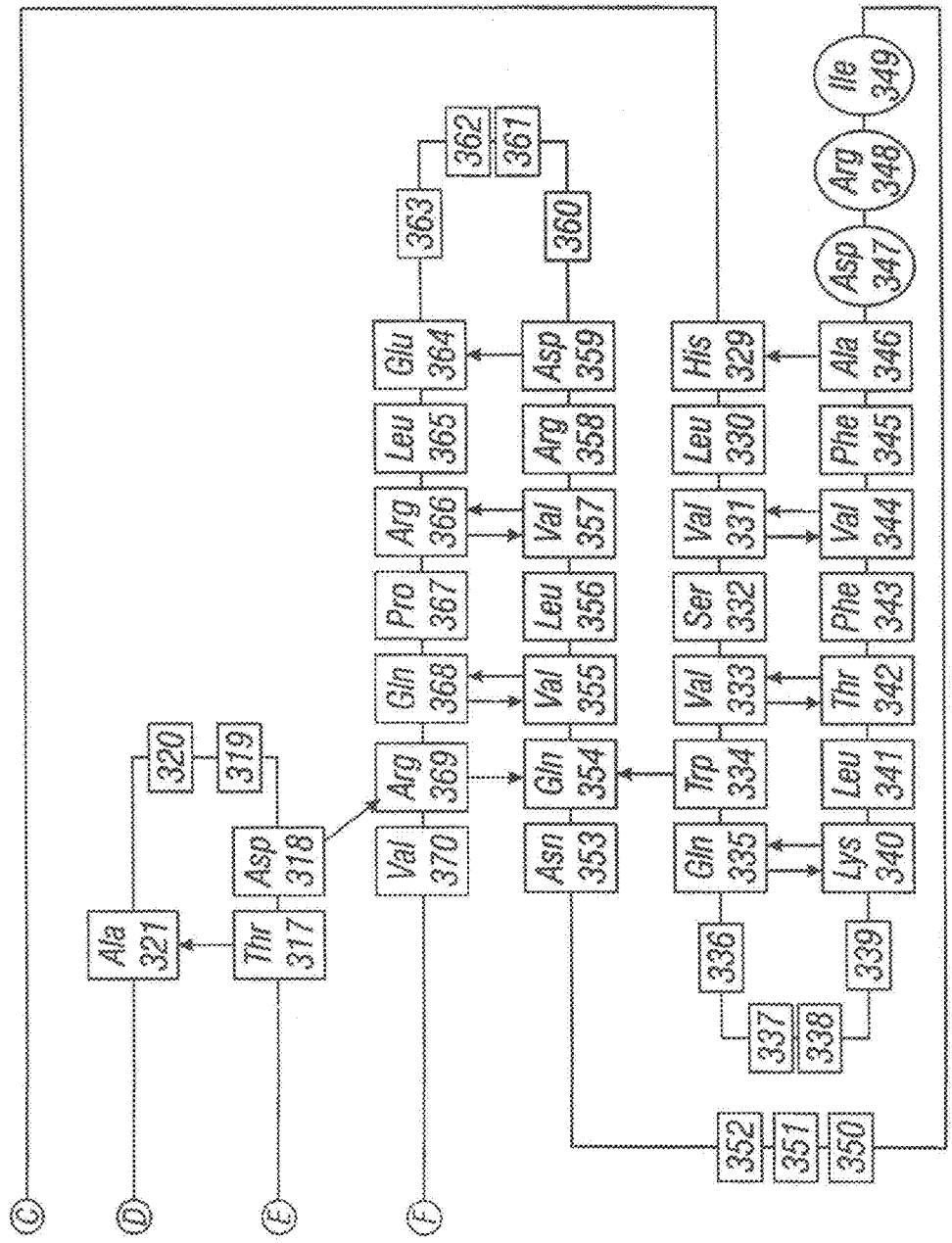
Figures 29D, 30A:
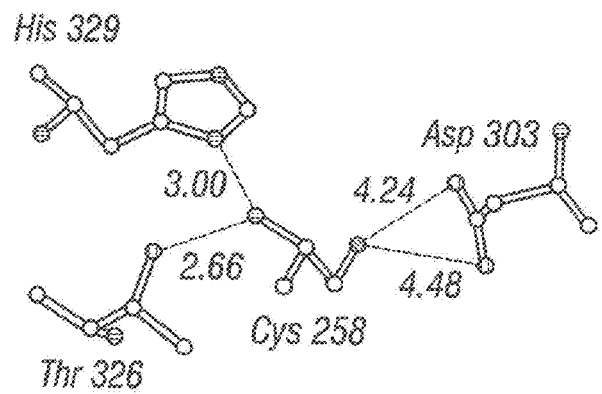
FIG. 29D is a structure-based alignment of the amino-acid sequences (SEQ ID Nos:38-45) of the two subdomains of Hh-$C_{17}$. Conserved amino acids are boxed. Active site residues are in bold. β strands are indicated with arrows. β1b and β2b are slightly longer than β1a and β2a, respectively, and are indicated with unshaded segments of the arrows. Fractional solvent accessibility (FSA) is shown above and below the rows of amino acid sequences for each residue in the Hh-$C_{17}$ structure. The FSA is the ratio of the solvent accessible surface area of residue X in a Gly-X-Gly tripeptide vs. in the Hh-$C_{17}$ structure. A value of 0 represents a value from 0.00 to 0.09, 1 represents 0.10 to 0.19, and so on. Type I β turns are conserved at homologous positions in both Hh-$C_{17}$ subdomains at residues 260-263 (homologous to residues 326-329) and residues 317-320 (homologous to residues 386-389). A type II β turn is conserved between both subdomains at residues 279-282 (homologous to residues 350-353), and a type IV β turn is conserved between both subdomains at residues 288-291 (homologous to residues 359-362). β bulges are found at homologous positions in both Hh-$C_{17}$ subdomains at residues 282 (homologous to residue 353) and 300 (homologous to 372).
FIG. 30A is a stereodiagram of the nucleophilic residue, Cys-258, and nearby residues. Distances (Å) between atoms are indicated.
Figure 30B:
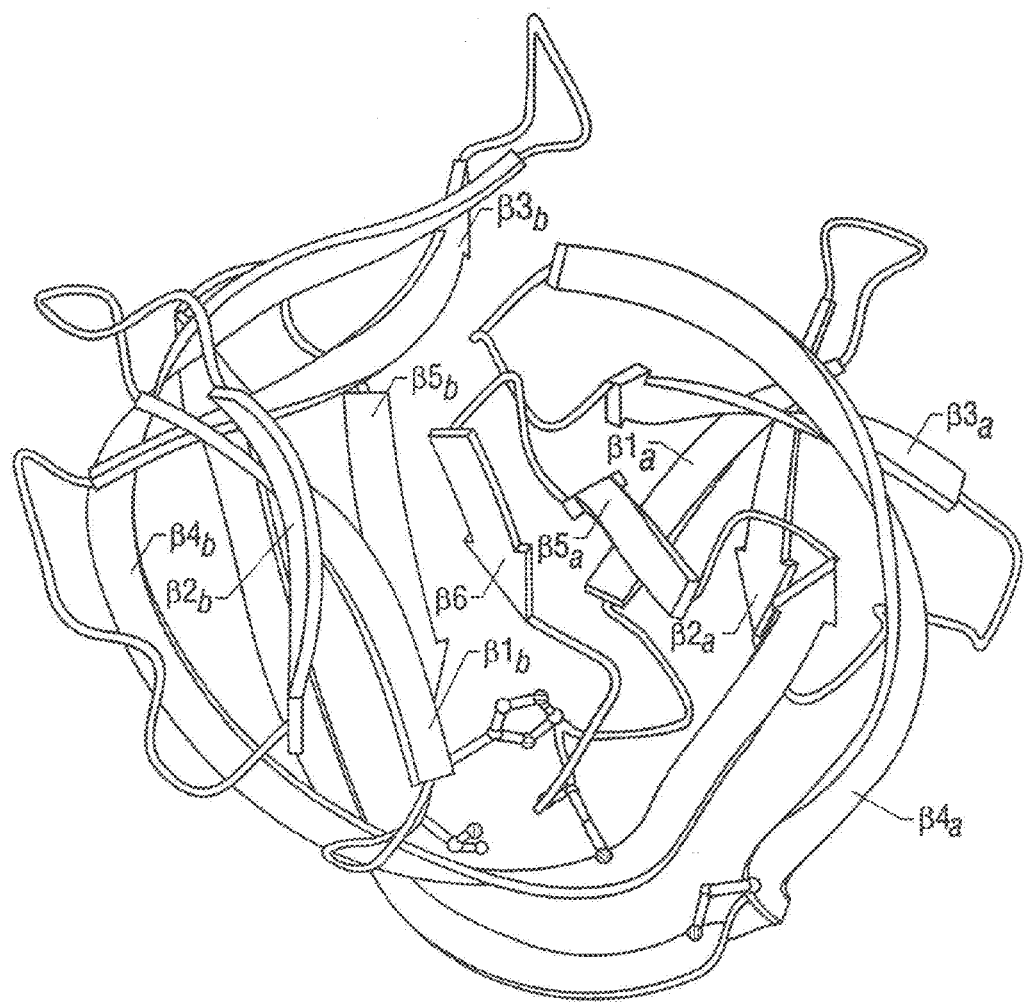
FIG. 30B is a ribbon diagram of Hh-$C_{17}$ with the side chains of Cys-258 and other putative active site residues indicated.
Figure 30C:
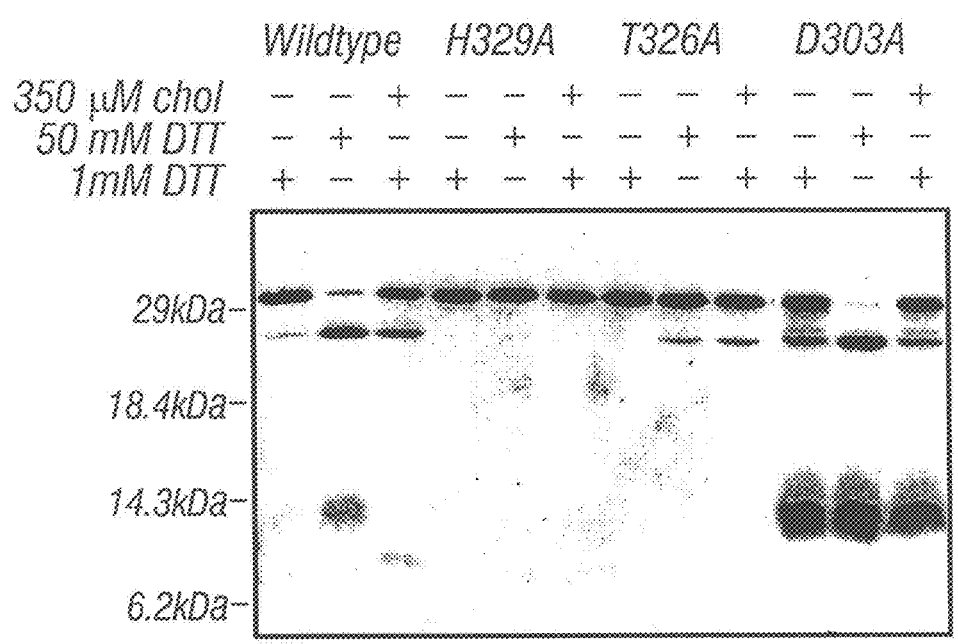
FIG. 30C shows a Coomassie Brilliant Blue-stained SDS-polyacrylamide gel showing in vitro autocleavage reactions of bacterially-expressed $His_6HhC$ wildtype (lanes 1-3) and mutant proteins, H329A (lanes 4-6), T326A (lanes 7-9), and D303A (lanes 10-12). Proteins were incubated with 1 mM DTT (lanes 1, 4, 7, and 10), 50 mM DTT (lanes 2, 5, 8, and 11) or 350 µM cholesterol/1 mM DTT (lanes 3, 6, 9, and 12). The uncleaved protein migrates as a ~29-kDa species. The carboxy-terminal cleavage product migrates as a ~25-kDa species and the amino-terminal product migrates as a ~7-kDa species when DTT-modified or as a ~5-kDa species when cholesterol-modified. The significant level of apparent cleavage seen with the D303A protein with 1 mM DTT results from preexisting cleavage products in the preparation; however, addition of 50 mM DTT greatly increases the amount of cleavage products and addition of cholesterol does not produce a cholesterol-modified product (~5-kDa species). D303A was also incubated with 46 µM [$^3$H]cholesterol/1 mM DTT, and no cholesterol-modified product was detected by autoradiography (data not shown). A cholesterol-transfer activity 1% of wildtype could have been detected by this radioassay.
Figures 2, 31A:
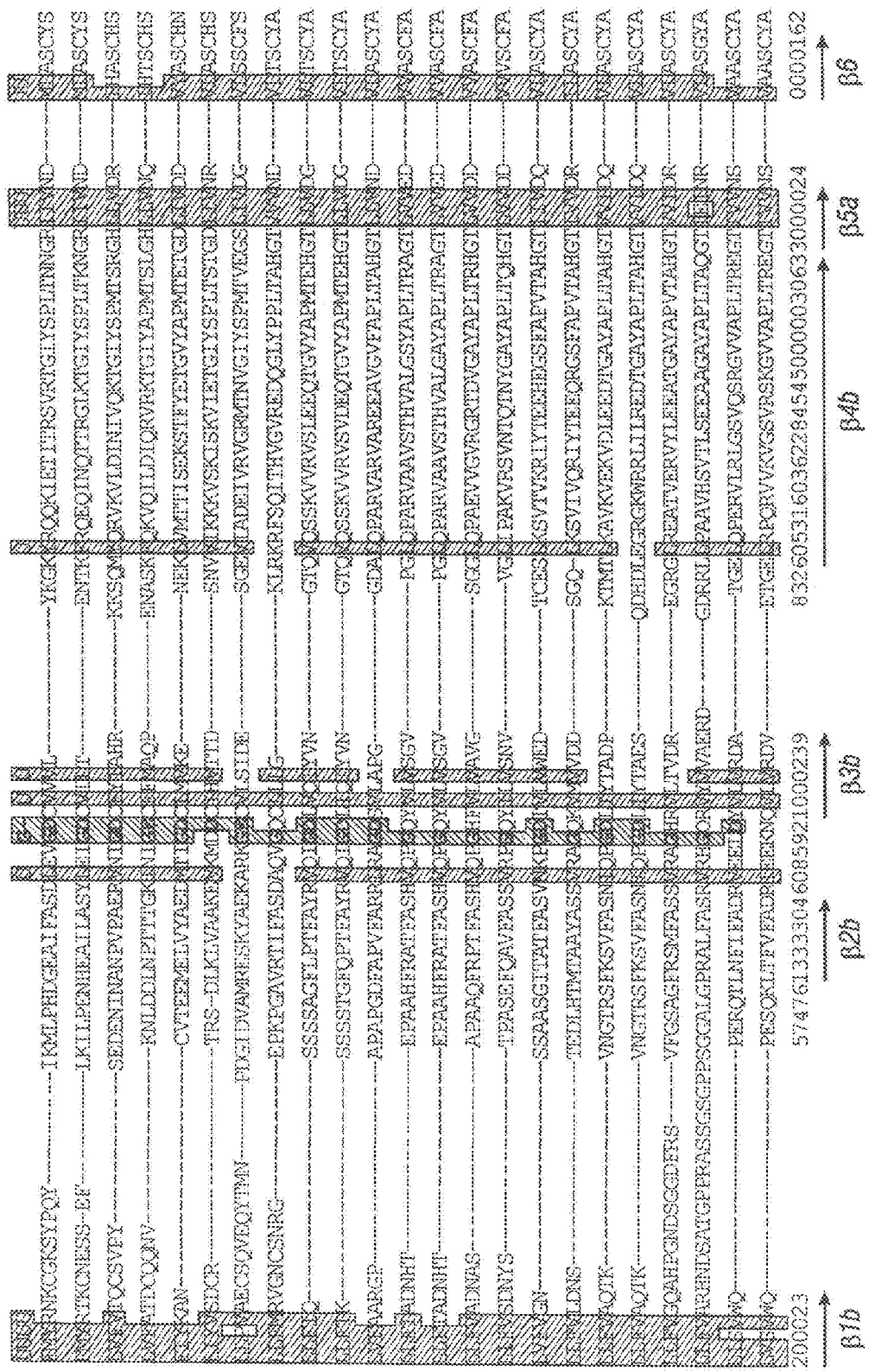
Figure 31B:
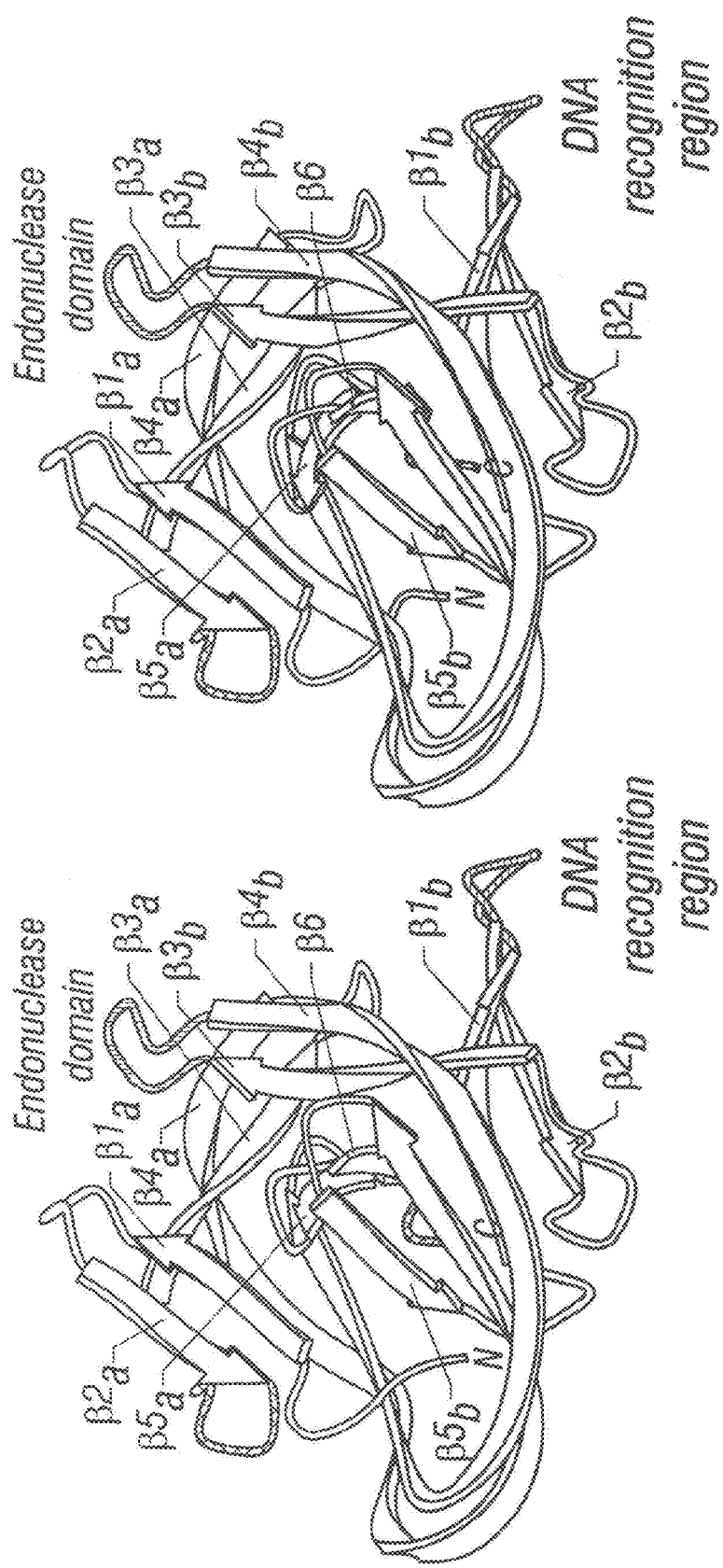
FIG. 31B is a stereo ribbon diagram of Hh-$C_{17}$, showing where the endonuclease domain and additional DNA recognition region of PI-SceI are inserted. The loop where the endonuclease domain is inserted is between β3b and β4b and the loop where the additional DNA recognition region ("the arm of the self-splicing domain" is inserted is between β1b and β2b. The orientation of the Hh-$C_{17}$ in this view is the same as the orientation of the PI-SceI intein in FIG. 2 of Duan, et al., 1997, supra. This panel was prepared with MOLSCRIPT.
Figure 32:
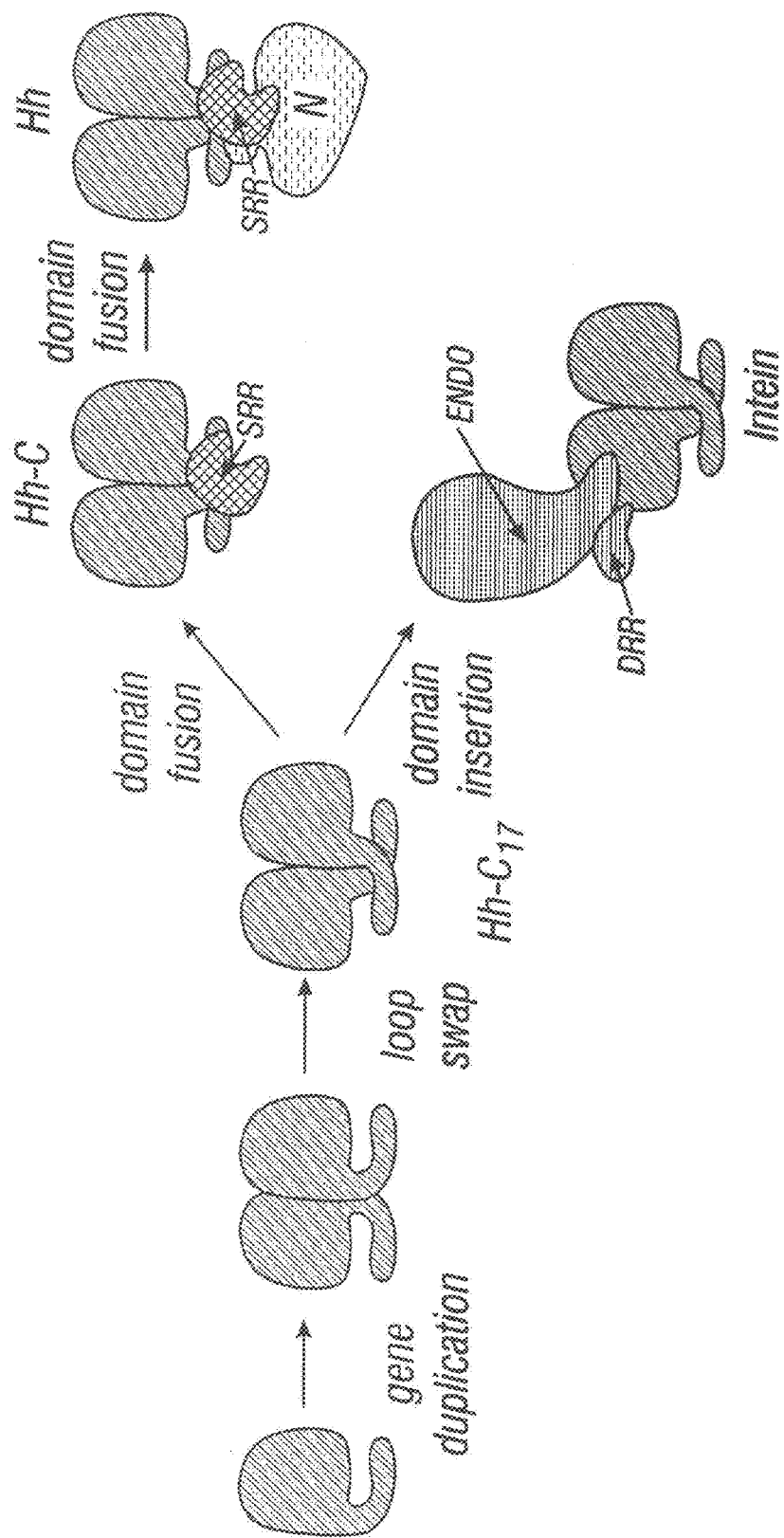
FIG. 32 is a schematic drawing illustrating the duplication and insertion events that appear to have occurred during the evolution of Hh proteins and interns. The insertion of the intein into a host protein is not shown. The order of some of these events is speculative. For example, dimerization through loop swapping may have preceded the gene duplication that produced an Hh-$C_{17}$-like protein. Abbreviations: Hh-C—Hh carboxy-endonuclease domain, DRR—DNA recognition region.

To determine whether this invariant His residue in the hh protein indeed plays a role in auto-proteolysis, two proteins from *E. coli* were purified: one carried the wild type sequence and the other a substitution of an Ala codon for the His codon at position 329 (H329A). Both of these proteins were engineered to contain a hexa-histidine tag at the amino terminus fused to *Drosophila* sequences extending from a residue just before the signal cleavage site to the carboxy-terminus (residues 83 to 471; the wild type form of this protein is referred to as $His_6$-U). Both proteins were extensively purified under denaturing conditions using a $Ni^{++}$-chelating matrix. FIG. 3(A) is a coomasie blue stained polyacrylamide gel that shows the production and purification of $His_6$-U and $His_6$-$UH_{329A}$ proteins from *E. coli*. Samples were molecular weight markers (lanes 1 and 2); lysates of *E. coli* cells carrying the $His_6$-U expression construct without (lane 3) and with (lane 4) induction by IPTG; purified $His_6$-U protein (lane 5); lysates of *E. coli* cells that carry the $His_6$-$UH_{329A}$ expression construct without (lane 6) and with (lane 7) induction by IPTG; purified $His_6$-$UH_{329A}$ protein (lane 8). Purified proteins were essentially homogeneous except for several minor species of lower relative mass; these species are endogenous breakdown products of the full-length proteins since they were absent in uninduced extracts and were detectable with hh antibodies. FIG. 3 (B) is an immunoblot detected with Ab2 showing transfected S2 cells induced to express hh (lane 1); $His_6$-U and $His_6$-$UH_{329A}$ proteins incubated in cleavage reaction buffer for 0 hours (lanes 2 and 5), for 20 hours (lanes 3 and 6), and for 20 hours in the presence of 20 mM TAME (a serine protease inhibitor) (lanes 4 and 7). Upon incubation the $His_6$-U, but not the $His_6$-$UH_{329A}$ protein, released a fragment presumed to be C on the basis of reactivity with Ab2 and co-migration with C produced in S2 cells. Release of C (lane 3) was only partially inhibited by TAME.

Preliminary proteinase inhibitor studies have been performed on in vitro translated Hh protein by adding various inhibitors at the start of the translation reaction. These studies have been complicated by the fact that numerous protease inhibitors lower or block translation efficiency. In some cases the effectiveness of an inhibitor was assayed by determining if addition of an inhibitor to a completed translation reaction will inhibit the self-processing that normally continues to occur. At this time we can only state the following with certainty: (i) the serine protease inhibitor TAME (p-toluene-sulfonyl-L-arginine methyl ester) inhibits auto-proteolysis of in-vitro translated Hh protein; (ii) soybean trypsin inhibitor, a, anti-trypsin, aprotitin, leupeptin, and E-64 do not block auto-proteolysis of translated Hh protein; and (iii) TAME partially inhibits auto-proteolysis of purified $His_6$-U protein (FIG. 3, panel B).

Figure 3B:
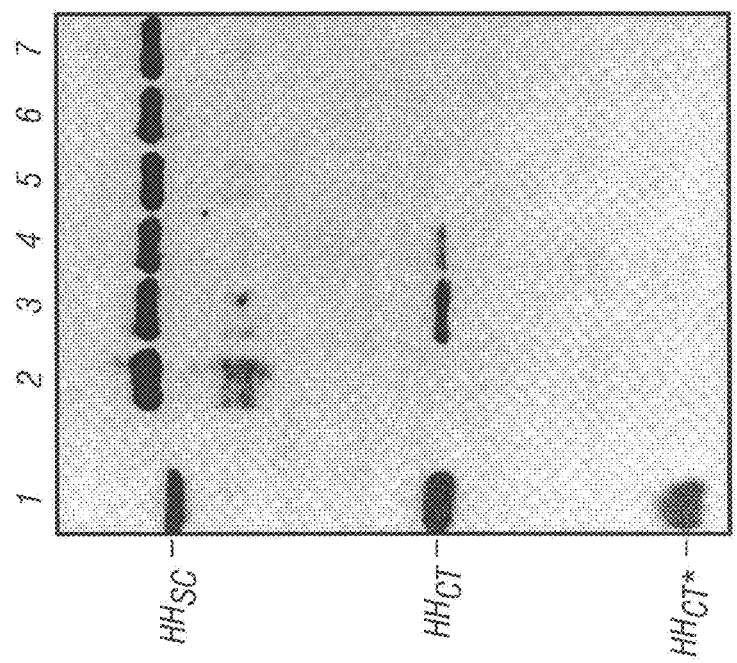
FIGS. 3A and 3B show autoproteolysis of the hh protein.
Figure 3A:
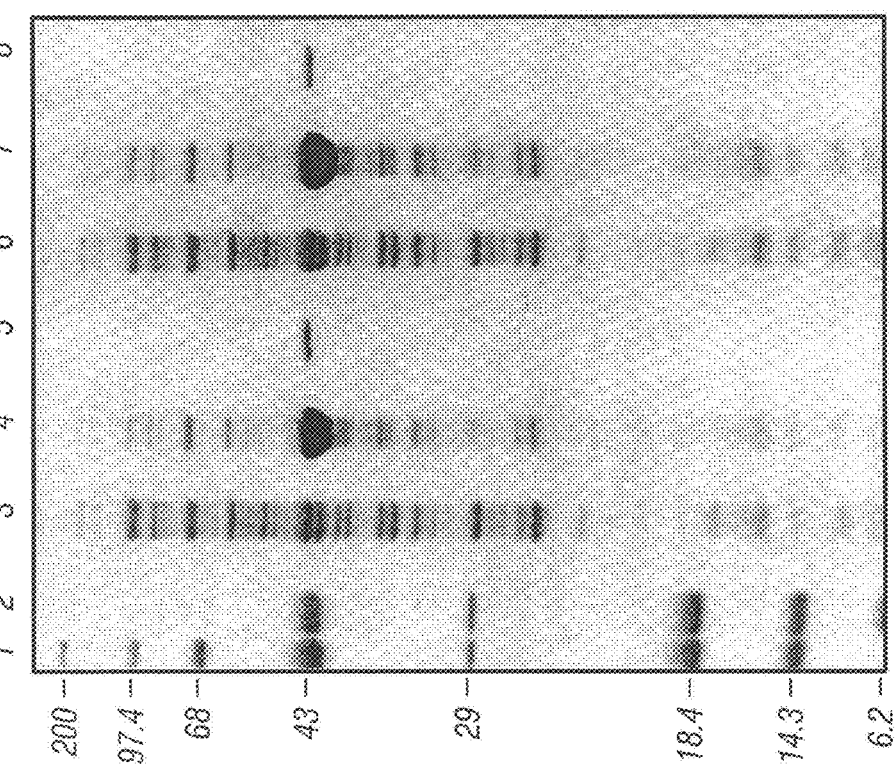

As seen in FIG. 3B, upon dilution of denaturant the wild type protein but not the H329A mutant protein released a 25 kD species detectable by Ab2 and identical in mobility with the C species produced from in vitro translations and various in vivo sources. This cleavage was also observed when the wild type protein was purified and renatured by other protocols and cleaved under distinct conditions. Plasmids encoding the $His_6$-U and His6-$UH_{329A}$ proteins were generated by inserting sequences corresponding to residues 83 to 471 from the wild-type or hh H329A ORF into the pRSETB expression vector (Invitrogen). Proteins were induced in BL21(DE3)-/pLysS *E. coli* cells as described (F. M. Ausubel et al., supra). The basic purification was performed on Ni-NTA agarose beads (Qiagen) by a denaturing protocol with the use of 6 M guanidinium HCl and 8 M urea essentially as recommended (a detailed protocol of exact conditions used is available upon request). Washes contained 0.2 percent Tween 20 and 5 mM b-mercaptoethanol. The final wash buffer was: 6 M urea, 100 mM Tris, 500 mM NaCl, 20 percent glycerol, (pH 7.4). Elutions were with the final wash buffer containing 250 mM imidazole. In vitro cleavage reactions were performed by incubating the purified protein (diluted 1:30 in the final mix) in cleavage buffer [50 mM Tris, 500 mM NaCl, 5 percent glycerol, 0.2% Triton X-100, 50 mM DTT, (pH 7.4)]. To isolate soluble full-length $His_6$-U protein free from denaturants or detergents, additional steps were taken (this refers to the other renaturation protocols mentioned in the text). Full-length protein from the eluate described above was further purified from breakdown products by precipitation, by urea removal through dialysis. The precipitate was then re-solubilized in a buffer containing guanidinium HCl and loaded onto another Ni-NTA agarose column. After washing as described, the protein was re-folded (while attached to the beads) by gradual dilution of urea (from 6M to 0.5M) with dilution buffer [(100 mM Tris, 500 mM NaCl, 20 percent glycerol, (pH 7.4)] over an 8 hour period at 4° C. The protein was eluted with dilution buffer containing 250 mM imidazole and 0.5M urea. The eluate was dialyzed in 100 mM Tris, 150 mM NaCl, 10 percent glycerol, (pH 7.4) at 4° C. and stored at −70° C.

Example 3

Mapping the Auto-Proteolytic Functions of hh

Figure 4E:
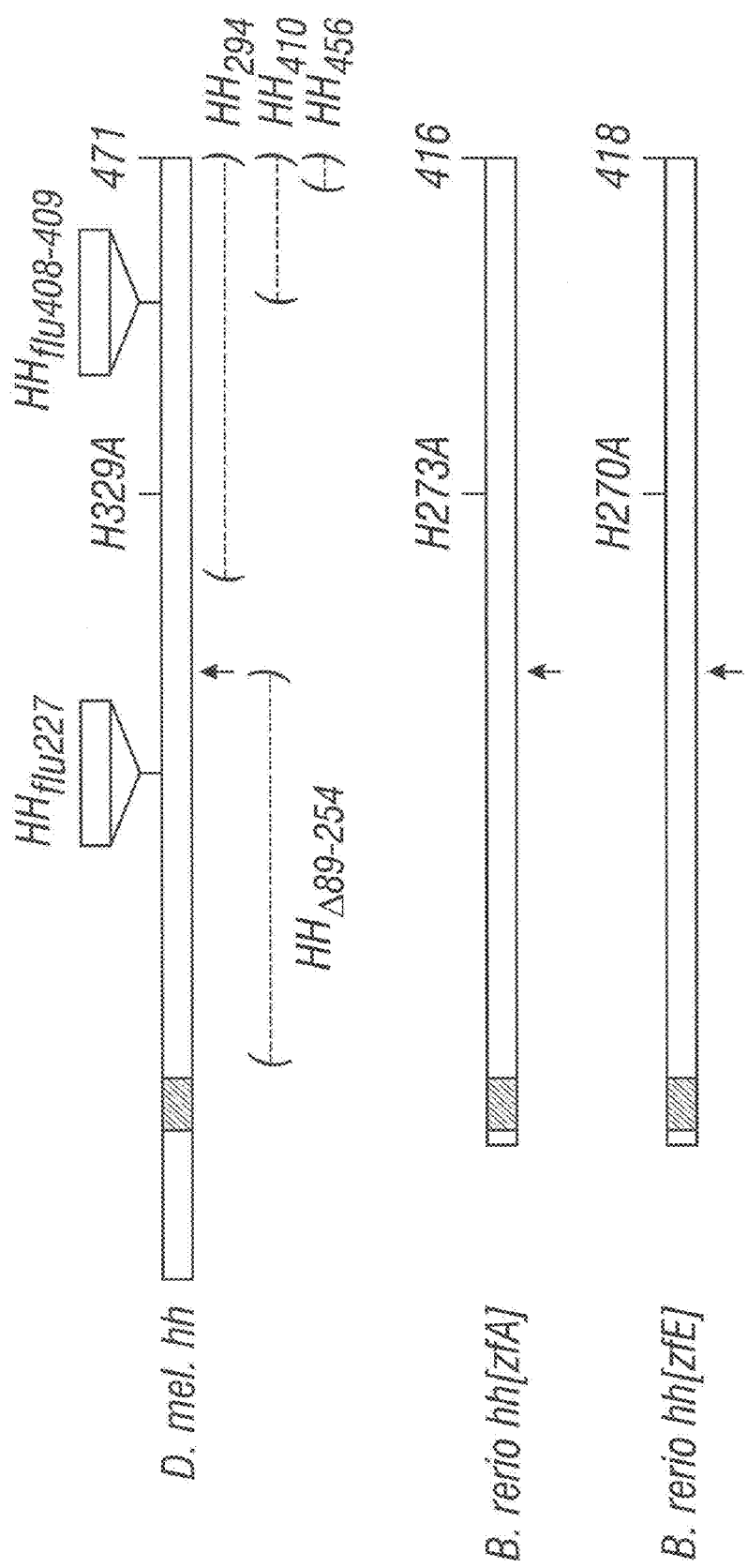

To more precisely define the domain of the hh protein responsible for this auto-proteolytic event, the effects of several distinct types of mutations upon in vitro processing were examined. The most informative mutation was a deletion that removes residues 89 to 254 (Δ89-254), which together constitute most of the amino acids within the portion of the molecule presumed to form the N fragment. In vitro translations of wild-type and mutant Hh proteins from *Drosophila* (FIGS. 4 A-C) and zebrafish (FIG. 4D) are shown. The locations of mutations and cleavage sites (arrows) in these proteins are schematically illustrated (FIG. 4E). In the *Drosophila* protein (FIGS. 4A, B, and C), auto-proteolysis is blocked or severely inhibited by several mutations in the COOH-terminus (H329A, 294 trunc, 410 trunc, flu408 and 456 trunc), but is unaffected by a large deletion (Δ89-254) or insertion of a flu-tag epitope trimer (flu227) in the $NH_2$-terminus. Auto-proteolysis thus depends primarily on residues within the C fragment (sequences to the right of the cleavage site in the diagram below; see FIG. 1). Furthermore, the H329A/flu227 double mutant is not cleaved by wild-type protein in a mixing experiment (lane 11), suggesting an intramolecular mechanism for auto-proteolysis. Hh proteins encoded by the zebrafish genes twhh and shh display a pattern of processing (D) similar to that of the *Drosophila* protein although the $NH_2$-terminal fragment of each zebrafish protein (23 kD for twhh and 22 kD for shh) has a lower apparent mass than the COOH-terminal fragment (25 kD for twhh and shh). This is the result of a shorter stretch of residues that precedes the signal sequences as compared to the *Drosophila* protein.

Processing is blocked by H273A and H270A mutations in twhh and shh proteins respectively (analogous to the H329A mutation in the *Drosophila* protein), which suggests an auto-proteolytic processing mechanism is used similar to that observed for the *Drosophila* protein.

In vitro translations were performed with the use of the TNT coupled transcription-translation system (Promega). $^{35}$S methionine (DuPont NEN) was used for detection by autoradiography. In the heparin binding experiment (FIG. 8C), in vitro translation lysate with microsomes that produce wild-type Hh protein was added to heparin agarose (Sigma) or Sepharose CL-4B (Pharmacia) beads pre-equilibrated with heparin binding buffer (HBB; 20 mM Tris (7.4), 150 mM NaCl, 0.1 percent Triton X-100). Samples were incubated at 4° C. for four hours with gentle rocking. After pelleting the beads, supernatants in some samples were analyzed (lanes 2 and 4). The beads were then washed 5 times with chilled HBB and samples (lanes 3 and 5) were subsequently eluted at 80° C. for 10 minutes in SDS PAGE loading buffer (F. M. Ausubel et al., supra).

All mutations in the hh gene were generated in the plasmid pFl (J. J. Lee, et al., supra). Mutations in the zebrafish twhh and shh genes were generated with the original cDNA clones as described (Ekker, et al., *Current Biology*, 5(8): 944, 1995). All point mutations were generated with the use of recombinant circle PCR (D. H. Jones and S. C. Winistorfer, *Biotechniques* 12: 528, 1992). The flu408 and flu227 mutations were generated by inserting a trimer of the influenza hemagglutinin antigen (42 residues for flu408 and 43 residues for flu227) into the AlwN 1 and Bgl I sites present in the hh ORF (nucleotide positions 1604 and 1058 respectively) (J. J. Lee, et al., supra). The Δ89-254 mutation was generated by removing sequences between the EcoN I site (644) and the Pml I site (1145). The 294 trunc mutation was generated by removing sequences between the Acc I site (1265) and the Xcm I site (1792). The 410 trunc mutation was previously generated and identified as $Hh_{410}$ (J. J. Lee, et al., supra). To map the mutation in the hh$^{13E}$ allele (base change $C_{1756}$ to A; coding change $Tyr_{457}$ to STOP), DNA isolated from hh$^{13E}$/TM3 was used to seed PCR reactions generating regions of the hh ORF and flanking sequences, which were subcloned into Bluescript KSM (Stratagene). Six clones each, derived from two different PCR amplifications were sequenced.

As seen in lanes 1 and 2 of FIG. 4A, this construct generates a full length species of a mobility corresponding to the expected relative mass of 33 kD, and two cleaved products whose apparent relative masses (25 and 9 kD) sum to give the relative mass of the larger species. The smaller of the cleaved products will occasionally migrate as two bands as seen in FIG. 4A. We have chosen the lower of the two bands between the 14.3-kD and 6.2-kD markers for our molecular weight measurement. The larger of the two cleaved products comigrates with the C species produced from the wild type protein, suggesting that the Δ89-254 hh protein contains the residues normally present in C and all of the determinants required for auto-proteolysis, including the normal cleavage site; most of the residues within N are dispensable for auto-proteolytic activity.

In contrast, lesions affecting residues presumed to lie within C block auto-proteolysis in vitro. All mutations tested by in vitro translation were also examined in S2 cells by immunoblotting. In all cases the patterns of cleavage in S2 cells were identical to those observed in translations except that C* was always present whenever C was formed. The former fragment was not observed in translations. These include the H329A mutation described above, a mutation that inserts an influenza virus epitope between residues 408 and 409 (flu408), and three mutations that cause premature termination of the protein at the carboxy terminus. The two most severe truncations, 294 trunc and 410 trunc, are mutations generated in vitro. They cause a loss of 177 and 61 residues, respectively, from the carboxyl-terminus of the protein, and neither undergoes proteolysis. The 456 trunc hh protein is like that encoded by the EMS-induced hh$^{13E}$ mutant allele, which results in the loss of 15 residues from the carboxy-terminus of the protein. This protein undergoes auto-proteolysis, as demonstrated by the appearance of a 24 kD band in place of C, but the efficiency of the reaction is much impaired in vitro (FIG. 4B). Auto-proteolysis of the hh protein relies mainly upon residues within C; deletion or alteration of residues within this domain is associated with reduced efficiency of processing, and one such deletion appears to be the cause of the hh$^{13E}$ mutation.

The sequence homology and auto-proteolytic function of the full length hh protein suggested the possibility that F or the C fragment is a sequence-specific protease. As a first step in clarifying the mechanism of auto-proteolysis, an influenza virus epitope tag was introduced into the N-terminus of a hh open reading frame that also carried a H329A mutation. FIG. 4C shows that the insertion of the epitope tag alone does not interfere with auto-proteolysis (lane 9), and yields a normal C fragment and an N fragment of increased relative mass (compare to wild type in lane 12). The protein carrying both mutations does not undergo proteolysis (lane 10), and since the epitope-tagged N fragment migrates differently from N, this double mutant provides an ideal substrate to look for intermolecular cleavage upon mixture with a wild type sequence. Lane 11 shows that in such a mixture, although normal N is formed, no tagged N can be detected. Thus, in this experiment, no appreciable intermolecular cleavage occurs. We also failed to detect intermolecular cleavage in the following two experiments: (i) co-transfection of wild type and 410 trunc sequences into S2 cells (the cleaved 410 trunc protein would yield a smaller and therefore identifiable form of C); (ii) mixing of excess unlabelled, purified His$_6$-U protein with labelled, in vitro translated H329A mutant protein. Thus, although an intermolecular mechanism for regulation of auto-proteolysis or for cleavage of other proteins can not be ruled out, the current evidence suggests that cleavage of the hh protein occurs predominantly by an intramolecular mechanism.

The hh gene has been broadly conserved in evolution, with single homologues unidentified in a wide variety of invertebrate species and multiple distinct homologues in each of several vertebrate species (Y. Echelard et al., *Cell* 75: 1417, 1993; S. Krauss, et al., *Cell* 75: 1431, 1993; H. Roelink et al., *Cell*, supra). As seen in FIG. 2, all of these coding sequences contain an invariant histidine and other conserved residues at a position corresponding to H329 in the *Drosophila* protein. In addition, the protein encoded by at least one of the mouse genes appears to be processed in vivo to yield two smaller species in a manner resembling the in vivo processing of the *Drosophila* protein. To determine whether auto-proteolysis may also play a role in vertebrates we examined the behavior of proteins encoded by two distinct hh homologues from the zebrafish, twhh and shh. FIG. 4D demonstrates that when these sequences are translated in vitro, smaller species are generated whose relative masses sum to yield approximately the relative mass of the full length protein (lanes 1 and 3). As seen in lanes 2 and 4, this cleavage reaction is blocked by substitution of Ala codons for the His codons at positions corresponding to H329 in *Drosophila* (see FIG. 2). Vertebrate hh proteins thus appear to be processed by a similar mechanism as the *Drosophila* protein.

Example 4

Role of Auto-Proteolysis in Embryos

Numerous functions for the hh gene have been described in Drosophila. At the morphological level these include a role in patterning of larval cuticular structures and adult structures such as the eye and appendages (C. Nüsslein-Volhard and E. Wieschaus, Nature 287: 795, 1980; and J. Mohler, Genetics 120: 1061, 1988).; the mechanistic basis for the morphological effects involves signaling for maintenance or induction of gene expression in embryos and imaginal discs (J. J. Lee, supra; T. Tabata and T. B. Kornberg, Cell 76: 89, 1994; and K. Basler and G. Struhl, Nature 368: 208, 1994). To ascertain the importance of auto-proteolysis for these functions, the H329A mutant gene under control of the hsp 70 promoter was introduced by P element-mediated transformation into the Drosophila germline. The hshh H329A construct was made identically to the hshh construct with the use of a hh ORF fragment containing the H329A mutation. Transgenic flies were generated from a $y^1$ $w^{1118}$ parental strain using standard methods of P element mediated transformation (A. C. Spradling and G. M. Rubin, Science 218: 341 1982). A line, HA3, carrying the hshh H329A P element on the second chromosome was maintained as a homozygous stock. To assay for expansion of wg stripes, embryos collected at 4 to 6 hours after egg laying (AEL) at 25° C. were subjected to the following heat shock protocols prior to fixation. Embryos receiving single shocks (10 or 30 minutes at 37° C.) were allowed to recover for 1 hour at 25° C. Embryos receiving double shocks (two 10 minute or two 30 minute shocks at 37° C.) were allowed to recover 90 minutes after the first shock and 40 minutes after the second (Both recoveries were at 25° C. The double 30 minute protocol was as previously described, (S. Krauss, supra). In situ hybridizations were performed as described (D. Tautz, Chromosoma 98: 81, 1989) using a wg specific probe (D. T. Chang et al., supra). Embryos assayed for cuticle phenotype were heat shocked 6 to 8 hours AEL for 30 minutes at 37° C., allowed to develop at 25° C. for 36 hours and then processed and mounted as described (M. Ashburner, Drosophila: A Laboratory Manual, Cold Spring Harbor Laboratory Press, New York, 1989). Immunolocalizations (single or double stains) were performed as described. With the use of affinity purified Ab1 or Ab2 for the primary antibody and alkaline phosphatase (AP) or horseradish peroxidase (HRP) conjugated anti rabbit or mouse IgG (Jackson Immuno-research) for the secondary. Embryos from a $hh^{13E}$/TM3 ftz-lacZ (the balancer chromosome was from the Bloomington Stock Center, strain 3218) stock homozygous for the $hh^{13E}$ allele were identified by the lack of staining with an anti b-galactosidase antibody (Promega) in a double stain with Ab2 (FIG. 9, panel D). Staining in FIG. 9, panels B and C were performed formaldehyde fixed Canton-S embryos with the use of an AP conjugated anti-rabbit IgG secondary. Although standard formaldehyde fixation was generally used, heat and acid—formaldehyde fixation also gave similar results. GST fusion proteins containing either residues 83 to 160 or 300 to 391 from the Hh protein were expressed in E. coli, purified as recommended (F. M. Ausubel et al., supra), and used to immunize rabbits by standard methods. The antibodies were affinity purified on a column of $His_6$-U protein (Harlow and Lane, supra) linked to Affi-Gel 10 beads (Bio-Rad). The purification was performed as described (Harlow and Lane, supra) except that the acid and base elutions contained 10 percent dioxane. Biotinylated hh antibodies were prepared by purifying the rabbit antisera over a protein A column, followed by biotinylation with the use of the Immunoprobe biotinylation kit (Sigma). Immunoprecipitations were performed as described (Harlow and Lane, supra) with the use of cold RIPA lysis buffer containing 0.25 mM PMSF and 5 mM EDTA for tissue homogenization. Lysates were precleared twice with pre-immune rabbit serum plus protein A beads (Gibco BRL). Affinity purified antibodies or pre-immune serum was then added, and the immunoprecipitation was performed with protein A beads, with the use of NP-40 lysis buffer for the washes.

FIGS. 5 (A) and (B) are immunoblots developed with the use of Ab1 and Ab2 antibodies respectively. Lanes 1 and 6, induced untransfected S2 cells; lanes 2 and 7, transfected S2 cells induced to express hh; lanes 3 and 8, heat shocked wild-type embryos; lanes 4 and 9, heat shocked hshh embryos; lanes 5 and 10, heat shocked hshh H329A embryos. In heat shocked hshh embryos, the wild-type Hh protein is both induced and properly processed to generate the U, N, C and C* species seen in other expression contexts. In contrast, the H329A is induced but not appreciably processed in hshh H329A embryos (the low levels of processed species in lanes 5 and 10 are probably from endogenous hh expression since they are seen at identical levels in heat shocked wild-type embryos in lanes 3 and 8).

FIG. 5 shows that heat shock induction results in the formation of an abundant species that corresponds to U based on its mobility and its interaction with Ab1 and Ab2 (lanes 5 and 10). In contrast, induction of wild type hh protein using a similar construct resulted in similar levels of the N and C processed products (lanes 4 and 9), with very little uncleaved U. Thus, as observed in vitro and in S2 cells, the H329A mutation in embryos appears to greatly reduce the efficiency of auto-proteolytic cleavage of the hh protein.

In FIG. 6, the embryonic distribution of wingless (wg) RNA as revealed by in situ hybridization is shown in FIG. 6 (A) wild-type (homozygous $y^1$ $w^{1118}$), (B) hshh, and (C) hshh H329A embryos that were exposed to two 10 minute heat shocks separated by a 90-minute recovery period. Wild-type embryos showed little change in wg expression, whereas the wild-type protein and, to a lesser extent, the H329A protein each induced ectopic wg expression (Table 1). Panels (D), (E), and (F) show the dorsal surfaces of $y^1$ $w^{1118}$, and hshh H329A larvae, respectively, at the level of the fourth abdominal segment. These larvae were shocked for 30 minutes as embryos and allowed to complete embryogenesis. Cuticle cell types (1°, 2°, 3°, and 4°) are labeled as described (J. Heemskerk and S. DiNardo, Cell 76: 449, 1994). Note the expansion of 2° cell types (naked cuticle) at the expense of 3° and some 4° types in the hshh embryo (E) under conditions where the phenotype of hshh H329A embryos (F) is identical to that of control embryos (D).

Perhaps the earliest known requirement for Hh protein is in maintenance of an adjacent stripe of wingless (wg) gene expression in each embryonic segment (A. Martinez Arias, et al., Development 103: 157, 1988; and S. DiNardo, et al., Nature 322: 604, 1988). This requirement is deduced from the loss of wg expression when hh function is absent; in addition, the ubiquitous expression of wild-type Hh protein induces expansion of the domain of wg gene expression (P. W. Ingham, Nature 366: 560, 1993). The effects of the H329A mutation upon wg expansion were examined by heat shocking embryos carrying the H329A mutant construct in parallel with embryos containing the wild-type construct. Although the H329A mutant protein is able to induce some expansion of the wg domain, the efficiency of this activity is impaired relative to that of the wild-type protein (FIGS. 6, B and C; Table 1). The difference in efficiency ranges nearly as high as threefold depending upon the heat shock regime, and these results suggest that auto-proteolysis of the Hh protein is important for optimal activity in embryonic signaling to induce wg expression.

TABLE 1

Wild-type and mutant hh activity in embryonic induction of wg expression*

| | minutes of heat shock | | | |
|---|---|---|---|---|
| | 10 | 30 | 10/10 | 30/30 |
| hshh | 1.0 ± 0.3 (93) | 1.5 ± 0.6 (120) | 2.9 ± 0.3 (41) | 2.8 ± 0.4 (54) |
| hshh H329A | 0.7 ± 0.5 (190) | 0.9 ± 0.4 (111) | 1.1 ± 0.4 (145) | 1.9 ± 0.5 (93) |

*Expansion of wg expression beyond wild-type controls is given as average number of cell diameters ± standard deviation with number of embryos scored in parentheses.

The effects of Hh protein on the patterning of cuticular structures are most clearly visible on the dorsal surface of the larva, where four distinctive cell types can be identified in each para-segment. These cell types have been designated 1°, 2°, 3°, and 4°, from anterior to posterior, with hh transcription occurring in precursors of the 10 cells (J. Heemskerk and S. DiNardo, supra). Differentiation of the first three cell types was shown to be dependent upon hh gene function, and it has been proposed that the fates of these cells are determined by the concentration of Hh protein, with highest concentrations producing the 1° fate, intermediate concentrations producing the 2° fate, and the lowest concentrations producing the 3° fate (J. Heemskerk and S. DiNardo, supra). This proposal was supported by observations that the most anterior cell types display the greatest sensitivity to a reduction of hh expression, and that all of the 3° and some of the 4° bristles are replaced by naked cuticle characteristic of the more anterior 2° cell type when hh is expressed ubiquitously at high levels. We have reproduced suppression 3° and some 4° fates by heat shock induction of embryos that carry our wild-type construct (FIG. 6E), but find that the H329A mutant is unable to alter cell fates in the dorsal cuticle of the larva (FIG. 6F). Auto-proteolysis, or perhaps some other function blocked by the H329A mutation, thus appears to be essential for the patterning influence of Hh protein upon the dorsal cuticle.

Example 5

Effects of the H329A Mutation Upon Signaling in Imaginal Discs

Studies of H329A mutant protein were extended to the function to the patterning of adult structures and signaling within imaginal discs. In the eye imaginal disc hh function is required for appropriate development of pattern (J. Mohler, *Genetics* 120: 1061, 1988; J. J. Lee, supra; and J. Mohler and K. Vani, supra) and more recently has been shown to control progression of a wave of differentiation via induction of decapentaplegic (dpp) gene expression in the morphogenetic furrow of the eye (U. Heberlein, et al., *Cell* 75: 913, 1993; and C. Ma, et al., *Cell* 75: 927, 1993). In leg and wing discs, ectopic expression of hh has also been shown to yield pattern duplications and defects and is associated with induction of ectopic expression of other signaling molecules normally expressed in a zone along the anterior/posterior compartment boundary (T. Tabata and T. B. Kornberg, *Cell* 76: 89, 1994; and K. Basler and G. Struhl, *Nature* 368: 208, 1994).

For studies of signaling in imaginal discs, a thermal cycler was utilized to subject larvae carrying heat shock-inducible hh constructs to successive rounds of heat shock and recovery. The effects of temperature cycling upon expression of dpp and wg in imaginal discs was examined by monitoring β-galactosidase expression from a reporter gene carrying dpp promoter sequences or from an enhancer detector P element inserted in the wg gene. In FIG. 7, X-gal staining was used to follow expression of wg FIG. 7 (A-C) or dpp FIG. 7 (D-L) in imaginal discs of late third-instar larvae that carry wg-lacZ or dpp-lacZ reporter genes. Leg (A-F), wing (G-I) and eye-antennal discs (J-L) from control larvae (A, D, G, J), larvae carrying the hshh transgene (B, E, H, K) and larvae carrying the hshh H329A transgene (C, F, I, L) are displayed. In all panels anterior is to the left. Arrows highlight the following features: an ectopic patch of dpp expression in the anterior compartment of wing discs in hshh H329A larvae (1); and an ectopic band of dpp expression in eye portion of the eye-antennal disc anterior to the morphogenetic furrow (marked by the other band of dpp expression more posteriorly) in hshh larvae (K). Expansion into the anterior compartment of wg expression in leg discs, and dpp expression in leg and wing discs in hshh larvae is similar to that described for the ectopic expression of hh. Morphological changes in the anterior compartment of leg (B and E) and wing discs (H) were also as described (K. Basler and G. Struhl, supra). In contrast, discs from hshh H329A and control larvae showed very little change in wg and dpp expression, even under prolonged heat shock conditions and morphological changes were never observed. (M-O) The eye phenotypes of adult control (M), hshh (N) and hshh H329A (O) flies that were shocked during larval development in a manner similar to that of the imaginal disc experiments above. Duplicated eye structures were observed in hshh flies, but never in hshh H329A flies. The arrow in (N) points to a thin strip of cuticle between the two eye structures. Other deformities were also seen in hshh flies (for example, compare the thorax in N to M).

Virgin female flies from the homozygous lines hshh (D. T. Chang et al., *Development*, 1994, in press), hshh H329A, and $y^1 w^{1118}$ were crossed to males from the homozygous BS3.0 line (bearing a P element dpp reporter construct on the 2nd chromosome, referred to as dpp-lacZ) (R. K. Blackman, et al., *Development* 111: 657, 1991) or the line y; Sco/CyO, enlacZ11::wg (bearing a wg reporter P element enhancer trap on a second chromosome balancer; called wg-lacZ) (J. A. Kassis, et al., *Proc. Natl. Acad. Sci. USA*. 89: 1919, 1992). Progeny were grown at 25° C. in aerated 0.5-ml microcentrifuge tubes containing yeast paste until the late second instar or early third instar stage of larval development. The larvae were then cycled continuously at 37° C. for 30 minutes followed by 25° C. for 90 minutes in a Perkin-Elmer thermal cycler until they reached the late third instar stage. They were subsequently dissected and stained with X-gal as described (M. Ashburner, supra) or allowed to grow to adulthood for phenotypic analysis.

Figure 7A:
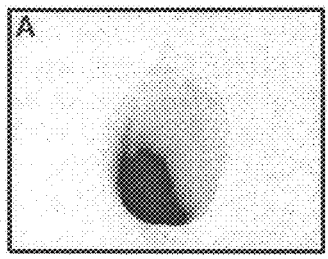
FIGS. 7A through 7O show X-gal staining to show imaginal disc effects of ubiquitous wild type and H329 hh proteins. X-gal staining was used to follow expression of wg (FIGS. 7A, 7B and 7C) or dpp (FIGS. 7D through FIG. 7O) in imaginal discs of late third-instar larvae that carry wg-lacZ or dpp-lacZ reporter genes. Leg (FIGS. 7A through 7F), wing (FIGS. 7G, 7H and 7I) and eye-antennal discs (FIGS. 7J, 7K and 7L) from control larvae (FIGS. 7A, 7D, 7G and 7J), larvae carrying the hshh transgene (FIGS. 7B, 7E, 7H and 7K) and larvae carrying the hshh H329A transgene (FIGS. 7C, 7F, 7I and 7L) are displayed. In all panels anterior is to the left.
Figure 7B:
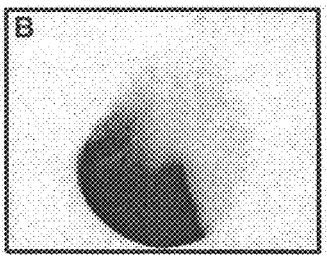
Figure 7C:
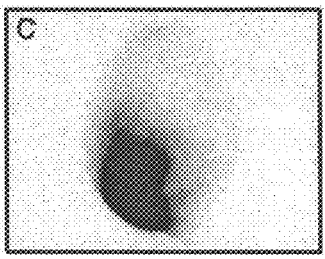
Figure 7D:
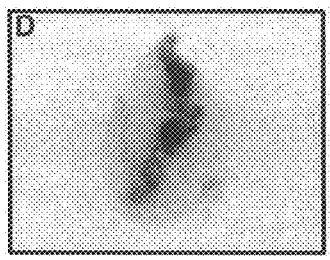
Figure 7E:
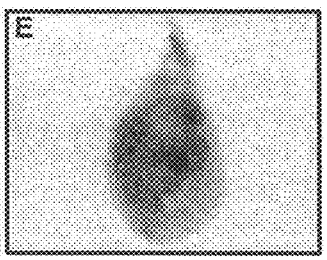
Figure 7F:
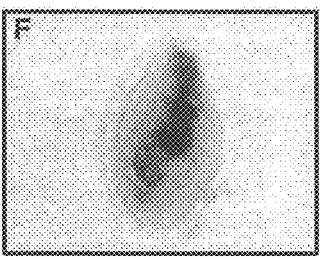
Figure 7G:
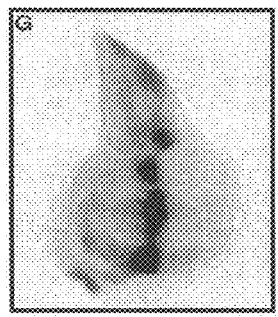
Figure 7H:
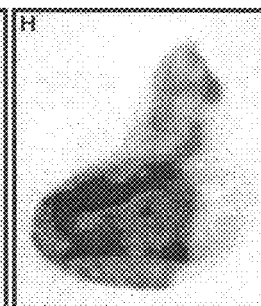
Figure 7I:
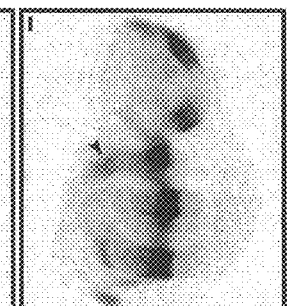
Figure 7J:
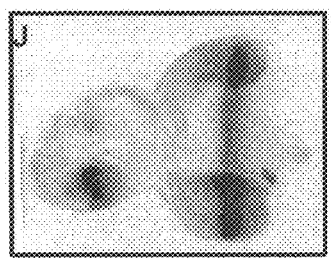
Figure 7K:
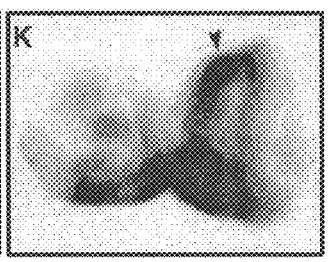
Figure 7L:
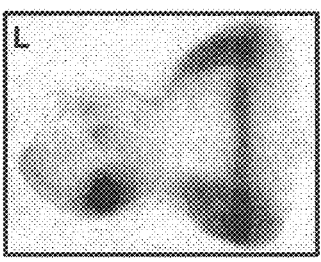
Figure 7M:
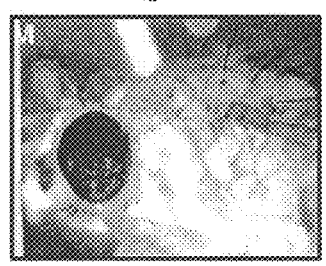
Figure 7N:
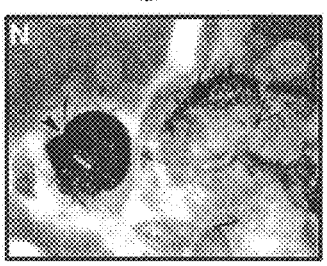
Figure 7O:
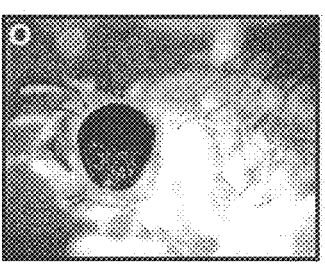

As shown in FIG. 7A, wg expression normally occurs in a ventral sector of the leg disc along the anterior/posterior compartment boundary while dpp is expressed in the dorsal portion of the disc along this boundary (FIG. 7D). Although thermal cycling of larvae carrying the wild-type hh gene produced abnormal leg disc morphology and extensive ectopic expression of both target genes, as previously reported for ectopic hh expression (FIGS. 7B and E), the H329A construct produced little if any detectable difference in these patterns of expression (FIGS. 7, C and F). Ectopic hh expression in the wing disc also leads to morphological changes and expanded expression of dpp (compare FIGS. 7, G and H), but the H329A construct produced only an occasional small patch of anterior ectopic expression (FIG. 7I).

Ubiquitous expression of wild-type hh also leads to ectopic expression of dpp in the eye-antennal disc (compare FIGS. 7, J and K). In the antennal portion of this disc the expansion of dpp expression resembles that observed in leg discs. In the eye portion of the disc dpp expression is observed at its normal location in the furrow; however, ectopic expression also occurs in the form of a second dorso-ventral band at a location somewhat anterior to the furrow, thus giving the appearance of an eye disc with two morphogenetic furrows (FIG. 7K). Indeed, in adults derived from temperature-cycled larvae that carry the wild-type hh construct, an apparently duplicated eye structure such as that in FIG. 7N can be observed, with two eye structures separated by a thin strip of cuticle (arrow). The H329A mutant protein, in contrast, did not induce expansion of dpp expression in either portion of the eye-antennal disc (FIG. 7L), and does not induce eye duplications or cuticle defects in the adult (FIG. 7O).

The experiments described thus far comprise multiple series of larvae subjected to two days of thermal cycling followed by immediate dissection for analysis of imaginal structures or further incubation at constant temperature for analysis of adult structures. Although the H329A protein appeared to have little activity in these experiments, the small patch of ectopic dpp expression induced in the wing disc (FIG. 7I, arrow) suggested that some residual activity remained. This suggestion was borne out in a similar experiment involving three days of cycling prior to dissection: the H329A protein clearly displayed some dpp-inducing activity in this experiment, presumably as a result of the higher amounts of protein that accumulated during the longer cycling period. The wing in particular, but also other imaginal discs, displayed low and variable amounts of ectopic dpp expression. This expression in all cases was far less extensive than that observed for the wild-type construct examined in parallel; furthermore, morphological deformations of the imaginal discs, although quite common with the wild-type protein, were extremely rare with the H329A protein. Although its potency is greatly reduced relative to wild-type, the H329A protein retained at least some activity in early embryonic and imaginal disc induction of wg and dpp expression; in contrast, even under heat shock conditions far more severe than those required for effects by the wild-type protein, the H329A mutant remained completely inert with respect to the re-specification of cell fates in the dorsal cuticle of the larva.

Example 6

Differential Release of N and C into Cultured Cell Supernatants

Figure 8C:
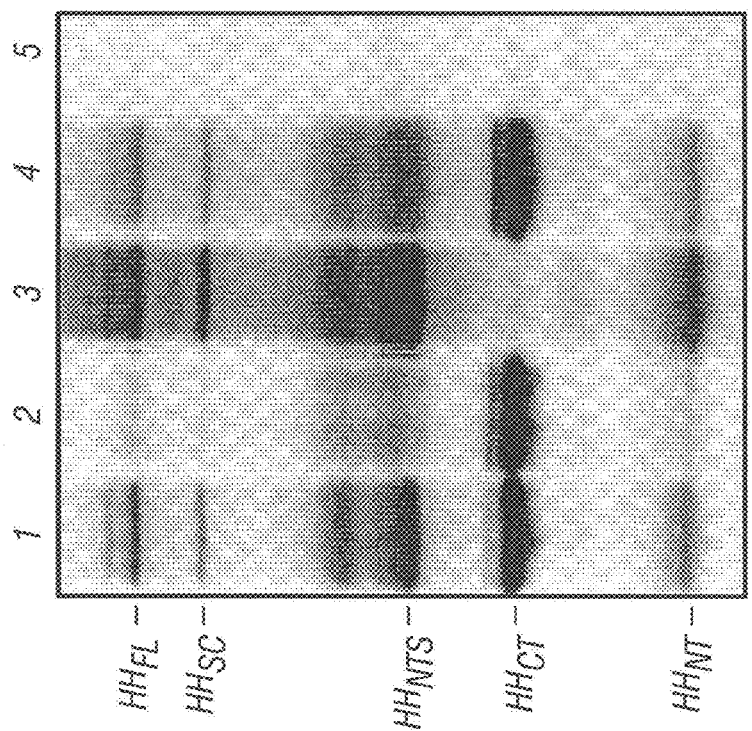
FIG. 8C demonstrates the heparin binding activity of various HH protein species generated by in vitro translations with microsomes (38). Samples were: total translation mix (lane 1); supernatant after incubation with heparin agarose or agarose (control) beads (lanes 2 and 4); and material eluted from heparin agarose or agarose beads after washing (lanes 3 and 5). F, U, $N_{25}$ and N fragments are depleted from reactions incubated with heparin agarose but not agarose beads (compare lanes 2 and 4 to 1), and the same species subsequently can be eluted from the heparin agarose but not the agarose beads (compare lanes 3 and 5 with lane 1).
Figure 8B:
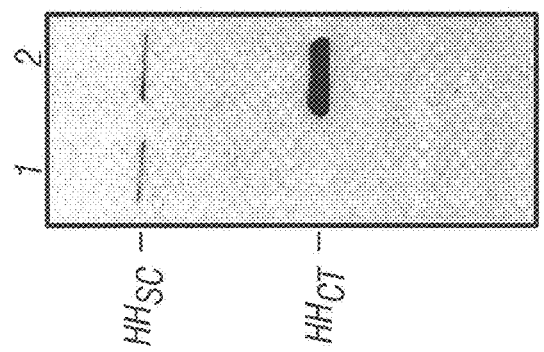
FIGS. 8A and 8B are immunoblots of cell pellets (lane 1) or supernatants (lane 2) from transfected S2 cell cultures expressing HH protein, developed with Ab1 (FIG. 8A) and Ab2 (FIG. 8B). Samples in each lane were from the same volume of resuspended total culture. Whereas N remained mostly associated with the cell pellet (compare lanes 1 and 2 in FIG. 8A), C was nearly quantitatively released into the supernatant (compare lanes 1 and 2 in FIG. 8B). U displayed partitioning properties in between those of N and C (FIG. 8A and FIG. 8B).
Figure 8A:
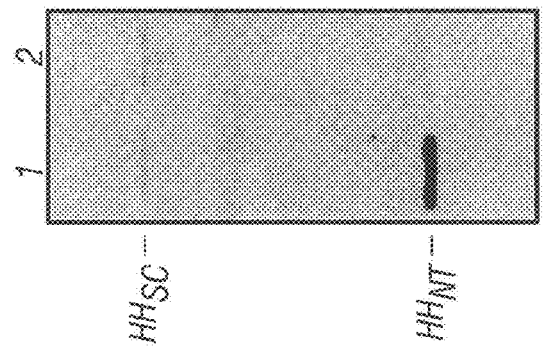

A puzzling feature of hh function is its apparent short-range action in settings such as embryonic and imaginal disc signaling to wg and dpp, and longer-range action in other settings, such as patterning of the dorsal larval cuticle. These observations and the existence of two major protein products in vivo prompted us to look for differences in the solubility or diffusibility of N and C expressed in S2 cultured cells. FIGS. 8 (A) and (B) are immunoblots of cell pellets (lane 1) or supernatants (lane 2) from transfected S2 cell cultures expressing Hh protein, developed with Ab1 (A) and Ab2 (B). Samples in each lane were from the same volume of resuspended total culture. Whereas N remained mostly associated with the cell pellet (compare lanes 1 and 2 in A), C was nearly quantitatively released into the supernatant (compare lanes 1 and 2 in B). U displayed partitioning properties in between those of N and C (A and B). (8C) demonstrates the heparin binding activity of various Hh protein species generated by in vitro translations with microsomes. Samples were: total translation mix (lane 1); supernatant after incubation with heparin agarose or agarose (control) beads (lanes 2 and 4); and material eluted from heparin agarose or agarose beads after washing (lanes 3 and 5). F, U, N, and N fragments are depleted from reactions incubated with heparin agarose but not agarose beads (compare lanes 2 and 4 to 1), and the same species subsequently can be eluted from the heparin agarose but not the agarose beads (compare lanes 3 and 5 with lane 1). FIGS. 8, A and B indeed show that these proteins behave differently, with most of the N fragment remaining cell-associated and all, or nearly all, of C being released into the culture supernatant.

One possible explanation for this differential behavior might be association of the N fragment with extracellular matrix proteins on the surfaces of the S2 cells. Accordingly, the relative affinity of these two proteins for heparin agarose was examined, since heparin binding is a common property of proteins that associate with the extracellular matrix. Given the obvious difficulty in obtaining soluble N from cultured cells, in vitro translation in the presence of microsomes was used to generate soluble, labelled N and C. As shown in FIG. 8C, N but not C is depleted from these translation extracts by treatment with heparin agarose beads, while treatment with unmodified agarose beads did not deplete either fragment. Furthermore, N but not C was retained upon the heparin agarose beads upon extensive washing with a solution that contains 0.1% Triton X-100 and 150 mM NaCl; in contrast, neither fragment was retained by unmodified agarose. N, but not C, binds tightly to heparin, and this behavior suggests that the low concentration of N released into culture supernatants may be the result of binding to the extracellular matrix. Another mechanism that might contribute to the differential release of N and C into culture supernatant would be the expression in S2 cells of a receptor for N but not for C. Our current data can not distinguish these possibilities.

Example 7

Distinct Embryonic Localizations of N and C

The differential release of N and C into cultured cell supernatants suggested the possibility that these fragments might also be differentially localized in embryos. Previously reported hh protein localizations utilized either antibodies specific for N epitopes or antibodies unable to distinguish between N and C. FIG. 9 shows the differential localizations of N and C in embryos by in situ localization of the hh transcript. FIG. 9 (A) is shown in comparison to the distribution of N and C epitopes detected with Ab1 and Ab2 in panels (9B) and (9C), respectively. Note that the distribution of N and C epitopes span approximately one-third and one-half of each segmental unit respectively, while the transcript is limited to approximately one-quarter of each unit. In (9D), the localization of C epitopes in embryos homozygous for the $hh^{13E}$ allele is detected with the use of Ab2. C epitopes in this mutant, which displays impaired auto-proteolytic activity are more restricted, and resemble the wild-type localization of N. Homozygous $hh^{13E}$ embryos were identified by loss of a marked balancer from a heterozygous parent stock. All embryos are at mid to late stage 9 (extended germ-band).

Figure 9A:
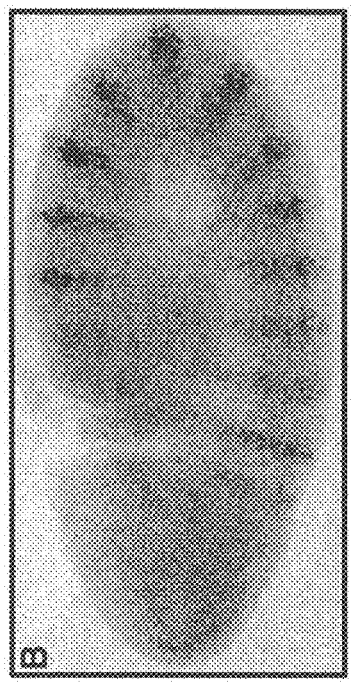
FIGS. 9A and 9B show the differential localizations of N and C in embryos by in situ localization of the hh transcript.
Figure 9B:
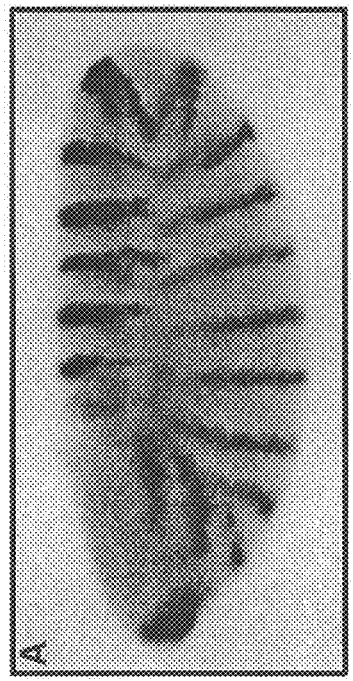
Figure 9C:
In FIG. 9D, the localization of C epitopes in embryos homozygous for the hh$^{13E}$ allele is detected with the use of Ab2. C epitopes in this mutant, which displays impaired auto-proteolytic activity (see text), are more restricted, and resemble the wild-type localization of N. Homozygous hh$^{13E}$ embryos were identified by loss of a marked balancer from a heterozygous parent stock. All embryos are at mid to late stage 9 (extended germ-band).

FIG. 9B shows in accordance with these reports, Ab1, which is specific for N epitopes, reveals a segmentally localized distribution that is slightly broader than that of the hh transcript at the same stage (FIG. 9A). Also consistent with these reports, we observed that N epitopes at later stages accumulate in large punctate structures. Our analysis here concentrates on the earlier stage, when antibody staining is weaker but before formation of the invaginations and grooves that later crease the epidermis and thereby complicate the interpretation. Ab2 was also utilized to detect C-specific epitopes with a variety of fixation and staining procedures. Although detection of C epitopes above background is more difficult than for N, we consistently observed a segmentally modulated pattern, albeit with a broader distribution than N (FIG. 9C). This localization is also distinctive in that C epitopes at early or late stages are not found in the punctate structures characteristic of N.

Figure 9D:

The $hh^{13E}$ mutation encodes a prematurely truncated protein that is missing 15 residues normally present at the COOH-terminus. Because this protein displays a much reduced efficiency in auto-proteolysis the distribution of C in this mutant background was examined. FIG. 9D shows that C epitopes in a homozygous $hh^{13E}$ embryo (identified by absence of a marked balancer) are distributed in a much tighter segmental pattern than in wild-type. This localization resembles that of N, and we thus conclude that the broad distribution of C epitopes normally seen is altered in $hh^{13E}$ by retention of the uncleaved precursor near the site of synthesis.

Example 8

The Role of Auto-Proteolysis in Biogenesis of Active Hedgehog Protein

In addition to signal cleavage, the hh protein undergoes auto-proteolysis at an internal site to generate the predominant protein species observed in vivo. All or most of the amino acid residues required for this auto-proteolysis function map to C, the carboxy-terminal product of this internal cleavage. In an effort to determine the importance of auto-proteolysis for function, we introduced a single residue mutation (H329A) that blocks auto-proteolysis of the hh protein in vitro and demonstrated that both processing and function of this protein is impaired in vivo. Since similar levels of induced protein were detected from a strain carrying the wild-type construct or from several strains carrying independent insertions of the mutant construct (FIG. 5), the impaired function of the H329A protein relative to wild-type is not the result of reduced levels of expression. Further evidence in support of a role for auto-proteolysis derives from the effect of the $hh^{13E}$ mutation, which reduces but does not eliminate auto-proteolysis of the hh protein in vitro (FIG. 4). Correspondingly, the $hh^{13E}$ mutation is associated with a phenotype of intermediate strength in vivo (J. Mohler, supra).

Curiously, the H329A Hh protein appears to retain weak activity in embryonic signaling to induce ectopic wg expression and, to a lesser degree, can function in imaginal disc signaling for induction of ectopic wg and dpp expression. In contrast to its retention of at least some signaling functions in embryonic and imaginal tissues, the H329 protein is completely inert when assayed for the ability to reprogram cell fates in the dorsal cuticle of the larva.

Figure 10A:
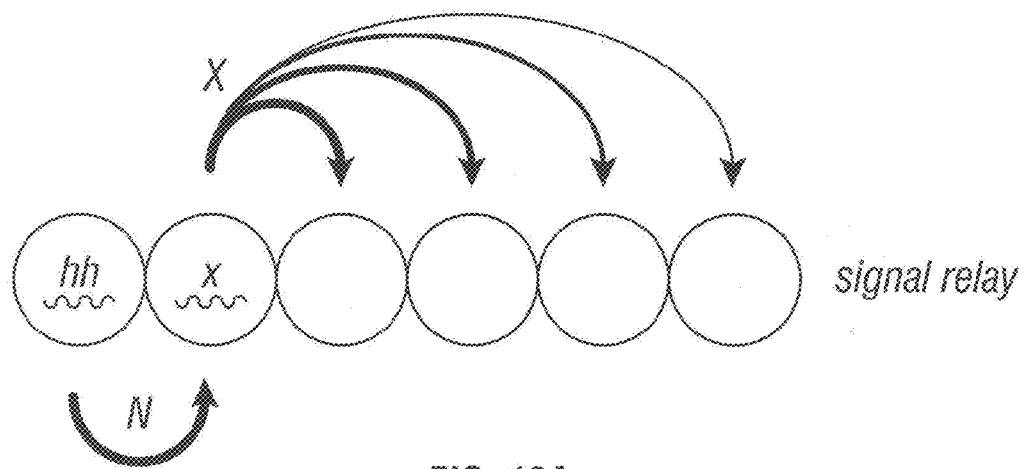
FIGS. 10A and 10B show a signal relay versus dual function models for hh protein action.
Figure 10B:
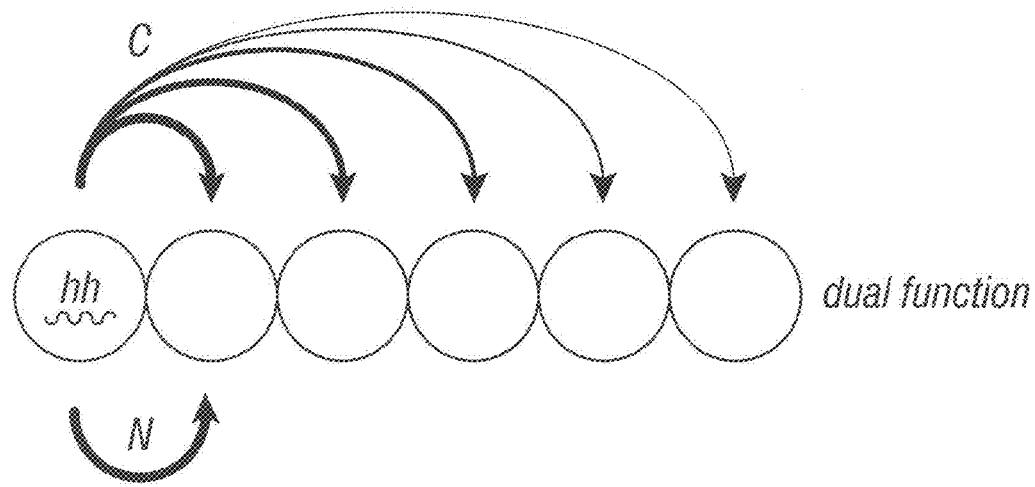

The assays in which the H329A protein is active or partially active involve short-range signaling that normally occurs across one or at most several cell diameters; in contrast, the H329A protein fails to exert any effect upon patterning of the dorsal cuticle, a long-range activity that normally operates across most of the segment. Previous proposals to account for long-range patterning activities have suggested that hh expression induces other signaling molecules which are then responsible for executing the patterning functions (the signal relay model; see FIG. 10A). FIG. 10 shows a signal relay versus dual function models for hh protein action. In FIG. 10 (A), the long-range effects of hh signaling are achieved indirectly through short-range induction of a second signaling molecule (X). Based on its biochemical properties and its restricted tissue localization, N is presumed to represent the active short-range signal while the role of C would be limited to supplying the catalytic machinery required for biogenesis of N. In (10B), the long- and short-range signaling functions of hh are supplied by the N and C proteins derived by internal auto-proteolysis of the U precursor. N is implicated in short-range signaling by retention near its cellular site of synthesis, while C is less restricted in its distribution and would execute long-range signaling functions. In both models, auto-proteolysis is required to generate fully active signaling proteins. See text for further discussion.

These proposals seek to maintain a consistent mode of hedgehog action by rationalizing the apparent long-range activities of hh products as indirect consequences of short-range signaling. Based on the distribution observed, the active molecule in this model might be N and the role of C would then be limited to supplying the catalytic machinery required for biogenesis of N.

Our evidence suggests an alternative model, the dual function model (FIG. 10B), in which long- and short-range activities of the hh protein might be executed by N and C, the two predominant forms of the molecule observed in vivo. The nearly quantitative release of C fragment into the culture medium of hh-expressing S2 cells and its broad, though segmentally modulated distribution within embryos suggests that C might execute or contribute to long-range signaling functions. The N fragment, on the other hand, predominantly remains associated with the expressing S2 cells and also binds to heparin, which suggests a possible association with the extracellular matrix. These properties and the segmentally restricted embryonic distribution of N are suggestive of a role in the execution of short-range hh signaling activities. Since the vertebrate Hh proteins we tested also appear to be auto-processed and also carry predicted heparin binding sites just carboxy-terminal to their signal sequences (H. Roelink et al., supra), many aspects of the dual function model discussed here in the context of *Drosophila* development may also apply to hh protein function in vertebrate development.

Execution of short-range functions by N would be consistent with the observation that the H329A mutant protein has at least partial function in signaling for the induction of wg and dpp, since this mutation does not alter residues located in the amino-terminal portion of the protein that normally would give rise to N. The uncleaved H329A protein thus would carry all the residues that normally interact with a presumed receptor for N, although there might be some effect on the affinity of the interaction due to the presence of carboxy-terminal sequences, thus accounting for the decreased potency of the H329A protein. Alternatively, the partial function of H329A protein may derive from an extremely small fraction of protein that appears to be cleaved, a very faint band with identical mobility to C appears in in vitro translations with the H329A protein (FIG. 4, lane 3). Execution of long-range functions by C is also consistent with our observations because long-range signaling might require the release of the C fragment or otherwise require the H329 residue for some function other than for cleavage.

When N is synthesized from a native construct (wild type hh), it remains primarily cell-associated (FIG. 10C), however, N generated from a truncated construct in cultured cells predomi-nantly enters the culture medium (FIG. 10D) (For constructs, see Porter, et al., *Nature*, 374:363, 1995). These results further confirm that autoprocessing by fragment C may regulate the degree of N association with the cell surface and therefore its range of action.

Example 9

Isolation of Hedgehog Homologues

The mouse and human hh-like sequences were isolated by polymerase chain reaction (PCR) using primers degenerate for all possible coding combinations of the sequences underlined in FIG. 1 of Chang, et al, (*Development,* 120: 1994). PCR amplifications contained from 100 ng to 2 µg genomic DNA (depending upon the genome size of the species), 2 µM of each primer, 200 µM dNTPs (Pharmacia), 1× reaction buffer (Boehringer-Mannheim) and 2.5 units Taq polymerase (Boehringer-Mannheim) in 50 µl reactions. Amplification was as follows: 94° C. 5 min, addition of Taq polymerase at 75° C., followed by 94° C. 1 min, 52° C. 1.5 min and 72° C. 1 min for 30 cycles and a final extension of 72° C. for 5 min. All PCR products were cloned into pBluescript (Stratagene) prior to sequence determination.

Mouse clones obtained in this manner contained 144 bases of sequence between the primer ends and were labelled with [$\alpha$-$^{32}$P]dATP and used for high stringency screens of mouse cDNA libraries made from whole 8.5 dpc embryonic RNA and from 14.5 dpc embryonic brain in the $\lambda$ZAP vector (a gift from A. Lanahan). Several clones corresponding to Hhg-1 were isolated and the largest, 2629 bp in length (pDTC8.0), was chosen for sequence analysis using dideoxy chain termination (Sanger, et al., 1977) and Sequenase v2.0 (US Biochemicals). Compressions were resolved by using 7-deazaguanosine (US Biochemicals). Sequence analysis made use of the Geneworks 2.0 (IntelliGenetics) and MacVector 3.5 (IBI) software packages.

One of the three mouse clones, Hhg-1, when used as a probe, yielded a 2.0 kb clone from a 8.5 dpc mouse embryonic cDNA library and a 2.7 kb clone from a 14.5 dpc embryonic cDNA library. The 2.7 kb cDNA appears to represent a nearly full length mRNA because it corresponds to a 2.7 kb band detected by hybridization on a Northern blot. The largest methionine-initiated open reading frame within this cDNA encompasses 437 codons, and is preceded by one in frame upstream stop codon. Sequence comparisons indicate that the protein encoded by Hhg-1 is identical to the independently characterized mouse Shh (Echelard, et al., *Cell,* 75:1417-1430, 1993) except for an arginine to lysine difference at residue 122. Hhg-1 also corresponds closely to the rat vhh-1 gene (97% amino acid identity; Roelink, et al., *Cell,* 76:761-775, 1994), the chicken Sonic hedgehog (81% identity; Riddle, et al., *Cell,* 75:1401-1416, 1993) and Shh from the zebrafish (68% identity; Krauss, et al., *Cell,* 75:1431-1444, 1993; Roelink, et al., *Cell,* 76:761-775, 1994). The PCR-generated fragments Hhg-2 and Hhg-3 appear to correspond to the Indian and Desert classes of mouse hedgehog genes, respectively (Echelard, et al., *Cell,* 75:1417-1430, 1993).

Alignment of the Hhg-1 open reading frame with the two *Drosophila* hh sequences showed that all three proteins contain hydrophobic amino acid sequences near their amino-termini; the hydrophobic stretches within the *D. melanogaster* protein (residues 64 to 83) and within the mouse protein are known to act efficiently as signal sequences for cleavage (Lee, et al, *Cell,* 71:33-50, 1992). Both *Drosophila* signal sequences are unusual in their internal locations, while the hydrophobic stretch of the mouse gene occurs at the extreme amino-terminus, a more conventional location for cleaved signal sequences. Although portions of sequence N-terminal to the *Drosophila* signal sequences are conserved, suggesting a functional role, the mouse gene lacks this region.

The overall level of amino acid identity between Hhg-1 and hh carboxy-terminal to the signal sequences is 46%. A closer examination shows that the amino terminal portion, from residues 25 to 187, displays 69% identity, while remaining residues in the carboxy-terminal portion display a much lower 31% identity. Like hh, the Hhg-1 coding sequence is divided into three exons, and the boundaries of these exons are at the same positions within coding sequence as those of the three *Drosophila* hh exons. Curiously, the boundary between coding sequences of the second and third exons occurs near the transition from high to low levels of overall sequence conservation. The coincidence of these two boundaries suggests a possible demarcation of functional domains within these proteins. This location within Hhg-1 coding sequence also coincides approximately with the site of a presumed proteolytic cleavage.

Example 10

Human Cloning of hh Genes

Partial sequence for two human hh genes has been obtained by DNA sequencing of clones derived by PCR amplification from genomic DNA with M-specific degenerate primers as outlined in Chang, et al., (*Development,* 120:3339, 1994) and EXAMPLE 9 (FIGS. 11A and B). More extensive screening by the same approach, either with the same primers or with other primers from the hh coding region or with the human hh fragments seen in FIGS. 11A and B, is expected to yield at the least a third gene, and possibly more, since at least three genes are found in the mouse. These segments of human hh genes can be used to obtain full coding sequences for human proteins by the following cloning method commonly used by those of skill in the art and which are extensively described in the literature.

For example, ready-made cDNA libraries or RNAs from a variety of human sources, including various fetal stages and organs (from abortuses) and specific infant or adult organs (from pathological or autopsy specimens), are being tested for the presence of hh sequences by PCR or RT-PCR using the primers described in Chang, et al., supra, and other primers derived directly from the sequence of the human fragments. Ready-made libraries containing hh sequences are being screened directly and, where necessary, new libraries are being constructed by standard methods from RNA sources containing hh sequences. The probe for these screens is a mixture of all the distinct human hh fragments. Sequences of cDNA clones can then be determined. Most clones containing the probe sequences, which are located in the N region, will also include a full C coding region since standard methods of library construction result in cDNA clones that are most complete at their 3' ends. All full length hh-coding sequences obtained previously in vertebrates and invertebrates contain N and C sequences encoded in a single RNA. Screening is continued until complete open reading frames that correspond to all of the fragments of human hh genes are obtained. Specifically, 1.2×10$^6$ clones from a human fetal brain library (-Stratagene, La Jolla, Calif.) was screened using a mixture of the two human hh fragments (FIGS. 11A and B) as probes. Twenty-nine clones were identified as specifically hybridizing with these probes.

Second, the RNA sources identified as containing hh sequences can be used as templates from anchored PCR (also referred to in the literature as RACE, for rapid amplification of cDNA ends). Briefly, this method provides a means to isolate further mRNA sequence in either the 5' or 3' direction provided that sequence is known from an internal starting point. Anchored PCR can also be used to isolate sequences from cDNA library.

Third, genomic libraries can be screened with the probes described in the first technique. Where necessary, human hh exons and coding sequences are being identified by hybridization to previously isolated human and mouse coding sequences by sequence determination, and by exon-trapping methods to identify all hh coding sequences within genomic clones; these coding sequences can be "stitched" together by standard recombinant DNA methods to generate complete hh open reading frames.

Figure 12D:
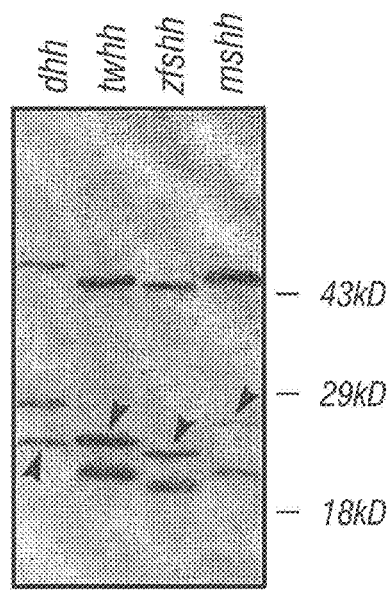
FIG. 12D shows a SDS-PAGE gel loaded with in vitro transcription/translation reactions as described in the previous Examples, using various hh genes as templates. dhh is *Drosophila*, twhh and zfshh are the twiggy-winkle and sonic hh genes of the zebrafish, and mshh is the shh/Hgh-1/vhh-1 gene of the mouse.

FIGS. 12 A and B show in vitro cleavage reactions of a *Drosophila* hh protein produced in *E. coli* and purified to homogeneity. This protein has residues 89-254 deleted, rendering it more soluble and easier to purify. It also contains a $His_6$ purification tag appended to the N-terminus. Autoproteolysis of this protein is triggered by the addition of reducing agents (DTT), and the resulting product corresponds to the C fragment identified in vivo. FIG. 12, Panel A shows a time course of cleavage after initiation by addition of DTT. Panel B shows incubations of concentrations ranging over three order of magnitude for a fixed time period (four hours), with no difference in the extent of conversion to the cleaved form. This concentration-independent rate of cleavage indicates an intramolecular mechanism of cleavage. Panel C shows the sequence around the cleavage site as determined by amino-terminal sequence of the cleaved fragment C. The cleavage site is denoted by the arrow, and the actual residues sequenced by Edman degradation of the C fragment are underlined. Panel C also shows an alignment of all published vertebrate hh sequences plus some of unpublished sequences from fish and *Xenopus*. The sequences shown correspond to the region of *Drosophila* hh where the cleavage occurs, and demonstrates the absolute conservation of the Gly-Cys-Phe sequence at the site of cleavage. Panel D shows a SDS-PAGE gel loaded with in vitro transcription/translation reactions as described in the previous Examples, using various hh genes as templates. dhh is *Drosophila*, twhh and zfshh are the twiggy-winkle and sonic hh genes of the zebrafish, and mshh is the shh/Hgh-1/vhh-1 gene of the mouse. The translation mix included $^{35}$S-labelled cysteine, used to visualize the resulting products by autoradiography. Note that each gene give a larger product (the precursor or U) and two smaller products of cleavage (N and C). The larger species is C for each of the vertebrate genes, whereas the *Drosophila* N is larger than C due to the presence of ~60 residues occurring amino-terminal to the signal sequence that are present in the vertebrate open reading frame. This panel shows that vertebrate hh proteins are processed similarly to the *Drosophila* protein. Panel E shows that Edman degradation of the C fragments releases $^{35}$S counts on the first but not subsequent rounds for all these proteins, indicating that the site of autoproteolytic cleavage for all of these hh proteins is the amide bond to the amino-terminal side of the Cys residue that forms the center of the conserved Gly-Cys-Phe sequence highlighted in panel C. This is a generalizable approach to establish the composition of protein fragments from any other hh family members.

Example 11

Differential Expression of Two hh Genes in Axial Mesoderm and in Neural Progenitors Partial sequences corresponding to five distinct zebrafish hh-like genes were isolated and the complete coding sequences for two of these genes were obtained from an embryonic cDNA library. One of these two sequences is identical to that of the zebrafish nhh-1 gene (Roelink, et al., *Cell,* 76:761, 1994), and appears to correspond to the shh gene reported by Krauss, et al., (*Cell,* 75:1431, 1993) (See FIG. 13 description); the other gene, twiggy-winkle (Potter, B., The Tale of Mrs. Tiggy-Winkle, *The Penguin Group*, London, 1905), represents a novel vertebrate hh. Coding sequences for both are shown in alignment to mouse and chicken sequences of the sonic/vhh-1 class (FIG. 13*b*). Like other vertebrate hh homologues, the twhh and shh proteins contain an amino-terminal stretch of hydrophobic residues. These residues function as signal sequences since cleavage is observed when coding sequences are translated in the presence of microsomoses; vertebrate hh genes thus appear to encode secreted proteins, as previously reported for *Drosophila* hh (Kimmel C. B. & Warga, R. M., *Developmental Biology,* 124:269-280, 1987; Warge, R. M., & Kimmel, C. B., *Development,* 108:569-580, 1990).

The first four sequences were isolated from zebrafish genomic DNA (a gift from J. Pellegrino) using degenerate primers in polymerase chain reactions as described (Chang, et al., supra). twhh and shh clones were isolated from a 20-28 hour cDNA library (a gift from R. Riggleman, K. Helde, D. Grunwald and J. Pellegrino) using the first three sequences as probes. The translational reading frames for twhh and shh were closed 12 and 16 codons, respectively, upstream of the putative initiating methionine.

FIG. 13 shows the predicted amino acid sequences are shown in single letter code. 13(*a*) shows sequences common to five distinct hh-like genes are shown with a dot indicating identity with the corresponding residue of zebrafish twiggy-winkle (twhh; Potter 1905; supra), hh[zfB] and hh[zfC] is more diverged and appears to represent a novel class. 13(*b*) shows amino acid sequences of twhh and shh are aligned to those of the soniclvhh-1 class from chick and mouse (Riddle, et al., *Cell,* 75:1401-1416, 1993; Chang, D. T., et al., *Development,* supra; Echelard, Y., et al., *Cell,* 75:1431-1444, 1993). Zebrafish sonic hedgehog (shh) is identical in sequence to z-vhh-1 reported by Roelink, et al., *Cell,* 76761-775, 1994. Based on expression and extensive sequence identity throughout most of the coding region, vhh-1 and the sonic sequence reported here probably correspond to shh of Krauss, et al., *Cell,* 75:1431-1444, 1993, diverges dramatically throughout a 26 residue stretch near the carboxy-terminus. Rat vhh-1/sonic hh (Roelink, et al., supra.) was excluded in this alignment because of its 97% sequence identity to the predicted mouse protein. Residues identical in all four sequences are boxed, and a dash indicates a gap in the alignment. The arrow indicates the predicted signal sequence cleavage site (von Heijine, G., *Nucleic Acids Res.,* 14, 4683-4690, 1986) for twhh. The amino-terminal hydrophobic stretch common to all four hh genes is shaded. 13(*c*) shows percent identity of residues carboxy-terminal to the hydrophobic region.

FIG. 14 shows a comparative expression of twhh, shh, and pax-2 during zebrafish embryogenesis Whole mount in situ hybridizations on 0-36 hour embryos were performed using a modification of the procedure of Tautz and Pfeifle, *Chronosoma,* 98:81-85, 1989, with antisense probes. Transcript localization is revealed by the purple product of an alkaline phosphatase enzymatic reaction. Staging of the embryos is according to Westerfield, M., (*The Zebrafish Book*, University of Oregon Press, Eugene, 1993). Transcripts were visualized by in situ hybridization to whole embryos. (a, b) twhh expression in a single late shield stage embryo. (a) Dorsal view, animal pole is to the top. The triangular shape of expression is characteristic of axial mesoderm-forming cells of the hypoblast (Statchel, S. E., et al., *Development*, 17:1261-1274, 1993). (b) Lateral view: the thicker layer of cells on the left (dorsal) side of the embryo is the embryonic shield; the two arrows indicate the twhh-expressing hypoblast cells and the non-expressing epiblast. Anterior is to the left in all subsequent embryos. Dorsal is to the top in all lateral views. (c, d) A single embryo at the end of gastrulation (100% epiboly) with /Wi/i-expressing cells. (d) Caudal-dorsal view. Note the wide patch of stain in the presumptive tailbud which narrows anteriorly. (e, j) Early somitogenesis (11.5 hour, 3-4 somite) embryos; optic vesicles have not begun to evaginate from the wall of the diencephalon. (e, h, k) Lateral views of developing brain. (f, i, l) Dorsal views of developing brain. (e, f, g) Localization twhh-expressing in a single row of cells that will form the flood plate. The arrowhead marks a parch of twhh-expressing cells lateral to the tailbud. (h, i, j) Localization of shh. shh is also expressed strongly in the protuberance. (j) Lateral view of the developing tail. shh is also expressed strongly in the protuberance. (j) Lateral view of developing tail. shh is expressed in cells that will form both floor plate and notochord. (k, l, m) Localization of pax-2 during early optic vesicle formation; (m) also shows twhh expression. (k) 12 hour (4-5 somites) embryo. (l) 12.5 hour (5-6 somites) embryo. Expression of pax-2 in the developing optic vesicle is in a gradient away from the protuberance. Note the expression of pax-2 (asterisk) at the future midbrain-hindbrain border. (m) twhh (arrow) and pax-2 expression in a 6-7 somite (13 hour) stage embryo. Note differential expression of twhh in ventral neural keel (corresponding to neural tube in other vertebrates). (n-s) Embryos at end of somitogenesis (22-24 hours). (m, o, p) Localization of twhh. (m, o) Developing brain. Note isolated groups of cells staining in the diencephalon (filled triangles) and the protuberance (arrowhead), and floor plate expression underlying the midbrain and hindbrain. The floor plate expression is contiguous caudally along the axis. (n) Lateral view. (o) Dorsal view. (p) Lateral view of tail. Expression is restricted to the floor plate. (q, r, s) Localization of shh. (q, r) Developing brain (q) Lateral view. pax-2 expression in the otic vesicle is indicated. (r) Dorsal view. Expression in the protuberance (arrowhead) and in the neural keel. (s) Lateral view of tail. Expression is strongest in the floor plate, but contrary to the report of Krauss, et al., supra., is still also in the notochord. Abbreviations: white e—epiblast; h—hypoblast; tb—tailbud; p—protuberance; e—eye; ov—optic vesicle; ot—otic vesicle; fp—floor plate; nc—notochord; asterisk—midbrain-hindbrain boundary or pax-2-labeled prospective midbrain-hindbrain boundary; t—telencephalon.

Figures 14H, 14I, 14J:
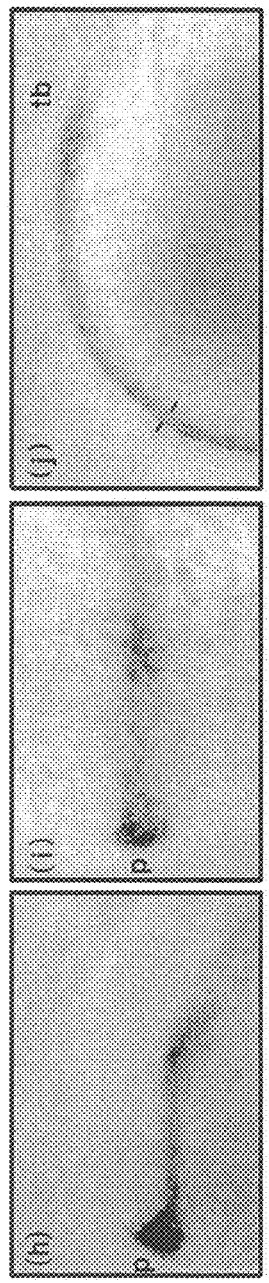
FIGS. 14A through 14S show a comparative expression of twhh, shh, and pax-2 during zebrafish embryogenesis.

Comparison of twhh and shh expression patterns (Krauss, et al, supra), reveals that both gene are predominantly expressed in midline structures, albeit with notable differences in regard to timing, rostra-caudal extent, and tissue restriction. Expression of twhh is first detected during gastrulation in the dorsal mesoderm (FIGS. 14*a, b*); this expression occurs in a band corresponding to a subset of the embryonic shield, a structure, analogous to Spemann's organizer in *Xenopus* (Stachel, et al., *Dev.*, 117:1261-1274, 1993, and reference therein; Ho., R., *Seminars in Developmental Biology*, pg. 3, 1992). In concert with the movements of convergence and extension, this band of twhh expression shortens along the equatorial plane and extends along the incipient embryonic axis until, by the end of gastrulation, expression occurs throughout the entire axis (FIGS. 14*c,d*). Early in somitogenesis, twhh RNA is found restricted to presumptive ventral neural tissue along the entire body (FIGS. 14*e, f, g*), the only exception being cells in and near the tailbud (FIG. 14*g*). In contrast to the neural restriction of twhh, shh is localized both to presumptive neural and notochordal cells (FIG. 14*j*).

As somitogenesis proceeds, ventral midline expression of shh and twhh is reduced in most of the prospective forebrain, but remains strong in an anterior patch of midline cells within the floor of the prospective diencephalon (FIGS. 14*e, f*, for twhh; FIGURES h, i for shh). This patch later will give rise to the protuberance (Schmitt, E. A. and Dowling, J. D., *J. Comp. Neur.*, 344 532-542, 1994), an anterior extension of the diencephalon. This structure, which is medial and just rostral to the developing optic stalks, is the site we propose as the focus of early patterning activity for the developing eyes (see below). By the end of somitogenesis, both twhh and shh are strongly expressed in the floor plate (FIGS. 14*p, s*), although shh transcripts remain detectable in the notochord at this stage and at 36 hours of development (FIG. 14*s*; later stage not shown). At 28 hours, twhh transcripts are also found in a small cluster of cells within the first gill arch (not shown), as also reported for shh at 33 hours of development (Krauss, et al., supra).

Differences between twhh and shh expression are apparent from the beginning of gastrulation, since twhh RNA can be detected as early as the shield stage while shh is first detected later, at about 60% epiboly (not shown; (Krauss, et al., supra). In addition, twhh transcripts are restricted to neural tissues early in development, and are never detected in the notochord (compare FIG. 14*g* to FIG. 14*j*). Later differences in expression include differential rostra-caudal restriction within the diencephalon and midbrain and weaker and more restricted expression of twhh in the protuberance (compare FIGS. 14*n* and 14*q*), such that the later domain of twhh expression in the brain appears to constitute a subset of the shh domain. In addition, shh but not twhh is expressed in the developing fin bud (Krauss, et al., supra). Comparison of shh and twhh expression patterns to this previously reported for hh homologues in zebrafish and other vertebrate species indicates that shh is the zebrafish homologue of the sonic/vhh-1 class while twhh represents a novel class of vertebrate hh.

Example 12

Developmental Consequences of Ectopic hh Expression During Zebrafish Embryogenesis To gain insight into the potential roles of hh products in development, synthetic twhh and shh mRNA was injected into 1-8 cell embryos. This technique yields a mosaic but fairly uniform pattern of expression, as determined for the control mRNA encoding β-galactosidase (not shown). Uniformity of expression is in good agreement with fate mapping studies of the early zebrafish embryo (Kimmel & Warga, supra; Warga & Kimmel, supra; Heide, et al., *Science*, 265: 517-520, 1994), which indicate that blastomeres undergo extensive cell mixing during the cleavages prior to gastrulation. We note that masochism of expression caused surprisingly little variation in the phenotypes of the hh injected embryos, possibly due to secretion of hh gene products.

Embryos injected with synthetic twhh or shh mRNA (hh RNA) exhibited numerous yet highly reproducible abnormalities in comparison to control embryos injected with lacZ mRNA. These abnormalities, discussed below, are primarily defects in the brain and eyes. Although the effects of ectopic twhh and shh expression were qualitatively similar, the incidence and severity were greater with twhh RNA (see text below, FIG. 15 and FIG. 16). The proteins encoded by these two genes have qualitatively similar biological activities, but apparent differences in potency.

FIG. 15 shows the effects of ectopic hh on zebrafish development. Wild type zebrafish, *Danio rerio*, Ekkwill Waterlife Resources) were maintained at 28.5° C., some embryos were then cultured overnight at RT. Zebrafish embryos were injected at the 1-8 cell stage with twhh, shh, or lacZRNA and examined at 28 h of development, (a-c) Dorsal view of the midbrain-hindbrain region; anterior is left, (a) lacZ. (b) twhh. (c) shh. (d-f) Frontal optical section of the forebrain region; anterior is up. (d) lacZ. (h) twhh. (f) shh. (g-l) Lateral view of the eye region; anterior is left (g) lacZ (h) twhh. (i) twhh. At levels caudal to the prospective brain, the notochord, somites, and neural keel formed by most M-injected embryos appeared grossly normal except for an overall shortening and dorsal curvature of the axis. A minority of hh-injected embryos (15% are not shown) displayed partially bifurcated axes, containing duplicated axial mesoderm and parallel neural keels, each neural keel comprising ventral midline cells and some bilaterally symmetric lateral cells (not shown). Although we have not determined the primary cause of these axial defects, analysis of late gastrulation stage embryos suggests that the bifurcation may result from difficulties in epiboly and convergence. Abbreviations: mv—mesencaphalic ventricle; rv—rhombencephalic rentricle; asterisk—midbrain-hindbrain boundary; ot—otic vesicle; tv—third (diencephalic) ventricle; r—retina or retina-like structure; l—lens or lens-like structure; pe—pigmented retinal epithelium.

Morphological defects in the brain and other rostral neural derivatives occur at high frequency in hh-injected embryos. The three ventricles of the fish brain normally apparent at 28 hours of development—the rhombencephalic, mesencephalic (FIG. 15a), and diencephalic (third ventricle; FIG. 15d)—are not formed in the brains of hh injectees (FIGS. 15b, c; FIGS. 15e, f)), despite the obvious presence of a lumen. The prominent construction normally present at the midbrain-hindbrain boundary also is absent (compare FIG. 15a to FIGS. 15b, c). Formation of this constriction requires function of pax-2 (Krauss, et al., *Nature*, 353:267-270, 1991; Krauss, et al, *Nature*, 360:87-89, 1992), which normally is expressed in a band at the midbrain-hindbrain boundary (Krauss, et al, supra; Krauss, et al, *Development*, 113:1193-1206, 1991) pax2 expression at this boundary is not disrupted by hh RNA injection, however, indicating that this phenotype does not result from disruption of rostra-caudal information.

Defects in eye development also occur at high frequency in embryos injected with hh RNA. Thus, while at 28 hours the normal zebrafish eye has a lens and a retina with pigmented epithelium (FIGS. 15d, g), hh-injected embryos usually fail to develop lenses and retinal pigmentation (FIGS. 15e, h). Eye duplications are also observed at low frequencies (FIG. 15i). The poorly developed eyes do not appear to result from a simple delay in development since pigmentation elsewhere in injected embryos appears in its normal time course. Examined at three days of development, the consequences of hh RNA injection include defects that range from complete absence of eyes to partially formed eyes lacing a ventral portion of the retina.

The eye phenotypes caused by hh RNA injection resemble those produced by treatment of zebrafish and *Xenopus laevis* embryos with retinoic acid. In *Xenopus*, phenotypes range from reduction of the eye and absence of the lends to eyes with retinal folds (resembling duplicated dyes) and multiple small lenses (Manns, M. & Fritzsch, B., *Neurosci. Lett.,* 127: 150-154, 1991). In zebrafish, exposure to retinoic acid during gastrulation interferes with the formation of the eye (Holder, N. & Hill, J., *Development,* 113:1159-1170, 1991), while exposure during formation of the optic primordia induces formation of duplicated retinas and extra lenses (Hyatt, et al, *Proc. Natl. Acad. Sci. USA,* 89:8293-8297, 1992). Patterning effects of retinoic acid upon the developing chick limb appear to be mediated through ectopic activation of the endogenous sonic hh gene (Riddle, et al, supra), these results with ectopic hh expression suggest the possibility of a similar mechanism underlying the patterning effects of retinoid acid treatment in the vertebrate eye.

Figures 14K, 14L, 14M:
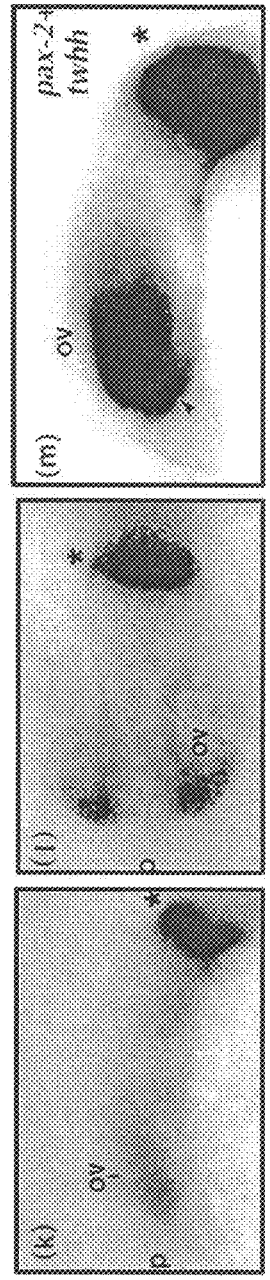

Example 13 hh Expression in the Optic Vesicle Specifies Proximal Fates at the Expense of Distal Fates To further elucidate the role of hh in eye development we utilized pax-2 and pax-6 (Krauss, et al., *EMBO J.,* 10:3609-3619, 1991; Pitischel, et al., *Development,* 114:643-651, 1992) were utilized as positional markers to examine the effects of ectopic hh expression on the optic vesicle. As the optic vesicle evaginates from the lateral walls of the zebrafish forebrain (Schmitt, E. A. & Dowling, J. D., *J. Comp. Neur.,* 344:532-542. 1994), pax-2 is expressed in a gradient, with highest RNA levels in the anterior and ventral regions of the optic vesicle (Krauss, et al., supra; FIGS. 14k, l, m). Immediately adjacent to the maximum of this pax-2 expression gradient is the region of the dicnecphalon termed the protuberance (Schmitt & Dowling, supra), where both twhh and shh but not pax-2 are strongly expressed (FIGS. 14e, f, h, i, m). The concentration gradient of pax-2 expression in the eptic vesicle thus appears to incline downward from its maximum at a location adjacent to the site of twhh and shh expression in the protuberance. Superposition of developmental fate within the optic vesicle (Schmitt, et al, supra), upon the pattern of pax-2 expression suggests that the gradient of pax-2 RNA prefigures the future proximal/distal axis of the eye.

Ectopic hh alters the expression of pax-2, pax-6, and F-spondin. Zebrafish embryos were injected at the 1-8 cell stage with twhh or shh RNA and the pattern of pax-2, pax-6, or F-spondin expression was examined by whole mount in situ hybridization. Control embryos injected with lacZ RNA were performed in every case and displayed wild-type expression patterns. At embryo stage, the anterior-posterior axis of the optic vesicle corresponds to the future proximal-distal axis of the eye. During the next hour of development, the posterior edge of the optic vesicle will separate from the diencephalon (Schmitt and Dowling, *Comp. Neur.,* 344:532-542. 1994).

Injection of either hh RNA causes uniform initiation of pax-2 expression along both the proximal-distal and dorsal-ventral axes of the optic vesicle as it begins to evaginate. The ectopic pax-2 expression appears at the same time as normal pax-2 expression is initiated in the eye, and in some cases, is also seen in the diencephalon between the optic vesicles. At the end of somitogenesis, a time when pax-2 would normally be restricted to the optic stalk, pax-2 RNA in hh injected embryos is detected in all but the most distal portion of the optic vesicle.

The effects of ectopic hh on expression of pax-6, which encodes a transcription factor critical for eye development was also studied. At 22 hours of zebrafish development, pax-6 is normally expressed in the lens and in most of the distal part of the optic cup (Krauss, et al, supra; Puschel, et al, *Development,* 114:643-651, 1992). In M-injected embryos, pax-6 is repressed in the optic vesicle, although many embryos retain pax-6 expression in the most distal cells. With regard to pax-2 and pax-6 as markers of positional identity, hh expression in the optic vesicle can be characterized as inducing proximal fates and repressing distal fates.

The distal part of the optic vesicle is the most refractory to M-induced changes in both pax-2 and pax-6 gene expression. Due to a later rotation, this distal portion of the optic vesicle will give rise to the dorsal portion of the mature eye (Schmitt, et al, supra); interestingly, this is the portion of the eye that remains in 3-day old injected embryos with intermediate phenotypes (see above).

Lesions in the pax-6 gene have been assigned as the basis for the Aniridia (Ton, et al., *Cell,* 67:1059-1074, 1991; Glaser, et al, *Nat. Genetics,* 2:232-239, 1992), Small eye (Hill, et al, *Nature,* 354:522-525, 1992), and eyeless mutations (Quiring, et al. *Science* 265:785-789, 1994), in humans, mice and *Drosophila*, respectively; pax-6 function thus appears to be critically required for eye development in *Drosophila* and mammals. As we argue here, M-encoded activities also appear to play a role in vertebrate eye development, and this suggests a further molecular parallel between vertebrates and insects, since the role of hh in *Drosophila* eye development is well established (Mohler, et al, supra; Ma, et al, supra; Heberlein, et al, supra; Lee, et al, supra). The reciprocal and non-overlapping patterns of hh and pax-6 expression in the developing *Drosophila* eye (Ma, et al, supra; Quiring, et al, *Science,* 265:785-789, 1994), suggest the possibility of pax-6 repression by hh, but whether hh functions by similar mechanisms in vertebrate and *Drosophila* eye development is a questions that requires further investigation.

In mice, the dosage of pax-6 protein is crucial for normal eye development (Hill, et al, supra). Small eye heterozygotes develop an abnormally small lens (Hogan, et al, *J. Embryol Exp. Morph.,* 97:95-110, 1986; Hogan, et al. *Development,* 103 Suppl., 115-119, 1988), as do hh-injected embryos with weaker phenotypes (FIG. 14*f*). Small eye homozygotes lacking lenses eventually generate and the animals lack eyes at birth (Hogan, et al, supra; Hogan, et al, supra), as do many of the hh-injected embryos at three days of development. These parallels suggest that many of the later eye defects observed in hh-injected zebrafish may be caused by partial or complete repression of pax-6 during eye development.

Example 14

Genetic Ablation of hh Forebrain Expression Causes Loss of Proximal Fates in the Optic Vesicle The patterns of twhh and shh expression (FIG. 14) and the effects of ectopic hh expression (FIG. 15) are consistent with a normal role for shh and twhh in eye development. If hh activities indeed play a normal role in promoting proximal fates within the developing eye, removal of hh activities would be expected to result in a loss of proximal fates. In embryos homozygous for the cyclops mutation ventral neural structures fail to form and the developing eyes fuse at the midline, yielding an embryo with a single eye (Hatta, et al, *Nature,* 350:339-341, 1991). The missing ventral structures in cyclops mutants include the regions where we observe expression of twhh and shh, and we therefore examined the effects of the cyclops mutation on hh expression.

$cyc^{b16}$ (Hatta, et al, *Nature,* 350:339-341, 1991), heterozygous adults (a kind gift of R. Riggle-man) were spawned and their offspring analyzed by whole mount in situ hybridization. Detection of pax-2 and either twhh or shh RNAs in embryos homozygous for the eye mutation or their wild-type siblings, twhh RNA is only expressed in the presumptive tailbud (caret) of cyc embryos. As reported by Krauss, et al, *Cell,* supra, neural expression of shh is abolished in cyc embryos. Strong pax-2 expression was observed in the optic vesicles of wild-type embryos which is significantly reduced in cyc mutant embryos.

twhh RNA in Cyclops embryos is found only in a small patch of cells at the presumptive tailbud and neural expression was not detected at any later stage examined. Neural expression of shh is also lost in eye mutants, although expression in the notochord is reunited (Krauss, et al, supra; data not shown).

Since the eye mutation appears to ablate M-expressing cells in the developing brain, this mutation can be used as a genetic tool to examine the requirement for hh function in eye development. Iiatta, et al; Hatta, et al, *Proc. Natl. Acad. Sci. USA,* 91:2061-2065, 1994), recently demonstrated that pax-6 expression is fused at the midline due to loss of ventral midline cells that normally do not express pax-6 and, in addition, pax-2 expression in the fused eye of eye mutant embryos is reduced. We extended these observations to an earlier stage when the optic vesicles first form and found that pax-2 expression is weak and fails to extend within the vesicles in eye mutants. In conjunction with the results of ectopic hh expression, these observations suggest that hh signaling that activity promotes and is required for the induction of proxima fates within the eye vesicle. In this model, we propose that the protuberance acts as a proximal patterning center for the developing zebrafish eye by providing a localized source of hh activity.

Example 15 hh Activity Ventralizes the Developing Brain

Previous work has established an important role of signals from the floor plate and notochord in ventral patterning of the neural tube (Jessell, T. M., & Dodd, J., *Cell,* 69:95-110, 1992). For example, Goulding, et al, *Development,* 117:1001-1016, 1993, recently demonstrated that notochord and floor plate grafts can repress the normal lateral expression of pax-6 in the neural tube. Other recent work has implicated hh activity in at least some aspects of ventral neural tube patterning (Echelard, et al, *Cell,* 75:1417-1430, 1993; Krauss, et al, supra; Roelink, et al, supra); consequently, we examined M-injected embryos for effects on pax-6 expression in the brain.

In the zebrafish at 22 hours of development, pax-6 is expressed in dorso-lateral regions of the diencephalon and in a ventro-lateral domain of the hindbrain and spinal cord that excludes the floor plate and adjacent cells (Krauss, et al., supra; Puschel, et al, supra). This pattern of expression is reciprocal to that of both twhh and shh in the diencephalon (compare FIGS. 14*q* and 14*i*) and in the hindbrain. hh RNA injection caused repression of pax-6 in the more ventral domain in the diencephalon, while more dorsal expression persisted. In addition, pax-6 expression was significantly reduced ventrally in rhombomeres 1, 2, and 4 and, in some cases, was completely abolished in these rhombomeres. The repressing effect of ectopically expressed hh and pax-6 in normal embryos are due to repression of pax-6 by nearby hh expressing cells.

Since absence of pax-6 expression is a feature of the ventral midline, repression of pax-6 in lateral positions suggests ventralization. Consequently, twhh was injected into embryos for analysis of induction of a floor plate marker, F-spondin (Riddle, et al, supra). As described above, ectopic twhh induces F-spondin expression at more dorsal levels in the midbrain and anterior hindbrain. The effects of hh upon expression of both pax-6 and F-spondin indicate a ventralization of the brain. Adoption of ventral cell identity by lateral cells might explain their failure to form ventricles (FIG. 15*a-f*).

The ventralizing activities of twhh confirm and extend those previously reported for shh/vhh-1 class genes of chicken, zebrafish, and rat (Echelard, et al, supra; Krauss, et al, supra; Roelink et al, supra). The early restriction of twhh to midline neural progenitors, however, suggests that it may play a specific role in the homeogentic mechanisms of floor plate maintenance and expansion (Placzek, et al, *Dev.*, 117: 205-218, 1993). In the zebrafish, wild type cells in cyclops hosts can contribute to and induce adjacent cells to form floor plate, but only when the transplanted cells populate the neural plate and not the notochord (Hatta, et al, *Nature*, 350:339-341, 1991) We have demonstrated that, in cyclops mutants, midline expression of twhh is lost while shh expression is maintained in the notochord (FIG. 18; Krauss, et al., supra for shh); taken together, these results suggest that the homogenetic floor plate signal lost in the cyclops mutant may be encoded by the twhh gene. In the chick and rat, the floor plate retains auto-inductive potential long after the loss of floor plate inducing properties by the notochord, despite continued expression of shh/vhh1 in the notochord (Roelink, et al, supra; Placzek, et al, supra; Yamada, et al, *Cell*, 73:673-686, 1993). Although no homologues of the twhh class have been reported in other vertebrates, expression of other hh homologues in patterns more like those of twhh might help explain these discrepancies.

Example 16

Two Distinct Signaling Proteins Derive from the twhh-Encoded Precursor

Endogenous hh protein in *Drosophila* is fund predominantly as an amino- and a carboxy-terminal fragment (N and C, respectively) derived by an internal auto-proteolytic cleavage of a larger precursor (U for uncleaved), which also occurs in vivo but at lower levels (Lee, et al, supra). Determinants within the amino-terminal domain appear not to be required for auto-proteolytic activity, whereas mutations affecting the carboxy-terminal domain can block auto-proteolysis and reduce activity in vivo (Lee, et al., supra). The auto-proteolysis is blocked by a substitution of alanine for the histidine normally present at position 329. This histidine is absolutely invariant in alignments of all known hh genes, and its sequence context suggests a catalytic role in auto-proteolysis (Lee, et al., supra).

Figure 17A:
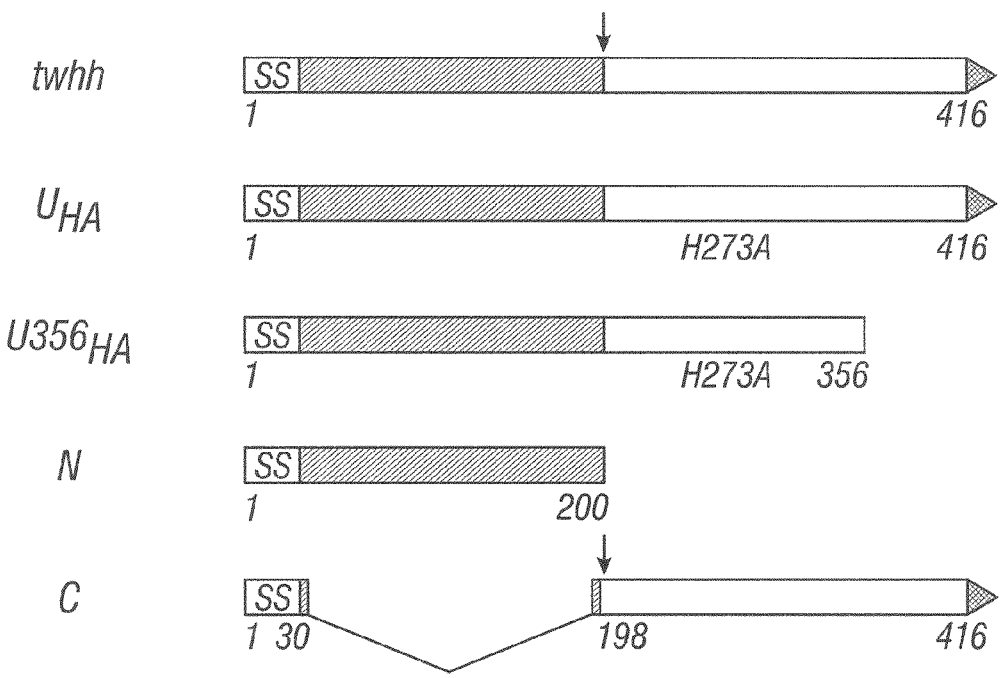
FIGS. 17A and 17B show zebrafish twiggy-winkle hedgehog derivatives.
Figure 17B:
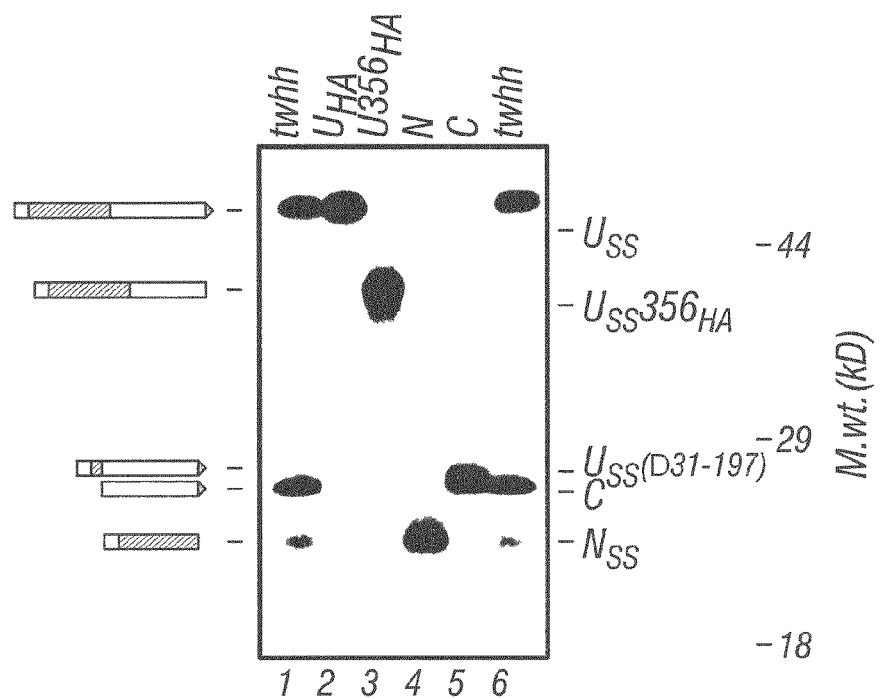

FIG. 17 shows zebrafish twiggy-winkle hedgehog derivatives. 17(*a*) Cartoons of various twhh open reading frames. SS (shaded) is the predicted N-terminal signal sequence for secretion of these proteins and encompasses the first 27 amino acids of each open reading frame. The arrow indicates the predicted internal site of auto-proteolytic cleavage. Amino acid residue numbers are according to FIG. 13*b*. The filled triangle denotes the normal termination codon for the twhh open reading frame. Construct $U_{HA}$ contains a mutation that blocks auto-proteolysis (the histidine at residue 273 is changed to an alanine; see Lee, J. J., et al, supra.). Construct $U356_{HA}$ contains a stop codon in place of amino acid residue 357 as well as the H273A mutation in $U_{HA}$. Construct N encodes just the first 200 amino acids of twhh. Construct C has had the codons for residues 31-197 deleted. 17(*b*) shows in vitro translation of the expression constructs shown schematically in part a. Constructs were translated in vitro in the presence of $^{35}$S methionine and analyzed by autoradiography after SDS-PAGE. The protein products are shown schematically to the left. Lanes 1 and 6: Auto-proteolysis of the full-length ($U_{SS}$) protein creates two fragments, an N-terminal fragment (Nss) and a C-terminal fragment (C). Lane 2: Construct $U_{HA}$ only makes an uncleaved form of twhh protein that comigrates with $U_{SS}$twhh via auto-cleavage. Lane 5: Construct C encodes processed and unprocessed forms which are visible as two bands migrating closely together. The bottom band is the C protein made from auto-proteolysis of the $U_{SS}$ (Δ31-197). All constructs were made by in vitro mutagenesis of expression construct T7TStwhh (see FIG. 15) using the method of RPCR. The sequence of all constructs were confirmed by dideoxy sequencing. In vitro translations were performed according to manufacturer's instructions (Promega).

The vertebrate hh proteins encoded by shh, twhh and mouse-shh/Hhg-1 also undergo auto-proteolysis to yield two smaller species from a single larger precursor (Lee, et al, supra; Chang, et al, supra; see lanes 1 and 6 in FIG. 17*b*). The invariant histidine to alanine mutation to generate a construct encoding a form of the twhh protein that is not auto-proteolytically cleaved ($U_{HA}$). We have also introduced a nonsense codon and deleted a segment of coding sequence to generate constructs that produce either the amino- or the carboxy-terminal domains of twhh (N and C, respectively; see lanes 4 and 5 in FIG. 17*b*); constructs are schematically diagrammed in FIG. 17*a*). To target these proteins to the secretory pathway, all constructs retained the normal twhh signal sequence.

Synthetic mRNAs transcribed from these constructs were injected to examine the role of processing and to assay the activities of individual protein fragments; the results are summarized in Table I and are based on the activities presented in FIG. 15. The most striking conclusion from these experiments is that N and C both exhibit activity, and that these activities are distinguishable. Thus, although both N and C are capable of ectobpicaily activating pax-2 in the developing eye, thereby providing an internal injection control, only N was capable of efficiently repressing pax-6 (FIG. 16). Later effects on lens development were also more extreme for N, consistent with the role of pax-6 in lens development suggested by its mutant phenotypes in mice. (See Ton, C. C., et al, *Cell* 67:1059-1074, 1991; Glaser, T., et al, *Nat. Genetics* 2:232-239, 1992; Hill, R. E., et al, *Nature* 354:522-525, 1991; Hogan, B. L., et al, *J. Embryol. Exp. Morph.*, 97:95-110, 1986; and Hogan, B. L., et al., *Development*, 103 Suppl.: 115-119, 1988.)

In considering the activity of delta N—C, it is important to recognize the activity of endogenous hh genes in these experiments, which are inhibited by delta N—C and fragments thereof. (see Example 18 and FIG. 18 for further discussion).

The uncleaved $U_{HA}$ protein is only somewhat less active than C in inducing pax-2, but it also was not able to repress pax6 efficiently (FIG. 16). The latter is particularly notable since the $U_{HA}$ protein ($U356_{HA}$; see FIGS. 17*a*, *b*) has activities not significantly different from N (FIG. 16). Thus, in addition to carrying determinants important for auto-proteolysis and pax-2-induction, the C-terminus also contains a domain inhibitory to N-terminal function when in the context of the uncleaved hh protein. The C-terminus can also inhibit N action by an intermolecular mechanism (Lai, et al, supra). The existence of such an inhibitory domain in C suggests that if autoproteolyis can be modulated, such modulation might regulate the activity of hh in vivo. This possibility highlights the importance of ascertaining the processed state of hh proteins expressed in any particular patterning center to understand the potential hh activities generated.

Example 17

Dual Roles of hh Signaling Proteins in Early Eye and Brain Patterning

In understanding the normal roles of N and C in eye and brain patterning, the N and C derivatives of the *Drosophila* hh gene may offer some insight. The *Drosophila* N derivative is retained close to its embryonic site of synthesis in a segmentally striped pattern (Tabata and Kornberg, *Cell,* 76:89-102, 1994; Taylor, et al, *Mech. Dev.,* 42 89-96, 1993), is cell-associated when expressed in cultured cells, and is effectively bound by heparin agarose in vitro, suggesting the possibility of extracellular matrix association. The C-terminal fragment, in contrast, is not bound effectively by heparin agarose, is almost quantitatively released into the culture supernatant of expressing cultured cells, and is only diffusely localized in embryos. Although the activities of individual fragments have not been assayed, the biochemical differences and tissue distributions of *Drosophila* N and C may account for the short and long range nature of the functions associated with hh during *Drosophila* development.

Although the tissue distributions of zebrafish N and C are not known, their activities in ectopic expression assays are also suggestive of short- and long-range functions when considered in the context of normal expression patterns of hh, pax-2 and pax-6. The normal gradient of pax-2 expression in the optic vesicle extends a substantial distance from its maximum adjacent to the site of hh expression in the protuberance; the ability of ectopic C to activate pax-2 therefore suggests that, consistent with the distribution of C in *Drosophila*, zebrafish C may carry out a long-range function. Repression of endogenous pax-6 expression, in contrast, appears to be a short-range function since pax-6 expression occurs close to endogenous hh expression. Efficient repression of pax-6 is an attribute of constructs producing N, and a short-range function for N would be consistent with the distribution of N in *Drosophila*.

Two types of M-dependent activity have been reported for hh-transfected cultured cells. One is the apparent contact-dependent induction of floor plate markers (Roelink, H., et al, *Cell* 76:761-775, 1994); the second induction of sclerotome markers in presomitic mesoderm, is diffusible and acts at long-range.

Example 18

Characterization of *Xenopus* hh

1. Materials and Methods cDNAs encoding full-length *Xenopus* hedgehogs, or encoding amino terminal or carboxy terminal domains linked to secretory leader sequences were transcribed in vitro to yield translatable messenger RNA. The synthetic messenger RNAs, and control mRNAs, were microinjected into the animal poles of cleavage stage *Xenopus* embryos, which were allowed to develop to the blastula stage, at which time the animal cap explants were prepared from the upper one fourth of the embryo. These blastula cap explants were then cultured in vitro in physiological saline in the presence or absence of the transforming growth factor beta family member, recombinant human activin A. All explants were allowed to develop until control embryos had grown to neurula stage, or to tadpole stage. Importantly, blastula caps left untreated differentiate from ectoderm into atypical epidermis. Blastula caps treated with activin differentiate into mesodermal and neural cell types. Thus, the question was whether hedgehog, or its proteolytic derivatives, would change the differentiation of cells away from becoming epidermis, and into another cell type. A second question was whether hedgehog can work with activin to alter the normal response of the tissue to either factor by itself.

Explants were then extracted to yield mRNA by methods commonly used by those of skill in the art, which was used as template with reverse transcriptase to yield cDNA. The cDNA was then used as template with various sets of primers for PCR for specific genes, reverse-transcriptase-polymerase chain reaction, or RT-PCR. This results in specific amplification of radioactive products which are diagnostic for the presence and level of the messenger RNAs which were present in the explants. Samples were separated on polyacrylamide gels, which were exposed to X-ray film to yield the bands shown in the figures. Thus, the darker bands correspond to a greater level of the specific mRNA.

Figure 18A:
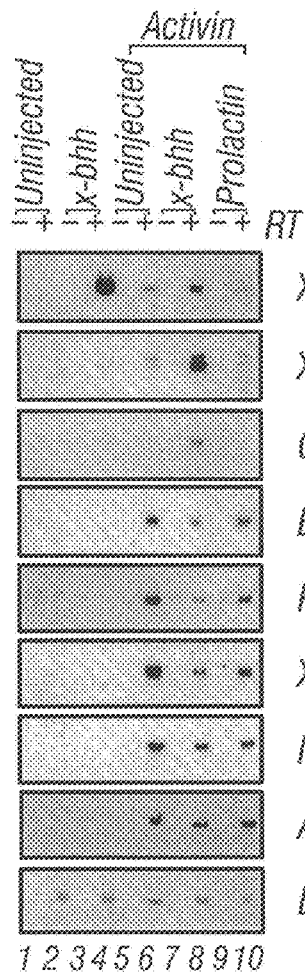
FIGS. 18A and 18B show Northern blot analysis of the effect of hedgehog on expression of various neural markers.

FIGS. 18A and B demonstrate that hedgehog induces pituitary and anterior brain genes, and can cooperate with activin or with neural inducers such as noggin and follistatin which are induced by activin to elevate expression of these genes in explanted embryonic tissue. All odd numbered lanes lack reverse transcriptase in the RT-PCR reaction and are negative controls. All even numbered lanes have this enzyme, and thus give specific bands to mRNA. In Panel A, Lanes 1-2 are control blastula caps, lanes 3-4 are *Xenopus* hedgehog-expressing blastula caps, lanes 5-6 are control blastula caps treated with activin, lanes 7-8 are hedgehog-expressing blastula caps treated with activin, and 9-10 are prolactin-expressing blastula caps treated with activin to serve as a control for simply expressing a secreted protein in the blastula cap. The primers used for the assay are shown to the left of each panel, i.e., XAG 1 is a cement gland marker, XANF1B is a pituitary marker, otx-A is an anterior brain marker, en-2 is a midbrain-hindbrain boundary marker, krox 20 is a rhombomere-specific hindbrain marker, HTHbox 6 is a posterior hindbrain marker, NCAM is a general neural marker, activin is a control for mesoderm induction, and elongation factor is a positive control to shown that all even numbered lanes did in fact have cDNA present.

The panel labelled XANF1B detects a pituitary gene. Lane 4 (panel A) shows that hedgehog induces this pituitary marker, and thus likely pituitary cell types, in blastula cap explants (see also FIG. 20, lane 6, for a stronger signal showing this), when compared to control explants in the absence of hedgehog (lane 2), which do not express this gene. Lane 6 shows that explants treated with activin, in the absence of hedgehog, also express the pituitary gene. Lane 8 shows that explants treated with both hedgehog, and with activin, give highest levels of the pituitary gene. Lane 10 proves that this effect of hedgehog is specific, since prolactin, another secreted protein, does not lead to this elevated level of pituitary gene.

The panel labelled OTX-A detects this anterior brain gene. Lane 4 (and 6 in FIG. 20) shows that hedgehog can induce this neural-specific gene. Lane 8 shows that the level of this neural gene is highest in tissue treated with both activin and hedgehog, relative to hedgehog alone (lane 4), or activin along (lane 6), and control explants do not express this gene (lane 2). Again, this effect is specific to hedgehog, since prolactin (lane 10) did not lead to elevated expression of this gene. The panel labelled XAG-1 detects a cement gland-specific gene, and lane 4 shows that hedgehog induces this gene at high level.

Figure 18B:
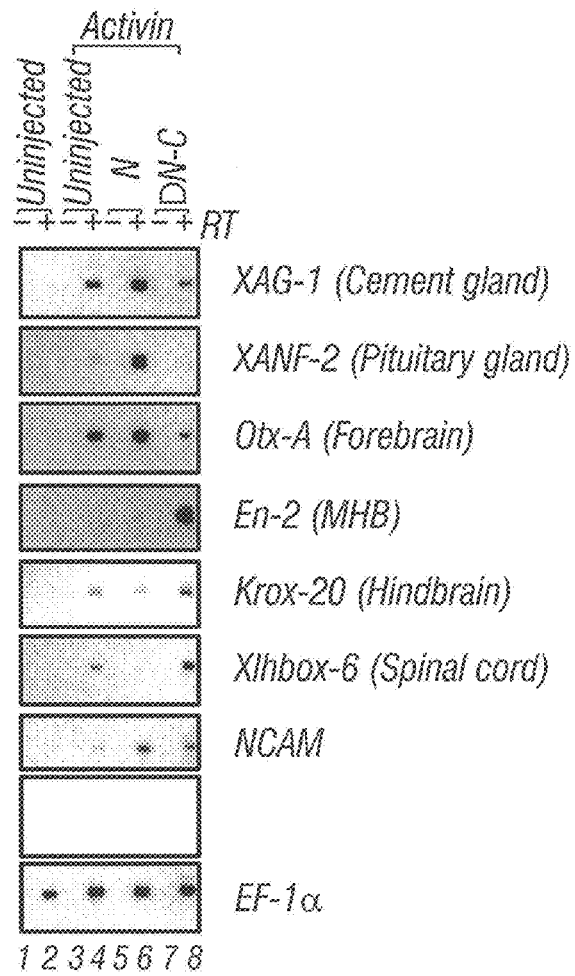

In panel 18B, embryos were injected with N or ΔN-C, and some animal cap explants were treated with activin before culturing until sibling embryos reached tailbud stage. Lanes 1, 2: control animal caps from uninjected embryos. Lanes 3, 4: control animal caps from uninjected embryos, treated with activin. Lanes 5, 6: animal caps from embryos injected with N and treated with activin. Lanes 7, 8: animal caps from embryos injected with ΔN-C and treated with activin. Whereas N displays activities in activin-treated explants similar to those of X-bhh (see B) ΔN-C produces the opposite effect, decreasing anterior and increasing posterior neural marker expression. As shown in FIG. 18B, N behaves like X-bhh in that it induces elevated levels of XANF-2 and Otx-A (lane 6) relative to control activin-treated animal caps (lane 4). Moreover, N also leads to a decrease in the expression of more posterior markers, such as krox-20 and X/Hbox-6, as observed following injection of X-bhh. In contrast to the activity of N (FIG. 4C, lane 6), ΔN-C decreases the expression of the anterior neural genes XANF-2 or Otx-A (FIG. 4C, lane 8) in activin-treated animal caps when compared to uninjected controls (lane 4). Moreover, ΔN-C also leads to an increase in the expression of more posterior markers, such as En-2 and Xlhbox-6.

Figure 19A:
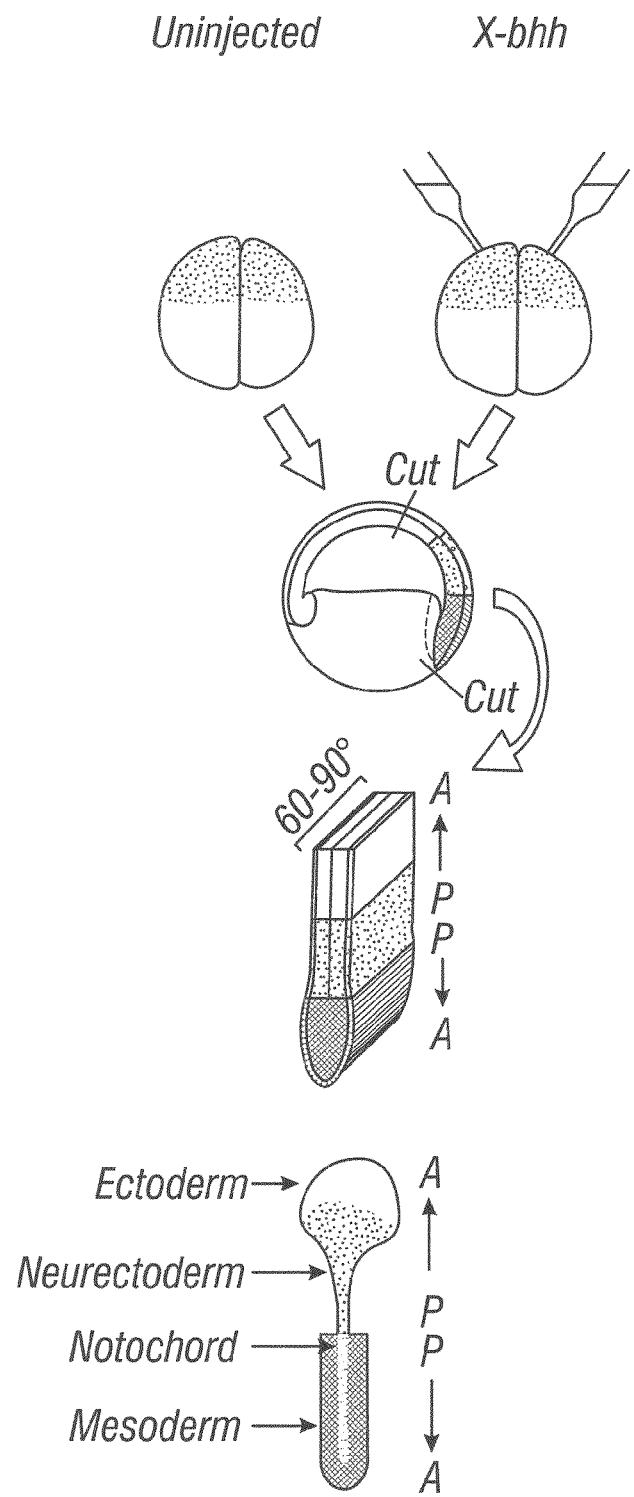
FIGS. 19A and 19B show hh synergy with naturally occurring neural markers or agents (e.g., XAG-1, XANF-2, Otx-A, En-2, Krox-20, Xlh box-6, NCAM, and EF-1α).
Figure 19B:
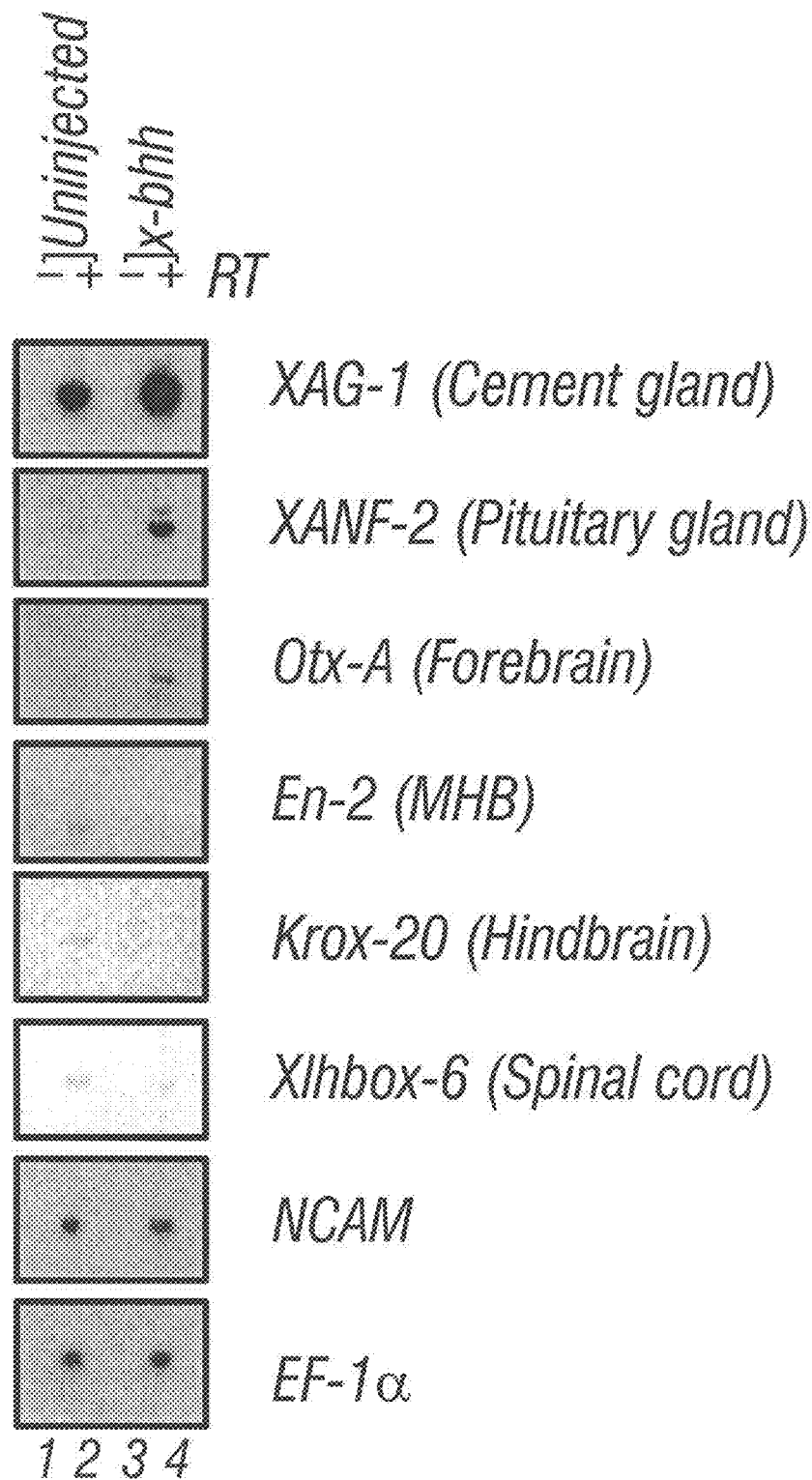

FIG. 19 shows X-bhh modifies the anteroposterior pattern of neural gene expression in explants under the influence of endogenous neural inducers. (A) Isolation of dorsal explants from injected embryos for the preparation of Keller sandwiches (Keller and Danilchik, 1988; Doniach, et al, 1992; redrawn from Doniach, 1993). (B) Keller sandwiches were made from uninjected (lanes 1 and 2) and X-bhh-injected (lanes 3 and 4) embryos, total RNA was isolated when control embryos reached stage 20, and RT-PCR was used to analyze the expression of XAG-1 and neural markers. XAG-1 is a cement gland marker, XANF-2 is an anterior pituitary marker, Otx-A is a forebrain marker, En-2 demarcates the midbrain-hindbrain boundary, Krox-20 marks rhombomeres 3 and 5 of the hindbrain and X/Hbox-6 is a spinal cord marker. N-CAM is a general neural marker whose expression is not restricted along the anteroposterior axis. The EF-1α control demonstrates that a comparable amount of RNA was assayed in each set. Note that expression of XAG-1 and anterior neural markers is stimulated by X-bhh treatment, whereas expression of posterior neural markers is suppressed.

Figure 20A:
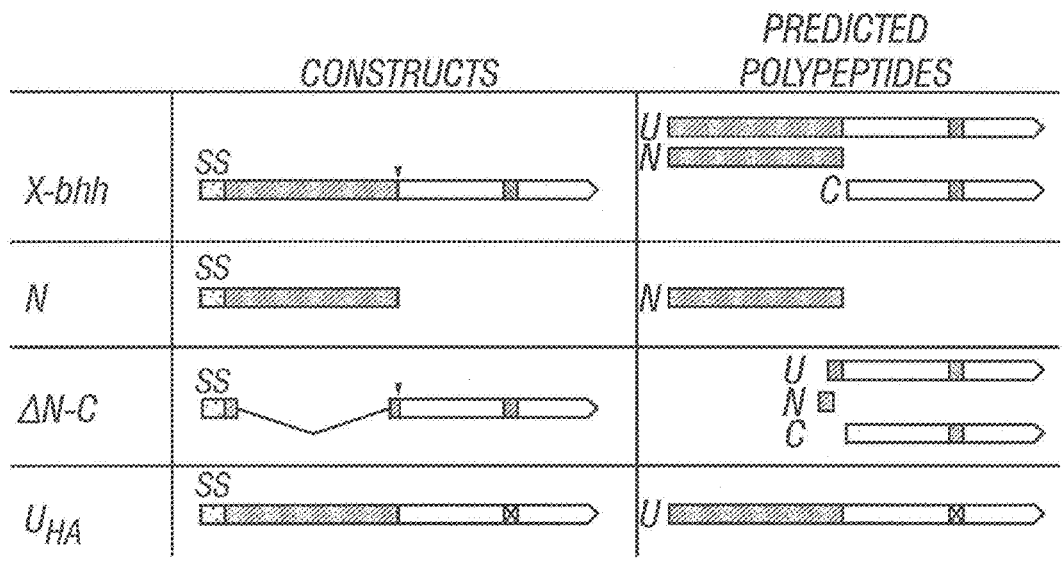
FIG. 20A shows hh constructs including delta N-C.
Figure 20B:
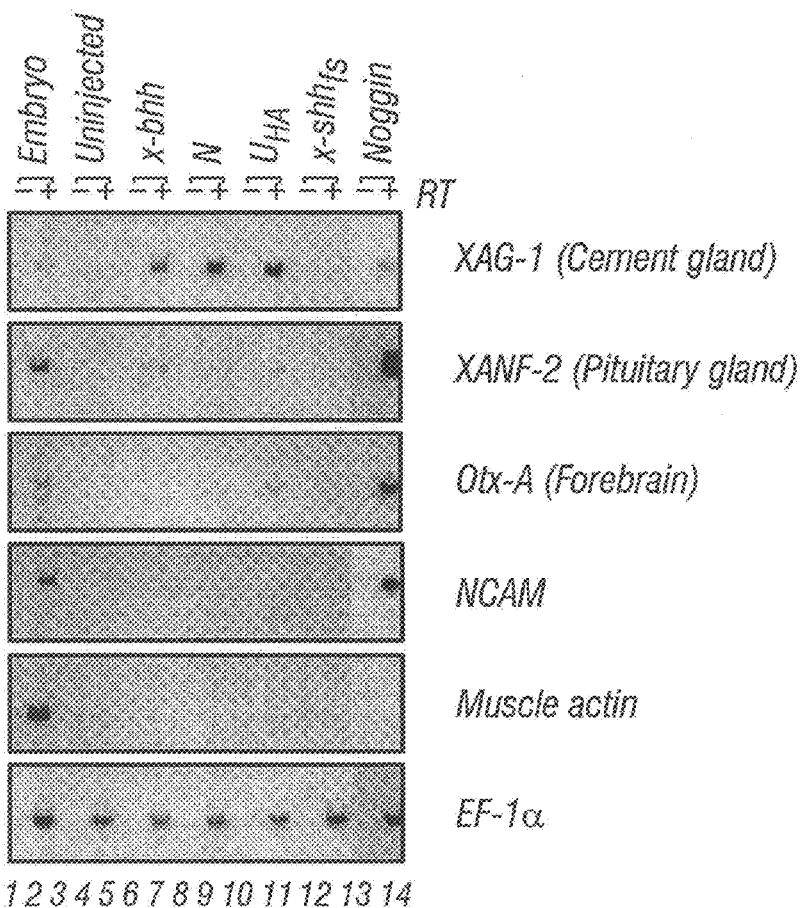
FIG. 20B shows a Northern blot analysis of the effect of hedgehog N or C on various neural markers.

FIG. 20 demonstration of differential activities of N and C domains of hedgehog proteins. As in FIG. 18 above, odd numbered lanes are negative control lanes, and positive numbered lanes show specific gene expression for the markers described above. The N domain of hedgehog is encoded in the construct called Xhh1208 (lane 8), and the C domain is encoded in the construct called Xhh1delta 27-208 (lane 10). The construct Xhhl 1-1270A (lane 12) is specifically mutated so that it is unable to undergo self-processing. The ability of the N and C domains to induce the genes described above is compared to control blastula cap explants (lane 4), entire embryos as a positive control (lane 2), blastula cap explants expressing a mutated hedgehog as a negative control (lane 14), blastula caps expressing the entire hedgehog 1 (lane 6), and blastula cap explants treated with an independent neural inducer, noggin (lane 16) (discovered by Richard Harland at University of California at Berkeley).

Examining the first panel for the cement gland marker XAG-1 clearly shows that intact hedgehog (lane 6) and the N domain (lane 8) and the processing defective hedgehog (lane 12) are much better than inducing the cement gland than is the C domain (lane 1). Examining the second panel demonstrates that the C domain (lane 10) is better at inducing the pituitary gene XANF1B than is the N domain (lane 8). Since the N domain induces the XAG-1 marker better, described in point A above, the two results together clearly demonstrate that the N and C domains have distinguishable activities. Examination of the remaining panels shows that all described activities of the normal hedgehog (lane 6) can be defined in terms of the activities of the N and C domain.

Examining the third panel, for the forebrain gene otx-A, shows that both the N domain (lane 8) and C domain (lane 10) induce similar levels of this gene, but the processing defective hedgehog (lane 12) is better than either at inducing this gene.

Examining the fourth panel of this figure (NCAM), (as well as the FIG. 18 panels EN-2, krox20, XIHbox6, and NCAM), shows that hedgehog does not induces these more posterior neural genes. Notably, noggin (lane 16) is able to induce pituitary gene and forebrain gene, but it also induces the general neural gene, NCAM, which hedgehog does not. This clearly shows that hedgehog is a distinct activity from the neural inducer noggin, and has a more restricted ability to induce neural genes.

Experiments in the *Xenopus* embryo were conducted by injecting full-length hedgehog RNA, and immunoprecipitating with a C-domain specific antibody, which proves that full length hedgehog does in fact get processed in vivo in vertebrates, consistent with the data shown in earlier Examples in *Drosophila*. Thus, the ideas for the utility of detecting hedgehog N and C domains is based on knowledge that such domains do appear through hedgehog processing in vertebrates. Moreover, the knowledge that hedgehog processing does occur in vivo naturally raised the question of whether the resulting N and C domains have independent activity.

The results in FIG. 18 are novel insofar as they establish that the activity of hedgehog in inducing a pituitary gene, and an anterior brain gene, may be enhanced by the TGFβ family of growth factors. This enhancement likely applies to the N and C domains described in FIG. 20, since the genes analyzed are the same. This enhancement is due to hh synergizing with neural inducing factors which are themselves induced by TGF-β family members, including but not limited to such molecules as noggin and follistatin.

The data in FIG. 20 makes several important points. First, the data show that the N and C domains have different though somewhat overlapping activities, and that the N and C activities added together account for all of the observed activity of the intact hedgehog protein. Thus, any clinical or diagnostic uses of hedgehog might be improved by use of the N or C domain, as one generally wishes to use the smallest protein which has an activity for clinical work, as it is less likely to evoke adverse immune responses, or other adverse side effects. Second, the data show that the C domain is better than the N domain in inducing pituitary gene expression and, since it has less induction of cement gland genes that intact hedgehog, or N domain, it suggests that the C domain might be useful in clinical situations where one wishes to enhance the development or expression of the pituitary as specifically as possible. As the pituitary is the source of a number of hormones, any treatment for enhancing pituitary cell growth and activity would ideally have as few side effects as possible, and the C domain is thus a viable candidate for therapies with enhanced pituitary cell growth and function in mind. Third, relating to studies regarding noggin, FIG. 20 shows clearly that while both hedgehog and noggin can induce pituitary gene expression, hedgehog is more specific, since hedgehog does not induce the general neural marker NCAM, whereas noggin induces NCAM as well as pituitary. Fourth, the hedgehog which was mutated to prevent processing (lane 12) is as active as full-length and wild-type hedgehog (lane 6) in inducing pituitary gene expression, but the processing defective hedgehog is better at inducing the forebrain marker otx-A. Thus, for some clinical applications of hedgehog in inducing specific cell types, it is possible that the processing-defective hedgehog will be superior compared to normal hedgehog.

FIG. 21 shows ΔN-C interferes with X-bhh and N activity in animal cap explants. Embryos were injected with various RNAs, animal cap explants were cultured until sibling embryos reached tailbud (stage 25), at which time RT-PCR was used to analyze the expression of the cement gland marker XAG-1 and the control RNA, EF-1α. Lanes 1, 2: control animal caps from uninjected embryos. Lanes 3, 4: animal caps from embryos injected with both X-bhh and prolactin RNAs. Lanes 5, 6: animal caps from embryos injected with box X-bhh and ΔN-C. Lanes 7, 8: animal caps from embryos injected with both N and prolacting RNAs. Lanes 9, 10: animal caps from embryos injected with both N and ΔN-C. The N and X-bhh experiments were conducted independently and thus absolute levels in lanes 3-6 should not be compared to those in lanes 7-10. Note that the induction of XAG-1 expression by X-bhh or N is reduced by co-injection of ΔN-C.

An internal deletion of X-bhh (ΔN-C) blocked the activity of X-bhh and N in explants and reduced dorsoanterior structures in embryos. As elevated hh activity increases the expression of anterior neural genes, and as ΔN-C reduces dorsoanterior structures, these complementary data support a role for hh in neural induction and anteroposterior patterning.

ΔN-C deletes amino acids 28-194 of X-bhh. The primary translation product is predicted to undergo signal sequence cleavage removing amino acids 1-23, and to undergo autoproteolysis. Based on the cleavage site in *Drosophila* hh (Porter, et al, *Nature,* 374:363.1995) autoproteolysis would generate a C domain of X-bhh amino acids 198-409, as well as a predicted seven amino acid polypeptide, representing amino acids 24-27, and 195-197 (Lai, et al, *Development* 121:2349. 1995). Analysis of the effect of ΔN-C on neural markers was by standard methods including Northern blot analysis and in situ hybridization (Lai, et al, supra, incorporated herein by reference).

Although ΔN-C does not induce the cement gland marker XAG-1, it decreases the expression of anterior ectodermal and neural markers in activin-treated animal caps. Thus, ΔN-C has the capacity to affect neural patterning. ΔN-C also promotes an increase in posterior neural markers in activin-treated animal caps. Mixing ΔN-C with N or full length X-bhh at a 1:1 ratio led to a dramatic inhibition of the induction of cement gland in animal cap assays, supporting the hypothesis that ΔN-C interfered with X-hh.

Example 19

Cholesterol Modification of Hedgehog Polypeptide

In addition to peptide bond cleavage, Hh autoprocessing causes the covalent attachment of a lipophilic adduct to the COOH-terminus of Hh-$N_p$ (J. A. Porter et al., *Cell* 86, 21, 1996). This modification is critical for the spatially restricted tissue localization of the Hh signal; in its absence, the signaling domain exerts an inappropriate influence beyond its site of expression (J. A. Porter et al., *Cell* 86, 21, 1996). Physical and biochemical characterization of this lipophilic adduct indicates that it is not the glycosyl phosphatidyl inositol (GPI) anchor, the only other known lipophilic modification associated with secreted cell surface proteins in eukaryotes (S. Udenfriend and K. Kodukula, *Annu. Rev. Biochem.* 64, 563, 1995; and P. J. Casey, *Science* 268, 221, 1995).

In vitro studies of Hh autoprocessing were performed using a bacterially expressed derivative of the *Drosophila* protein, $His_6$Hh-C, in which the majority of the $NH_2$-terminal signaling domain and the signal sequence are replaced by a hexa-histidine tag. Cleavage of this protein occurs between residues corresponding to Gly 257 and Cys 258 (J. A. Porter et al., *Nature* 374, 363, 1995) and likely proceeds through a labile thioester intermediate formed by the cysteine thiol and the glycine carbonyl carbon. In the presence of high concentrations of thiols or other small molecules with strongly nucleophilic properties at neutral pH, cleavage of the peptide results from nucleophilic attack upon the thioester carbonyl, causing displacement of the thiol group and formation of an adduct to Gly 257 by the attacking nucleophilic (FIG. 22A). Thus, in reactions with 50 raM dithiothreitol, in vitro cleavage of $His_6$Hh-C proceeded to greater than 50% completion within three hours at 30° C. (FIG. 22B). At 1 mM dithiothreitol, however, the reaction yielded no visible cleavage product (FIG. 22B).

FIG. 22 shows lipid stimulation of Hh autoprocessing in vitro. Panel A illustrates the mechanism of Hh processing. The reaction is initiated by formation of a thioester between the thiol side chain of cysteine 258 and the carbonyl carbon of glycine 257, and N to S shift. This activated intermediate then undergoes a nucleophilic attack by DTT in vitro or by a piophilic nucleophilic in vivo resulting in cleavage as well as a formation of a covalent adduct at the carboxy-terminus of the amino-terminal product, X denotes the attacking nucleophilic. Panel B shows a coomassie blue stained SDS-polyacrylamide gel showing in vitro autocleavage reactions of the bacterially expressed His6Hh-C protein (~29 kD) incubated for 3 hours at 30° C. with no additions (lane 1), 50 mMDTT (lane 2), 1 mMDTT (lane 3), or 1 mMDTT plus bulk S2 cell lipids (lane 4). The Hh-C product of the autoprocessing reaction migrates as an ~25 kD species (lanes 2 and 4); the ~5 kD $NH_2$-terminal product is not resolved in this gel.

The in vivo reaction resulted in lipophilic modification of the $NH_2$-terminal signaling domain. The most direct mechanism by which this could occur, by analogy to the in vitro mechanism (FIG. 22A), would be for a lipid to function as the displacing nucleophilic in attack of the thioester. To explore this possibility, bulk lipids extracted from *Drosophila* S2 cultured cells (I. Schneider, *J Embryol Exp Morph* 27, 353 (1972); and F. M. Ausubel et al., *Current protocols in molecular biology* (Greene Publishing Associates and Wiley-Interscience, New York, 1995) were added to the in vitro processing reaction in the presence of 1 mM dithiothreitol. Cleavage was observed and the reaction proceeded to 20% completion in a three hour period (FIG. 22B). The reaction continues beyond this time and reaches ~50% completion by 18 hours.

To identify the components active in the reaction, the bulk S2 lipids were separated into two classes, neutral and complex, by silicic acid column chromatography (W. W. Christie, *Lipid analysis* (Pergamon, Oxford, ed. 2nd, 1982). FIG. 23A is a thin layer chromatography (TLC) plate coated with silica gel G (Merck) showing the fractionation of bulk S2 cell lipids using a heptane:ether:formic acid solvent (80:20:2). Six major spots are visualized by acid charring and are indicated by letters A-F. FIG. 23B is a Coomassie blue-stained SDS-polyacrylamide gel showing in vitro autocleavage reactions of the bacterial expressed $His_6$Hh-C protein incubated with 1 mMDTT plus either unfractionated S2 cell lipids (lane 1), or spots A through F (lanes 2-7, respectively). Addition of lipid spot B but no other resulted in processing of $His_6$Hh-C protein. FIG. 23C is TLC of S2 cell lipids (lane 1) along with selected lipid standards: phospha-tidylcholine (lane 2), a diacylglycerol (lane 3), cholesterol (lane 4), stearic acid (lane 5), a tnacylglycerol (lane 6), and cholesteryl ester (lane 7). Lipid spot B comigrates with cholesterol, as also demonstrated by mixing radio-labeled cholesterol with S2 lipids before TLC fractionation. FIG. 23D is a Coomassie blue stained SDS-polyacrylamide gel showing that relative to 1 mMDTT alone (lane 1) cholesterol (0.35 mM)+1 mMDTT (lane 2) stimulates $His_2Hh-C$ autocleavage in vitro. FIG. 23E is an autoradiogram of electrophoretically-resolved products of $His_6Hh-C$ autocleavage reactions driven by 20 mMDTT (lane 1) or 1 mMDTT+0.35 mM cholesterol (lane 2). For lane 1 [$^3H$]cholesterol (3 µCi) was added at the end of the incubation period just prior to electrophoresis; for lane 2[$^3H$]cholesterol was present throughout the incubation period and is incorporated into the amino-terminal product of the reaction. To resolve the ~5 kD product of His6Hh-C autocleavage, reaction products were separated in 17% SDS-polyacrylamide gels.

The activity was found exclusively in the neutral class, so the lipids were subjected to preparative thin layer chromatography (TLC) using a solvent system that resolved neutral lipids (W. W. Christie, *Lipid analysis* (Pergamon, Oxford, ed. 2nd, 1982) (FIG. 23A). Lipid spots were visualized with iodine vapor or acid charring, and adsorbent at the corresponding positions of identical uncharred plates was excised and extracted with chloroform/methanol/water. Only lipids extracted from spot B displayed stimulatory activity in the in vitro cleavage reaction (FIG. 23B).

With the use of various lipid standards, it was found that spot B comigrated with cholesterol (FIG. 23C). In addition, the active S2 cell-derived lipid displayed the same mobility as cholesterol in two other solvent systems and gave a positive color test when sprayed with a specific reagent that reacts with sterols; W. W. Christie, *Lipid analysis* (Pergamon, Oxford, ed. 2nd, 1982); and R. R. Lowry, *Journal of Lipid Research* 9, 397, 1968). Taken together these results imply that the active lipid component is in the sterol fraction of the S2 lipids. Indeed, it was found that cholesterol, which is the principal sterol in eukaryotic cell membranes (W. W. Christie, *Lipid analysis* (Pergamon, Oxford, ed. 2nd, 1982)), displayed stimulatory activity similar to that observed with lipids extracted from spot B when added in pure form to the in vitro processing reaction (FIG. 23D). To establish that the stimulatory activity of cholesterol is a result of its participation as a modifying group, it was shown that $^3H$-labeled cholesterol added to the 1 mM dithiothreitol reaction was incorporated into the $NH_2$-terminal product (FIG. 23E). No incorporation was seen, however, when [$^3H$]cholesterol was added just prior to electrophoresis to a reaction incubated for 3 hours with 20 mM dithiothreitol (FIG. 23E). Also consistent with covalent cholesterol addition, the $NH_2$-terminal fragment of $His_6Hh-C$ generated by the cholesterol-driven reaction migrated just beneath the 6 kD marker, whereas the product of the reaction driven by 20 mM dithiothreitol migrated just above this marker (FIG. 24A). Such a shift in mobility, thought to result from an increase capacity for SDS binding to the covalently linked lipid (M. L. Cardoso de Almeida and M J. Turner, *Nature* 302, 349, 1983), was also noted for Ffh-$N_f$, as compared to the precisely truncated $NH_2$-terminal fragment (Hh-N, truncated following Gly257).

The part of the sterol most likely to act as attacking is the 3P hydroxyl. Such an attack would leave cholesterol as a covalent adduct in ester linkage to the carboxylate of the terminal residue of the NH2-terminal fragment (GLY 257). FIG. 24A shows Coomassie stained gels of $His_6Hh-C$ autocleavage reactions carried out in the presence of 20 mMDTT (lane 1), or 1 mMDTT+0.35 mM cholesterol (lane 2). Lane 3 contains a mixture of the samples loaded in lanes 1 and 2. The amino-terminal product of the cholesterol driven reaction migrates approximately 2 kD faster than the DTT-driven reaction fragment. FIG. 24B is Coomassie stained gels showing protein products of $His_6Hh-C$ autocleavage reactions carried out in the presence of 1 mM DTT+0.35 mM cholesterol (lanes 1 and 2) or with 20 mM DTT (lane 3). Prior to loading the gel, samples in lane 2 and 3 were incubated for 60 minutes with 50 mMKOH in 90% methanol (M. C. Field and A. K. Menon, in *Lipid modification of proteins* N. M. Hooper, A. J. Turner, Eds. (Oxford University Press, New York 1992) pp. 155). Base treatment causes the cholesterol-driven amino-terminal reaction product to comigrate with the corresponding DTT-driven reaction product.

FIG. 24C is an autoradiogram of immunoblotted Hh amino-terminal domains purified from cultured S2 cells. Amino-terminal domains were derived either from a construct truncated after glycine 257 (Hh-N lanes 1, 3, 4, 8, and 9) or from a construct encoding wild-type Hh that produces the amino-terminal domain via the processing reaction (Hh-$N_P$, lane 2, 3, 5, 6, 7, 8, and 9). Proteins were either directly loaded (lanes 1 and 2) or base-treated (M. C. Field and A. K. Menon, in *Lipid modification of proteins* N. M. Hooper, A. J. Turner, Eds. (Oxford University Press, New York 1992) pp. 155) for 5 minutes (lane 5), 20 minutes (lane 6) or 1 hour (lanes 7 and 4) prior to electrophoresis. Lane 3 contains a mixture of the samples loaded in lanes 1 and 2, lane 8 contains a mixture of the samples loaded in lanes 7 and 4, and lane 9 contains a mixture of the samples loaded in lanes 7 and 2. Upon base treatment, Hh-$N_p$ undergoes a shift in mobility from 18.5 kD to 19.5 kD, the mobility of the unmodified Hh-N protein.

Figure 25A:
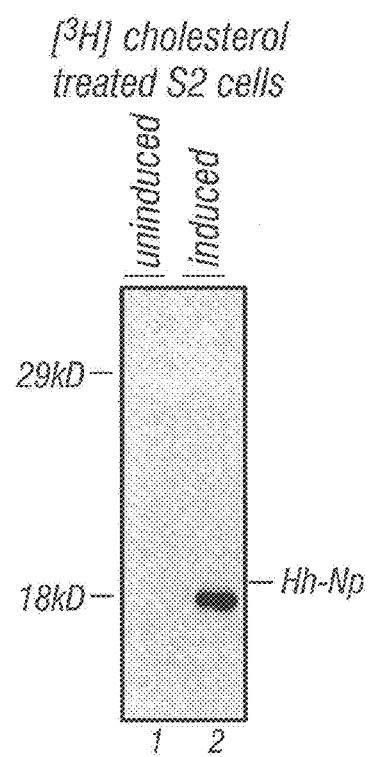
FIG. 25A is an autoradiogram of a gel loaded with total cell proteins from S2 cells containing a stably integrated Cu++-inducible hedgehog gene.
Figure 25B:
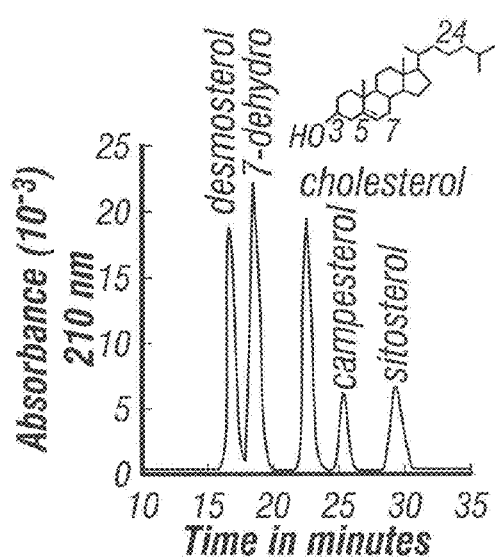
FIG. 25B is an HPLC profile of sterols separated on a C18 column by isocratic elution with a solvent containing methanol:ethanol:water (86:10:4).
Figure 25C:
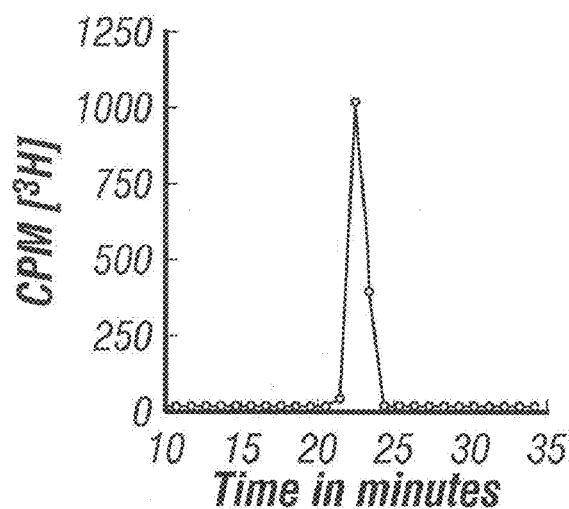
FIG. 25C shows HPLC analysis as in FIG. 25B of the adduct released by base treatment of Hh-$N_p$ metabolically labeled with [3H]cholesterol (A).
Figure 25D:
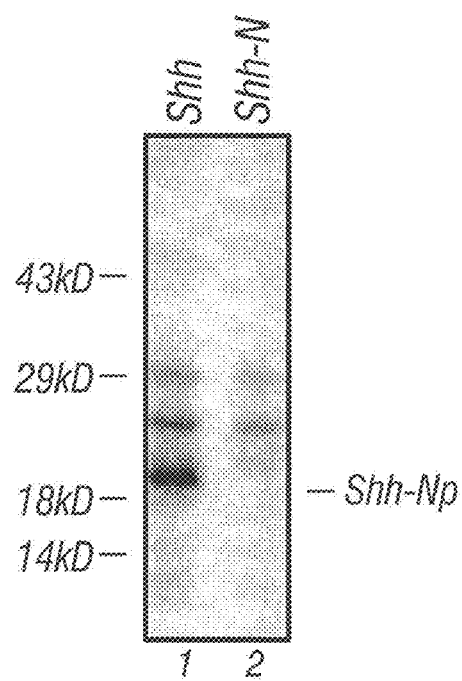
FIG. 25D shows metabolic labeling of vertebrate Sonic hedgehog protein with [3H]cholesterol. Autoradiogram of a gel loaded with total cell proteins from COS-7 cells transfected with a wild-type Sonic hedgehog expression construct (Shh, lane 1) or a construct that generates an unprocessed amino-terminal protein truncated after the conserved glycine at the site of autocleavage (Shh-N, lane 2).
Figure 26A:
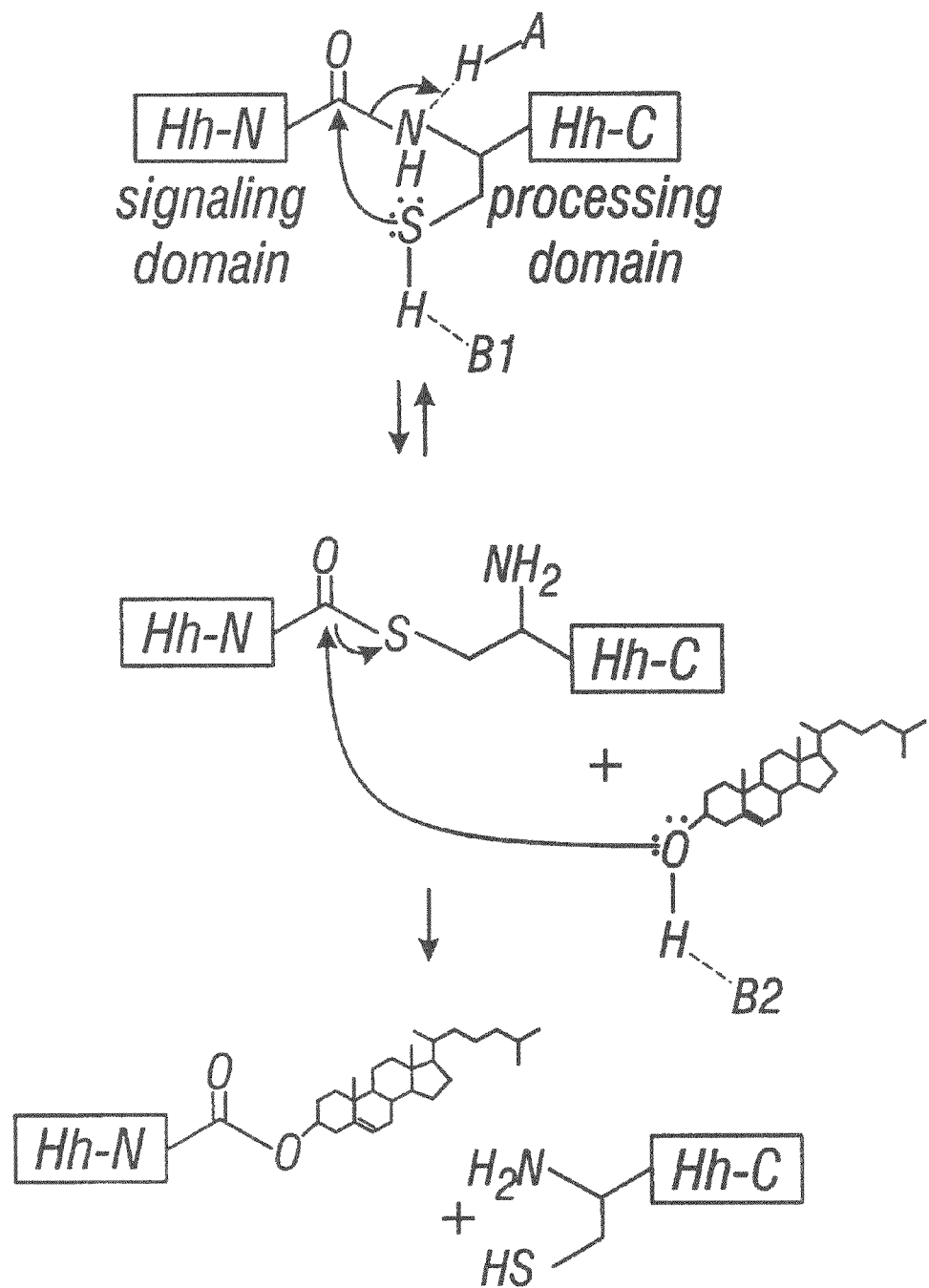
FIG. 26A is a schematic drawing of a two-step mechanism for Hh autoprocessing. Aided by deprotonation by either solvent or a base (B1), the thiol group of Cys-258 initiates a nucleophilic attack on the carbonyl carbon of the preceding residue, Gly-257. This attack results in replacement of the peptide bond between Gly-257 and Cys-258 by a thioester linkage (step 1). The emerging α-ammo group of Cys-258 likely becomes protonated, and an acid (A) is shown donating a proton. The Thioester is subject to a second nucleophilic attack from the 3β-hydroxyl group of a cholesterol molecule, shown here facilitated by a second base (B2), resulting in a cholesterol-modified amino-terminal domain and a free carboxy-terminal domain. In vitro cleavage reactions may also be stimulated by addition of small nucleophiles including DTT, glutathione, and hydroxylamine.
Figure 26B:
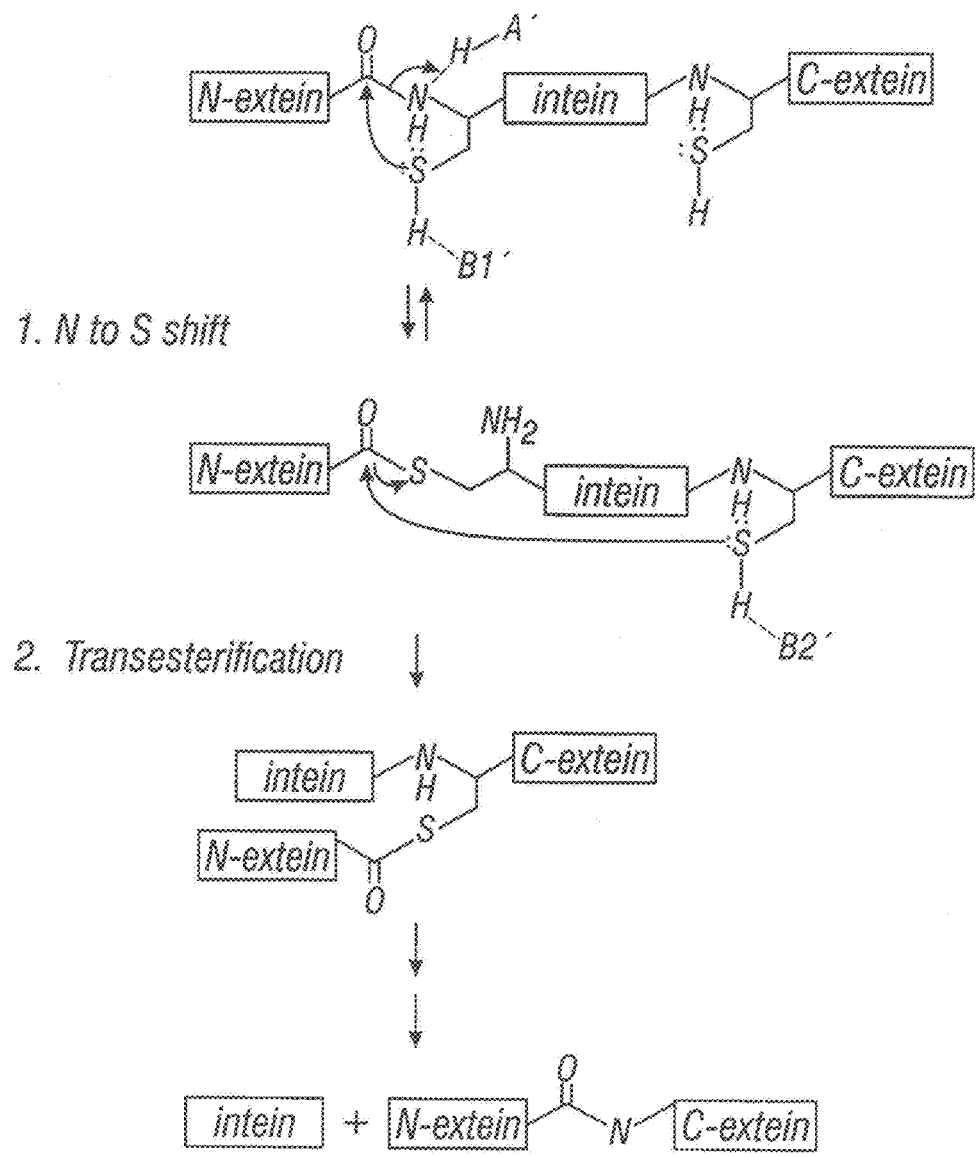
FIG. 26B is a schematic drawing of a mechanism for intein self-splicing. A base (B1') or solvent deprotonates a cysteine or serine residue at the N-extein/intein junction (shown here as a cysteine residue) for attack on the carbonyl group of the preceding amino-acid residue resulting in the formation of a thioester/ester intermediate. An acid (A') may protonate the α-amino group of the cysteine/serine residue promoting its release. The thioester/ester is then subject to a second nucleophilic attack from a cysteine, serine, or threonine residue at the intein/C-extein junction (shown here as a cysteine residue). A second base (B2') is shown facilitating deprotonation of the second nucleophile, although this function may also be carried out by B1'. This reaction produces a branched protein intermediate that ultimately resolves to a free intein and ligated exteins.
Figure 27:
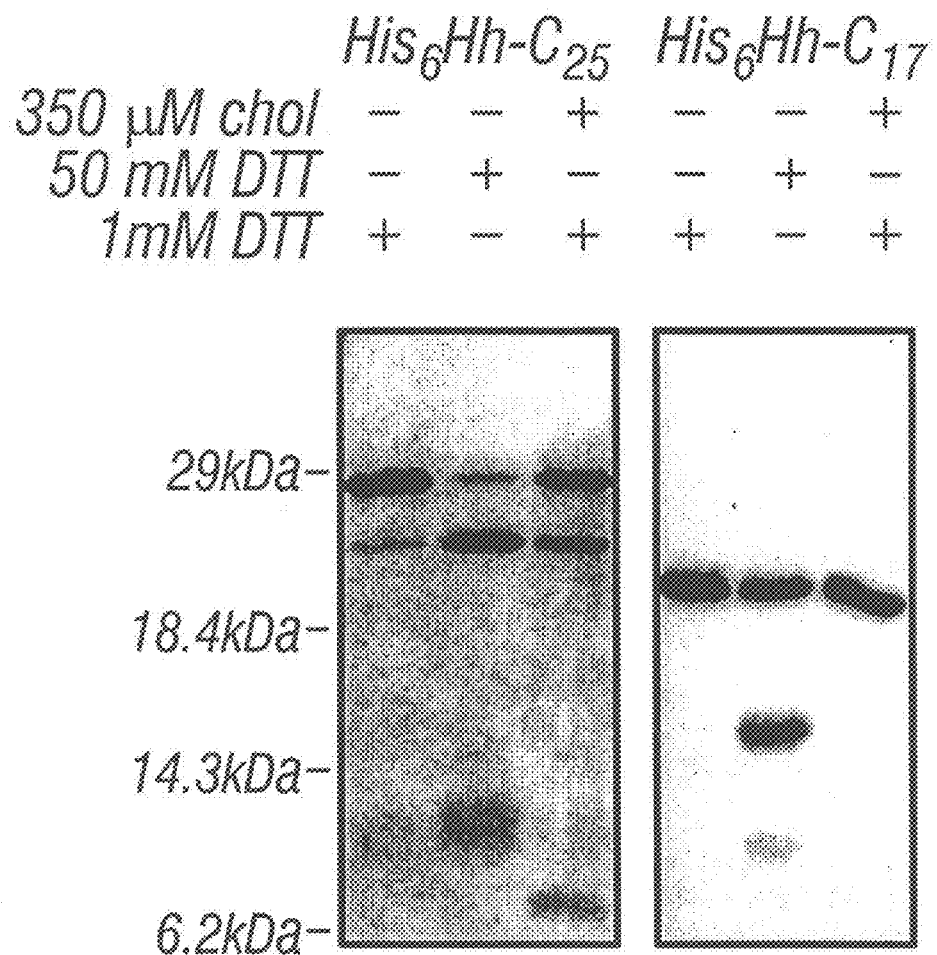
FIG. 27 is a Coomassie Brilliant Blue-stained SDS-polyacrylamide gel showing in vitro autocleavage reactions of bacterially-expressed $His_6Hh-C_{25}$ (lanes 1-3) and $His_6Hh-C_{17}$ (lanes 4-6) proteins. Proteins were incubated with 1 mM DTT (lanes 1 and 4), 50 mM DTT (lanes 2 and 5) or 350 μM cholesterol/1 mM DTT (lanes 3 and 6). The uncleaved $His_6Hh-C_{25}$ protein migrates as a ~29-kDa species, and the carboxy-terminal cleavage product of this protein migrates as a ~25-kDa species (Porter et al., 1996). The uncleaved $His_6Hh-C_{17}$ protein migrates as a ~21-kDa species, and the carboxy-terminal product of this truncated protein migrates as a ~14-kDa species. The amino-terminal product of the $His_6Hh-C_{25}$ and $His_6Hh-C_{17}$ proteins migrates as a ~7-kDa species when DTT-modified or as a ~5-kDa species when cholesterol-modified. $His_6Hh-C_{17}$ was also incubated with 46 μM [3H]cholesterol/1 mM DTT, and no cholesterol-modified product was detected by autoradiography. A cholesterol-transfer activity 1% of wildtype could have been detected by this radioassay.

Ester bonds are subject to hydrolysis in alkaline conditions and base treatment prior to electro-phoresis indeed reduced the migration of the cholesterol-driven reaction product to a position coinciding with that of the dithiothreitol-driven reaction product. These results are consistent with stimulation of the in vitro processing reaction by direct nucleophilic attack of cholesterol on the thioester intermediate to form an ester-linked adduct. If processing of Hh also results in formation of an ester-linked cholesterol adduct in vivo, then the protein-lipid linkage should be subject to base hydrolysis with a concomitant shift in electrophoretic mobility of the protein (normally 18.5 kD). The immunoblot in FIG. 24C shows the base-induced appearance of a species of reduced mobility (19.5 kD), which increased in abundance from ~⅓ of the total after five minutes of treatment to most of the immunoreactive protein after one hour. This novel species comigrated with truncated, unprocessed Hh-N, which is not affected by base treatment. These data are consistent with an ester bond as the protein-lipid linkage in Hh-$N_p$. To confirm the involvement of cholesterol in formation of the Hh-$N_p$ adduct in vivo, S2 cells containing an inducible wild-type Hh construct were metabolically labeled with [$^3H$]cholesterol. FIG. 25A is an audio-radiogram of a gel loaded with total cell proteins from S2 cells containing a stably integrated Cu++-inducible hedgehog gene. Prior to harvesting, these cells were grown in media supplemented with [$^3H$]cholesterol in the absence (lane 1) or presence (lane 2) of 1 mM CuS04. [$^3H$]cholesterol incorporation is dependent upon Cu++ induction (lane 2) and is restricted to a single protein species migrating at a position corresponding to Hh-$N_p$. FIG. 25B is an HPLC profile of sterols separated on a C18 column by isocratic elution with a solvent containing methanol:ethanol:water (86:10:4) (R. J. Rodriguez and L. W. Parks, *Methods of Emymology* 111, 37, 1985). ~5 µg of each sterol was mixed, loaded, and elution monitored by absorbance at 210 nM. The structure of cholesterol is shown above cholesterol peak. Other sterols include:

1) 10 desmosterol, which contains one additional double bond between carbon 24 and 25; 2) 20 7-dehydrocholesterol, which contains one additional double bond between carbon 7 and 8; 3) campesterol which contains an additional methyl group on carbon 24; and 4) sitosterol, which contains an additional ethyl group on carbon 24. FIG. 25C shows HPLC analysis as in (B) of the adduct released by base treatment of Hh-N$_p$ metabolically labeled with pHlcholesterol (A). The radioactive species recovered from the metabolically labeled protein collates with cholesterol. FIG. 25D shows metabolic labeling of vertebrate Sonic hedgehog protein with [$^3$H]cholesterol. Autoradiogram of a gel loaded with total cell proteins from COS-7 cells transferred with a wild-type Sonic hedgehog expression construct (Shh, lane 1) or a construct that generates an unprocessed ammo-terminal protein truncated after the conserved glycine at the site of autocleavage (Shh-N, lane 2). The COS-7 cells were incubated in culture medium supplemented with [$^3$H]cholesterol for 24 hours prior to and 36 hours after transfection (COS-7 cells grown at 37° C. in DMEM supplemented with 10% fetal calf serum were plated at −35% confluence onto two 35 mm dishes in 1 ml of Optimem media (Gibco) containing 1.5% fetal bovine sera and 25 µCi of [$^3$H]cholesterol, giving ~40 µg/ml as the final concentration of cholesterol with a specific activity of 2 Ci/mmol (labeling medium). After 24 hours the labeling medium was removed and the cells were transfected for 6 hours with Shh or Shh-N expression constructs using lipofectamine (Gibco) and serum-free DMEM media. After transfection, 1 ml of fresh labeling medium was added to each dish and the cells were incubated for 36 hours at 37° C. The cells were then harvested without washing, lysed on the plate with Tris buffered saline plus 1% Triton X-100 and the total cell proteins were precipitated with acetone, washed and analyzed as described above for the S2 cell proteins). A strongly labeled species with the Shh but not Shh-N construct. Several other less heavily labeled species are apparent in both lanes, and may represent other cholesterol-modified proteins.

After 48 hours of growth in the presence of [$^3$H]cholesterol, induced and uninduced cultured cells were detergent extracted and total cell proteins were subjected to SDS-PAGE followed by fluorography (Metabolic labeling of S2 cultured cells with [$^3$H]cholesterol was performed essentially as described (Silberkang, et al, *J. Biol. Chem.* 258:8503. 1983). Briefly, cells containing a stably integrated Cu$^{++}$-inducible hedgehog gene were grown at 23° C. for two weeks in Schneider cell media (Gibco) containing a 5% fetal bovine serum depleted of lipoprotein (low cholesterol media, ~20 µg/ml cholesterol). These cells were then plated at 40% confluence onto two 35 mm tissue culture dishes (Nunc) in 1 ml of low cholesterol media supplemented with 300 µCi of labeled cholesterol, [1.2.6.7-$^3$H(N)] 65 Ci/mM (NEN) giving a specific activity for cholesterol in tins medium of ~5 Ci/mmol. After 24 hours (1 doubling time) one plate of cells was induced to express Hh protein by the addition of CuSO$_4$ (1 mM final concentration). After an additional 24 hours the cells from both dishes were harvested, lysed in Tris buffered saline containing 1% Triton X-100, and total cell protein was precipitated with 5 volumes of cold acetone. The protein pellet was resuspended in 2% SDS in H$_2$O and reprecipitated with acetone several times to remove unincorporated radioactivity prior to loading onto SDS polyacrylamide gels for analysis. Initial labeling experiments in which 25 µCi of cholesterol was added resulted in ~10 fold decrease in extent of label incorporated into the inducible Hh-N$_p$ protein). Whereas uninduced cells showed no incorporation of [$^3$H]cholesterol into cellular proteins, cells induced to express Hh showed a single strong band with a mobility corresponding to that of Hh-N$_p$ (FIG. 25A). Given the hydrophobic character of Hh-N$_p$, these results suggest that either cholesterol itself or a sterol derivative constitutes the lipophilic adduct of Hh-N$_p$. To determine whether cholesterol is the final form of the adduct, radio-labeled Hh-N$_p$ protein excised from a gel was base-treated to release the adduct, which was then isolated by either extraction (HPLC analysis of the Hh-N$_p$ adduct involved gel isolation of the radioactive band, KOH/methanol treatment of the band to break the ester linkage as described, followed by neutralization of the solution with acetic acid, drying in a speedvac, resuspension in H$_2$O and extraction of the hydrophobic radioactivity with ether. After evaporation of the ether the sample was resuspended in isopropa-nol and applied to the C18 column for analysis. Radio-labeled adduct was then subjected to analysis by HPLC with a method specifically designed to resolve various sterols (R. J. Rodriguez and L. W. Parks, *Methods of Enzymology* 111, 37, 1985) (FIG. 25B). The radioactive adduct released from Hh-N$_p$ eluted at the same position as the cholesterol standard, and no radioactivity was detected in any other fraction (FIG. 25C).

The amount of radioactive cholesterol incorporated is consistent with that expected if all of the Hh-N$_p$ synthesized upon induction received a cholesterol adduct (The specific activity of [$^3$H]cholesterol in the S2 cell labeling medium was ~5 Ci/mmol. Assuming after a 24 hour doubling time that this concentration approximately represents that within the S2 cell membrane, then any protein subsequently expressed and receiving cholesterol as an adduct would also be labeled at the same specific activity. As determined by standardized coomassie blue staining, ~50-100 ng or 2.5 to 5 picomoles of Hh-N$_p$ is produced by one 35 mm dish of S2 cells containing the Cu$^{++}$-inducible Hh construct during 24 hours of induction with 1 mM CuSO$_4$ (13). This predicts ~12.5 to 25 nCi or $2.75 \times 10^4$ to $5.5 \times 10^4$ dpm of radioactivity would be incorporated into Hh-N$_p$ protein produced in our labeling experiment assuming it is cholesterol modified. Total incorporation of radioactivity into Hh-N$_p$ during the in vivo labeling experiment described above was measured at ~$5 \times 10^4$ dpm by excision and scintillation counting of an Hh-N$_p$ gel band), suggesting that other cellular components do not complete effectively as nucleophilic adducts in the in vivo autoprocessing reaction. Also consistent with a homogenous adduct, the mass of cholesterol is consistent with the mass previously measured by mass spectrometry of processed protein purified from cultured cells. A recent MALDI mass spectral analysis gave a mass of ~430 daltons for the Hh-N$_p$ adduct, ~9% larger than the mass of cholesterol (386.6). Detection of this modification required that Hh-N$_p$ be treated with CNBr/70% formic acid, i.e. full length Hh-N$_p$ could not be detected. The mass discrepancy noted above could be accounted for by the net addition of formic acid (45 daltons) during CNBr digestion. This reaction could involve the addition of H$_2$O across the 5,6 double bond of cholesterol, a common reaction of secondary alkenes in strong acids [R. T. Morrison, R. N. Boyd, *Organic Chemistry* (Allyn and Bacon, Boston, ed. 3rd, 1973)], followed by esterification of formate via this newly formed alcohol [B. I. Cohen, G. S. Tint, T. Kuramoto, E. H. Mosbach, *Steroids* 25, 365-378, 1975. To test whether the sterol backbone could be modified by the CNBr treatment, a positively charged cholesterol derivative (3β(N—(N',N'-dimethylamino) ethanecarbamoyl)-cholesterol, Sigma) detectable by MALDI was examined. It was found that incubation of this sterol derivative in 70% formic acid alone resulted in the addition of 45 mass units to the sterol (13), a mass consistent with the net addition of a formic acid molecule). These in vitro and in vivo results show that the Hh-C processing domain functions as a cholesterol transferase; as a result of this activity, a cholesterol adduct is attached via an ester linkage to the COOH-terminus of the $NH_2$-terminal signaling domain of the Hh protein.

To test whether processing of vertebrate hedgehog proteins results in the incorporation of cholesterol as a covalent adduct to the signaling domain, cultured green monkey kidney cells (COS-7) were metabolically labeled with [$^3$H]cholesterol and transfected with expression constructs containing (i) the full length murine Sonic hedgehog (Shh) open reading frame, leading to production of an autocatalytically processed signaling domain (Shh-$N_p$) or (ii) Shh coding sequences precisely truncated at the site of cleavage, thus producing an unprocessed amino terminal signaling domain (Shh-N) (COS-7 cells grown at 37° C. in DMEM supplemented with 10% fetal calf serum were plated at −35% confluence onto two 35 mm dishes in 1 ml of Optimem media (Gibco) containing 1.5% fetal bovine sera and 25 μCi of [$^3$H]cholesterol, giving ~40 μg/ml as the final concentration of cholesterol with a specific activity of 2 Ci/mmol (labeling medium). After 24 hours the labeling medium was removed and the cells were transfected for 6 hours with Shh or Shh-N expression constructs using lipofectamine (Gibco) and serum-free DMEM media. After transfection, 1 ml of fresh labeling medium was added to each dish and the cells were incubated for 36 hours at 37° C. The cells were then harvested without washing, lysed on the plate with Tris buffered saline plus 1% Triton X-100 and the total cell proteins were precipitated with acetone, washed and analyzed as described above for the S2 cell proteins). Cells expressing the full length construct contained a prominent radio-labeled species migrating at ~19 kD, suggesting that cholesterol is covalently added to Shh-$N_p$ (FIG. 25D). This band was not present in cultures expressing the truncated Shh-N protein (FIG. 25D), indicating that the incorporation of [$^3$H]cholesterol is dependent on the presence of the Shh processing domain. These data strongly suggest that the ability to attach cholesterol as a covalent adduct during autocatalytic processing and cleavage is a universal property of Hh proteins. Several other protein species in addition to the Shh amino terminal domain also appeared to incorporate cholesterol in cells transfected with either construct, suggesting that covalent modification by cholesterol extends to proteins beyond the Hh family. This possibility is consistent with the recently reported occurrence of several sequences homologous to the Hh processing domain in association with amino terminal sequences distinct from hedgehog.

Example 20

Figure 33A:
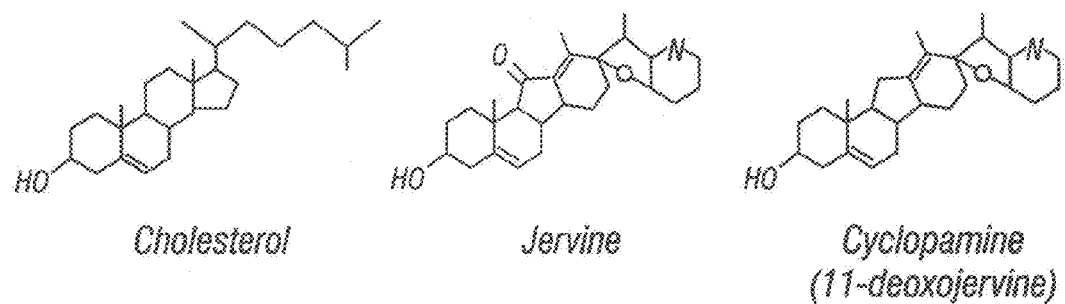
FIGS. 33A and 33B show inhibition of cholesterol biosynthesis by the plant steroidal alkaloid, jervine.
Figure 33B:
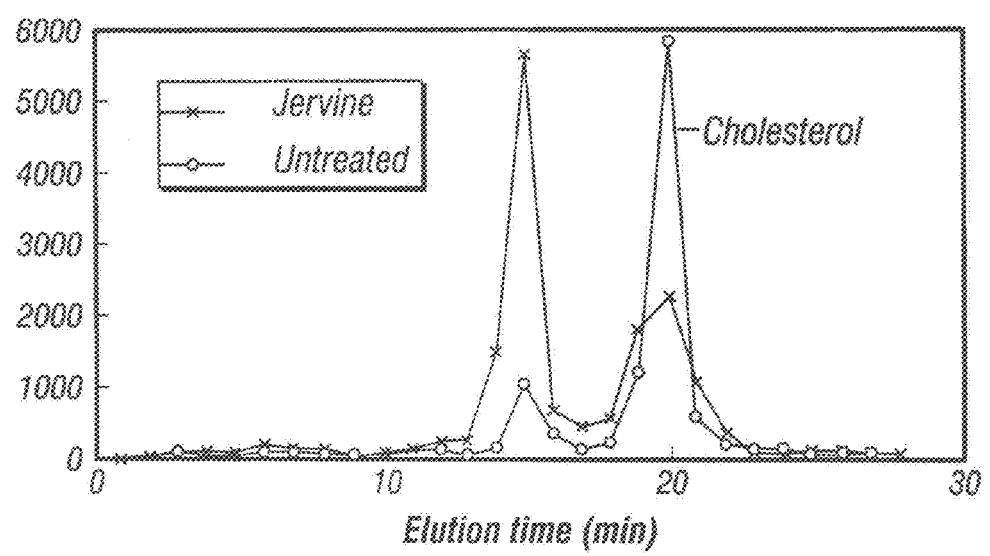

An experimental model for holoprosencephaly derives from the occurrence of epidemics of congenital craniofacial malformations among newborn lambs on sheep ranches in several National Forests of the western United States. The most dramatically affected lambs showed severe holoprosencephaly, including true cyclopia and other craniofacial malformations characteristic of holoprosencephaly. The occurrence of these defects was traced to grazing by pregnant ewes on the range plant *Veratrum californicum*. The compounds responsible were identified as a family of steroidal alkaloids; the structures of two of these, cyclopamine and jervine, are shown as compared to cholesterol in FIG. 33. In FIG. 33, sterols were extracted and analyzed by HPLC from COS 7 cells metabolically labelled with [$^3$H]-mevalonic acid in the presence or absence of jervine, a teratogenic plant steroidal alkaloid. In the presence of 28 mM jervine, radiolabeled cholesterol levels were reduced and another radiolabeled sterol was found to accumulate. On the basis of its retention time in this reverse phase HPLC method, this abnormal sterol is tentatively identified as zymosterol, an intermediate in the cholesterol biosynthetic pathway.

Given the structural similarities of these compounds to cholesterol and the similar teratogenic effects of cholesterol synthesis inhibitors upon the offspring of pregnant rats, a reasonable mechanism to consider for the effects of these plant sterol derivatives was the inhibition of cholesterol biosynthesis. Accordingly, COS7 cultured cells treated with jervine were tested for defects in cholesterol biosynthesis by labelling with [3H]-mevalonic acid and then extracting and analyzing radiolabeled, non-saponifiable lipids.

Metabolic labeling and sterol analysis was essentially as described (Popjak et al. *J. Biol. Chem.* 264: 630-6238.1989; Rilling et al. 1993 *Arch. Biochem. Biophys.* 301: 210-215.), with minor modifications. Briefly, COS-7 cells were plated at ~35% confluence into two 60 mm dishes at 37° C. in 4 ml each of Dulbecco's modified Eagle's medium (DMEM) supplemented with 10% fetal bovine serum (FBS). After 24 hr of growth the medium in each dish was replaced with 2 ml fresh medium with 10% FBS; [$^3$H]-mevalonic acid (NEN #NET 176) brought to a specific activity of 0.8 Ci/mmol in a 1% solution of bovine serum albumin was added to this medium to a final concentration of 20 mM. At this time, one dish received 6 ml of a 4 mg/ml solution of jervine in ethanol (final concentration 28 mM jervine), and the other received 6 ml of ethanol. After 24 hr further incubation, cells were washed in PBS, extracted with methanol, and 1 M potassium hydroxide (KOH) added to 10%. Following a three hour incubation at 60° C., the methanol/KOH mixture was extracted with diethyl ether, the extract dried down, resuspended in isopropanol, and subjected to reverse phase HPLC analysis by the method of Rodriguez and Parks (*Methods in Enzymology* 111: 37-51 1985).

Treated cells synthesized reduced levels of cholesterol and accumulated increased levels of another sterol that we have provisionally identified as the cholesterol precursor, zymosterol. The natural product jervine at these concentrations thus inhibits cholesterol biosynthesis in cultured cells in much the same manner as the synthetic drugs discussed above, although the specific enzyme(s) affected appear to differ. Given the similarities in their teratogenic effects, this inhibition seems likely to underlie the teratogenic effects of both the synthetic and natural compounds.

Example 21

Protein expression and purification: *Drosophila melanogaster* Hh protein in which most of the amino-terminal signaling domain and signal sequence have been replaced by a hexa-histidine tag ($His_6$Hh-$C_{25}$) was expressed as previously described (Porter et al., 1995). SeMet $His_6$Hh-$C_{25}$ was prepared by expression in *E. coli* strain B834 (DE3) pLysS, a methionine auxotroph, and growth in minimal media as previously described (Leahy et al., 1994). This $His_6$-tagged protein was purified on a $Ni^{++}$-NTA agarose column and autocleavage stimulated by addition of 50 mM DTT. After removal of the DTT by dialysis, the cleaved protein was passed over a $Ni^{++}$-NTA agarose column and the Hh carboxy-terminal domain, Hh-$C_{25}$, collected in the column run through. Hh-$C_{25}$ was subjected to limited proteolysis by overnight incubation with 1:500 (w:w) subtilisin (Boehringer Mannheim) at 4° C. A protease-stable fragment of approximately 17 kDa, Hh-$C_{17}$, was identified by SDS-PAGE and purified by anion-exchange chromatography utilizing a Mono-Q column (Pharmacia). The amino- and carboxy-terminal residues of Hh-$C_{17}$ were determined to be Cys-258 and Ser-408, respectively, by mass spectral analysis of cyanogen bromide-cleaved fragments. Mass spectral analysis was performed as previously described (Porter et al., 1996a).

Crystallization: Crystals were grown from hanging drops by the method of vapor diffusion (Wlodawer et al., 1975). 6 μl cf of a 1.4 mg/ml solution of Hh-$C_{17}$ in 1.4 mM β-mercaptoethanol were mixed with 2 μl of a 1:1 dilution of reservoir solution (20% PEG 3550, 80 mM ammonium sulfate, and 10 mM sodium cacodylate, pH 5.8) with distilled water and equilibrated over the reservoir solution. Crystals typically grew to a final size of 0.2 mm×0.2 mm×0.1 mm over 3-7 days. Crystals are in space group $I2_1 3$ with unit cell dimension a=b=c=101.54 Å.

Data collection and processing: All data were collected from crystals soaked in mother liquor made 10% (w/v) ethylene glycol and flash frozen in a gaseous nitrogen stream at −180° C. MAD data were collected at four wavelengths from a single SeMet crystal at beamline X-4A of the National Synchrotron Light Source at Brookhaven National Laboratory. Data were collected using Fuji HR-V phosphor-imaging plates and digitized using a Fuji BA-3000 scanner. 2° oscillations at φ and φ+180° were collected with no overlap for each oscillation range ac each wavelength. All diffraction images were processed using the program DENZO and scaled with the program SCALEPACK (Otwinowski and Minor, 1997). <I+> and <I−> were used for MAD phase determination and partially recorded reflections were used in all cases. Diffraction data from different wavelengths were scaled with WVLSCL, and values for $F_A$ and optimal f' and f'' were calculated with MADLSQ (Hendrickson, 1991). Data collection statistics are shown in Table I.

Structure determination: Three selenium sites were deduced from $F_A$ amplitudes using both the program SHELXS (Sheldrick, 1991) and Patterson methods. MAD phase determinations were made which the program MLPHARE (Collaborative Computational Project, 1994; Ramakrishnan and Biou. 1997), and solvent-flattening and histogram-matching were performed with the program DM (Collaborative Computational Project, 1994). An atomic model consisting of Cys-258 to Tyr-401 was readily built into electron density maps computed with MAD-derived phases for reflections in the range 20.0-2.0 Å using the program "O" (Jones et al., 1991). One round of simulated annealing and several rounds of Powell minimization using X-PLOR (Brunger, 1992) alternated with model building with "O" yielded the current model of Hh-$C_{17}$ consisting of 145 residues, Cys-258 to Ala-402, and 126 water molecules. The model was refined using the data collected at 0.9919 Å. One molecule is present in the asymmetric unit, and the solvent content is approximately 59%. All backbone torsion angles are within energetically acceptable regions. No electron density was observed for residues 403 to 408, but additional electron density was observed near the thiol group of Cys-258. As the crystallization buffer contained cacodylic acid, both $AsO(CH_3)_2$ or an As atom were modeled in this density, but neither the crystallographic R-factor ncr the free R-factor improved with these atoms added to the refinement and no atoms have been included in this region in the final atomic model.

Site-directed mutagenesis and in vitro autocleavage assays: His-329, Thr-325, and Asp-303 were each mutated to alanine (H329A, T326A, and D303A, respectively) and Leu-409 was mutated to a stop coden ($His_6$Hh-$C_{17}$) by the method of recombinant circle PCR (Jones and Winistorfer, 1992). $His_6$-tagged proteins containing residues 83-471 of *Drosophila* Hh protein with residues 89-254 deleted and with the mutated residues were expressed in *E. coli* and purified to near homogeneity as previously described (Porter et al., 1995). Autocleavage activity of the mutant proteins was assessed in 15 μl reactions by incubating 1 μg of protein in 150 mM NaCl, 100 mM Tris-HCl (pH 7.4), 0.05% Triton X-100, 1.25 mM β-mercaptoethanol, and 2.5% glycerol with either 50 mM DTT or 350 μM cholesterol/1 mM DTT for 6 hours at 30° C. The cleavage products were then fractionated by SDS-PAGE and detected by Coomassie Brilliant Blue staining. The activity of D303A and $His_6$ Hh-$C_{17}$ were also assessed by incubating 1 μg of protein with 46 μM [$^3$H] cholesterol (11.6 Ci/mmole)/1 mM DTT for 6 hours at 30° C. The proteins were then subjected to SDS-PAGE and labeled proteins detected by autoradiography.

Database searching and sequence alignment: Screening of the non-redundant protein sequence database at the National Center for Biotechnology Information (NIH) was performed using the BLASTPGP program, which is an enhanced version of BLAST that produces gapped alignments (Altschul and Gish, 1996). Additional searches were performed using the PSI-BLAST (Position-Specific Iterative BLAST) program, which constructs position-specific weight matrices from the BLASTPGP output and employs them for subsequent iterations of database screening using a modLficauon of the BLAST statistics (Altschul et al., in press). Alignments of multiple protein sequences were constructed using the CLUSTALW program (Thompson et al., 1994) or the MACAW program (Schuler et al., 1991).

Domain Identification and Structure Determination

*Drosophila melanogaster* Hh in which the signal sequence and most of the amino-terminal signaling domain have been replaced by a hexahistidine tag was expressed in *E. coli* as previously described (Porter et al., 1995). Following purification with Ni$^{++}$-NTA agarose, this protein cleaves itself in vitro in the presence of either DTT or cholesterol to liberate the 25 kDa Hh-C fragment (Hh-$C_{25}$, residues Cys-258 to Asp-471). Hh-$C_{25}$ prepared by this method was found to be poorly soluble in the absence of detergents and susceptible to further proteolytic breakdown when concentrated to 1 mg/ml or greater. Treatment of Hh-$C_{25}$ with subtilisin, however, resulted in a protease-stable fragment of ~17 kDa molecular weight (Hh-$C_{17}$) with improved solubility. Mass spectrometric analysis of cyanogen bromide cleavage fragments of Hh-$C_{17}$ showed it to consist of residues Cys-25S to Ser-408 (data not shown). All residues absolutely conserved in Hh-C homologues (Porter et al., 1996a), including the nematode sequences, are contained in Hh-$C_{17}$. To determine if Hh-$C_{17}$ retained autoprocessing activity, a mutant version of His-tagged Hh-C containing a termination codon at residue position 409 ($His_6$Hh-$C_{17}$) was expressed and assayed for autocleavage in the presence of DTT and cholesterol. As shown in FIG. 2, $His_6$Hh-$C_{17}$ is capable of cleaving itself in the presence of DTT but not cholesterol, indicating that $His_6$Hh-$C_{17}$ is able to form the thioester intermediate (see FIG. 1A) but that some portion of the carboxy-terminal 63 residues of Hh-$C_{25}$ (Leu-409 to Asp-471) is required for cholesterol transfer.

Crystals of Hh-$C_{17}$ that diffracted to at least 1.9 Å Bragg spacings were readily produced from both native and selenomethionyl-substituted (SeMet) protein. The crystal structure of Hh-$C_{17}$ was determined by the method of multiwavelength anomalous diffraction (MAD) using SeMet crystals, (Hendrickson et al., 1990; *Hendrickson,* 1991). High quality experimental electron density maps allowed construction of an atomic model for Hh-$C_{17}$ residues Cys-258 to Ala-402 that readily refined to low R-factor with good stereochemistry. Final refinement and stereochemical statistics are summarized in Table 1.

Description of Hh-C$_{17}$ Structure

Hh-C17 possesses an all-β structure that is roughly disk-shaped with a diameter of ~35 Å and width of ~20 Å. The amino and carboxy termini emerge from the same surface of Hh-C$_{17}$ ~6 Å apart. A ribbon drawing and topology diagram of the Hh-C$_{17}$ structure are shown in FIG. 3. An unexpected feature of the Hh-C$_{17}$ structure is the presence of two homologous subdomains related by a pseudo-twofold axis of symmetry (FIGS. 4A and 4B). The subdomains adopt an irregular fold characterized by three extended β-hairpin loops and are intimately associated, burying 1372 Å$^2$ of surface area at a hydrophobic interface such that a single hydrophobic core exists for the entire Hh-C$_{17}$ molecule. The topology of the Hh-C$_{17}$ subdomains matches that of snake toxins such as cardiotoxin VII4 (Rees et al., 1990) and α-bungarotoxin (Love and Stroud, 1986), but the toxin and Hh-C$_{17}$ structures do not superimpose well and these: structures do not seem otherwise related. As discussed below, the full Hh-C$_{17}$ fold can be detected in the self-splicing region of inteins (Duan et al., 1997), and the evidence for a divergent evolutionary relationship in this case is strong.

Despite a low level of sequence conservation, the two *Drosophila* Hh-C$_{17}$ subdomains are superimposable with an r.m.s. deviation in α-carbon positions of 1.38 Å, and several notable structural features, including β-bulges and specific β-turn types, are conserved between the subdomains (FIG. 4C). A structure-based alignment of the *Drosophila* Hh-C$_{17}$ subdomain sequences is shown in FIG. 4D. While 8 out of 50 amino-acid residues (16%) in this alignment are conserved, none of these 8 residues is absolutely conserved in both subdomains of all Hh-C homologues. A characteristic pattern of conserved amino-acid types, mostly hydrophobic residues, is discernible in an alignment of these homologues, however.

The level of structural similarity between the two Hh-C$_{17}$ subdomains suggests that Hh-C$_{17}$ could have arisen by tandem duplication of a primordial gene. The duplicated sequences do not, however, correspond directly to the compact subdomains observed in the Hh-C$_{17}$ structure. As can be seen in FIGS. 4B and 4C, the Hh-C$_{17}$ subdomains have exchanged homologous loop regions. Examination of FIG. 4B shows how the loop exchange in Hh-C$_{17}$ could be achieved by a simple pivot of the loops about a single flex point. The structurally cohesive subdomains of Hh-C$_{17}$ are thus mosaics composed of elements from both units of the tandem sequence duplication. To illustrate, if the three successive loops in each Hh-C$_{17}$ subdomain are labeled 1-2-3 and A1-A2-A3-B1-B2-B3 in the duplicated molecule prior to loop swapping, then the exchange of the third loop between subdomains can be represented as A1-A2-(A3-B1-B2)-B3 where the structurally distinct subdomains are composed of loops either inside or outside of the parentheses (see FIG. 4B). We note that duplication coupled with an interdomain structural exchange such as appears to have occurred in Hh-C$_{17}$ provides a mechanism to generate permutations in the order in which specific structural elements occur in the amino-acid sequence. Such permutations have been noted m other systems including saposin homologues (Ponting and Russell, 1995) and bacterial glucanases (Heinemann and Hahn, 1995).

The exchange of domains or elements of secondary structure has been observed in several proteins and is believed to result in a more stable association of subunits in multidomain proteins (Bennett et al., 1995). Exchange of structural regions has principally been observed between independent polypeptide chains within homodimers, but the lac operon repressor and homologues also appear to represent a case of exchange between duplicared domains within a single polypeptide chain (Schumacher et al., 1994; Lewis et al., 1996).

Active Site Residues

Figure 5B:
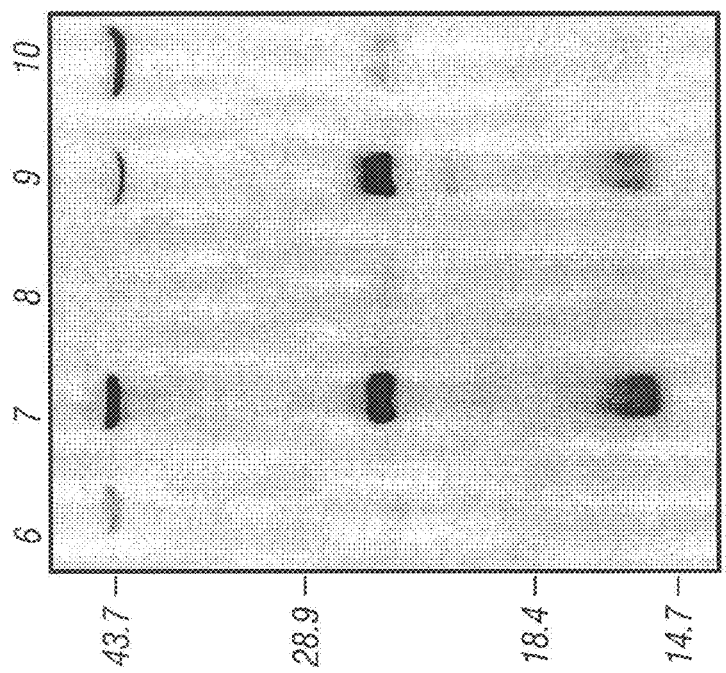
FIGS. 5A and 5B show immunoblots showing heat shock induced expression of wild type and H329A mutant hh proteins in *Drosophila* embryos.
Figure 5A:
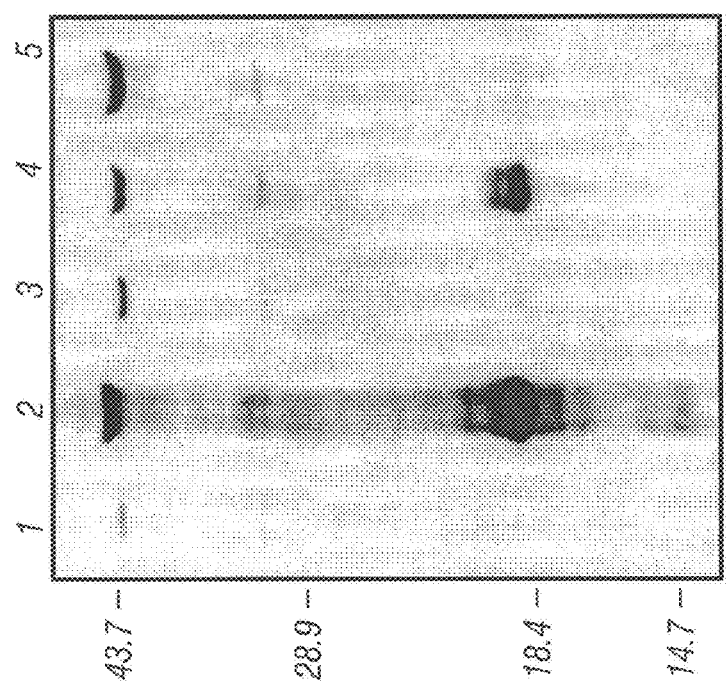

The amino-terminal residue of Hh-C$_{17}$, Cys-258, is involved in both the thioester formation and cholesterol transfer steps of Hh autoprocessing (see FIG. 1A). Amino-acid side chains participating directly in Hh autoprocessing chemistry will most likely possess polar groups, and the only such residues near Cys-258 in the Hh-C$_{17}$ structure are His-329, Thr-326, and Asp-303. The arrangement of these three amino acids in relation to Cys-258 is shown in FIGS. 5A and 5B. His-329 and Thr-326 are absolutely conserved in all Hh-C homologues, and the side chains of both of these residues are within hydrogen bonding distance of the α-amino group of Cys-258 in the Hh-C$_{17}$ structure. Asp-303 is invariably aspartic acid or histidine in Hh-C domains, and the side chain of Asp-303 is exposed to solvent 4.2-4.5 Å away from the Cys-258 thiol group. Significant structural rearrangements would appear necessary for additional residues in Hh-C$_{17}$ to participate directly in Hh autoprocessing. Cys-258, His-329, and Asp-282 do not form a serine protease-like catalytic triad as had been proposed (Lee et al., 1994; Porter et al., 1996a).

To assess the involvement of His-329, Thr-326, and Asp-303 in Hh autoprocessing, each of these residues was mutated to alanine within the context of the full-length His$_6$Hh-C$_{25}$ protein, and the mutant proteins were expressed and assayed for Hh autoprocessing activity. The autocleaving activity of the mutant proteins in the presence of high concentrations of DTT was used as an assay for thioester formation, the first step in the Hh autoprocessing reaction, while the autocleaving activity in the presence of cholesterol was used to assay for cholesterol transfer, the second step in the autoprocessing reaction. The results of these assays are shown in FIG. 5C. His-329 is known from earlier experiments to be essential for Hh autoprocessing activity (Lee et al., 1994), and the His-329 to alanine mutant (H329A) was inactive in both the DTT- and cholesterol-stimulated reactions. The Thr-326 to alanine mutant (T326A) also showed greatly reduced activity in both assays. By contrast, the Asp-303 to alanine mutant (D303A) was active in the DTT-stimulated reaction but inactive in the cholesterol-stimulated reaction.

The loss or dramatic reduction of autocleaving activity in the presence of both DTT and cholesterol for H329A and T326A implicates both His-329 and Thr-326 in formation of the internal thioester during Hh autoprocessing. The interaction of the side chains of both of these residues with the α-amino group of Cys-258, a component of the cleaved peptide bond, strongly implies a direct role for these residues in thioester formation. Possible roles for His-329 during thioester formation include stabilization of negative charge on the carbonyl oxygen of Gly-257, donation of a proton to the free α-amino group of Cys-258, and maintenance of an appropriate orientation of reaction components through polar interactions. His-329 may also deprotonate the thiol group of Cys-258 prior to thioester formation, but if this is the case some rearrangement of Cys-258 relative to its position in the Hh-C$_{17}$ crystal structure would be required to bring the thiol group cf Cys-258 into proximity with His-329. As the pK$_a$ of the thiol group in free cysteine is 8.3, a base may not be needed to catalyze thiol deprotonation. Possible roles far Thr-326 in thioester formation seem more limited. The high pK$_a$ of a threonine hydroxyl group (>15) makes Thr-326 an unlikely candidate for proton transfers, suggesting that this residue is needed to form polar interactions that stabilize reactive conformations within the Hh protein.

The activity of the D303A mutant in DTT- but not cholesterol-stimulated autoprocessing shows that Asp-303 is nor needed for thioester formation but is required for cholesterol transfer. The negatively-charged aspartic acid residue seems unlikely to be involved in binding a hydrophobic cholesterol molecule. A role in activating the cholesterol molecule for nucleophilic attack of the thioester appears more plausible. For cholesterol to become an effective nucleophile, the 3β-hydroxyl group must become deprotonated, and Asp-303 is a good candidate for the general base that catalyzes this deprotonation. Substitution of Asp-303 with histidine in Hh-C homologues is consistent with this hypothesis as histidine is also capable of functioning as a general base.

As indicated by the inactivity of $Hh-C_{17}$ in cholesterol transfer assays, residues in the 63 amino acids removed from the $Hh-C_{25}$ carboxy terminus are also involved in cholesterol transfer. The proximity of the carboxy terminus of $Hh-C_{17}$ to the active site implies a direct role for these residues in cholesterol binding or activation. The decreased solubility of $Hh-C_{25}$ is relative to $Hh-C_{17}$ suggests that the carboxy-terminal 63 residues of $Hh-C_{25}$ may possess an exposed hydrophobic region that could serve as a cholesterol binding site.

Relationship Between $Hh-C_{17}$ and Self-Splicing Proteins

An earlier analysis identified a 36 amino acid conserved motif in the amino-terminal regions of Hh-C homologues and inteins (Koonin, 1995). A greatly expanded database of Hh-C and intein sequences coupled with recent enhancements of the BLAST method for database searching enabled extension of the detectable region of sequence similarity to the amino-terminal ~100 amino acids of Hh-C and intein sequences ($p \sim 10^{-3}$-$10^{-4}$). The improved methods for database searching include statistical analysis of gapped alignments and iterative database scanning with position-specific matrices derived from previous BLAST outputs (Altschul et al., in press). When a database search was initiated with any of the Hh-C sequences or with most of the intein sequences, members of the respective second protein family were the only additional sequences retrieved from the database at a statistically significant level.

Solution of the $Hh-C_{17}$ crystal structure showed the expanded region of Hh-C/intein sequence homology to terminate halfway through one of the subdomains in the turn region of an exposed loop between β strands 3b and 4b (sec FIG. 3 A). This observation, coupled with the presence of characteristic endonuclease motifs in intein sequences shortly after the end of the detectable Hh-C/intein homology suggested that the intein endonuclease domain had been inserted into the β3b-β4b loop of an $Hh-C_{17}$-like structure. This hypothesis focused the search for resumption of the Hh-C/intein sequence similarity in intein sequences likely to follow the endonuclease region. The recently determined crystal structure of the PI-SceI intein indeed shows the insertion of the endonuclease region of the intein in the β3b-β4b loop of an $Hh-C_{17}$-like structure and indicates that the region of the intein sequence in which the similarity to $Hh-C_{17}$ must resume is immediately amino-terminal to the second extein (Duan et al., 1997). An alignment of $Hh-C_{17}$ and intein sequences is shown in FIG. 6A. A fully structure-based alignment of the $Hh-C_{17}$ and intein sequences awaits direct comparison of the atomic coordinates of $Hh-C_{17}$ and PI-SceI.

As can be seen in FIG. 6A, aside from sites with conserved hydrophobic character the only residues absolutely or nearly absolutely conserved between Hh-C homologues and inteins are those identified in the active site of $Hh-C_{17}$ and shown to be important for thioester formation by site-directed mutagenesis. The amino-terminal cysteine residue directly involved in thioester formation in Hh-C homologues is replaced by serine in some inteins, and these inteins form an ester rather than a thioester intermediate. The yeast HO endonuclease, which lacks an amino-terminal serine or cysteine residue, does not have self-splicing activity (Perler et al., 1997), and the only intein homologue in which this residue is replaced by alanine (KIbA protein homologue from *Methanococcus jannaschii*) is suspected to be inactive as well.

The only residue absolutely conserved between Hh-C homologues and inteins is a histidine corresponding to His-329 in *Drosophila* Hh-C. The presence of His-329 in the active site of *Drosophila* Hh-C and the loss of thioester formation activity when His-329 is mutated strongly imply that this histidine is conserved because it performs a vital role in thioester formation and that it functions similarly in inteins and Hh-C homologues. The only other residue conserved in the active site of Hh-C homologues and shown by mutagenesis to be required for efficient thioester formation, Thr-326, is also extremely conserved in intein sequences. Of the 39 intein sequences in the database at the time of our comparison, 34 sequences contain a threonine at a homologous position to Thr-326, while three inteins have serine, and one each have asparagine or glutamic acid at this position. The high level of conservation of threonine al this active site position and its substitution with similar amino acids suggests a conserved role for this threonine in inteins and Hh-C homologues. A conserved residue homologous to Asp-303, also found in the $Hh-C_{17}$ active site, is not found in intein sequences, consistent with its role in cholesterol activation rather than thioester formation.

As expected from the sequence homology, the structures of the self-splicing region of the PI-SceI intein (Duan et al. 1997) and $Hh-C_{17}$ are clearly homologous. Although not previously noted, the self-splicing region of PI-SceI contains homologous subdomains related by pseudosymmetry. The PI-SceI subdomains are homologous to the $Hh-C_{17}$ subdomains and possess the same loop exchange observed in $Hh-C_{17}$. However, these features are obscured by insertion of endonuclease-associated sequences. In addition to insertion of the core endonuclease domain in the region homologous to the β3b-β4b loop, the PI-SceI intein contains an additional insertion of amino acids relative to the $Hh-C_{17}$ structure. The site of this insertion occurs in the turn between β strands 1b and 2b in the $Hh-C_{17}$ structure (see FIG. 3A), and this inserted region is believed to be involved in aiding DNA recognition by the PI-SceI intein (Duan et al., 1997). FIG. 6B shows a stereodiagram of the $Hh-C_{17}$ structure depicted in the same orientation as the PI-SceI intein structure in Duan, et al. (1997) with the sites of die endonuclease-associated insertions indicated.

The conservation of structure, sequence, and cleavage mechanism between Hh-C homologues and the intein regions of self-splicing proteins firmly establishes the divergence of these two protein families from a common precursor. FIG. 7 shows a plausible evolutionary scenario for the development of the Hh-C and intein protein families from a primordial domain of unknown function. The $Hh-C_{17}$ module is sufficient only for the initial replacement of a peptide bond with a thioester or ester in both the Hh autoprocessing and self-splicing reactions. In both protein families, residues carboxy terminal to the $Hh-C_{17}$ module are needed for selecting or contributing the second nucleophile that resolves the inidal ester/thioester and determines the products of the overall reaction. The loss of detectable sequence similarity in the region of the *C. elegans* Hh-C homologues following the $Hh-C_{17}$ module (R. Mann, personal communication) raises the possibility that these residues may transfer a molecule older than cholesterol. The ongoing expansion of sequence databases provides the prospect of additional $Hh-C_{17}$ modules being discovered that initiate novel splicing or transfer reactions by formation of ester or thioester intermediates.

Table Legend
Table I. Statistics for Data Collection, Phase Determination and Refinement (A) $R_{sym}$ and completeness values were calculated considering Bijvoets equivalent. Values in parentheses for $<I/\sigma I>$ are for the highest resolution shell (1.98-1.9 Å). $R_{sym}$=100× $\Sigma_h \Sigma_i |I_i(h) - <I(h)>|/\Sigma_h \Sigma_i(h)$. (B) r.m.s. ($\Delta|F|$)/r.m.s. (|F|) where $\Delta F$ is the Bijvoet difference at one wavelength (values on the diagonal) or the dispersive difference between two wavelengths (values off the diagonal). Also shown are the anomalous components of the Se scattering factors as a function of wavelength as determined by MADLSQ (Hendrickson, 1991). (C) All data for which $|F|>2\sigma$ were used in the refinement. A subset of the data (10%) was excluded from the refinement and used to calculate the free R-value (Brunger, 1992). A final round of refinement including this data was performed to produce the final set of coordinates and crystallographic R-value. R-value=$\Sigma||_o|F_c||/\Sigma|F_o|$.

TABLE I

Statistics for Data Collection, Phase Determination and Refinement (A) Data Collection Statistics (30.0 to 1.9 Å)

| Wavelength (Å) | Reflections (N) | Redundancy | Completeness (%) | Signal ($<I/\sigma I>$) | $R_{sym}$ (%) |
|---|---|---|---|---|---|
| 0.9919 | 26,790 | 10.3 | 100.0 | 19.9 (4.2) | 9.2 |
| 0.9793 | 26,791 | 10.6 | 100.0 | 19.4 (3.8) | 9.9 |
| 0.9791 | 26,792 | 10.4 | 100.0 | 18.8 (3.6) | 10.4 |
| 0.96S6 | 26,792 | 10.5 | 100.0 | 18.7 (3.5) | 10.3 |

(B) MAD Structure Factor Ratios and Anomalous Scattering Factors

| Wavelength (Å) | 0.9919 | 0.9793 | 0.9791 | 0.9686 | f' (e) | f" (e) |
|---|---|---|---|---|---|---|
| 0.9919 | 0.041 | 0.064 | 0.059 | 0.053 | −3.94 | 0.51 |
| 0.9793 |  | 0.055 | 0.049 | 0.062 | −9.45 | 3.28 |
| 0.9791 |  |  | 0.076 | 0.058 | −8.05 | 6.03 |
| 0.9686 |  |  |  | 0.063 | −4.15 | 4.12 |

(C) Refinement and stereochemical statistics

| | |
|---|---|
| R-value | 0.218 (F > 2σ, 6.0-1.9 Å) 0.222 (all F, 6.0-1.9 Å) |
| free R-value | 0.275 (F > 2σ, 6.0-1.9 Å) 0.283 (all F, 6.0-1.9 Å) |
| Average B (Å$^2$) | 21.5 for protein, 39.6 for solvent |
| Rms deviations | |
| Bonds (Å) | 0.008 |
| Angles (°) | 1.97 |
| B-values (Å$^2$) | 1.30/1.45 bonds/angles of main chain |
| | 2.83/3.20 bonds/angles of side chains |

REFERENCES

Altschul, S. F. and Gish, W. (1996). Local Alignment Statistics. Meth. Enzymol. 266, 460-481.

Altschul, S. F., Madden, T. L., Schaffer, A. A., Zhang, J., Zhang, Z, Miller, W. and Lipman, D. J. Gapped BLAST and PSI-BLAST—A New Generation Of Protein Database Search Programs. Nucleic Acids Res., in press.

Bennett, M. J., Schlunegger, M. P. and Eisenberg, D. (1995). 3D Domain Swapping: A Mechanism For Oligomer Assembly. Prot. Sci. 4, 2455-2468.

Brannigan, J. A., Dodson, G., Duggleby, H. J., Moody, P. C. E., Smith, J. L., Tomchick, D. R. and Murzin, A. G. (1995). A Protein Catalytic Framework with an N-terminal Nucleophile is Capable of Self-activation. Nature 378, 416-419.

Brünger, A. T. (1992). X-PLOR, Version 3.1 A System for X-Ray Crystallography and NMR. New Haven, Conn., Yale University.

Bumcrot, D. A., Takada, R. and McMahon, A. P. (1995). Proteolytic Processing Yields Two Secreted Forms of Sonic Hedgehog. Mol. Cell. Biol. 15, 2294-2303.

Burglin, T. R. (1996). Warthog and Groundhog, Novel Families Related to Hedgehog. Curr. Biol. 6, 1047-1050.

Collaborative Computational Project. N. 4. (1994). The CCP4 Suite: Programs for Protein Crystallography. Acta Crystaliogr. D50, 760-763.

Cooper, A. A. and Stevens, T. H. (1995). Protein Splicing: Self-Splicing of Genetically Mobile Elements at the Protein Level. Trends Biochem. Sci. 20, 351-356.

Duan, X., Gimble, F. S, and Quiocho, F. A. (1997). Crystal Structure of PI-SceI, a Homing Endonuclease with Protein Splicing Activity. Cell 89, 555-564.

Ekker, S. C, McGrew, L. L., Lai, C. J., Lee, J. J., von Kessler, D. P., Moon, R. T. and Beachy, P. A. (1995). Distinct Expression and Shared Activities of Members of the Hedgehog Gene Family of *Xenopus laevis*. Development 121, 2337-2347.

Ekker, S. C, Ungar, A. R., Greenstein, P., von Kessler, D. P. Porter. J. A., Moon, R. T. and Beachy, P. A. (1995). Patterning Activities of Vertebrate Hedgehog Proteins in the Developing Eye and Brain. Curr. Biol. 5, 944-955.

Fan, C. M., Porter, J. A., Chiang, C., Chang, D. T., Beachy, P. A. and Tessier-Lavigne, M. (1995). Long-Range Sclerotome Induction by Sonic Hedgehog: Direct Role of the Amino-Terminal Cleavage Product and Modulation by the Cyclic AMP Signaling Pathway. Cell 81, 457-465.

Fietz, M. J., Jacinto, A., Taylor, A. M., Alexandre. C. and Ingham, P. W. (1995). Secretion of the Amino-Terminal Fragment of the Hedgehog Protein is Necessary and Sufficient for Hedgehog Signalling in *Drosophila*. Curr. Biol. 5, 643-650.

Hammerschmidt, M., Brook, A. and McMahon, A. P. (1997). The World According to Hedgehog. Trends Genet. 13, 14-21.

Heinemann, U. and Hahn, M. (1995). Circular Permutations of Protein Sequence: Not So Rare? Trends in Biochemical Sciences 20, 349-350.

Hendrickson, W. A. (1991). Determination of Macromolecular Structures from Anomalous Diffraction of Synchrotron Radiation. Science 254, 51-58.

Hendrickson, W. A., Honon, J. R. and LeMasler, D. M. (1990). Selenomethionyl Proteins Produced for Analysis by Multiwavelength Anomalous Diffraction (MAD): A Vehicle for Direct Determination of Three-Dimensional Structure. EMBO J. 9, 1665-1672.

Hutchinson, E. G. and Thornton, J. M. (1996). PROMOTIF—A Program to Identify and Analyze Structural Motifs in Proteins. Prot. Sci. 5, 212-220.

Hynes, M., Porter, J. A., Chiang, C., Chang, D., Tessier-Lavigne, M., Beachy, P. A. and Rosenthal, A. (1995). Induction of Midbrain Dopaminergic Neurons by Sonic Hedgehog. Neuron 15, 35-44.

Jones, D. H. and Winistorfer. S. C. (1992). Recombinant Circle PCR and Recombination PCR for Site-Specific Mutagenesis Without PCR Product Purification. Biotechniques 12, 528-530.

Jones, T. A., Zou, J. Y., Cowan, S. W. and Kjeldgaard, M. (1991). Improved Methods for the Building of Protein Methods in Electron Density Maps and the Location of Errors in these Models. Acta Crystallographica, A 47, 110-119.

Koonin, E. V. (1995). A Protein Splice-Junction Motif in Hedgehog Family Proteins. Trends Biochem. Sci. 20, 141-142.

Kraulis, P. J. (1991). MOLSCRIPT: A Program to Produce Both Detailed and Schematic Plots of Protein Structures. L Appl. Cryst. 24, 946-950.

Lai, C.-J., Ekker, S. C., Beachy, P. A. and Moon, R. T. (1995). Patterning of the Neural Ectoderm of Xenopus laevis by the Amino-terminal Product of Hedgehog Autoproteolytic Cleavage. Development 121, 2349-2360.

Leahy, D. J., Erickson, H. P., Aukhil, I, Joshi, P. and Hendrickson, W. A. (1994). Crystallization of a Fragment of Human Fibronectin: Introduction of Methionine by Site-Directed Mutagenesis to Allow Phasing by Selenomethionine. Proteins 19, 48-54.

Lee, J. J., Ekker, S. C., von Kessler, D. P., Porter, J. A., Sun, B. I. and Beachy, P. A. (1994). Auto-proteolysis in Hedgehog Protein Biogenesis. Science 266, 1528-1537.

Lewis, M., Chang, G., Horton, N. C., Kercher, M. A., Pace, H. C., Schumacher, M. A., Brennan, R. G. and Lu, P. (1996). Crystal Structure of the Lactose Operon Repressor and its Complexes with DNA and Inducer. Science 271, 1247-1254.

Lopez-Martinez, A., Chang, D. T., Chiang, C., Porter, J. A., Ros, M. A., Simandl, B. K., Beachy, P. A. and Fallon, J. F. (1995). Limb-Patterning Activity and Restricted Posterior Localization of the Ammo-Terminal Product of Sonic Hedgehog Cleavage. Curr. Biol. 5(791-796).

Love, R. A. and Stroud, R. M. (1986). The Crystal Structure of Alpha-Bungarotoxin at 2.5 Å Resolution: Relation to Solution Structure and Binding to Acetylcholine Receptor. Prol. Eng. 1, 37-46.

Marti, E., Bumcrot, D. A., Takada, R. and McMahon, A. P. (1995). Requirement of 19K Form of Sonic Hedgehog for Induction of Distinct Ventral Cell Types in CNS Explants. Nature 375, 322-325.

Murzin, A. G. (1996). Structural Classification of Proteins: New Superfamilies. Curr. Opin. Struct Biol. 6, 386-394.

Otwinowski, Z. and Minor, V. (1997). Processing of X-Ray Diffraction Data Collected in Oscillation Mode. Meth. Enzymol. 276, 307-326.

Perler, F. B., Olsen, G. J. and Adam, E. (1997). Compilation and Analysis of Intein Sequences. Nucleic Acids Res. 25, 1087-1093.

Pietrokovski, S. (1994). Conserved Sequence Features Of Inteins (Protein Introns) and their Use in Identifying New Inteins and Related Proteins. Prot. Sci. 3, 2340-2350.

Ponting, C. P. and Russell, R. B. (1995). Swaposins: Circular Permutations within Genes Encoding Saposin Homologues. Trends Biochem. Sci. 20, 179-180.

Porter, J. A., Ekker, S. C., Park, W.-J., von Kessler, D. P., Young. K. E., Chen, C.-H., Ma, Y., Woods, A. S., Cotter, R. J., Koonin, E. V. and Beachy. P. A. (1996a). Hedgehog Patterning Activity: Role of a Lipophilic Modification Mediated by the Carboxy-terminal Autoprocessing Domain. Cell 86, 21-34.

Porter, J. A., von Kessler, D. P., Ekker, S. C., Young, K. E., Lee, J. J., Moses, K. and Beachy, P. A. (1995). The Product of hedgehog Autoproteolytic Cleavage Active in Local and Long-Range Signalling. Nature 374, 363-366.

Porter, J. A., Young, K. E. and Beachy, P. A. (1996b). Cholesterol Modification of Hedgehog Signaling Proteins in Animal Development. Science 274, 255-259.

Ramakrishnan, V, and Bieu, V. (1997). Treatment of Multi-wavelength Anomalous Diffraction Data as a Special Case of Multiple Isomorphous Replacement. Meth. Enzymol. 276, 538-557.

Rees, B., Bilwes, A., Samama, J. P. and Moras, D. (1990). Cardiotoxin VII4 from Naja Mossambica Mossambica. The Refined Crystal Structure. J. Mol. Biol. 214, 281-297.

Roelink, H., Porter, J. A., Chiang, C., Tanabe, Y., Chang, D. T., Beachy, P. A. and Jessell, T. M. (1995). Floor Plate and Motor Neuron Induction by Different Concentrations of the Amino-Terminal Cleavage Product of Sonic Hedgehog Autoproteolysis. Cell 81, 445-455.

Schuler, G. D., Altschul, S. F. and Lipman, D. J. (1991). A Workbench for Multiple Alignment Construction and Analysis. Proteins 9, 180-190.

Schumacher, M. A., Choi, K. Y., Zalkin, H. and Brennan, R. G. (1994). Crystal Structure of LacI Member, PurR, Bound to DNA: Minor Groove Binding by a Helices. Science 266, 763-770.

Sheldrick, G. (1991). Patterson Interpretation and the Use of Macromolecular Delta-F Data. Daresbury, UK.

Thompson, J. D., Higgins, D. G. and Gibson, T. J. (1994). CLUSTAL W: Improving the Sensitivity of Progressive Multiple Sequence Alignment Through Sequence Weighting, Position-Specific Gap Penalties and Weight Matrix Choice. Nucleic Acids Res. 22, 4673-4680.

Wlodawer, A., Hodgson, K. O. and Shooter, E. M. (1975). Crystallization of Nerve Growth Factor from Mouse Submaxillary Glands. Proc. Natl. Acad. Sci. USA 72, 777-779.

Xu, M.-Q. and Perier, F. B. (1996). The Mechanism of Protein Splicing and its Modulation by Mutation. EMBO J. 15, 5146-5153.

The above disclosure generally describes the present invention. A more complete understanding can be obtained by reference to the following specific examples which are provided herein for purposes of illustration only and are not intended to limit the scope of the invention.

What is claimed is:

1. An isolated antibody fragment which binds specifically to:
   a) an N-terminal fragment of a vertebrate hedgehog polypeptide or a fragment thereof, wherein the N-terminal fragment or the fragment thereof, has a Glycine reside at its carboxy terminus, resulting from specific cleavage of a G↓CF cleavage site specifically recognized by a proteolytic activity of the carboxy terminal fragment of a native hedgehog polypeptide; or
   b) a C-terminal fragment of a vertebrate hedgehog polypeptide or a fragment thereof, wherein the C-terminal fragment or the fragment thereof, has Cys Phe residues at its amino terminus, resulting from specific cleavage of a G↓CF cleavage site contained within the hedgehog polypeptide.

2. The antibody fragment of claim 1, wherein the antibody fragment comprises an Fab, Fab', (Fab')$_2$, Fv, or combination thereof.

3. The antibody fragment of claim 1, wherein the antibody fragment is a fragment of a monoclonal antibody.

4. The antibody fragment of claim 1, wherein the antibody fragment is a fragment of a polyclonal antibody.

5. The antibody fragment of claim 1, wherein the antibody fragment is a pool of monoclonal antibody fragments that recognizes only epitopes of the N-terminal or C-terminal of the hedgehog polypeptide or fragment thereof.

6. The antibody fragment of claim 1, wherein the antibody is generated by immunizing an animal with the N-terminal or C-terminal fragment.

7. The antibody fragment of claim 1, wherein the antibody is generated by immunizing an animal with a recombinant N-terminal or C-terminal fragment.

8. The antibody fragment of claim 1, wherein the N-terminal fragment epitope recognized by the antibody includes a sterol moiety.

9. A method of generating an antibody fragment which binds specifically to:
   a1 an N-terminal fragment of a vertebrate hedgehog polypeptide or a fragment thereof, wherein the N-terminal fragment or the fragment thereof, has a Glycine reside at its carboxy terminus, resulting from specific cleavage of a G↓CF cleavage site specifically recognized by a proteolytic activity of the carboxy terminal fragment of a native hedgehog polypeptide; or
   b) a C-terminal fragment of a vertebrate hedgehog polypeptide or a fragment thereof, wherein the C-terminal fragment or the fragment thereof, has Cys Phe residues at its amino terminus, resulting from specific cleavage of a G↓CF cleavage site contained within the hedgehog polypeptide,
   comprising immunizing a mammalian subject with the N-terminal fragment or the fragment thereof, or the C-terminal fragment or the fragment thereof.

10. The method of claim 9, wherein the antibody fragments or antibody-producing cells are isolated from the mammalian subject.

11. The method of claim 9, wherein the immunization is performed with an N-terminal fragment comprising a sterol moiety.

12. The method of claim 9, wherein the immunization is performed with an N-terminal or C-terminal fragment having the amino acid sequence of a Zebrafish, Xenopus, chicken, murine, or human hedgehog N-terminal or C-terminal fragment.

13. The method of claim 9, wherein the immunization is performed with a mammalian hedgehog N-terminal or C-terminal fragment.

14. The method of claim 9, wherein the immunization is performed using a human hedgehog N-terminal or C-terminal fragment.

15. The method of claim 9, wherein the immunization is performed using a recombinant N-terminal or C-terminal fragment.

* * * * *

SEQUENCE LISTING

```
<160> NUMBER OF SEQ ID NOS: 108

<210> SEQ ID NO 1
<211> LENGTH: 144
<212> TYPE: DNA
<213> ORGANISM: Homo sapiens

<400> SEQUENCE: 1
gtgaaactgc gggtgaccga gccctgggac gaagatggcc accactcaca ggagtctctg      60
cactacgagg gccgcgcagt ggacatcacc acgtctgacc gcgaccgcag caagtacggc     120
atgctggccc gcctggcggt ggag                                            144
```

```
<210> SEQ ID NO 2
<211> LENGTH: 144
<212> TYPE: DNA
<213> ORGANISM: Homo sapiens

<400> SEQUENCE: 2
gtgaagctgc gggtgaccga gggctgggac gaggacggcc accactcaga ggagtccctg      60
cattatgagg gccgcgcggt ggacatcacc acatcagacc gcgaccgcaa taagtatgga     120
ctgctggcgc gcttggcagt ggag                                            144

<210> SEQ ID NO 3
<211> LENGTH: 14
<212> TYPE: PRT
<213> ORGANISM: Drosophila melanogaster

<400> SEQUENCE: 3

Ile Ser Ser His Val His Gly Cys Phe Thr Pro Glu Ser Thr
1               5                   10

<210> SEQ ID NO 4
<211> LENGTH: 14
<212> TYPE: PRT
<213> ORGANISM: Drosophila hydei

<400> SEQUENCE: 4

Ser Ile Ser His Met His Gly Cys Phe Thr Pro Glu Ser Thr
1               5                   10

<210> SEQ ID NO 5
<211> LENGTH: 14
<212> TYPE: PRT
<213> ORGANISM: Mouse

<400> SEQUENCE: 5

Val Ala Ala Lys Ser Gly Gly Cys Phe Pro Gly Ser Ala Thr
1               5                   10

<210> SEQ ID NO 6
<211> LENGTH: 14
<212> TYPE: PRT
<213> ORGANISM: Rat

<400> SEQUENCE: 6

Val Ala Ala Lys Ser Asp Gly Cys Phe Pro Gly Ser Ala Thr
1               5                   10

<210> SEQ ID NO 7
<211> LENGTH: 14
<212> TYPE: PRT
<213> ORGANISM: Chicken

<400> SEQUENCE: 7

Val Ala Ala Lys Ser Gly Gly Cys Phe Pro Gly Ser Ala Leu
1               5                   10

<210> SEQ ID NO 8
<211> LENGTH: 14
<212> TYPE: PRT
<213> ORGANISM: Zebrafish

<400> SEQUENCE: 8

Val Ala Ala Lys Ser Gly Gly Cys Phe Pro Gly Ser Gly Thr
1               5                   10
```

```
<210> SEQ ID NO 9
<211> LENGTH: 14
<212> TYPE: PRT
<213> ORGANISM: Zebrafish

<400> SEQUENCE: 9

Val Ala Ala Lys Ser Gly Gly Cys Phe Pro Ala Gly Ala Arg
1               5                   10

<210> SEQ ID NO 10
<211> LENGTH: 14
<212> TYPE: PRT
<213> ORGANISM: Xenopus

<400> SEQUENCE: 10

Val Ala Ala Lys Thr Gly Gly Cys Phe Pro Ala Gly Ala Gln
1               5                   10

<210> SEQ ID NO 11
<211> LENGTH: 14
<212> TYPE: PRT
<213> ORGANISM: Mouse

<400> SEQUENCE: 11

Val Ala Ala Lys Thr Gly Gly Cys Phe Pro Gly Glu Ala Leu
1               5                   10

<210> SEQ ID NO 12
<211> LENGTH: 14
<212> TYPE: PRT
<213> ORGANISM: Xenopus

<400> SEQUENCE: 12

Leu Gly Val Arg Ser Gly Gly Cys Phe Pro Gly Thr Ala Met
1               5                   10

<210> SEQ ID NO 13
<211> LENGTH: 14
<212> TYPE: PRT
<213> ORGANISM: Mouse

<400> SEQUENCE: 13

Leu Ala Val Arg Ala Gly Gly Cys Phe Pro Gly Asn Ala Thr
1               5                   10

<210> SEQ ID NO 14
<211> LENGTH: 8
<212> TYPE: PRT
<213> ORGANISM: Drosophila

<400> SEQUENCE: 14

His Gly His Gly Cys Phe Thr Pro
1               5

<210> SEQ ID NO 15
<211> LENGTH: 7
<212> TYPE: PRT
<213> ORGANISM: Zebrafish

<400> SEQUENCE: 15

Ile Thr Leu Thr Ala Ala His
1               5

<210> SEQ ID NO 16
```

```
<211> LENGTH: 8
<212> TYPE: PRT
<213> ORGANISM: Zebrafish

<400> SEQUENCE: 16

Lys Ser Gly Gly Cys Phe Pro Gly
1               5

<210> SEQ ID NO 17
<211> LENGTH: 416
<212> TYPE: PRT
<213> ORGANISM: Zebrafish

<400> SEQUENCE: 17

Met Asp Val Arg Leu His Leu Lys Gln Phe Ala Leu Leu Cys Phe Ile
1               5                   10                  15

Ser Leu Leu Leu Thr Pro Cys Gly Leu Ala Cys Gly Pro Gly Arg Gly
            20                  25                  30

Tyr Gly Lys Arg Arg His Pro Lys Lys Leu Thr Pro Leu Ala Tyr Lys
        35                  40                  45

Gln Phe Ile Pro Asn Val Ala Glu Lys Thr Leu Gly Ala Ser Gly Lys
    50                  55                  60

Tyr Glu Gly Lys Ile Thr Arg Asn Ser Glu Arg Phe Lys Glu Leu Ile
65                  70                  75                  80

Pro Asn Tyr Asn Pro Asp Ile Ile Phe Lys Asp Glu Glu Asn Thr Asn
                85                  90                  95

Ala Asp Arg Leu Met Thr Lys Arg Cys Lys Asp Lys Leu Asn Ser Leu
            100                 105                 110

Ala Ile Ser Val Met Asn His Trp Pro Gly Val Lys Leu Arg Val Thr
        115                 120                 125

Glu Gly Trp Asp Glu Asp Gly His His Leu Glu Glu Ser Leu His Tyr
    130                 135                 140

Glu Gly Arg Ala Val Asp Ile Thr Thr Ser Asp Arg Asp Lys Ser Lys
145                 150                 155                 160

Tyr Gly Met Leu Ser Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Gly Thr Val
        195                 200                 205

Thr Leu Gly Asp Gly Thr Arg Lys Pro Ile Lys Asp Leu Lys Val Gly
    210                 215                 220

Asp Arg Val Leu Ala Ala Asp Glu Lys Gly Asn Val Leu Ile Ser Asp
225                 230                 235                 240

Phe Ile Met Phe Ile Asp His Asp Pro Thr Thr Arg Arg Gln Phe Ile
                245                 250                 255

Val Ile Glu Thr Ser Glu Pro Phe Thr Lys Leu Thr Leu Thr Ala Ala
            260                 265                 270

His Leu Val Phe Val Gly Asn Ser Ser Ala Ala Ser Gly Ile Thr Ala
        275                 280                 285

Thr Phe Ala Ser Asn Val Lys Pro Gly Asp Thr Val Leu Val Trp Glu
    290                 295                 300

Asp Thr Cys Glu Ser Leu Lys Ser Val Thr Val Lys Arg Ile Tyr Thr
305                 310                 315                 320

Glu Glu His Glu Gly Ser Phe Ala Pro Val Thr Ala His Gly Thr Ile
                325                 330                 335
```

```
Ile Val Asp Gln Val Leu Ala Ser Cys Tyr Ala Val Ile Glu Asn His
            340                 345                 350

Lys Trp Ala His Trp Ala Phe Ala Pro Val Arg Leu Cys His Lys Leu
            355                 360                 365

Met Thr Trp Leu Phe Pro Ala Arg Glu Ser Asn Val Asn Phe Gln Glu
370                 375                 380

Asp Gly Ile His Trp Tyr Ser Asn Met Leu Phe His Ile Gly Ser Trp
385                 390                 395                 400

Leu Leu Asp Arg Asp Ser Phe His Pro Leu Gly Ile Leu His Leu Ser
                405                 410                 415

<210> SEQ ID NO 18
<211> LENGTH: 418
<212> TYPE: PRT
<213> ORGANISM: Zebrafish

<400> SEQUENCE: 18

Met Arg Leu Leu Thr Arg Val Leu Leu Val Ser Leu Leu Thr Leu Ser
1               5                   10                  15

Leu Val Val Ser Gly Leu Ala Cys Gly Pro Gly Arg Gly Tyr Gly Arg
                20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
50                  55                  60

Lys Ile Thr Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ser Leu Ala Ile Ser
            100                 105                 110

Val Met Asn His Trp Pro Gly Val Lys Leu Arg Val Thr Glu Gly Trp
        115                 120                 125

Asp Glu Asp Gly His His Phe Glu Glu Ser Leu His Tyr Glu Gly Arg
130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
            260                 265                 270

Phe Val Leu Asp Asn Ser Thr Glu Asp Leu His Thr Met Thr Ala Ala
        275                 280                 285

Tyr Ala Ser Ser Val Arg Ala Gly Gln Lys Val Met Val Val Asp Asp
290                 295                 300
```

-continued

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
            325                 330                 335

Asp Arg Ile Leu Ala Ser Cys Tyr Ala Val Ile Glu Asp Gln Gly Leu
            340                 345                 350

Ala His Leu Ala Phe Ala Pro Ala Arg Leu Tyr Tyr Val Ser Ser
        355                 360                 365

Phe Leu Phe Pro Gln Asn Ser Ser Arg Ser Asn Ala Thr Leu Gln
370                 375                 380

Gln Glu Gly Val His Trp Tyr Ser Arg Leu Leu Tyr Gln Met Gly Thr
385                 390                 395                 400

Trp Leu Leu Asp Ser Asn Met Leu His Pro Leu Gly Met Ser Val Asn
            405                 410                 415

Ser Ser

<210> SEQ ID NO 19
<211> LENGTH: 425
<212> TYPE: PRT
<213> ORGANISM: Chicken

<400> SEQUENCE: 19

Met Val Glu Met Leu Leu Leu Thr Arg Ile Leu Leu Val Gly Phe Ile
1               5                   10                  15

Cys Ala Leu Leu Val Ser Ser Gly Leu Thr Cys Gly Pro Gly Arg Gly
            20                  25                  30

Ile Gly His Arg Arg His Pro Lys Lys Leu Thr Pro Leu Ala Tyr Lys
        35                  40                  45

Gln Phe Ile Pro Asn Val Ala Glu Lys Thr Leu Gly Ala Ser Gly Arg
    50                  55                  60

Tyr Glu Gly Lys Ile Thr Arg Asn Ser Glu Arg Phe Lys Glu Leu Ile
65                  70                  75                  80

Pro Asn Tyr Asn Pro Asp Ile Ile Phe Lys Asp Glu Glu Asn Thr Gly
                85                  90                  95

Ala Asp Arg Leu Met Thr Cys Arg Cys Lys Asp Lys Leu Asn Ala Leu
            100                 105                 110

Ala Ile Ser Val Met Asn Cys Trp Pro Gly Val Met Leu Arg Val Thr
        115                 120                 125

Glu Gly Trp Asp Glu Asp Gly His His Ser Lys Glu Ser Leu His Tyr
130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile Cys Ser Val Lys Ala Glu Asn Ser
            180                 185                 190

Val Ala Ala Lys Ser Gly Gly Cys Phe Pro Gly Ser Ala Thr Val His
        195                 200                 205

Leu Glu His Gly Gly Thr Lys Leu Val Lys Asp Leu Ser His Gly Asp
    210                 215                 220

Arg Val Leu Ala Ala Asp Ala Asp Gly Arg Leu Leu Val Ser Asp Phe
225                 230                 235                 240

Leu Leu Thr Phe Leu Asp Arg Met Asp Ser Ser Arg Lys Leu Phe Tyr
                245                 250                 255

Val Ile Glu Thr Arg Gln Pro Arg Ala Arg Leu Leu Leu Thr Ala Ala

```
                260                 265                 270
His Leu Leu Phe Val Ala Pro Gln His Asn Gln Ser Glu Ala Thr Gly
                275                 280                 285

Ser Thr Ser Gly Gln Ala Leu Phe Ala Ser Asn Val Lys Pro Gly Gln
                290                 295                 300

Pro Val Val Leu Gly Glu Gly Gln Gln Leu Leu Pro Ala Ser
305                 310                 315                 320

Val His Ser Val Ser Leu Arg Glu Glu Ala Ser Gly Ala Tyr Ala Pro
                325                 330                 335

Thr Thr Ala Cys Gly Thr Ile Leu Ile Asn Arg Val Leu Ala Ser Cys
                340                 345                 350

Tyr Ala Val Ile Glu Glu His Ser Trp Ala His Ala Ala Phe Ala Pro
                355                 360                 365

His Arg Leu Ala Gln Gly Leu Leu Ala Ala Leu Cys Pro Asp Gly Ala
                370                 375                 380

Ile Pro Thr Ala Ala Thr Thr Thr Thr Gly Ile His Trp Tyr Ser Arg
385                 390                 395                 400

Leu Leu Tyr Arg Ile Gly Ser Trp Val Leu Asp Gly Asp Ala Leu His
                405                 410                 415

Pro Leu Gly Met Val Ala Pro Ala Ser
                420                 425

<210> SEQ ID NO 20
<211> LENGTH: 437
<212> TYPE: PRT
<213> ORGANISM: Mouse

<400> SEQUENCE: 20

Met Leu Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
                20                  25                  30

Lys Arg Arg His Pro Lys Lys Leu Thr Pro Leu Ala Tyr Lys Gln Phe
                35                  40                  45

Ile Pro Asn Val Ala Glu Lys Thr Leu Gly Ala Ser Gly Arg Tyr Glu
50              55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
                100                 105                 110

Ser Val Met Asn Gln Trp Pro Gly Val Lys Leu Arg Val Thr Glu Gly
                115                 120                 125

Trp Asp Glu Asp Gly His His Ser Glu Glu Ser Leu His Tyr Glu Gly
                130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Glu Asn Ser Val
                180                 185                 190

Ala Ala Lys Ser Gly Gly Cys Phe Pro Gly Ser Ala Thr Val His Leu
                195                 200                 205

Glu Gln Gly Gly Thr Lys Leu Val Lys Asp Leu Arg Pro Gly Asp Arg
```

```
                210                 215                 220
Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Thr Ala Ala His Leu
                260                 265                 270

Leu Phe Val Ala Pro His Asn Asp Ser Gly Pro Thr Gly Pro Ser
275                 280                 285

Ala Leu Phe Ala Ser Arg Val Arg Pro Gly Gln Arg Val Tyr Val Val
                290                 295                 300

Ala Glu Arg Gly Gly Asp Arg Arg Leu Leu Pro Ala Ala Val His Ser
305                 310                 315                 320

Val Thr Leu Arg Glu Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
                340                 345                 350

Ile Glu Glu His Ser Trp Ala His Arg Ala Phe Ala Pro Phe Arg Leu
                355                 360                 365

Ala His Ala Leu Leu Ala Ala Leu Ala Pro Ala Arg Thr Asp Gly Gly
370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
                420                 425                 430

Ala Val Lys Ser Ser
            435

<210> SEQ ID NO 21
<211> LENGTH: 48
<212> TYPE: PRT
<213> ORGANISM: Homo sapiens

<400> SEQUENCE: 21

Val Lys Leu Arg Val Thr Glu Pro Trp Asp Glu Asp Gly His His Ser
1               5                   10                  15

Gln Glu Ser Leu His Tyr Glu Gly Arg Ala Val Asp Ile Thr Thr Ser
                20                  25                  30

Asp Arg Asp Arg Ser Lys Tyr Gly Met Leu Ala Arg Leu Ala Val Glu
            35                  40                  45

<210> SEQ ID NO 22
<211> LENGTH: 48
<212> TYPE: PRT
<213> ORGANISM: Homo sapiens

<400> SEQUENCE: 22

Val Lys Leu Arg Val Thr Glu Gly Trp Asp Glu Asp Gly His His Ser
1               5                   10                  15

Glu Glu Ser Leu His Tyr Glu Gly Arg Ala Val Asp Ile Thr Thr Ser
                20                  25                  30

Asp Arg Asp Arg Asn Lys Tyr Gly Leu Leu Ala Arg Leu Ala Val Glu
            35                  40                  45

<210> SEQ ID NO 23
```

```
<211> LENGTH: 7
<212> TYPE: PRT
<213> ORGANISM: Drosophila melanogaster

<400> SEQUENCE: 23

Leu Thr Val Thr Pro Ala His
1               5

<210> SEQ ID NO 24
<211> LENGTH: 7
<212> TYPE: PRT
<213> ORGANISM: Chicken

<400> SEQUENCE: 24

Leu Leu Leu Thr Ala Ala His
1               5

<210> SEQ ID NO 25
<211> LENGTH: 7
<212> TYPE: PRT
<213> ORGANISM: Mouse

<400> SEQUENCE: 25

Leu Leu Leu Thr Pro Trp His
1               5

<210> SEQ ID NO 26
<211> LENGTH: 7
<212> TYPE: PRT
<213> ORGANISM: Mouse

<400> SEQUENCE: 26

Leu Ala Leu Thr Pro Ala His
1               5

<210> SEQ ID NO 27
<211> LENGTH: 7
<212> TYPE: PRT
<213> ORGANISM: Bovine

<400> SEQUENCE: 27

Trp Val Val Thr Ala Ala His
1               5

<210> SEQ ID NO 28
<211> LENGTH: 7
<212> TYPE: PRT
<213> ORGANISM: Bovine

<400> SEQUENCE: 28

Trp Val Val Ser Ala Ala His
1               5

<210> SEQ ID NO 29
<211> LENGTH: 7
<212> TYPE: PRT
<213> ORGANISM: Porcine

<400> SEQUENCE: 29

Trp Val Met Thr Ala Ala His
1               5

<210> SEQ ID NO 30
<211> LENGTH: 7
<212> TYPE: PRT
<213> ORGANISM: Homo sapiens
```

<400> SEQUENCE: 30

Trp Val Ile Ser Ala Thr His
1               5

<210> SEQ ID NO 31
<211> LENGTH: 7
<212> TYPE: PRT
<213> ORGANISM: Homo sapiens

<400> SEQUENCE: 31

Trp Ile Leu Thr Ala Ala His
1               5

<210> SEQ ID NO 32
<211> LENGTH: 7
<212> TYPE: PRT
<213> ORGANISM: Homo sapiens

<400> SEQUENCE: 32

Trp Val Leu Thr Ala Ala His
1               5

<210> SEQ ID NO 33
<211> LENGTH: 7
<212> TYPE: PRT
<213> ORGANISM: Rat

<400> SEQUENCE: 33

Phe Val Leu Thr Ala Ala His
1               5

<210> SEQ ID NO 34
<211> LENGTH: 7
<212> TYPE: PRT
<213> ORGANISM: Homo sapiens

<400> SEQUENCE: 34

Tyr Val Leu Thr Ala Ala His
1               5

<210> SEQ ID NO 35
<211> LENGTH: 7
<212> TYPE: PRT
<213> ORGANISM: Homo sapiens

<400> SEQUENCE: 35

Trp Ile Leu Ser Ala Ala His
1               5

<210> SEQ ID NO 36
<211> LENGTH: 8
<212> TYPE: PRT
<213> ORGANISM: Artificial sequence
<220> FEATURE:
<223> OTHER INFORMATION: Synthetic construct: proteolytic domain
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 36

Xaa Thr Xaa Xaa His Leu Xaa Xaa
1               5

<210> SEQ ID NO 37
<211> LENGTH: 7
<212> TYPE: PRT
<213> ORGANISM: Zebrafish

<400> SEQUENCE: 37

Leu Thr Leu Thr Ala Ala His
1               5

<210> SEQ ID NO 38
<211> LENGTH: 10
<212> TYPE: PRT
<213> ORGANISM: Drosophila

<400> SEQUENCE: 38

Phe Thr Pro Glu Ser Thr Ala Leu Leu Glu
1               5                   10

<210> SEQ ID NO 39
<211> LENGTH: 10
<212> TYPE: PRT
<213> ORGANISM: Drosophila

<400> SEQUENCE: 39

Val Thr Pro Ala His Leu Val Ser Val Trp
1               5                   10

<210> SEQ ID NO 40
<211> LENGTH: 21
<212> TYPE: PRT
<213> ORGANISM: Drosophila

<400> SEQUENCE: 40

Ser Gly Val Arg Lys Pro Leu Gly Glu Leu Ser Ile Gly Asp Arg Val
1               5                   10                  15

Leu Ser Met Thr Ala
            20

<210> SEQ ID NO 41
<211> LENGTH: 21
<212> TYPE: PRT
<213> ORGANISM: Drosophila

<400> SEQUENCE: 41

Lys Leu Thr Phe Val Phe Ala Asp Arg Ile Glu Glu Lys Asn Gly Val
1               5                   10                  15

Leu Val Arg Asp Val
            20

<210> SEQ ID NO 42
<211> LENGTH: 10
<212> TYPE: PRT
<213> ORGANISM: Drosophila

<400> SEQUENCE: 42

Gln Ala Val Tyr Ser Glu Val Ile Leu Phe
1               5                   10

<210> SEQ ID NO 43

```
<211> LENGTH: 10
<212> TYPE: PRT
<213> ORGANISM: Drosophila

<400> SEQUENCE: 43

Glu Leu Arg Pro Gln Arg Val Val Lys Val
1               5                   10

<210> SEQ ID NO 44
<211> LENGTH: 9
<212> TYPE: PRT
<213> ORGANISM: Drosophila

<400> SEQUENCE: 44

Phe Val Gln Leu His Thr Asp Gly Gly
1               5

<210> SEQ ID NO 45
<211> LENGTH: 9
<212> TYPE: PRT
<213> ORGANISM: Drosophila

<400> SEQUENCE: 45

Val Val Ala Pro Leu Thr Arg Glu Gly
1               5

<210> SEQ ID NO 46
<211> LENGTH: 145
<212> TYPE: PRT
<213> ORGANISM: Drosophila
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (22)..(24)
<223> OTHER INFORMATION: Xaa can be any naturally occurring amino acid
<220> FEATURE:
<221> NAME/KEY: misc_feature
<222> LOCATION: (32)..(34)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (69)..(71)
<223> OTHER INFORMATION: Xaa can be any naturally occurring amino acid
<220> FEATURE:
<221> NAME/KEY: misc_feature
<222> LOCATION: (79)..(82)
<223> OTHER INFORMATION: Xaa can be any naturally occurring amino acid
<220> FEATURE:
<221> NAME/KEY: misc_feature
<222> LOCATION: (93)..(95)
<223> OTHER INFORMATION: Xaa can be any naturally occurring amino acid
<220> FEATURE:
<221> NAME/KEY: misc_feature
<222> LOCATION: (103)..(106)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (137)..(138)
<223> OTHER INFORMATION: Xaa can be any naturally occurring amino acid
```

```
<220> FEATURE:
<221> NAME/KEY: misc_feature
<222> LOCATION: (144)..(145)
<223> OTHER INFORMATION: Xaa can be any naturally occurring amino acid

<400> SEQUENCE: 46

Xaa Xaa Xaa Xaa Xaa Ser Thr Ala Leu Leu Xaa Xaa Val Arg Lys
1               5                   10                  15

Pro Leu Gly Glu Leu Xaa Xaa Xaa Asp Arg Val Leu Ser Met Thr Xaa
            20                  25                  30

Xaa Xaa Gln Ala Val Tyr Ser Glu Val Ile Leu Phe Met Asp Arg Asn
        35                  40                  45

Leu Glu Gln Met Gln Asn Phe Val Gln Leu His Thr Asp Xaa Xaa Ala
    50                  55                  60

Val Leu Thr Val Xaa Xaa Xaa His Leu Val Ser Val Trp Gln Xaa Xaa
65                  70                  75                  80

Xaa Xaa Lys Leu Thr Phe Val Phe Ala Asp Arg Ile Xaa Xaa Xaa Asn
            85                  90                  95

Gln Val Leu Val Arg Asp Xaa Xaa Xaa Xaa Glu Leu Arg Pro Gln Arg
            100                 105                 110

Val Val Lys Val Gly Ser Val Arg Ser Lys Gly Val Val Ala Pro Leu
            115                 120                 125

Thr Arg Xaa Gly Thr Ile Val Val Xaa Xaa Val Ala Ala Ser Cys Xaa
    130                 135                 140

Xaa
145

<210> SEQ ID NO 47
<211> LENGTH: 151
<212> TYPE: PRT
<213> ORGANISM: Caenorhabditis elegans

<400> SEQUENCE: 47

Cys Phe Ser Leu Asp Thr Trp Val Thr Thr Pro Gly Lys Lys Arg
1               5                   10                  15

Met Asp Gln Ile Asp Ile Gly Asp Tyr Val Leu Thr Ala Asp Leu Glu
            20                  25                  30

Lys Thr Tyr Phe Thr Pro Ile Thr Leu Trp Ile His Arg Glu Pro Glu
        35                  40                  45

Lys Val Gln Glu Phe Leu Thr Ile Met Thr Glu Tyr Gly Lys Thr Leu
    50                  55                  60

Arg Ile Thr Ser Arg His Phe Met Tyr Arg Asn Lys Cys Gly Lys Ser
65                  70                  75                  80

Tyr Pro Gln Tyr Ile Lys Met Leu Pro His Asp Gly Glu Ala Ile Phe
            85                  90                  95

Ala Ser Asp Leu Glu Val Gly Asp Cys Val Val Val Leu Tyr Lys Gly
            100                 105                 110

Lys Tyr Arg Gln Gln Lys Ile Glu Thr Ile Thr Arg Ser Val Arg Thr
            115                 120                 125

Gly Ile Tyr Ser Pro Leu Thr Asn Asn Gly Arg Ile Ile Val Asn Asp
    130                 135                 140

Met Leu Ala Ser Cys Tyr Ser
145                 150

<210> SEQ ID NO 48
<211> LENGTH: 150
<212> TYPE: PRT
<213> ORGANISM: Caenorhabditis elegans
```

<400> SEQUENCE: 48

```
Cys Phe Ser Ser Asp Thr Leu Val Thr Thr Pro Ser Gly Lys Lys Arg
1               5                   10                  15
Met Asp Glu Ile Asp Val Gly Asp Tyr Val Leu Thr Ala Asn Arg Val
            20                  25                  30
Lys Thr His Phe Thr Pro Val Thr Leu Trp Ile His Arg Glu Ser Glu
        35                  40                  45
Lys Leu Glu Glu Phe Leu Thr Ile Thr Thr Glu Arg Gly Ser Thr Leu
    50                  55                  60
Gln Leu Thr Pro Leu His Phe Met Tyr Arg Thr Lys Cys Asn Glu Ser
65                  70                  75                  80
Ser Glu Phe Leu Lys Ile Leu Pro Glu Asn His Glu Ala Ile Leu Ala
                85                  90                  95
Ser Tyr Leu Glu Ile Gly Asp Cys Val Ile Leu Thr Glu Asn Thr Lys
            100                 105                 110
Phe Arg Gln Glu Lys Ile Asn Gln Thr Thr Arg Gly Leu Lys Thr Gly
        115                 120                 125
Ile Tyr Ser Pro Leu Thr Lys Asn Gly Arg Ile Ile Val Asn Asp Met
    130                 135                 140
Leu Ala Ser Cys Tyr Ser
145                 150
```

<210> SEQ ID NO 49
<211> LENGTH: 154
<212> TYPE: PRT
<213> ORGANISM: Caenorhabditis elegans

<400> SEQUENCE: 49

```
Cys Phe Pro Gly Asp Ala Met Val Asn Val Tyr Asn Gly Gly Phe Lys
1               5                   10                  15
Arg Met Asp Glu Leu Ala Val Gly Asp Trp Val Gln Ala Leu Asp Lys
            20                  25                  30
Asn Gly Ser Gln Val Thr Phe Ile Pro Val Gln Tyr Trp Leu His Arg
        35                  40                  45
Asp Pro Lys Gln Val Ala Asp Phe Val Glu Phe Thr Leu Asp Asn Gly
    50                  55                  60
Glu Thr Phe Ser Leu Thr Glu Lys His Leu Val Phe Val Thr Gln Cys
65                  70                  75                  80
Ser Val Pro Tyr Ser Glu Asp Glu Asn Ile Asn Ala Asn Pro Val Pro
                85                  90                  95
Ala Glu Arg Val Asn Ile Gly Asp Cys Phe Tyr Ile Ala His Arg Lys
            100                 105                 110
Lys Ser Gln Met Tyr Gln Arg Val Lys Val Leu Asp Ile Asn Ile Val
        115                 120                 125
Gln Lys Thr Gly Ile Tyr Ser Pro Met Thr Ser Arg Gly His Leu Leu
    130                 135                 140
Val Asp Arg Ile His Ala Ser Cys His Ser
145                 150
```

<210> SEQ ID NO 50
<211> LENGTH: 150
<212> TYPE: PRT
<213> ORGANISM: Caenorhabditis elegans

<400> SEQUENCE: 50

```
Cys Phe Pro Ala Asp Ala Glu Val Asn Val Tyr Glu Lys Gly Val Lys
```

```
                1               5                  10                 15
Arg Met Asp Glu Leu Glu Val Gly Asp Trp Val Gln Ala Leu His Gly
                20                 25                 30

Lys Glu Thr Thr Tyr Ser Pro Val Lys Tyr Trp Leu His Arg Asp Pro
                35                 40                 45

Glu Gln Glu Ala Glu Phe Val Glu Phe Leu Leu Glu Asn Gly Glu Ser
                50                 55                 60

Phe Thr Leu Thr Glu Lys His Leu Val Phe Ala Thr Asp Cys Gln Gln
65                 70                 75                 80

Asn Val Lys Asn Leu Asp Asp Leu Asn Pro Thr Thr Gly Lys Ile
                85                 90                 95

Asn Ile Gly Glu Cys Phe Phe Met Ala Gln Pro Glu Asn Ala Ser Lys
                100                105                110

Phe Gln Lys Val Gln Ile Leu Asp Ile Gln Arg Val Arg Lys Thr Gly
                115                120                125

Ile Tyr Ala Pro Met Thr Ser Leu Gly His Leu Leu Val Asn Gln Ile
                130                135                140

His Thr Ser Cys His Ser
145                150

<210> SEQ ID NO 51
<211> LENGTH: 141
<212> TYPE: PRT
<213> ORGANISM: Caenorhabditis elegans

<400> SEQUENCE: 51

Cys Phe Thr Gly Asn Ser Lys Val Met Thr Pro Ala Gly Glu Lys Ser
1               5                  10                 15

Met Ala Asp Leu Ser Val Gly Asp Met Val Met Thr Tyr Glu Tyr Gly
                20                 25                 30

Lys Met Thr Tyr Thr Arg Val Ala Ser Trp Leu His Arg Leu Pro Asp
                35                 40                 45

Thr Lys Ala Ala Phe Ile Lys Leu Thr Thr Glu Gln Gly Ala Ile Ile
                50                 55                 60

Asp Met Thr Pro Gln His Phe Ile Tyr Lys Ala Asn Cys Val Thr Glu
65                 70                 75                 80

Glu Met Glu Leu Val Tyr Ala Glu Asp Met Thr Ile Gly Asp Cys Leu
                85                 90                 95

Met Val Lys Glu Asn Glu Lys Leu Val Met Thr Thr Ile Ser Glu Lys
                100                105                110

Ser Thr Phe Tyr Glu Thr Gly Val Tyr Ala Pro Met Thr Glu Thr Gly
                115                120                125

Asp Leu Ile Val Asp Asp Val Tyr Ala Ser Cys His Asn
                130                135                140

<210> SEQ ID NO 52
<211> LENGTH: 143
<212> TYPE: PRT
<213> ORGANISM: Caenorhabditis elegans

<400> SEQUENCE: 52

Cys Phe Ser Gly Asp Met Glu Val Glu Thr Glu Asp Gly Ile Lys Met
1               5                  10                 15

Ile Lys Asp Leu Lys Ile Gly Asp Lys Val Leu Ser Met Asp Glu Ala
                20                 25                 30

Phe Val Thr Tyr Ser Pro Val Ile Met Phe Leu His Lys Arg Asp Glu
                35                 40                 45
```

```
Glu Ile Ala Glu Phe Asn Leu Ile Glu Thr Ala Asn Gly His Ser Ile
 50                  55                  60

Lys Leu Thr Asp Asn His Leu Ile Tyr Val Ser Asp Cys Arg Thr Arg
 65                  70                  75                  80

Ser Asp Leu Lys Leu Val Ala Ala Lys Glu Val Lys Met Asp Asp Cys
                 85                  90                  95

Ile His Val Thr Thr Asp Ser Asn Val Val Ile Lys Lys Lys Val Ser
            100                 105                 110

Lys Ile Ser Lys Val Ile Glu Thr Gly Ile Tyr Ser Pro Leu Thr Ser
            115                 120                 125

Thr Gly Asp Ile Ile Val Asn Arg Val Leu Ala Ser Cys His Ser
130                 135                 140
```

<210> SEQ ID NO 53
<211> LENGTH: 155
<212> TYPE: PRT
<213> ORGANISM: Caenorhabditis elegans

<400> SEQUENCE: 53

```
Cys Phe Ser Ala Asp Ser Leu Val Thr Thr Val Thr Gly Gln Lys Arg
 1               5                  10                  15

Met Asp Glu Leu Gln Ile Gly Asp Tyr Val Leu Val Pro Ser Ser Gly
                20                  25                  30

Asn Val Leu Lys Tyr Glu Lys Val Glu Met Phe Tyr His Arg Glu Pro
            35                  40                  45

Lys Thr Arg Thr Asn Phe Val Val Leu Tyr Thr Lys Ser Gly Arg Lys
 50                  55                  60

Leu Ser Leu Thr Gly Arg His Leu Leu Pro Val Ala Glu Cys Ser Gln
 65                  70                  75                  80

Val Glu Gln Tyr Thr Met Asn Asp Gly Ile Asp Val Ala Met Arg Glu
                 85                  90                  95

Ser Lys Tyr Ala Glu Lys Ala Arg Lys Gly Glu Cys Val Leu Ser Ile
            100                 105                 110

Asp Glu Ser Gly Glu Val Ile Ala Asp Glu Ile Val Arg Val Gly Arg
            115                 120                 125

Met Thr Asn Val Gly Ile Tyr Ser Pro Met Thr Val Glu Gly Ser Leu
130                 135                 140

Ile Val Asp Gly Val Leu Ser Ser Cys Phe Ser
145                 150                 155
```

<210> SEQ ID NO 54
<211> LENGTH: 153
<212> TYPE: PRT
<213> ORGANISM: Danio rerio

<400> SEQUENCE: 54

```
Cys Phe Pro Gly Arg Ala Leu Val Thr Met Lys Asp Gly Ser His Arg
 1               5                  10                  15

Gln Ile Arg Asp Leu Gln Ala Gly Asp Leu Val Leu Ala Ser Glu Gly
                20                  25                  30

Ser Asp Gly Thr Gly Asp Leu Ile Tyr Ser Glu Val Leu Thr Phe Leu
            35                  40                  45

Asp Arg Arg Pro Ile Thr Gln Lys His Phe Tyr Val Ile Arg Thr Glu
 50                  55                  60

Asp Gly Ala Ser Val Ser Leu Thr Ala Ala His Leu Leu Phe Met Arg
 65                  70                  75                  80
```

```
Val Gly Asn Cys Ser Asn Arg Gly Glu Pro Lys Pro Gly Ala Val Arg
             85                  90                  95

Thr Ile Phe Ala Ser Asp Ala Gln Val Gly Gln Cys Leu Leu Leu Gly
            100                 105                 110

Lys Leu Arg Lys Arg Phe Ser Gln Ile Thr His Val Gly Val Arg Glu
        115                 120                 125

Asp Gln Gly Leu Tyr Pro Pro Leu Thr Ala His Gly Thr Val Val Val
        130                 135                 140

Asn Asp Val Leu Thr Ser Cys Tyr Ala
145                 150
```

```
<210> SEQ ID NO 55
<211> LENGTH: 145
<212> TYPE: PRT
<213> ORGANISM: Xenopus laevis

<400> SEQUENCE: 55

Cys Phe Pro Gly Thr Ala Met Val Met Gly Thr Gly Glu Arg Lys
1               5                   10                  15

Pro Leu Ser Glu Leu Lys Ile Gly Asp Thr Val Tyr Thr Thr Asp Glu
            20                  25                  30

Thr Gly Gln Leu Ile Thr Ser Val Leu Leu Phe Leu His Arg Asn
        35                  40                  45

Pro Tyr Lys Thr Ala Thr Phe Val Leu Ile Glu Ala Glu Gly His Pro
50                  55                  60

Ser Lys Leu Leu Val Thr Pro Asn His Leu Leu Phe Ile Gln Ser Ser
65                  70                  75                  80

Ser Ser Ala Gly Phe Leu Pro Thr Phe Ala Tyr Arg Val Gln Ile Gly
             85                  90                  95

Asp Leu Val Gln Ile Tyr Val Asn Gly Thr Gln Val Gln Ser Ser Lys
            100                 105                 110

Val Val Arg Val Ser Leu Glu Glu Gln Thr Gly Val Tyr Ala Pro Met
        115                 120                 125

Thr Glu His Gly Thr Leu Leu Val Asp Gly Val Leu Thr Ser Cys Tyr
        130                 135                 140

Ala
145
```

```
<210> SEQ ID NO 56
<211> LENGTH: 145
<212> TYPE: PRT
<213> ORGANISM: Xenopus laevis

<400> SEQUENCE: 56

Cys Phe Pro Gly Thr Ala Met Val Met Glu Thr Gly Lys Lys Lys
1               5                   10                  15

Pro Leu Ser Glu Leu Lys Leu Gly Asp Thr Val Phe Thr Thr Asp Glu
            20                  25                  30

Thr Gly Leu Leu Ile His Ser Val Leu Leu Phe Leu His Arg Asp
        35                  40                  45

Pro Tyr Lys Thr Ala Thr Phe Val Leu Ile Glu Ala Glu Gly His Pro
50                  55                  60

Thr Lys Leu Leu Val Thr Pro Asn His Leu Leu Phe Ile Lys Ser Ser
65                  70                  75                  80

Ser Ser Thr Gly Phe Gln Pro Thr Phe Ala Tyr Arg Tyr Gln Ile Gly
             85                  90                  95

Asp Leu Ile Gln Ile Tyr Val Asn Gly Thr Gln Val Gln Ser Ser Lys
```

```
                    100                 105                 110
Val Val Arg Val Ser Val Asp Glu Gln Thr Gly Val Tyr Ala Pro Met
        115                 120                 125

Thr Glu His Gly Thr Leu Leu Val Asp Gly Val Leu Thr Ser Cys Tyr
        130                 135                 140

Ala
145

<210> SEQ ID NO 57
<211> LENGTH: 147
<212> TYPE: PRT
<213> ORGANISM: Mouse

<400> SEQUENCE: 57

Cys Phe Pro Gly Asn Ala Thr Val Arg Leu Arg Ser Gly Glu Arg Lys
1               5                   10                  15

Gly Leu Arg Glu Leu His Arg Gly Asp Trp Val Leu Ala Ala Asp Ala
            20                  25                  30

Ala Gly Arg Val Val Pro Thr Pro Val Leu Leu Phe Leu Asp Arg Asp
        35                  40                  45

Leu Gln Arg Arg Ala Ser Phe Val Ala Val Glu Thr Glu Arg Pro Pro
    50                  55                  60

Arg Lys Leu Leu Leu Thr Pro Trp His Leu Val Phe Ala Ala Arg Gly
65                  70                  75                  80

Pro Ala Pro Ala Pro Gly Asp Phe Ala Pro Val Phe Ala Arg Arg Leu
                85                  90                  95

Arg Ala Gly Asp Ser Val Leu Ala Pro Gly Gly Asp Ala Leu Gln Pro
            100                 105                 110

Ala Arg Val Ala Arg Val Ala Arg Glu Glu Ala Val Gly Val Phe Ala
        115                 120                 125

Pro Leu Thr Ala His Gly Thr Leu Leu Val Asn Asp Val Leu Ala Ser
    130                 135                 140

Cys Tyr Ala
145

<210> SEQ ID NO 58
<211> LENGTH: 147
<212> TYPE: PRT
<213> ORGANISM: Mouse

<400> SEQUENCE: 58

Cys Phe Pro Ala Gly Ala Gln Val Arg Leu Glu Asn Gly Glu Arg Val
1               5                   10                  15

Ala Leu Ser Ala Val Lys Pro Gly Asp Arg Val Leu Ala Met Gly Glu
            20                  25                  30

Asp Gly Thr Pro Thr Phe Ser Asp Val Leu Ile Phe Leu Asp Arg Glu
        35                  40                  45

Pro Asn Arg Leu Arg Ala Phe Gln Val Ile Glu Thr Gln Asp Pro Pro
    50                  55                  60

Arg Arg Leu Ala Leu Thr Pro Ala His Leu Leu Phe Ile Ala Asp Asn
65                  70                  75                  80

His Thr Glu Pro Ala Ala His Phe Arg Ala Thr Phe Ala Ser His Val
                85                  90                  95

Gln Pro Gly Gln Tyr Val Leu Val Ser Gly Val Pro Gly Leu Gln Pro
            100                 105                 110

Ala Arg Val Ala Ala Val Ser Arg His Val Ala Leu Gly Ser Tyr Ala
        115                 120                 125
```

```
Pro Leu Thr Arg His Gly Thr Leu Val Val Glu Asp Val Val Ala Ser
    130                 135                 140

Cys Phe Ala
145
```

<210> SEQ ID NO 59
<211> LENGTH: 147
<212> TYPE: PRT
<213> ORGANISM: Homo sapiens

<400> SEQUENCE: 59

```
Cys Phe Pro Ala Gly Ala Gln Val Arg Leu Glu Ser Gly Ala Arg Val
1               5                   10                  15

Ala Leu Ser Ala Val Arg Pro Gly Asp Arg Val Leu Ala Met Gly Glu
            20                  25                  30

Asp Gly Ser Pro Thr Phe Ser Asp Val Leu Ile Phe Leu Asp Arg Glu
        35                  40                  45

Pro His Arg Leu Arg Ala Phe Gln Val Ile Glu Thr Gln Asp Pro Pro
    50                  55                  60

Arg Arg Leu Ala Leu Thr Pro Ala His Leu Leu Phe Thr Ala Asp Asn
65                  70                  75                  80

His Thr Glu Pro Ala Ala Arg Phe Arg Ala Thr Phe Ala Ser His Val
                85                  90                  95

Gln Pro Gly Gln Tyr Val Leu Val Ala Gly Val Pro Gly Leu Gln Pro
            100                 105                 110

Ala Arg Val Ala Ala Val Ser Thr His Val Ala Leu Gly Ala Tyr Ala
        115                 120                 125

Pro Leu Thr Lys His Gly Thr Leu Val Val Glu Asp Val Val Ala Ser
    130                 135                 140

Cys Phe Ala
145
```

<210> SEQ ID NO 60
<211> LENGTH: 148
<212> TYPE: PRT
<213> ORGANISM: Chicken

<400> SEQUENCE: 60

```
Cys Phe Pro Gly Arg Ala Leu Ala Thr Leu Glu Asn Gly Ala Arg Thr
1               5                   10                  15

Pro Leu Trp Ala Leu Arg Pro Gly Gln Arg Val Leu Ala Met Asp Gly
            20                  25                  30

Ala Gly Arg Pro Thr Tyr Ser Asp Phe Leu Ala Phe Leu Asp Lys Glu
        35                  40                  45

Pro Arg Ala Leu Thr Ala Phe His Val Ile Glu Thr Arg Gln Pro Pro
    50                  55                  60

Arg Arg Leu Ala Leu Thr Pro Thr His Leu Leu Phe Val Ala Asp Asn
65                  70                  75                  80

Ala Ser Ala Pro Ala Gln Phe Arg Pro Thr Phe Ala Ser His Val
                85                  90                  95

Gln Pro Gly His Phe Val Leu Val Ala Val Gly Ser Gly Leu Gln
            100                 105                 110

Pro Ala Glu Val Val Gly Val Arg Gly Arg Thr Asp Val Gly Ala Tyr
        115                 120                 125

Ala Pro Leu Thr Arg His Gly Thr Leu Val Val Asp Asp Val Val Ala
    130                 135                 140
```

```
Ser Cys Phe Ala
145

<210> SEQ ID NO 61
<211> LENGTH: 147
<212> TYPE: PRT
<213> ORGANISM: Xenopus laevis

<400> SEQUENCE: 61

Cys Phe Pro Gly Glu Ala Leu Ala Thr Leu Glu Ser Gly Glu Lys Ile
1               5                   10                  15

Pro Val Ser Gln Leu Ser Pro Gly Leu Arg Val Leu Ala Met Asp Asn
            20                  25                  30

Ser Gly Arg Pro Thr Tyr Ser Asp Phe Leu Ser Phe Leu Asp His Ser
        35                  40                  45

Pro Lys Glu Glu His Met Phe Gln Val Ile Lys Thr Gln Asp Pro His
    50                  55                  60

Arg Arg Leu Phe Leu Thr Pro Ala His Leu Ile Phe Val Ser Asp Asn
65                  70                  75                  80

Tyr Ser Thr Pro Ala Ser Glu Phe Gln Ala Val Phe Ala Ser Ser Val
                85                  90                  95

Arg Pro Gly Gln Tyr Ile Leu Val Ser Asn Val Val Gly Leu Ile Pro
            100                 105                 110

Ala Lys Val Arg Ser Val Asn Thr Gln Thr Asn Tyr Gly Ala Tyr Ala
        115                 120                 125

Pro Leu Thr Gln His Gly Thr Leu Val Val Asp Val Val Val Ser
    130                 135                 140

Cys Phe Ala
145

<210> SEQ ID NO 62
<211> LENGTH: 147
<212> TYPE: PRT
<213> ORGANISM: Danio rerio

<400> SEQUENCE: 62

Cys Phe Pro Gly Ser Gly Thr Val Thr Leu Gly Asp Gly Thr Arg Lys
1               5                   10                  15

Pro Ile Lys Asp Leu Lys Val Gly Asp Arg Val Leu Ala Ala Asp Glu
            20                  25                  30

Lys Gly Asn Val Leu Ile Ser Asp Phe Ile Met Phe Ile Asp His Asp
        35                  40                  45

Pro Thr Thr Arg Arg Gln Phe Ile Val Ile Glu Thr Ser Glu Pro Phe
    50                  55                  60

Thr Lys Leu Thr Leu Thr Ala Ala His Leu Val Phe Val Gly Asn Ser
65                  70                  75                  80

Ser Ala Ala Ser Gly Ile Thr Ala Thr Phe Ala Ser Asn Val Lys Pro
                85                  90                  95

Gly Asp Thr Val Leu Val Trp Glu Asp Thr Cys Glu Ser Leu Lys Ser
            100                 105                 110

Val Thr Val Lys Arg Ile Tyr Thr Glu Glu His Glu Gly Ser Phe Ala
        115                 120                 125

Pro Val Thr Ala His Gly Thr Ile Ile Val Asp Gln Val Leu Ala Ser
    130                 135                 140

Cys Tyr Ala
145
```

```
<210> SEQ ID NO 63
<211> LENGTH: 148
<212> TYPE: PRT
<213> ORGANISM: Danio rerio

<400> SEQUENCE: 63

Cys Phe Pro Gly Ser Ala Leu Val Ser Leu Gln Asp Gly Gly Gln Lys
 1               5                  10                  15

Ala Val Lys Asp Leu Asn Pro Gly Asp Lys Val Leu Ala Ala Asp Ser
            20                  25                  30

Ala Gly Asn Leu Val Phe Ser Asp Phe Ile Met Phe Thr Asp Arg Asp
        35                  40                  45

Ser Thr Thr Arg Arg Val Phe Tyr Val Ile Glu Thr Gln Glu Pro Val
    50                  55                  60

Glu Lys Ile Thr Leu Thr Ala Ala His Leu Leu Phe Val Leu Asp Asn
65                  70                  75                  80

Ser Thr Glu Asp Leu His Thr Met Thr Ala Ala Tyr Ala Ser Ser Val
                85                  90                  95

Arg Ala Gly Gln Lys Val Met Val Asp Asp Ser Gly Gln Leu Lys
            100                 105                 110

Ser Val Ile Val Gln Arg Ile Tyr Thr Glu Glu Gln Arg Gly Ser Phe
        115                 120                 125

Ala Pro Val Thr Ala His Gly Thr Ile Val Val Asp Arg Ile Leu Ala
    130                 135                 140

Ser Cys Tyr Ala
145

<210> SEQ ID NO 64
<211> LENGTH: 147
<212> TYPE: PRT
<213> ORGANISM: Xenopus laevis

<400> SEQUENCE: 64

Cys Phe Pro Ala Gly Ala Arg Val Met Val Glu Gly Gly Thr Lys
 1               5                  10                  15

Ala Val Lys Asp Leu Arg Pro Gly Asp Arg Val Leu Ser Ser Asp Pro
            20                  25                  30

Gln Gly Asn Leu Leu Tyr Ser Asp Phe Leu Met Phe Ile Asp Gln Glu
        35                  40                  45

Arg Asp Val Lys Lys Leu Phe Tyr Val Ile Glu Thr Ser Gln Arg Lys
    50                  55                  60

Ile Arg Leu Thr Ala Ala His Leu Leu Phe Val Ala Gln Thr Lys Val
65                  70                  75                  80

Asn Gly Thr Arg Ser Phe Lys Ser Val Phe Ala Ser Asn Ile Gln Pro
                85                  90                  95

Gly Asp Leu Ile Tyr Thr Ala Asp Pro Lys Thr Met Thr Leu Lys Ala
            100                 105                 110

Val Lys Val Glu Lys Val Asp Leu Glu Glu Asp Thr Gly Ala Tyr Ala
        115                 120                 125

Pro Leu Thr Ala His Gly Thr Val Val Ile Asp Gln Val Leu Ala Ser
    130                 135                 140

Cys Tyr Ala
145

<210> SEQ ID NO 65
<211> LENGTH: 148
<212> TYPE: PRT
<213> ORGANISM: Xenopus laevis
```

<400> SEQUENCE: 65

```
Cys Phe Pro Ala Gly Ala Arg Val Met Val Glu Phe Gly Gly Thr Lys
1               5                   10                  15

Ala Val Lys Asp Leu Arg Pro Gly Asp Arg Val Leu Ser Ser Asp Pro
            20                  25                  30

Gln Gly Asn Leu Leu Tyr Ser Asp Phe Leu Met Phe Ile Asp Gln Glu
        35                  40                  45

Arg Asp Val Lys Lys Leu Phe Tyr Val Ile Glu Thr Ser Gln Arg Lys
    50                  55                  60

Ile Arg Leu Thr Ala Ala His Leu Leu Phe Val Ala Gln Thr Lys Val
65                  70                  75                  80

Asn Gly Thr Arg Ser Phe Lys Ser Val Phe Ala Ser Asn Ile Gln Pro
                85                  90                  95

Gly Asp Leu Ile Tyr Thr Ala Glu Ser Gln Asp His Asp Leu Glu Gly
            100                 105                 110

Arg Gly Lys Trp Arg Arg Leu Ile Leu Arg Glu Asp Thr Gly Ala Tyr
        115                 120                 125

Ala Pro Leu Thr Ala His Gly Thr Val Val Ile Asp Gln Val Leu Ala
    130                 135                 140

Ser Cys Tyr Ala
145
```

<210> SEQ ID NO 66
<211> LENGTH: 158
<212> TYPE: PRT
<213> ORGANISM: Cynops pyrrhogaster

<400> SEQUENCE: 66

```
Cys Phe Pro Gly Ser Ala Thr Val Ala Leu Glu Gln Gly Val Arg Ile
1               5                   10                  15

Pro Val Lys Asp Leu Arg Pro Gly Asp Arg Val Leu Ala Ala Asp Gly
            20                  25                  30

Leu Gly Lys Leu Val Tyr Ser Asp Phe Leu Leu Phe Met Asp Lys Glu
        35                  40                  45

Glu Thr Val Arg Lys Val Phe Tyr Val Ile Glu Thr Ser Arg Glu Arg
    50                  55                  60

Val Arg Leu Thr Ala Ala His Leu Leu Phe Val Gly Gln Ala His Pro
65                  70                  75                  80

Gly Asn Asp Ser Gly Gly Asp Phe Arg Ser Val Phe Gly Ser Ala Gly
                85                  90                  95

Phe Arg Ser Met Phe Ala Ser Ser Val Arg Ala Gly His Arg Val Leu
            100                 105                 110

Thr Val Asp Arg Glu Gly Arg Gly Leu Arg Glu Ala Thr Val Glu Arg
        115                 120                 125

Val Tyr Leu Glu Glu Ala Thr Gly Ala Tyr Ala Pro Thr Ala His
    130                 135                 140

Gly Thr Val Val Ile Asp Arg Val Leu Ala Ser Cys Tyr Ala
145                 150                 155
```

<210> SEQ ID NO 67
<211> LENGTH: 168
<212> TYPE: PRT
<213> ORGANISM: Homo sapiens

<400> SEQUENCE: 67

```
Cys Phe Arg Gly Ser Ala Thr Val His Leu Glu Gln Gly Gly Thr Lys
```

-continued

```
                1               5                  10                 15
Leu Val Lys Asp Leu Arg Pro Gly Asp Arg Val Leu Ala Ala Asp
                20                 25                 30

Gln Gly Arg Leu Leu Tyr Ser Asp Phe Leu Thr Arg Leu Asp Arg Asp
                35                 40                 45

Asp Gly Ala Lys Lys Val Phe Tyr Val Ile Glu Thr Arg Glu Pro Arg
            50                 55                 60

Glu Arg Leu Leu Leu Thr Ala Ala His Leu Phe Val Ala Arg His
65                  70                 75                 80

Asn Asp Ser Ala Thr Gly Pro Pro Arg Ala Ser Ser Gly Ser Gly Pro
                85                 90                 95

Pro Ser Gly Gly Ala Leu Gly Pro Arg Ala Leu Phe Ala Ser Arg Val
            100                105                110

Arg His Gly Gln Arg Val Tyr Val Ala Glu Arg Asp Gly Asp Arg
                115                120                125

Arg Leu Leu Pro Ala Ala Val His Ser Val Thr Leu Ser Glu Glu Ala
            130                135                140

Ala Gly Ala Tyr Ala Pro Leu Thr Ala Gln Gly Thr Ile Glu Ile Asn
145                 150                155                160

Arg Val Leu Ala Ser Gly Tyr Ala
                165

<210> SEQ ID NO 68
<211> LENGTH: 144
<212> TYPE: PRT
<213> ORGANISM: Drosophila hydei

<400> SEQUENCE: 68

Cys Phe Thr Pro Glu Ser Thr Ala Leu Leu Glu Ser Gly Ala Glu Lys
1               5                  10                 15

Ala Leu Gly Glu Leu Ala Ile Gly Asp Arg Val Leu Ser Met Asp Val
                20                 25                 30

Lys Gly Gln Pro Val Tyr Ser Glu Val Ile Leu Phe Met Asp Arg Asn
                35                 40                 45

Leu Glu Gln Val Glu Asn Phe Val Gln Leu His Thr Asp Gly Gly Ala
            50                 55                 60

Val Leu Thr Val Thr Pro Ala His Leu Ile Ser Val Trp Gln Pro Glu
65                  70                 75                 80

Arg Gln Thr Leu Asn Phe Ile Phe Ala Asp Arg Val Glu Glu Leu Asp
                85                 90                 95

Tyr Val Leu Val Arg Asp Ala Thr Gly Glu Leu Gln Pro Gln Arg Val
            100                105                110

Leu Arg Leu Gly Ser Val Gln Ser Arg Gly Val Val Ala Pro Leu Thr
            115                120                125

Arg Glu Gly Thr Ile Val Val Asn Ser Val Ala Ala Ser Cys Tyr Ala
130                 135                140

<210> SEQ ID NO 69
<211> LENGTH: 145
<212> TYPE: PRT
<213> ORGANISM: Drosophila melanogaster

<400> SEQUENCE: 69

Cys Phe Thr Pro Glu Ser Thr Ala Leu Leu Glu Ser Gly Val Arg Lys
1               5                  10                 15

Pro Leu Gly Glu Leu Ser Ile Gly Asp Arg Val Leu Ser Met Thr Ala
                20                 25                 30
```

```
Asn Gly Gln Ala Val Tyr Ser Glu Val Ile Leu Phe Met Asp Arg Asn
            35                  40                  45

Leu Glu Gln Met Gln Asn Phe Val Gln Leu His Thr Asp Gly Gly Ala
 50                  55                  60

Val Leu Thr Val Thr Pro Ala His Leu Val Ser Val Trp Gln Pro Glu
 65                  70                  75                  80

Ser Gln Lys Leu Thr Phe Val Phe Ala Asp Arg Ile Glu Glu Lys Asn
                 85                  90                  95

Gln Val Leu Val Arg Asp Val Glu Thr Gly Glu Leu Arg Pro Gln Arg
                100                 105                 110

Val Val Lys Val Gly Ser Val Arg Ser Lys Gly Val Val Ala Pro Leu
                115                 120                 125

Thr Arg Glu Gly Thr Ile Val Val Asn Ser Val Ala Ala Ser Cys Tyr
    130                 135                 140

Ala
145

<210> SEQ ID NO 70
<211> LENGTH: 101
<212> TYPE: PRT
<213> ORGANISM: Yeast

<400> SEQUENCE: 70

Cys Phe Ala Lys Gly Thr Asn Val Leu Met Ala Asp Gly Ser Ile Glu
 1               5                  10                  15

Cys Ile Glu Asn Ile Glu Gly Val Asn Lys Val Met Gly Lys Leu Leu
                20                  25                  30

Lys Phe Thr Cys Asn Ala Thr His Glu Leu Val Val Arg Thr Ser Asn
            35                  40                  45

Lys Ala Tyr Phe Glu Trp Thr Ile Glu Ala Arg Asp Leu Ser Leu Leu
 50                  55                  60

Gly Ser His Val Leu Gln Glu Leu Lys Glu Asp Tyr Tyr Gly Ile
 65                  70                  75                  80

Thr Leu Ser Asp Asp Ser Asp His Gln Phe Leu Leu Ala Asn Gln Val
                 85                  90                  95

Val Val His Asn Cys
            100

<210> SEQ ID NO 71
<211> LENGTH: 99
<212> TYPE: PRT
<213> ORGANISM: Candida tropicalis

<400> SEQUENCE: 71

Cys Phe Thr Lys Gly Thr Gln Val Met Met Ala Asp Gly Ala Asp Lys
 1               5                  10                  15

Ser Ile Glu Ser Ile Glu Val Gly Asp Lys Val Met Gly Lys Phe Thr
                20                  25                  30

Val Ser Ala Asp His Lys Leu Ile Leu Lys Thr Ile Asp Ser Lys Glu
            35                  40                  45

Tyr Ile Asp Trp Ile Ile Glu Ala Arg Asp Tyr Val Gln Val Asp Glu
 50                  55                  60

Ile Val Leu Ile Lys Ser Ala Lys Glu Asn Tyr Tyr Gly Ile Thr Leu
 65                  70                  75                  80

Ala Glu Glu Thr Asp His Gln Phe Leu Leu Ser Asn Met Ala Leu Val
                 85                  90                  95
```

His Asn Cys

<210> SEQ ID NO 72
<211> LENGTH: 103
<212> TYPE: PRT
<213> ORGANISM: Mycobacterium leprae

<400> SEQUENCE: 72

Cys Val Ser Gly Asn Ser Leu Val Arg Leu Leu Phe Gly Lys Ser Ile
1               5                   10                  15

Arg Ile Gly Asp Ile Val Thr Gly Ala Gly Tyr Glu Ile Thr Gly Thr
            20                  25                  30

Ser Asn His Pro Leu Leu Cys Leu Val Asn Val Gly Gly Ile Pro Thr
        35                  40                  45

Leu Leu Trp Lys Leu Ile Gly Glu Ile Arg Ser Gly Asp Tyr Val Val
    50                  55                  60

Leu Gln Arg Ile Pro Val Ala Ser Val Thr Asp Thr Gly Ile Gln Pro
65                  70                  75                  80

Val Phe Ser Leu His Val Asp Thr Glu Asp His Ser Phe Leu Thr Asn
                85                  90                  95

Gly Phe Ile Ser His Asn Thr
            100

<210> SEQ ID NO 73
<211> LENGTH: 103
<212> TYPE: PRT
<213> ORGANISM: Mycobacterium xenopi

<400> SEQUENCE: 73

Cys Ile Thr Gly Asp Ala Leu Val Ala Leu Pro Glu Gly Glu Ser Val
1               5                   10                  15

Arg Ile Ala Asp Ile Val Pro Gly Ala Gly Leu Arg Val Thr Gly Thr
            20                  25                  30

Ala Asn His Pro Leu Leu Cys Leu Val Asp Val Ala Gly Val Pro Thr
        35                  40                  45

Leu Leu Trp Lys Leu Ile Asp Glu Ile Lys Pro Gly Asp Tyr Ala Val
    50                  55                  60

Ile Gln Arg Ser Ala Val Ala Ser Val Thr Asp Ala Gly Val Gln Pro
65                  70                  75                  80

Val Tyr Ser Leu Arg Val Asp Thr Ala Asp His Ala Phe Ile Thr Asn
                85                  90                  95

Gly Phe Val Ser His Asn Thr
            100

<210> SEQ ID NO 74
<211> LENGTH: 95
<212> TYPE: PRT
<213> ORGANISM: Mycobacterium tuberculosis

<400> SEQUENCE: 74

Cys Leu Ala Glu Gly Thr Arg Ile Phe Asp Pro Val Thr Gly Thr Thr
1               5                   10                  15

His Arg Ile Glu Asp Val Val Asp Gly Arg Gly Ala Ile Val Trp Ala
            20                  25                  30

Thr Pro Asp His Lys Val Leu Thr Glu Tyr Gly Trp Arg Ala Ala Gly
        35                  40                  45

Glu Leu Arg Lys Gly Asp Arg Val Ala Gln Pro Arg Arg Phe Ile Arg
    50                  55                  60

Glu Val Leu Pro Thr Arg Arg Ala Arg Thr Phe Asp Leu Glu Val Glu
65                  70                  75                  80

Glu Leu His Thr Leu Val Ala Glu Gly Val Val His Asn Cys
            85                  90                  95

<210> SEQ ID NO 75
<211> LENGTH: 92
<212> TYPE: PRT
<213> ORGANISM: Mycobacterium leprae

<400> SEQUENCE: 75

Cys Met Asn Tyr Ser Thr Arg Val Thr Leu Ala Asp Gly Ser Thr Glu
1               5                   10                  15

Lys Ile Gly Lys Ile Val Asn Asn Lys Lys Ser Gln Phe Ala Ala Thr
            20                  25                  30

Pro Asn His Leu Ile Arg Thr Pro Gly Gly Trp Thr Glu Ala Gly Asn
        35                  40                  45

Leu Ile Ala Gly Asp Arg Val Leu Ala Val Glu Pro His Val Lys Leu
    50                  55                  60

Ser Thr Arg Ser Met Asn Arg Phe Asp Ile Glu Val Glu Gly Asn His
65                  70                  75                  80

Asn Tyr Phe Val Asp Gly Val Met Val His Asn Ser
                85                  90

<210> SEQ ID NO 76
<211> LENGTH: 106
<212> TYPE: PRT
<213> ORGANISM: Mycobacterium leprae

<400> SEQUENCE: 76

Cys Leu Thr Ala Asp Ala Arg Ile Asn Val Lys Gly Lys Gly Leu Val
1               5                   10                  15

Ser Ile Ala Asp Val Gln Pro Gly Asp Gly Arg Ala Leu Glu Ala Thr
            20                  25                  30

Gly Asn His Gln Phe Leu Val Ala Arg Arg Val Glu Glu Gly Lys Arg
        35                  40                  45

Thr Arg Trp Thr Ala Val Trp Ala Pro Leu Glu Glu Ile Glu Ser Gly
    50                  55                  60

Glu Pro Ile Ala Val Ala Arg Val Leu Leu Lys Ser Lys Thr Leu Val
65                  70                  75                  80

Gly Glu Lys Pro Thr Tyr Asp Ile Gln Val Val Gly Leu Glu Asn Phe
                85                  90                  95

Val Ala Asn Gly Ile Val Ala His Asn Ser
                100                 105

<210> SEQ ID NO 77
<211> LENGTH: 93
<212> TYPE: PRT
<213> ORGANISM: Porphyra purpurea

<400> SEQUENCE: 77

Cys Ile Ser Lys Phe Ser His Ile Met Trp Ser His Val Ser Lys Pro
1               5                   10                  15

Leu Phe Asn Phe Ser Ile Lys Lys Glu Lys Tyr Leu Glu Leu Thr Ser
            20                  25                  30

Asn His Lys Ile Leu Thr Leu Arg Gly Trp Gln Arg Cys Asp Gln Leu
        35                  40                  45

Leu Cys Asn Asp Met Ile Thr Thr Gln Ile Gly Phe Leu Ala Asn Ile
    50                  55                  60

```
Asn Ile Ser Asn Phe Gln Asn Val Phe Asp Phe Ala Ala Asn Pro Ile
 65                  70                  75                  80

Pro Asn Phe Ile Ala Asn Asn Ile Ile Val His Asn Ser
                 85                  90
```

<210> SEQ ID NO 78
<211> LENGTH: 95
<212> TYPE: PRT
<213> ORGANISM: Synechocystis sp.

<400> SEQUENCE: 78

```
Cys Ile Ser Gly Asp Ser Leu Ile Ser Leu Ala Ser Thr Gly Lys Arg
  1               5                  10                  15

Val Ser Ile Lys Asp Leu Leu Asp Glu Lys Gly Arg Thr Ile Lys Ala
                 20                  25                  30

Thr Ala Asn His Arg Phe Leu Thr Ile Asp Gly Trp Lys Arg Leu Asp
             35                  40                  45

Glu Leu Ser Leu Lys Glu His Ile Ala Leu Pro Arg Lys Leu Ile Val
 50                  55                  60

Ser Ile Thr Glu Thr Gly Val Glu Val Phe Asp Leu Thr Val Pro
 65                  70                  75                  80

Gly Pro His Asn Phe Val Ala Asn Asp Ile Ile Val His Asn Ser
                 85                  90                  95
```

<210> SEQ ID NO 79
<211> LENGTH: 94
<212> TYPE: PRT
<213> ORGANISM: Synechocystis sp.

<400> SEQUENCE: 79

```
Cys Phe Ser Gly Asp Thr Leu Val Ala Leu Thr Asp Gly Arg Ser Val
  1               5                  10                  15

Ser Phe Glu Gln Leu Val Glu Glu Gly Ser Ile Ile Cys Thr
                 20                  25                  30

Pro Asp His Lys Phe Met Leu Arg Asp Gly Ser Tyr Lys Cys Ala Met
             35                  40                  45

Asp Leu Thr Leu Asp Asp Ser Leu Met Pro Leu His Arg Lys Ile Glu
 50                  55                  60

Ala Val Ser Glu Thr Ile Asp Val Tyr Asp Ile Glu Val Pro His Thr
 65                  70                  75                  80

His Asn Phe Ala Leu Ala Ser Gly Val Phe Val His Asn Ser
                 85                  90
```

<210> SEQ ID NO 80
<211> LENGTH: 96
<212> TYPE: PRT
<213> ORGANISM: Synechocystis sp.

<400> SEQUENCE: 80

```
Cys Leu Thr Gly Asp Ser Gln Val Leu Thr Arg Asn Gly Leu Met Ser
  1               5                  10                  15

Ile Asp Asn Pro Gln Ile Lys Gly Asn Ser Thr Val Arg Cys Thr Ala
                 20                  25                  30

Asn His Leu Ile Arg Thr Glu Gln Gly Trp Thr Arg Ala Glu Asn Ile
             35                  40                  45

Thr Pro Gly Met Lys Ile Leu Ser Pro Ala Ser Val Phe Glu Glu Val
 50                  55                  60

Glu Ser Val Thr Lys Gly Gln Val Glu Lys Val Tyr Asp Leu Glu Val
```

```
                65                  70                  75                  80
Glu Asp Asn His Asn Phe Val Ala Asn Gly Leu Leu Val His Asn Cys
                    85                  90                  95

<210> SEQ ID NO 81
<211> LENGTH: 103
<212> TYPE: PRT
<213> ORGANISM: Chlamydomonas

<400> SEQUENCE: 81

Cys Leu Thr Ser Asp His Thr Val Leu Thr Arg Gly Trp Ile Pro
1               5                   10                  15

Ile Ala Asp Val Thr Leu Asp Asp Gly Val Asp Leu Phe Val Thr Pro
                20                  25                  30

Asn His Arg Met Tyr Val Asn Thr Thr Asn Asn Thr Thr Asn Gln Asn
            35                  40                  45

Tyr Asn Leu Val Glu Ala Ser Ser Ile Phe Gly Lys Lys Val Arg Tyr
        50                  55                  60

Asn Thr Ser Thr Asn Asp Arg Phe Val Tyr Tyr Lys Pro Gly Val Tyr
65                  70                  75                  80

Cys Leu Thr Gly Pro Asn Asn Val Phe Tyr Val Gln Arg Asn Gly Lys
                85                  90                  95

Ala Val Trp Thr Gly Asn Ser
            100

<210> SEQ ID NO 82
<211> LENGTH: 106
<212> TYPE: PRT
<213> ORGANISM: Methanococcus jannaschii

<400> SEQUENCE: 82

Cys Leu Met Pro His Glu Lys Val Leu Thr Glu Tyr Gly Glu Ile Lys
1               5                   10                  15

Ile Glu Asp Leu Phe Lys Ile Gly Trp His Ser Ile Thr Thr Thr Pro
                20                  25                  30

Glu His Pro Phe Leu Thr Asn Asn Gly Trp Ile Lys Ala Glu Asn Ile
            35                  40                  45

Lys Lys Gly Met Tyr Val Ala Ile Pro Arg Lys Ile Tyr Gly Asn Glu
        50                  55                  60

Asp Phe Glu Lys Phe Ile Glu Phe Ile Val Glu Asp Val Glu Ile Ile
65                  70                  75                  80

Asp Tyr Asp Gly Tyr Val Tyr Asp Leu Thr Thr Glu Thr His Asn Phe
                85                  90                  95

Ile Ala Asn Gly Ile Val Val His Asn Thr
            100                 105

<210> SEQ ID NO 83
<211> LENGTH: 103
<212> TYPE: PRT
<213> ORGANISM: Methanococcus jannaschii

<400> SEQUENCE: 83

Cys Leu Asn Ala Asn Thr Glu Ile Leu Gln Glu Ser Gly Phe Arg Lys
1               5                   10                  15

Ile Thr Glu Leu Asn Lys Asp Glu Gly Leu Glu Ile Thr Thr Thr Pro
                20                  25                  30

Asn His Ile Phe Leu Val Lys Glu Asn Gly Ser Leu Lys Glu Lys Glu
            35                  40                  45
```

```
Ala Lys Asp Leu Lys Val Gly Asp Tyr Val Ala Thr Val Asp Arg Ile
 50                  55                  60

Ile Lys Glu Ile Lys Lys Ile Lys Val Asn Asp Lys Tyr Ala Tyr Asp
 65                  70                  75                  80

Ile Glu Leu Pro Asp Asp Gly Ser Asn Ser His Tyr Ile Val Ala Asn
                 85                  90                  95

Gly Phe Ile Val His Asn Ser
            100

<210> SEQ ID NO 84
<211> LENGTH: 101
<212> TYPE: PRT
<213> ORGANISM: Methanococcus jannaschii

<400> SEQUENCE: 84

Cys Leu Thr Gly Asp Thr Lys Val Ile Val Asn Gly Glu Ile Arg Glu
 1               5                  10                  15

Ile Gly Glu Val Ile Glu Ile Gly Arg Glu Leu Lys Val Thr Thr
                 20                  25                  30

Tyr His Pro Leu Leu Ile Asn His Lys Asn Gly Glu Ile Lys Trp Glu
             35                  40                  45

Lys Ala Glu Asn Leu Lys Val Gly Asp Lys Leu Ala Thr Pro Arg Tyr
 50                  55                  60

Ile Ile Val Glu Ile Glu Gln Leu Asn Gly Glu Phe Thr Ile Tyr Asp
 65                  70                  75                  80

Leu His Val Pro Arg Tyr His Asn Phe Ile Gly Gly Asn Leu Pro Thr
                 85                  90                  95

Ile Leu His Asn Thr
            100

<210> SEQ ID NO 85
<211> LENGTH: 107
<212> TYPE: PRT
<213> ORGANISM: Methanococcus jannaschii

<400> SEQUENCE: 85

Cys Leu Thr Gly Asp Ala Lys Ile Thr Leu Pro Asp Glu Arg Glu Ile
 1               5                  10                  15

Lys Ile Glu Asp Phe Ile Lys Met Phe Gly Arg Glu Ile Glu Ala Thr
                 20                  25                  30

Gly Asp His Lys Phe Leu Thr Arg Asp Gly Trp Lys Glu Val Tyr Glu
             35                  40                  45

Leu Lys Glu Asp Asp Glu Val Leu Val Tyr Pro Ala Leu Glu Gly Val
 50                  55                  60

Gly Phe Glu Val Asp Glu Arg Arg Ile Ile Ile Lys Lys Glu Cys
 65                  70                  75                  80

Ile Gly Tyr Arg Asp Val Tyr Asp Ile Thr Cys His Lys Asp Pro Ser
                 85                  90                  95

Phe Ile Ala Asn Gly Phe Val Ser His Asn Cys
            100                 105

<210> SEQ ID NO 86
<211> LENGTH: 95
<212> TYPE: PRT
<213> ORGANISM: Methanococcus jannaschii

<400> SEQUENCE: 86

Cys Leu Thr Ser Asn Ser Lys Ile Leu Thr Asp Asp Gly Tyr Tyr Ile
 1               5                  10                  15
```

```
Lys Leu Glu Lys Leu Lys Glu Lys Gly Arg Val Leu Glu Gly Ser Lys
         20                  25                  30

Asp His Pro Val Leu Thr Leu Asn Gly Tyr Val Pro Met Gly Met Leu
             35                  40                  45

Lys Glu Gly Asp Asp Val Ile Val Tyr Pro Tyr Glu Ile Lys Glu Ile
 50                  55                  60

Glu Glu Ile Ser Tyr Asp Ser Lys Leu Tyr Asp Val Gly Ile Val Ser
 65                  70                  75                  80

Lys Glu His Asn Phe Ile Ala Asn Ser Ile Val Val His Asn Cys
             85                  90                  95
```

<210> SEQ ID NO 87
<211> LENGTH: 98
<212> TYPE: PRT
<213> ORGANISM: Methanococcus jannaschii

<400> SEQUENCE: 87

```
Cys Leu His Pro Asp Thr Tyr Val Ile Leu Pro Asp Gly Arg Met Lys
 1               5                  10                  15

Lys Ile Ser Glu Ile Asp Glu Asp Glu Ser Glu Leu Ile Thr Thr Gly
             20                  25                  30

Glu His Lys Leu Phe Val Val Glu Asn Gly Lys Ile Val Glu Lys Cys
             35                  40                  45

Val Lys Asp Leu Asn Gly Ser Glu Leu Ile Gly Val Val Arg Lys Leu
 50                  55                  60

Phe Lys Ile Glu Glu Val Glu Ser Asp Val Glu Tyr Val Tyr Asp Leu
 65                  70                  75                  80

Glu Val Glu Asp Tyr His Asn Phe Ile Gly Asn Leu Ile Ile Asn His
             85                  90                  95

Asn Ser
```

<210> SEQ ID NO 88
<211> LENGTH: 94
<212> TYPE: PRT
<213> ORGANISM: Methanococcus jannaschii

<400> SEQUENCE: 88

```
Cys Val Asp Gly Asp Thr Thr Val Leu Leu Asp Gly Lys Leu Ile Lys
 1               5                  10                  15

Ile Lys Asp Leu Glu Asp Lys Trp Gly Arg Glu Ile Ile Ala Thr Glu
             20                  25                  30

Asp His Pro Phe Tyr Thr Thr Asn Gly Arg Lys Arg Cys Gly Glu Leu
             35                  40                  45

Lys Val Gly Asp Glu Val Ile Ile Tyr Pro Asn Asp Ile Val Ser Ile
 50                  55                  60

Glu Glu Thr Lys Val Asp Tyr Val Tyr Asp Ile Thr Thr Ile Ser Glu
 65                  70                  75                  80

Thr His Asn Phe Ile Ala Asn Gly Phe Leu Thr Gly Asn Cys
             85                  90
```

<210> SEQ ID NO 89
<211> LENGTH: 99
<212> TYPE: PRT
<213> ORGANISM: Methanococcus jannaschii

<400> SEQUENCE: 89

```
Cys Leu Thr Pro Asp Thr Tyr Val Val Leu Gly Asp Gly Arg Ile Glu
 1               5                  10                  15
```

```
Thr Ile Glu Asp Ile Val Asn Ala Lys Asn Tyr Glu Leu Lys Ala Thr
                20                  25                  30

Pro Asp His Cys Leu Leu Val Leu Arg Asp Asn Gln Leu Lys Trp Ile
            35                  40                  45

Pro Ala Lys Asp Ile Lys Glu Glu Asp Tyr Ile Ala Met Pro Phe Asn
 50                  55                  60

Tyr Val Lys Lys Val Glu Asn Ile Pro Tyr Asp Gly Tyr Val Tyr Asp
 65                  70                  75                  80

Leu Ser Ile Lys His Asn Gln Asn Phe Ile Ser Asn Gly Val Ile Ser
                85                  90                  95

His Asn Cys

<210> SEQ ID NO 90
<211> LENGTH: 104
<212> TYPE: PRT
<213> ORGANISM: Methanococcus jannaschii

<400> SEQUENCE: 90

Cys Ile Glu Gly Asp Ala Lys Ile Leu Thr Asp Arg Gly Phe Leu Lys
 1               5                  10                  15

Met Lys Glu Val Tyr Lys Leu Val Lys Asp Thr Ile Lys Ile Thr Pro
                20                  25                  30

Asp His Lys Pro Val Phe Val Asn Gly Glu Leu Ser Lys Val Gln Leu
            35                  40                  45

Cys Asp Ile Ile Asp Asn Asn Leu Ser Val Leu Ser Ile Asp Tyr Ile
 50                  55                  60

Lys Lys Val Gly Glu Asp Tyr Gly Val Tyr Asn Ile Thr Val Lys
 65                  70                  75                  80

Ala Glu Asn Glu Phe Asn His Asn Tyr Val Val Trp Thr Lys His Tyr
                85                  90                  95

Thr Pro Ile Val Val Phe Asn Cys
            100

<210> SEQ ID NO 91
<211> LENGTH: 102
<212> TYPE: PRT
<213> ORGANISM: Methanococcus jannaschii

<400> SEQUENCE: 91

Cys Phe His Pro Asp Glu Val Leu Phe Ile Asp Arg Gly Arg Gly Leu
 1               5                  10                  15

Glu Cys Ile Thr Phe Lys Glu Leu Phe Glu Leu Gly Arg Glu Ile
                20                  25                  30

Lys Ile Thr Lys Asp His Pro Val Val Ile Leu Glu Asp Gly Glu Leu
            35                  40                  45

Lys Ile Lys Leu Thr Ser Asp Val Lys Glu Gly Asp Lys Val Ile Leu
 50                  55                  60

Pro Tyr Gly Asn Val Lys Glu Ile Ile Lys Glu His Tyr Ser Gly Tyr
 65                  70                  75                  80

Val Tyr Ser Val Glu Thr Glu Asn Ser Leu Leu Ile Thr Ser Tyr Gly
                85                  90                  95

Ile Leu Ile His Asn Cys
            100

<210> SEQ ID NO 92
<211> LENGTH: 103
<212> TYPE: PRT
```

```
-continued
```

<213> ORGANISM: Methanococcus jannaschii

<400> SEQUENCE: 92

Cys Val Pro Pro Asp Thr Leu Leu Ile Leu Glu Asn Gly Phe Lys Arg
1               5                   10                  15

Ile Val Asp Ile Lys Val Gly Asp Lys Val Leu Thr His Pro Glu Glu
            20                  25                  30

Ile Ile Leu Thr Pro Glu His Pro Val Tyr Ala Ile Lys Thr Glu Lys
        35                  40                  45

Arg Cys Asp Gly Ser His Gly Ile Cys Lys Phe Asn Cys Leu Thr Gln
    50                  55                  60

Tyr Thr Asn Pro Ser Ile Ile Arg Ile Gly Arg Glu Tyr Tyr Asp Gly
65                  70                  75                  80

Phe Val Tyr Asn Leu Glu Val Glu Asp Ser Ser Tyr Val Thr Val
                85                  90                  95

Ser Gly Thr Leu His Asn Cys
            100

<210> SEQ ID NO 93
<211> LENGTH: 102
<212> TYPE: PRT
<213> ORGANISM: Pyrococcus furiosus

<400> SEQUENCE: 93

Cys Ile Asp Gly Lys Ala Lys Ile Ile Phe Glu Asn Glu Gly Glu Glu
1               5                   10                  15

His Leu Thr Thr Met Glu Glu Met Tyr Glu Arg Gly Thr Lys Ile Leu
            20                  25                  30

Thr Ser Pro Trp His Pro Phe Phe Val Leu Thr Pro Asp Phe Lys Ile
        35                  40                  45

Val Glu Lys Arg Ala Asp Glu Leu Lys Glu Gly Asp Ile Leu Ile Gly
    50                  55                  60

Gly Met Pro Asp Ile Thr Thr Thr Asn Glu Pro Arg Thr Phe Tyr Asp
65                  70                  75                  80

Leu Thr Val Glu Asn Tyr Gln Asn Tyr Leu Ala Gly Leu Asn Gly Met
                85                  90                  95

Ile Phe Val His Asn Thr
            100

<210> SEQ ID NO 94
<211> LENGTH: 97
<212> TYPE: PRT
<213> ORGANISM: Pyrococcus furiosus

<400> SEQUENCE: 94

Cys Val Val Gly Asp Thr Arg Ile Leu Thr Pro Glu Gly Tyr Leu Lys
1               5                   10                  15

Ala Glu Glu Ile Phe Ser Leu Ala Lys Glu Arg Glu Glu Lys Val Glu
            20                  25                  30

Tyr Glu Thr Val His Gly Lys Val Leu Ala Val Ala Asp Pro Val Ala
        35                  40                  45

Val Pro Ala Tyr Val Trp Lys Val Gly Arg Lys Lys Val Ala Arg Val
    50                  55                  60

Lys Thr Ser Val Glu Val Leu Gly Glu Ile Val Tyr Asp Phe Thr
65                  70                  75                  80

Val Pro Asn Tyr His Met Tyr Ile Ser Asn Gly Phe Met Ser His Asn
                85                  90                  95

Cys

<210> SEQ ID NO 95
<211> LENGTH: 93
<212> TYPE: PRT
<213> ORGANISM: Pyrococcus sp.

<400> SEQUENCE: 95

```
Cys His Pro Ala Asp Thr Lys Val Val Lys Gly Lys Gly Ile Ile
1               5                   10                  15

Asn Ile Ser Glu Val Gln Glu Gly Asp Leu Lys Cys Thr Pro Asn His
            20                  25                  30

Lys Leu Pro Val Val Thr Lys Asn Glu Arg Gln Thr Arg Ile Arg Asp
        35                  40                  45

Ser Leu Ala Lys Ser Phe Leu Thr Lys Val Glu Phe Asn Val Ser
    50                  55                  60

Thr Glu Tyr Tyr Glu Gly Lys Val Tyr Asp Leu Thr Leu Glu Gly Thr
65                  70                  75                  80

Pro Tyr Tyr Phe Ala Asn Gly Ile Leu Thr His Asn Ser
                85                  90
```

<210> SEQ ID NO 96
<211> LENGTH: 99
<212> TYPE: PRT
<213> ORGANISM: Methanococcus jannaschii

<400> SEQUENCE: 96

```
Cys His Pro Lys Gly Thr Lys Val Val Lys Gly Lys Gly Ile Val
1               5                   10                  15

Asn Ile Glu Asp Val Lys Glu Gly Asn Leu Lys Cys Thr Pro Met His
            20                  25                  30

Lys Ile Pro Leu Arg Tyr Lys Ile Lys His Lys Lys Ile Asn Lys Asn
        35                  40                  45

Asp Tyr Leu Val Arg Asp Ile Tyr Ala Lys Ser Leu Leu Thr Lys Phe
    50                  55                  60

Lys Asp Val Cys Val Ser Leu Glu Ser Tyr Lys Gly Glu Val Tyr Asp
65                  70                  75                  80

Leu Thr Leu Gly Glu Arg Pro Tyr Tyr Phe Ala Asn Gly Ile Leu Thr
                85                  90                  95

His Asn Ser
```

<210> SEQ ID NO 97
<211> LENGTH: 104
<212> TYPE: PRT
<213> ORGANISM: Methanococcus jannaschii

<400> SEQUENCE: 97

```
Ser Val Ser Lys Asp Thr Pro Ile Leu Val Lys Ile Asp Gly Lys Val
1               5                   10                  15

Lys Arg Thr Thr Phe Glu Glu Leu Asp Lys Ile Tyr Gly Gly Tyr Ile
            20                  25                  30

Glu Leu Thr Gly Asn His Ser Ile Met Met Leu Asp Glu Asn Gly Leu
        35                  40                  45

Val Ala Lys Lys Ala Ser Asp Ile Lys Val Gly Asp Cys Phe Leu Ser
    50                  55                  60

Phe Val Ala Asn Val Lys Glu Ile Glu Ile Asp Tyr Asn Asp Phe
65                  70                  75                  80

Val Tyr Asp Val Ser Val Pro Asn Asn Glu Met Phe Phe Ala Gly Asn
```

```
                 85                  90                  95

Val Pro Ile Leu Leu His Asn Ser
            100

<210> SEQ ID NO 98
<211> LENGTH: 104
<212> TYPE: PRT
<213> ORGANISM: Pyrococcus sp.

<400> SEQUENCE: 98

Ser Ile Leu Pro Glu Glu Trp Val Pro Leu Ile Lys Asn Gly Lys Val
1               5                   10                  15

Lys Ile Phe Arg Ile Gly Asp Phe Val Asp Gly Leu Gly Arg Lys Ile
            20                  25                  30

Thr Ile Thr Glu Gly His Ser Leu Phe Val Tyr Arg Asn Gly Asp Leu
        35                  40                  45

Val Glu Ala Thr Gly Glu Asp Val Lys Ile Gly Asp Leu Leu Ala Val
    50                  55                  60

Pro Arg Ser Val Val Glu Ile Lys Arg Glu Tyr Tyr Asp Gly Tyr
65                  70                  75                  80

Val Tyr Asp Leu Ser Val Asp Glu Asp Glu Asn Phe Leu Ala Gly Phe
                85                  90                  95

Gly Phe Leu Tyr Ala His Asn Ser
            100

<210> SEQ ID NO 99
<211> LENGTH: 104
<212> TYPE: PRT
<213> ORGANISM: Pyrococcus sp.

<400> SEQUENCE: 99

Ser Ile Leu Pro Glu Glu Trp Leu Pro Val Leu Glu Glu Gly Glu Val
1               5                   10                  15

His Phe Val Arg Ile Gly Glu Leu Ile Asp Arg Met Gly Arg Arg Ile
            20                  25                  30

Lys Ile Thr Ser Gly His Ser Leu Phe Ser Val Arg Asn Gly Glu Leu
        35                  40                  45

Val Glu Val Thr Gly Asp Glu Leu Lys Pro Gly Asp Leu Val Ala Val
    50                  55                  60

Pro Arg Arg Leu Val Glu Ser Val Asp Val Asp Tyr Asp Gly Tyr
65                  70                  75                  80

Val Tyr Asp Leu Ser Val Glu Asp Asn Glu Asn Phe Leu Val Gly Phe
                85                  90                  95

Gly Leu Val Tyr Ala His Asn Ser
            100

<210> SEQ ID NO 100
<211> LENGTH: 104
<212> TYPE: PRT
<213> ORGANISM: Thermococcus litoralis

<400> SEQUENCE: 100

Ser Ile Leu Pro Asn Glu Trp Leu Pro Ile Ile Glu Asn Gly Glu Ile
1               5                   10                  15

Lys Phe Val Lys Ile Gly Glu Phe Ile Asn Ser Tyr Gly Arg Lys Ile
            20                  25                  30

Asn Ile Thr Ala Gly His Ser Leu Phe Thr Val Arg Asn Gly Glu Ile
        35                  40                  45
```

-continued

Lys Glu Val Ser Gly Asp Gly Ile Lys Glu Gly Asp Leu Ile Val Ala
        50                  55                  60

Pro Lys Lys Ile Val Lys Ser Val Lys Glu Lys Asp Tyr Glu Gly Tyr
 65                  70                  75                  80

Val Tyr Asp Leu Ser Val Glu Asp Asn Glu Asn Phe Leu Val Gly Phe
                85                  90                  95

Gly Leu Leu Tyr Ala His Asn Ser
                100

<210> SEQ ID NO 101
<211> LENGTH: 99
<212> TYPE: PRT
<213> ORGANISM: Thermococcus litoralis

<400> SEQUENCE: 101

Ser Val Ser Gly Glu Ser Glu Ile Ile Ile Arg Gln Asn Gly Lys Ile
 1               5                  10                  15

Arg Phe Val Lys Ile Lys Asp Leu Phe Ser Lys Val Ser Trp Tyr Ile
                20                  25                  30

Asp Val Thr Glu Asp His Ser Leu Ile Gly Tyr Leu Asn Thr Ser Lys
            35                  40                  45

Thr Lys Thr Ala Lys Lys Ile Gly Glu Arg Leu Lys Glu Val Lys Pro
 50                  55                  60

Phe Val Lys Lys Val Glu Ile Pro Tyr Glu Gly Tyr Val Tyr Asp
 65                  70                  75                  80

Ile Glu Val Glu Glu Thr His Arg Phe Phe Ala Asn Asn Ile Leu Val
                85                  90                  95

His Asn Thr

<210> SEQ ID NO 102
<211> LENGTH: 102
<212> TYPE: PRT
<213> ORGANISM: Methanococcus jannaschii

<400> SEQUENCE: 102

Ser Ile Leu Pro Asp Glu Tyr Leu Thr Ile Glu Glu Asp Gly Ile
 1               5                  10                  15

Lys Val Val Lys Ile Gly Glu Tyr Ile Asp Asp Leu Gly Arg Thr Ile
                20                  25                  30

Lys Val Thr Arg Gly His Ser Leu Phe Lys Tyr Glu Asn Gly Lys Ile
            35                  40                  45

Val Glu Val Lys Gly Asp Asp Val Arg Phe Gly Asp Leu Ile Val Val
 50                  55                  60

Pro Lys Lys Leu Val Lys Glu Ile Glu Ala Phe Glu Tyr Ser Gly Tyr
 65                  70                  75                  80

Val Tyr Asp Leu Ser Val Glu Asp Asn Glu Asn Phe Leu Val Asn Asn
                85                  90                  95

Ile Tyr Ala His Asn Ser
                100

<210> SEQ ID NO 103
<211> LENGTH: 105
<212> TYPE: PRT
<213> ORGANISM: Methanococcus jannaschii

<400> SEQUENCE: 103

Ser Val Asp Tyr Asn Glu Pro Ile Ile Ile Lys Glu Asn Gly Glu Ile
 1               5                  10                  15

```
Lys Val Val Lys Ile Gly Glu Leu Ile Asp Lys Ile Asn Lys Lys Val
            20                  25                  30

Arg Val Thr Arg Ser His Ser Val Phe Thr Ile Arg Asp Asn Glu Val
        35                  40                  45

Val Pro Ile Arg Val Asp Glu Leu Lys Val Gly Asp Ile Leu Val Leu
 50                  55                  60

Ala Lys Glu Leu Ile Lys Glu Ile Asn Lys Val Glu Pro Thr Ser Gly
 65                  70                  75                  80

Tyr Ala Tyr Asp Leu Thr Val Pro Asn Ala Glu Asn Phe Val Ala Gly
                85                  90                  95

Phe Gly Gly Phe Val Leu His Asn Thr
            100                 105

<210> SEQ ID NO 104
<211> LENGTH: 120
<212> TYPE: PRT
<213> ORGANISM: Methanococcus jannaschii

<400> SEQUENCE: 104

Ser Leu Gly Arg Asp Glu Leu Ile Phe Ile Lys Glu Gly Gly Asp Lys
 1               5                   10                  15

Leu Lys Val Cys Lys Ile Gly Glu Ala Ile Asp Glu Phe Gly Thr Ser
            20                  25                  30

Ile Ile Val Thr Glu Asp His Ser Leu Phe Asn Tyr Asp Glu Asn Gly
        35                  40                  45

Asn Leu Val Cys Val Lys Pro Arg Gln Met Lys His Ile Ile Arg Asn
 50                  55                  60

Phe Asn Asn Pro Tyr Asp Val Glu Tyr Arg Ile Gly Asp Tyr Ile Glu
 65                  70                  75                  80

Thr Asn Tyr Gln Arg Ile Lys Glu Ile Lys Glu Ile Asp Tyr Asn Gly
                85                  90                  95

Tyr Val Tyr Asp Leu Ser Val Glu Asp Asn Glu Asn Phe Ile Thr Ala
                100                 105                 110

Thr Gly Ile Leu Cys His Asn Thr
        115                 120

<210> SEQ ID NO 105
<211> LENGTH: 106
<212> TYPE: PRT
<213> ORGANISM: Methanococcus jannaschii

<400> SEQUENCE: 105

Ser Leu Pro Tyr Asp Glu Lys Ile Leu Ile Phe Glu Asn Asn Glu Tyr
 1               5                   10                  15

Lys Leu Val Lys Ile Gly Glu Phe Val Glu Lys Tyr Gly Lys Lys Val
            20                  25                  30

Arg Val Thr Gly Asp His Ser Val Phe Thr Ile Asn Asp Asn Leu Asp
        35                  40                  45

Val Val Glu Val Lys Ala Ser Asp Leu Lys Val Gly Asp Phe Ile Ile
 50                  55                  60

Thr Pro Lys Ile Ile Ile Lys Ser Ile Arg Val Leu Asp Glu Ile Pro
 65                  70                  75                  80

Glu Tyr Val Tyr Asp Ile Ser Val Glu Gly Thr Glu Asn Phe Ile Gly
                85                  90                  95

Gly Glu Gly Phe Ile Cys Leu His Asn Thr
            100                 105
```

```
<210> SEQ ID NO 106
<211> LENGTH: 104
<212> TYPE: PRT
<213> ORGANISM: Methanococcus jannaschii

<400> SEQUENCE: 106

Ser Leu Pro Tyr Glu Glu Lys Ile Ile Ile Lys Glu Gly Glu Phe Ile
1               5                   10                  15

Lys Pro Val Glu Ile Gly Lys Leu Val Asp Glu Met Gly Arg Glu Ile
            20                  25                  30

Thr Ala Thr Pro Tyr His Ser Phe Val Ile Arg Lys Asp Asn Lys Ile
        35                  40                  45

Ile Pro Val Lys Gly Ser Glu Leu Lys Ile Gly Asp Arg Ile Pro Val
    50                  55                  60

Val Lys His Ile Ile Val Lys Ile Glu Glu Ile Ser Cys Asp Lys Lys
65                  70                  75                  80

Tyr Val Tyr Asp Ile Ser Val Glu Gly Leu Glu Thr Phe Thr Thr Phe
                85                  90                  95

Asp Gly Val Leu Thr His Asn Thr
            100

<210> SEQ ID NO 107
<211> LENGTH: 101
<212> TYPE: PRT
<213> ORGANISM: Methanococcus jannaschii

<400> SEQUENCE: 107

Ala Leu Ala Tyr Asp Glu Pro Ile Tyr Leu Ser Asp Gly Asn Ile Ile
1               5                   10                  15

Asn Ile Gly Glu Phe Val Asp Lys Phe Arg Arg Glu Ile Thr Leu Thr
            20                  25                  30

His Asp His Pro Val Tyr Ile Ser Lys Thr Gly Glu Val Leu Glu Ile
        35                  40                  45

Asn Ala Glu Met Val Lys Val Gly Asp Tyr Ile Tyr Ile Pro Lys Asn
    50                  55                  60

Asn Ile Lys Val Glu Thr Val Asp Tyr Asn Gly His Ile Tyr Asp Leu
65                  70                  75                  80

Thr Val Glu Asp Asn His Thr Tyr Ile Ala Gly Lys Asn Glu Gly Phe
                85                  90                  95

Ala Val Ser Asn Cys
            100

<210> SEQ ID NO 108
<211> LENGTH: 72
<212> TYPE: PRT
<213> ORGANISM: Yeast

<400> SEQUENCE: 108

Met Leu Ser Glu Asn Thr Thr Ile Leu Met Ala Asn Gly Glu Ile Lys
1               5                   10                  15

Asp Ile Ala Asn Val Thr Ala Asn Ser Tyr Val Met Arg Leu Ala Leu
            20                  25                  30

Gln Cys Thr Ala Gly His Lys Leu Ser Val Arg Val Pro Thr Lys Pro
        35                  40                  45

Leu Leu Glu Lys Ser Gly Arg Asn Ala Thr Lys Tyr Lys Val Arg Trp
    50                  55                  60

Arg Asn Leu Gln Gln Cys Gln Thr
65                  70
```